US012686680B2

(12) United States Patent
Ashweek et al.

(10) Patent No.: US 12,686,680 B2
(45) Date of Patent: Jul. 21, 2026

(54) SUBSTITUTED PYRAZOLO[1,5-α]PYRIMIDINES AS CRF RECEPTOR ANTAGONISTS

(71) Applicant: Neurocrine Biosciences, Inc., San Diego, CA (US)

(72) Inventors: Neil J. Ashweek, San Diego, CA (US); John P. Williams, San Diego, CA (US); Lev Alexander Zegelman, San Diego, CA (US); Christina Marie Costa, San Diego, CA (US); Scott Stirn, San Diego, CA (US); Shawn Branum, San Diego, CA (US); Jackie Le, San Diego, CA (US); John Lloyd Tucker, San Diego, CA (US); Brian M. Cochran, San Diego, CA (US); David Kucera, San Diego, CA (US); Donald Hettinger, San Diego, CA (US); Max A. Mellmer, San Diego, CA (US)

(73) Assignee: Neurocrine Biosciences, Inc., San Diego, CA (US)

( * ) Notice: Subject to any disclaimer, the term of this patent is extended or adjusted under 35 U.S.C. 154(b) by 881 days.

(21) Appl. No.: 17/782,615

(22) PCT Filed: Dec. 1, 2020

(86) PCT No.: PCT/US2020/062747
§ 371 (c)(1),
(2) Date: Jun. 3, 2022

(87) PCT Pub. No.: WO2021/113263
PCT Pub. Date: Jun. 10, 2021

(65) Prior Publication Data

US 2023/0065034 A1 Mar. 2, 2023

Related U.S. Application Data

(60) Provisional application No. 62/943,517, filed on Dec. 4, 2019.

(51) Int. Cl.

| | |
|---|---|
| ***A61K 31/519*** | (2006.01) |
| ***A61P 5/00*** | (2006.01) |
| ***C07D 231/54*** | (2006.01) |
| ***C07D 233/20*** | (2006.01) |
| ***C07D 487/04*** | (2006.01) |
| ***G01N 33/74*** | (2006.01) |

(52) U.S. Cl.
CPC .............. *C07D 487/04* (2013.01); *A61P 5/00* (2018.01); *C07D 231/54* (2013.01); *C07D 233/20* (2013.01); *G01N 33/74* (2013.01)

(58) Field of Classification Search
CPC ............................ A61K 31/519; C07D 487/04
USPC ........................................ 514/259.3; 544/282
See application file for complete search history.

(56) References Cited

U.S. PATENT DOCUMENTS

| | | | |
|---|---|---|---|
| 5,464,847 | A | 11/1995 | Courtemanche et al. |
| 6,344,470 | B1 | 2/2002 | Fontaine et al. |
| 6,365,180 | B1 | 4/2002 | Meyer et al. |
| 6,531,475 | B1 | 3/2003 | Haddach et al. |
| 6,586,456 | B1 | 7/2003 | Fontaine et al. |
| 6,610,678 | B2 | 8/2003 | Huang et al. |
| 6,664,261 | B2 | 12/2003 | Chen et al. |
| 6,806,282 | B2 | 10/2004 | Geslin et al. |
| 7,276,526 | B2 | 10/2007 | Termin et al. |
| 7,297,708 | B2 | 11/2007 | Termin et al. |
| 7,951,803 | B2 | 5/2011 | Cole et al. |
| 8,030,304 | B2 | 10/2011 | Chen et al. |
| 8,153,127 | B2 | 4/2012 | Paez-Pereda et al. |
| 8,314,249 | B2 | 11/2012 | Fazekas et al. |
| 8,420,679 | B2 | 4/2013 | Fontaine et al. |
| 9,351,517 | B2 | 5/2016 | Bromley |
| 10,758,490 | B2 | 9/2020 | Viladot Petit et al. |
| 10,849,908 | B2 | 12/2020 | Howerton et al. |
| 10,898,477 | B2 | 1/2021 | Madhavi et al. |
| 10,905,690 | B2 | 2/2021 | Grigoriadis |
| 11,007,201 | B2 | 5/2021 | Howerton et al. |
| 11,304,950 | B2 | 4/2022 | Howerton et al. |
| 11,311,544 | B2 | 4/2022 | Grigoriadis |
| 11,583,502 | B2 | 2/2023 | Wu et al. |
| 11,730,739 | B2 | 8/2023 | Grigoriadis |
| 11,858,932 | B2 | 1/2024 | Barnes et al. |
| 12,128,033 | B2 | 10/2024 | Becker et al. |
| 12,214,084 | B2 | 2/2025 | Osaki et al. |

(Continued)

FOREIGN PATENT DOCUMENTS

| | | |
|---|---|---|
| CN | 1370154 | 9/2002 |
| CN | 101381314 A | 3/2009 |

(Continued)

OTHER PUBLICATIONS

[No Author Listed], "Assessing the Effects of Food on Drugs in INDs and NDAs—Clinical Pharmacology Considerations Guidance for Industry," U.S. Department of Health and Human Services, Food and Drug Administration, Center for Drug Evaluation and Research (CDER), Feb. 2019, Clinical Pharmacology, 17 pages.

(Continued)

*Primary Examiner* — Douglas M Willis
(74) *Attorney, Agent, or Firm* — Fish & Richardson P.C.

(57) ABSTRACT

Compounds are provided herein that antagonize corticotropin-releasing factor (CRF) receptors, in particular CRF receptor 1 ($CRF_1$), as well as related preparations, compositions and methods for treating diseases and/or disorders that would benefit from the same such as congenital adrenal hyperplasia (CAH).

36 Claims, 18 Drawing Sheets

(56) References Cited

U.S. PATENT DOCUMENTS

| | | | |
|---|---|---|---|
| 12,383,536 | B2 | 8/2025 | Smith et al. |
| 12,582,634 | B2 | 3/2026 | Becker et al. |
| 2005/0209250 | A1 | 9/2005 | Romano |
| 2006/0078623 | A1 | 4/2006 | Dhoot et al. |
| 2007/0281919 | A1 | 12/2007 | Fontaine et al. |
| 2009/0203755 | A1 | 8/2009 | Richard |
| 2010/0216751 | A1 | 8/2010 | Jacob et al. |
| 2010/0222339 | A1 | 9/2010 | Chen et al. |
| 2013/0183383 | A1 | 7/2013 | Phang et al. |
| 2015/0094310 | A1 | 4/2015 | Holsboer |
| 2015/0284362 | A1 | 10/2015 | Bersot et al. |
| 2017/0020877 | A1 | 1/2017 | Grigoriadis |
| 2019/0231781 | A1 | 8/2019 | Grigoriadis |
| 2020/0255436 | A1 | 8/2020 | Howerton et al. |
| 2021/0137926 | A1 | 5/2021 | Grigoriadis |
| 2021/0361659 | A1 | 11/2021 | Grigoriadis |
| 2022/0023266 | A1 | 1/2022 | Farber et al. |
| 2022/0133742 | A1 | 5/2022 | Ghosh et al. |
| 2022/0211711 | A1 | 7/2022 | Howerton et al. |
| 2022/0409592 | A1 | 12/2022 | Smith et al. |
| 2023/0233534 | A1 | 7/2023 | Palmer et al. |
| 2023/0255942 | A1 | 8/2023 | Farber et al. |
| 2023/0286932 | A1 | 9/2023 | Palmer et al. |
| 2023/0295161 | A1 | 9/2023 | Barnes et al. |
| 2024/0024330 | A1 | 1/2024 | Loewen et al. |
| 2024/0058342 | A1 | 2/2024 | Grigoriadis |
| 2024/0238257 | A1 | 7/2024 | Becker et al. |

FOREIGN PATENT DOCUMENTS

| | | | |
|---|---|---|---|
| CN | 102414185 | | 4/2012 |
| CN | 106102740 | | 11/2016 |
| CN | 107438606 | | 12/2017 |
| EP | 3784233 | B1 | 6/2024 |
| JP | 2002-030048 | A | 1/2002 |
| JP | 4949582 | | 3/2012 |
| JP | 2012-525368 | A | 10/2012 |
| JP | 2013-231063 | | 11/2013 |
| JP | 2015-516979 | A | 6/2015 |
| JP | 2018-516231 | A | 6/2018 |
| RU | 2523793 | C2 | 7/2014 |
| RU | 2667977 | C2 | 9/2018 |
| WO | WO 1987/005297 | | 9/1987 |
| WO | WO 1998/008846 | | 3/1998 |
| WO | WO 1998/011075 | | 3/1998 |
| WO | WO 1999/010350 | | 3/1999 |
| WO | WO 2000/059888 | | 10/2000 |
| WO | WO 2001/005776 | | 1/2001 |
| WO | WO 2003/006015 | | 1/2003 |
| WO | WO 2003/022820 | A1 | 3/2003 |
| WO | WO 2006/044821 | | 4/2006 |
| WO | WO 2006/044958 | | 4/2006 |
| WO | WO 2006/102194 | | 9/2006 |
| WO | WO 2006/107784 | | 10/2006 |
| WO | WO 2006/116412 | | 11/2006 |
| WO | WO 2006/126718 | | 11/2006 |
| WO | WO 2007/069565 | | 6/2007 |
| WO | WO 2007/069671 | | 6/2007 |
| WO | WO 2007/090631 | | 8/2007 |
| WO | WO 2007/104053 | A2 | 9/2007 |
| WO | WO 2007/105113 | | 9/2007 |
| WO | WO 2007/137227 | | 11/2007 |
| WO | WO 2008/036541 | | 3/2008 |
| WO | WO 2008/036579 | | 3/2008 |
| WO | WO 2008/051533 | | 5/2008 |
| WO | WO 2008/082003 | | 7/2008 |
| WO | WO 2008/083070 | | 7/2008 |
| WO | WO 2008/136377 | | 11/2008 |
| WO | WO 2009/008552 | | 1/2009 |
| WO | WO 2009/144632 | | 12/2009 |
| WO | WO 2010/014280 | | 2/2010 |
| WO | WO 2010/014687 | | 2/2010 |
| WO | WO 2010/015628 | | 2/2010 |
| WO | WO 2010/015655 | | 2/2010 |
| WO | WO 2010/062718 | | 6/2010 |
| WO | WO 2010/096426 | | 8/2010 |
| WO | WO 2010/125414 | | 11/2010 |
| WO | WO 2011/043381 | | 4/2011 |
| WO | WO 2011/043387 | | 4/2011 |
| WO | WO 2011/092290 | | 8/2011 |
| WO | WO 2011/092293 | | 8/2011 |
| WO | WO 2011/095450 | | 8/2011 |
| WO | WO 2011/128783 | A2 | 10/2011 |
| WO | WO 2013/155464 | | 10/2013 |
| WO | WO 2013/160315 | | 10/2013 |
| WO | WO 2013/160317 | | 10/2013 |
| WO | WO 2014/151109 | A1 | 9/2014 |
| WO | WO 2015/112642 | | 7/2015 |
| WO | WO 2015/155664 | A1 | 10/2015 |
| WO | WO 2015/159170 | A2 | 10/2015 |
| WO | WO 2016/065177 | | 4/2016 |
| WO | WO 2016/127133 | | 8/2016 |
| WO | WO 2016/156575 | A2 | 10/2016 |
| WO | WO 2016/156576 | | 10/2016 |
| WO | WO 2017/031325 | A1 | 2/2017 |
| WO | WO 2017/218379 | A1 | 12/2017 |
| WO | WO 2018/102552 | | 6/2018 |
| WO | WO 2018/213634 | A1 | 11/2018 |
| WO | WO 2018/219804 | | 12/2018 |
| WO | WO 2019/036472 | | 2/2019 |
| WO | WO 2019/036503 | | 2/2019 |
| WO | WO 2019/210266 | | 10/2019 |
| WO | WO 2020/115555 | | 6/2020 |
| WO | WO 2021/016208 | | 1/2021 |
| WO | WO 2021/062246 | | 4/2021 |
| WO | WO 2021/111179 | A1 | 6/2021 |
| WO | WO 2021/113263 | | 6/2021 |
| WO | WO 2021/250468 | | 12/2021 |
| WO | WO 2021/252669 | | 12/2021 |
| WO | WO 2022/036123 | A1 | 2/2022 |
| WO | WO 2022/046905 | | 3/2022 |
| WO | WO 2022/153062 | A1 | 7/2022 |
| WO | WO 2022/184549 | A1 | 9/2022 |
| WO | WO 2024/206769 | | 10/2024 |

OTHER PUBLICATIONS

[No Author Listed], "Form 8-K: Current Report," Securities and Exchange Commission, Washington, D.C., Apr. 5, 2000, 4 pages.

[No Author Listed], "IUPAC-IUB, Commission on Biochemical Nomenclature—Abbreviated Nomenclature of Synthetic Polypeptides (Polymerized Amino Acids)*—Revised Recommendations (1971)," Biochemistry, 1972, 11(5):942-944.

[No Author Listed], "Neurocrine announces top-line results of corticotropin releasing factor antagonist GSK561679 for treatment of major depressive disorder," Neurocrine Biosciences, Inc., Sep. 14, 2010, 1 page.

[No Author Listed], "Sanofi-Aventis: strong performance of growth platforms in Q1 2011," Sanofi Press Release, Apr. 28, 2011, 13 pages.

[No Author Listed], "Neurocrine Biosciences Reports Positive Phase II Data for Crinecerfont in Adults with Congenital Adrenal Hyperplasia at ENDO Online 2020," Neurocrine Biosciences Inc., Jun. 8, 2020, 3 pages.

[No Author Listed], "Neurocrine Biosciences to Present New Data Analyses for Crinecerfont in Adults with Classical Congenital Adrenal Hyperplasia at ENDO 2021," Neurocrine Biosciences Inc., Mar. 20, 2021, 5 pages.

[No Author Listed], "Spruce Biosciences Presents Phase 1 and 2 Data for Tildacerfont in Adults with Congenital Adrenal Hyperplasia from Endocrine Society's 2021 Annual Meeting," Spruce Biosciences, Mar. 17, 2021, 2 pages.

Abdellatif, "Microparticles Formulation as a Targeting Drug Delivery System," J Nanomed Res., 2017, 6(2):00151.

Alejandro et al., "Behavioral, Adrenal, and Sympathetic Responses to Long-Term Administration of an Oral Corticotropin-Releasing Hormone Receptor Antagonist in a Primate Stress Paradigm," The Journal of Clinical Endocrinology & Metabolism, Nov. 1, 2004, 89(11):5729-5737.

(56) References Cited

OTHER PUBLICATIONS

Allen et al., "Psychometric evaluation and tests of validity of the Medical Outcomes Study 12-item Sleep Scale (MOS sleep)," Sleep Medicine, May 1, 2009;10(5):531-9.
Ambroziak et al., "Congenital adrenal hyperplasia due to 21-hydroxylase deficiency—management in adults," Polish Journal of Endocrinology, 2010, 61:142-155.
Anthenelli et al., "Sex Differences in the ACTH and Cortisol Response to Pharmacological Probes are Stressor-Specific and Occur Regardless of Alcohol Dependence History," Psychoneuroendocrinology, Aug. 2018, 94:72-82.
Arlt et al., "Health status of adults with congenital adrenal hyperplasia: a cohort study of 203 patients," J Clin Endocrinol Metab., Nov. 2010, 95(11):5110-21.
Arvanitis, AG., et al., "Non-Peptide Corticotropin-Releasing Hormone Antagonists: Syntheses and Structure-Activity Relationships of 2-Anilinopyrimidines and—triazines," J. Med. Chem., 1999, 42(5): 805-818.
Auchus et al., "A pharmacokinetic and biomarker study of the corticotropin-releasing factor receptor antagonist NBI-77860 in adult females with classic, 21-hydroxylase deficiency, congenital adrenal hyperplasia (CAH)," OR06 HPA Axis and Adrenal: Receptors to Clinical Impact, Platform presentation at the 97th annual meeting of the Endocrine Society (ENDO 2015), Mar. 2015, 1 page.
Auchus et al., "Approach to the patient: the adult with congenital adrenal hyperplasia," J Clin Endocrinol Metab., Jul. 2013, 98(7):2645-55.
Auchus et al., "Crinecerfont (NBI-74788), a novel CRFI receptor antagonist, reduces adrenal androgens and precursors in patients with classic congenital adrenal hyperplasia: Results from a phase 2, multiple-dose study," Poster Presentation, Presented Virtually at The 22nd European Congress of Endocrinology, Sep. 5- 9, 2020, 1 page.
Auchus et al., "Crinecerfont lowers elevated hormone markers in adults with 21-hydroxylase deficiency congenital adrenal hyperplasia," The Journal of Clinical Endocrinology & Metabolism, 2022, 107(3):801-812.
Auchus et al., "OR18-4 Crinecerfont (NBI-74788), a Novel CRFI Receptor Antagonist, Lowers Adrenal Androgens and Precursors in Adolescents with Classic Congenital Adrenal Hyperplasia," Journal of the Endocrine Society, 2022, 6(Supplement 1):A618.
Auchus et al., "Response to Crinecerfont Treatment in Adults with Classic Congenital Adrenal Hyperplasia Is Correlated with Elevated Baseline Hormone Levels But Not Glucocorticoid Dose," Abstract submitted to ECE for consideration at 2023 annual meeting, prepared on Mar. 2023, 2 pages.
Auchus et al., "The Effects of Crinecerfont (NBI-74788), a Novel CRF1 Receptor Antagonist, on Adrenal Androgens and Precursors in Patients with Classic Congenital Adrenal Hyperplasia: Results from A Multiple-Dose Phase 2 Study," J Endocrin Soc., 2020, 4(Supplement 1):OR25-03.
Auchus et al., "The effects of crinecerfont (NBI-74788), a novel CRF1 receptor antagonist, on adrenal androgens and precursors in patients with classic congenital adrenal hyperplasia: Results from a multiple-dose phase 2 study," Journal of the Endocrine Society, 2020, 4(Abstract Supplement):A111.
Auchus RJ, et al., "Management of the adult with congenital adrenal hyperplasia," Int J Ped Endocrinol., 2010, Article ID 614107: 1-9.
Bachelot A, et al., "Bone health should be an important concern in the care of patients affected by 21 hydroxylase deficiency," Int J Ped Endocrinol., 2010, Article ID 326275: 1-7.
Bakshi VP, et al., "Reduction of Stress-Induced Behavior by Antagonism of Corticotropin-Releasing Hormone 2 (CRH2) Receptors in Lateral Septum or CRH1 Receptors in Amygdala", J. Neurosci., 2002, 22(7): 2926-2935.
Bale et al., "Overview on Therapeutic Applications of Microparticulate Drug Delivery Systems," Crit Rev Ther Drug Carrier Syst., 2016, 33(4):309-361.
Barreau F et al., "Pathways involved in gut mucosal barrier dysfunction induced in adult rats by maternal deprivation: corticotrophin-releasing factor and nerve growth factor interplay," Journal of Physiology-London, 2007, 580(1):347-356.
Behan DP et al., "Neurobiology of corticotropin releasing factor (CRF) receptors and CRF-binding protein: implications for the treatment of CNS disorders," Molecular Psychiatry, 1996, 1(4):265-277.
Belza et al., "A systematic review of studies using the multidimensional assessment of fatigue scale," Journal of Nursing Measurement, May 1, 2018;26(1):36-74.
Belza, "Comparison of self-reported fatigue in rheumatoid arthritis and controls," J Rheumatol., Apr. 1995, 22(4):639-643.
Benedetti et al., "The Biochemical and Neuroendocrine Bases of the Hyperalgesic Nocebo Effect," J Neurosci., Nov. 15, 2006, 26(46):12014-12022.
Berge et al., "Pharmaceutical salts," Journal of Pharmaceutical Sciences, 1977, 66(1):1-9.
Bleicken B, et al., "Improvement of health-related quality of life in adult women with 21-hydroxylase deficiency over a seven-year period," Endocr J., 2012, 59(10):931-939.
Blume et al., "Oral medicine acceptance in infants and toddlers: measurement properties of the caregiver-administered Children's acceptance tool (CareCAT)," BMC pediatrics, 2018, 18:117.
Bonfig et al., "Reduced final height outcome in congenital adrenal hyperplasia under prednisone treatment: deceleration of growth velocity during puberty," J Clin Endocrinol Metab., May 2007, 92(5):1635-1639.
Bonfig W et al., "Hydrocortisone Dosing During Puberty in Patients With Classical Congenital Adrenal Hyperplasia: An Evidence-Based Recommendation," J Clin Endocrinol Metab., 2009, 94(10):3882-3888.
Bornstein et al., "Chronic effects of a nonpeptide corticotropin-releasing hormone type I receptor antagonist on pituitary-adrenal function, body weight, and metabolic regulation," Endocrinology, 1998, 139(4): 1546-1555.
Brazier et al., "Validating the SF-36 health survey questionnaire: new outcome measure for primary care," BMJ, Jul. 18, 1992, 305(6846):160-164.
Brunson KL, et al., "Corticotropin-Releasing Hormone (CRH) Downregulates the Function of Its Receptor (CRF1) and Induces CRF1 Expression in Hippocampal and Cortical Regions of the Immature Rat Brain," Experimental Neurology, 2002, 176(1):75-86.
Buxton et al., "Pharmacokinetics: The Dynamics of Drug Absorption, Distribution, Metabolism, and Elimination," Goodman & Gilman's The Pharmacological Basis of Therapeutics., Brunton L.L. ed., 12th ed. 2011, Chapter 2, 29 pages.
Caira, "Crystalline polymorphism of organic compounds," Design of Organic Solids, 1998, pp. 163-208.
Caresfoundation.org [Online], "Emergency Instructions - Treatment for Congenital Adrenal Hyperplasia in times of stress," 2014, [retrieved on Mar. 6, 2023], retrieved from: URL<https://caresfoundation.org/wp-content/uploads/2014/08/EmergencyBrochure2014.pdf>, 2 pages.
CAS Registry No., 321839-75-2, Feb. 15, 2001, 1 page.
Chakhtoura Z. et al., "Impact of total cumulative glucocorticoid dose on bone mineral density in patients with 21-hydroxylase deficiency," Eur J Endocrinol., 2008, 158(6):879-887.
Charmandari et al., "Bioavailability of oral hydrocortisone in patients with congenital adrenal hyperplasia due to 21-hydroxylase deficiency," J Endocrinol, Apr. 2001, 169(1):65-70.
Chatzaki, E, et al., "CRF receptor type 1 and 2 expression and anatomical distribution in the rat colon," Journal of Neurochemistry, 2004, 90: 309-316.
Chen C, et al., "NBI 30775 (R121919), an Orally Active Antagonist of the Corticotropin-releasing Factor (CRF) Type-1 Receptor for the Treatment of Anxiety and Depression," Drug Development Research, 2005, 65(4):216-226.
Chen C, et al., "1-Alkyl-3-amino-5-aryl-1H-[1,2,4]triazoles: novel synthesis via cyclization of N-Acyl-S-methylisothioureas with alkylhydrazines and their potent corticotropin-Releasing factor-1 (CRF1) receptor antagonist activities," Bioorganic & Medicinal Chemistry Letters, 2001, 11(24): 3165-3168.

(56) References Cited

OTHER PUBLICATIONS

Chen C, et al., "Design and Synthesis of a Series of Non-Peptide High-Affinity Human Corticotropin-Releasing Factor1 Receptor Antagonists," J. Med. Chem., 1996, 39(22): 4358-4360.
Chen C, et al., "Optimization of 3-phenylpyrazolo[1,5-a]pyrimidines as potent corticotropin-releasing factor-1 antagonists with adequate lipophilicity and water solubility" Bioorganic & Medicinal Chemistry Letters, 2004, 14(14): 3669-3673.
Chen et al., "Design of 2,5-dimethyl-3-(6-dimethyl-4-methylpyridin-3-yl)-7-dipropylaminopyrazolo[1,5-a] pyrimidine (NBI 30775/R121919) and structure-activity relationships of a series of potent and orally active corticotropin-releasing factor receptor antagonists," Journal of Medicinal Chemistry, 2004, 47(19):4787-4798.
Chen Y, et al., "Cellular and molecular mechanisms of hippocampal activation by acute stress are age-dependent," Molecular Psychiatry, 2006, 11: 992-1002.
Chen Y, et al., "Modulation of dendritic differentiation by corticotropin-releasing factor in the developing hippocampus," Proceedings of the National Academy of Sciences, 2004, 101(44): 15782-15787.
Cheng and Speiser, "Treatment outcomes in congenital adrenal hyperplasia," Adv Pediatr., 2012, 59(1):269-281.
Claahsen-van der Grinten et al., "Prevalence of testicular adrenal rest tumours in male children with congenital adrenal hyperplasia due to 21- hydroxylase deficiency," Eur J Endocrinol., Sep. 2007, 157(3):339-344.
Claustre et al., "Effects of the Vasopressin ($V_{1b}$) Receptor Antagonist, SSR149415, and the Corticotropin-Releasing Factor 1 Receptor Antagonist, SSR125543, on FG 7142-induced Increase in Acetylcholine and Norepinephrine Release in the Rat," Neuroscience, 2006, 141:1481-1488.
Clinicaltrials.gov [Online], "Safety, Tolerability, Pharmacokinetics, and Pharmacodynamics of NBI-74788 in Pediatric Subjects With Congenital Adrenal Hyperplasia," First Posted Aug. 5, 2019, [Retrieved on Nov. 30, 2022], retrieved from: URL<https://clinicaltrials.gov/ct2/show/NCT04045145>, 7 pages.
Clinicaltrials.gov, "A study in patients with irritable bowel syndrome to measure hormone response after dosing with GW876008 and Gsk561679," U.S. National Library of Medicine, Aug. 6, 2007, retrieved on Jun. 11, 2020, retrieved from URL: https://clinicaltrials.gov/ct2/show/NCT00511563?term=NCT00511563&draw=1&rank=1, 5 pages.
Clinicaltrials.gov, "A study of the effects of a new antidepressant treatment (GSK561679) in females with major depressive disorder," U.S. National Library of Medicine, Aug. 13, 2008, retrieved on Jun. 11, 2020, retrieved from URL: https://clinicaltrials.gov/ct2/show/NCT00733980?term=NCT00733980&draw=2&rank=1, 14 pages.
Clinicaltrials.gov, "A study to compare the putative anxiolytic effect of 2 new drugs in subjects with social anxiety disorder," U.S. National Library of Medicine, Nov. 7, 2007, retrieved on Jun. 11, 2020, retrieved from URL: https://clinicaltrials.gov/ct2/show/NCT00555139?term=NCT00555139&draw=2&rank-1, 10 pages.
Clinicaltrials.gov, "CRF1 antagonist GSK561679 in alcoholism," U.S. National Library of Medicine, Aug. 24, 2010, retrieved on Sep. 25, 2020, retrieved from URL: https://clinicaltrials.gov/ct2/show/NCT01187511?term=NCT01187511&draw=2&rank=1, 20 pages.
Clinicaltrials.gov, "Evaluation of GSK561679 in women with post-traumatic stress disorder," U.S. National Library of Medicine, Nov. 25, 2009, retrieved on Jun. 11, 2020, retrieved from URL: https://clinicaltrials.gov/ct2/show/NCT01018992?term=NCT01018992&draw=2&rank=1, 9 pages.
Collier et al., "Radiosynthesis and In-Vivo Evaluation of the Pseudopeptide δ-Opioid Antagonist [$^{125}$I]-ITIPP(Ψ)," XIIIth International Symposium on Radiopharmaceutical Chemistry, J. Labelled Cpd. Radiopharm., 1999, 42(Suppl. 1):S264-S266.
Cottone P, et al., "CRF system recruitment mediates dark side of compulsive eating," Proceedings of the National Academy of Sciences, 2009, 106(47): 20016-20020.
Cui et al., "Modification of sample size in group sequential clinical trials," Biometrics, 1999, 55(3):853-857.
Curtis AL, et al., "Pharmacological comparison of two corticotropin-releasing factor antagonists: in vivo and in vitro studies," Journal of Pharmacology and Experimental Therapeutics, 1994, 268(1): 359-365.
Dai et al., "A Generic Headspace GC Method for Residual Solvents in Pharmaceuticals: Benefits, Rationale, and Adaptations for New Chemical Entities," LCGC North America, 2010, 28(1):54-66.
Dauber et al., "Nocturnal dexamethasone versus Hydrocortisone for the treatment of children with congenital adrenal hyperplasia," Int. J. of Pediatric Endocrinology, 2010, 2010(1):347636.
de Vries et al., "Mental health of a large group of adults with disorders of sex development in six European countries," Psychosomatic Medicine, 2019, 81(7):629-640.
Deak et al., "The impact of the nonpeptide corticotropin-releasing hormone antagonist antalarmin on behavioral and endocrine responses to stress," Endocrinology, 1999, 140(1):79-86.
Derendorf et al., "Pharmacokinetics and oral bioavailability of hydrocortisone," J Clin Pharmacol. May 1991, 31(5):473-476.
Douma et al., "CRF1 receptor antagonists do not reverse pharmacological disruption of prepulse inhibition in rodents," Psychopharmacology, 2014, 231:1289-1303.
Dournes et al., "Deep brain stimulation in treatment-resistant depression in mice: comparison with the $CRF_1$ antagonist, SSR125543," Progress in Neuro-Psychopharmacology & Biological Psychiatry, 2013, 40:213-220.
Doyon et al., "Effects of the $CRF_1$ receptor antagonist SSR125543 on energy balance and food deprivation-induced in neuronal activation in obese Zucker rats," J. of Endocrinology, 2007, 193:11-19.
Dudzinska B, et al., "Sexual Well-Being in Adult Male Patients with Congenital Adrenal Hyperplasia," Int J Endocrinol., 2014, ID 469289: 1-9.
Dunn et al., "Physiological and behavioral responses to corticotropin-releasing factor administration: is CRF a mediator of anxiety or stress responses?" Brain Res Brain Res Rev., May 1990-Aug. 15(2):71-100.
Dyck B, et al., "Potent, Orally Active Corticotropin-Releasing Factor Receptor-1 Antagonists Containing a Tricyclic Pyrrolopyridine or Pyrazolopyridine Core," J. Med. Chem., 2005, 48(12): 4100-4110.
Elder et al., "The utility of sulfonate salts in drug development," Journal of Pharmaceutical Sciences, Jan. 1, 2010, 99(7):2948-2961.
El-Maouche et al., "Adrenal morphology and associated comorbidities in congenital adrenal hyperplasia," Clinical Endocrinology, 2019, 91(2):247-255.
El-Maouche et al., "Longitudinal assessment of illnesses, stress dosing, and illness sequelae in patients with congenital adrenal hyperplasia," The Journal of Clinical Endocrinology & Metabolism, 2018, 103(6):2336-2345.
El-Maouche et al., "Congenital Adrenal Hyperplasia," Lancet., Nov. 11, 2017, 390:2194-2210.
Elnecave et al., "Bone mineral density in girls with classical congenital adrenal hyperplasia due to CYP21 deficiency," J Pediatr Endocrinol Metab., Dec. 2008, 21(12):1155-62.
Esteban et al., "Daily cortisol production rate in man determined by stable isotope dilution/mass spectrometry," J Clin Endocrinol Metab., Jan. 1991, 72(1):39-45.
EU Clinical Trials Register, "Abbreviated Style Clinical Study Report," Sanofi- Aventis Group, Sep. 5, 2011, 4 pages.
Fahmy et al., "Structure and Function of Small Non-Peptide CRF Antagonists and their Potential Clinical Use," Curr Mol Pharmacol., 2017, 10(4):270-281.
Falhammar et al., "Fertility, sexuality and testicular adrenal rest tumors in adult males with congenital adrenal hyperplasia," Eur J Endocrinol., Mar. 2012, 166(3):441-449.
Falhammar et al., "Fractures and bone mineral density in adult women with 21-hydroxylase deficiency," J Clin Endocrinol Metab. Dec. 2007; 92(12):4643-4649.
Falhammar et al., "Increased mortality in patients with congenital adrenal hyperplasia due to 21-hydroxylase deficiency," J Clin Endocrinol Metab., Dec. 2014, 99(12):E2715-21.
Falhammar et al., "Quality of life, social situation, and sexual satisfaction, in adult males with congenital adrenal hyperplasia," Endocrine, 2014, 47:299-307.

(56) References Cited

OTHER PUBLICATIONS

Finkielstain et al., "Clinical Characteristics of a Cohort of 244 Patients with Congenital Adrenal Hyperplasia," J Clin Endocrinol Metab, 2012, 97(12):4429-4438.
Fleck et al., "Binding Kinetics Redefine the Antagonist Pharmacology of the Corticotropin-Releasing Factor Type 1 Receptor," The Journal of Pharmacology and Experimental Therapeutics, 2012, 341(2):518-531.
Forest, "Recent advances in the diagnosis and management of congenital adrenal hyperplasia due to 21-hydroxylase deficiency," Human Reproduction Update, 2004, 10(6): 469-485.
Frederic et al., "Radiosynthesis of [C-11]SSR126374, a new selective CRF1 antagonist," Journal of Labelled Compounds & Radiopharmaceuticals, 2011, 54(1):273.
Fuqua et al., "Duration of suppression of adrenal steroids after glucocorticoid administration," International Journal of Pediatric Endocrinology, 2010, 2010:1-8.
Gilban D, et al., "Health related quality of life of children and adolescents with congenital hyperplasia in Brazil," Health Qual Life Outcomes, 2014, 12:107 (9 pages).
Gilligan et al., "Corticotropin-releasing factor antagonists: recent advances and exciting prospects for the treatment of human diseases," Curr. Opin. In Drug Discov. & Develop., 2004, 7(4)487-497.
Grammatopoulos et al., Functional characteristics of CRH receptors and potential clinical applications of CRH-receptor antagonists, TRENDS in Endocrinology & Metabolism, 2002, 13(10):436-444.
Griebel et al., "4-(2-Chloro-4-methoxy-5-methylphenyl)-N-[(1S)-2-cyclopropyl-1-(3-fluoro-4-methylphenyl)ethyl]5-methyl-N-(2-propynyl)-1,3-thiazol-2-amine Hydrochloride (SSR125543A), a Potent and Selective Corticotrophin-Releasing factor(1) Receptor Antagonist. II. Characterization in Rodent Models of Stress-Related Disorders," J. Pharmacol. Exp. Ther., 2002, 301(1):333-345.
Grigoriadis DE, "Corticotropin-Releasing Factor Receptor Antagonists: Potential Novel Therapies for Human Disease," Celltransmissions, 2003, 19(4): 3-10.
Grigoriadis DE, "The corticotropin-releasing factor receptor: a novel target for the treatment of depression and anxiety-related disorders," Expert Opin. Ther. Targets, 2005, 9(4): 651-684.
Grigoriadis DE, et al., "$^{125}$I-Tyr$^{0}$-Sauvagine: A Novel High Affinity Radioligand for the Pharmacological and Biochemical Study of Human Corticotropin-Releasing Factor 20 Receptors," Molecular Pharmacology, 1996, 50:679-686.
Grigoriadis DE, et al., "Drugability of Extracellular Targets: Discovery of Small Molecule Drugs Targeting Allosteric, Functional, and Subunit-Selective Sites on GPCRs and Ion Channels," Neuropsychopharmacology, 2009, 34: 106-125.
Grigoriadis, DE, et al., "The CRF Receptor Structure, Function and Potential for Therapeutic Intervention," Current Medicinal Chemistry—Central Nervous System Agents, 2001, 1(1): 63-97.
Gross RS, et al., "Design and Synthesis of Tricyclic Corticotropin-Releasing Factor-1 Antagonists," J. Med. Chem., 2005, 48(18): 5780-5793.
Grossi et al., "Development and validation of the short version of the Psychological General Well-Being Index (PGWB-S)," Health and Quality of Life Outcomes, 2006, 4(1):1-8.
Gully et al., "4-(2-Chloro-4-methoxy-5-methylphenyl)-*N*-[(1S)-2-cyclopropyl-1-(3- fluoro-4-methylphenyl)ethyl]5-methyl-*N*-(2-propynyl)-1,3-thiazol-2-amine hydrochloride (SSR125543A): A potent and selective corticotrophin-releasing factor$_1$ receptor antagonist. I. Biochemical and Pharmacological Characterization," Journal of Pharmacology and Experimental Therapeutics, 2002, 301(1):322-332.
Guo Z, et al., "Design and Synthesis of Tricyclic Imidazo[4,5-b]pyridin-2-ones as Corticotropin-Releasing Factor-1 Antagonists," J. Med. Chem., 2005 , 48(16): 5104-5107.
Habib et al., "Oral administration of a corticotropin-releasing hormone receptor antagonist significantly attenuates behavioral, neuroendocrine, and autonomic responses to stress in primates," Proceedings of the National Academy of Sciences, 2000, 97(11):6079-6084.
Halper et al., "Health-related quality of life in children with congenital adrenal hyperplasia," Health Qual. Life Outcomes, 2017, 15(1):194.
Hamilton, "Needle Phobia: A Neglected Diagnosis," J Fam Pract., Aug. 1995, 41(2):169-175.
Han et al., "Quality of life in adults with congenital adrenal hyperplasia relates to glucocorticoid treatment, adiposity and insulin resistance: United Kingdom Congenital Adrenal Hyperplasia Adult Study Executive (CaHASE)" Eur J Endocrinol., May 3, 2013, 168(6):887-893.
Han TS, et al., "Glucocorticoid treatment regimen and health outcomes in adults with congenital adrenal hyperplasia," Clin Endocrinol, 2013, 8:197-203.
Han TS, et al., "Relationship Between Final Height and Health Outcomes in Adults with Congenital Adrenal Hyperplasia: United Kingdom Congenital Adrenal Hyperplasia Adult Study Executive (CaHASE)," J Clin Endocrinol Metab., 2014, 99(8):E1547-E1555.
Han TS, et al., "Treatment and health outcomes in adults with congenital adrenal hyperplasia," Nat Rev Endocrinol., 2014, 10:115-124.
Hannah-Shmouni et al., "Genetics of Congenital Adrenal Hyperplasia," Best Pract Res Clin Endocrinol Metab., Apr. 2009, 23(2):181-192.
Hauger RL, et al., "International Union of Pharmacology. XXXVI. Current Status of the Nomenclature for Receptors for Corticotropin-Releasing Factor and Their Ligands," Pharmacological Reviews, 2003, 55(1): 21-26.
He et al., "Changes in adrenal and gonadal androgens after 14-day treatment with a CRF1 receptor antagonist, crinecerfont (NBI-74788), in men with classic 21-hydroxylase deficiency," Journal of the Endocrine Society, 2021, 5(Supplement_1):A78.
Heike et al., "Treatment of depression with the CRH-1-receptor antagonist R121919: endocrine changes and side effects", J Psych Res., Nov. 1, 2003, 37(8):525-533.
Heinrichs SC, et al., "Brain Penetrance, Receptor Occupancy and Antistress In Vivo Efficacy of a Small Molecule Corticotropin Releasing Factor Type I Receptor Selective Antagonist," Neuropsychopharmacology, 2002, 27:194-202.
Herdman et al., "Development and preliminary testing of the new five-level version of EQ-5D (EQ-5D-5L)," Qual Life Res., Dec. 2011, 20(10):1727-1736.
Hertzberg et al., "Birth prevalence rates of newborn screening disorders in relation to screening practices in the United States," J Pediatr., Oct. 2011, 159(4):555-560.
Hines et al., "Spatial abilities following prenatal androgen abnormality: targeting and mental rotations performance in individuals with congenital adrenal hyperplasia," Psychoneuroendocrinology, Nov. 2003, 28(8):1010-1026.
Hoare et al., "Mechanism of Corticotropin-Releasing Factor Type I Receptor Regulation by Nonpeptide Antagonists," Molecular Pharmacology, 2003, 63(3):751-756.
Hoare SRJ, et al., "Allosteric Ligands for the Corticotropin Releasing Factor Type 1 Receptor Modulate Conformational States Involved in Receptor Activation," Molecular Pharmacology, 2008, 73(5): 1371-1380.
Hoare SRJ, et al., "Conformational states of the corticotropin releasing factor 1 (CRF1) receptor: detection, and pharmacological evaluation by peptide ligands," Peptides, 2003, 24(12): 1881-1897.
Hoare SRJ, et al., "Ligand Affinity for Amino-Terminal and Juxtamembrane Domains of the Corticotropin Releasing Factor Type I Receptor: Regulation by G-Protein and Nonpeptide Antagonists," Biochemistry, 2004, 43(13): 3996-4011.
Hoare SRJ, et al., "Single amino acid residue determinants of non-peptide antagonist binding to the corticotropin-releasing factor1 (CRF1) receptor," Biochemical Pharmacology, 2006, 72(2): 244-255.
Holm, "A simple sequentially rejective multiple test procedure," Scandinavian Journal of Statistics, 1979, 65-70.
Huang CQ, et al., "Design and synthesis of 3-(2-pyridyl)pyrazolo[1,5-a]pyrimidines as potent CRF1 receptor antagonists," Bioorganic & Medicinal Chemistry Letters, 2004, 14(15): 3943-3947.
Huang CQ, et al., "Design, synthesis, and SAR of 2-dialkylamino-4-arylpyrimidines as potent and selective corticotropin-releasing

(56) References Cited

OTHER PUBLICATIONS factor1 (CRF1) receptor antagonists," Bioorganic & Medicinal Chemistry Letters, 2004, 14(9): 2083-2086.
Huang CQ, et al., "Synthesis and SAR of 8-Arylquinolines as potent corticotropin-Releasing factor1 (CRF1) receptor antagonists," Bioorganic & Medicinal Chemistry Letters, 2003, 13(19): 3375-3379.
Huang CQ, et al., "Synthesis of 1-methyl-3-phenylpyrazolo[4,3-b]pyridines via a methylation of 4-phthalimino-3-phenylpyrazoles and optimization toward highly potent corticotropin-releasing factor type-1 antagonists," Bioorganic & Medicinal Chemistry Letters, 2003, 13(19): 3371-3374.
Iranmanesh et al., "Glucose Ingestion Selectively Amplifies ACTH and Cortisol Secretory-Burst Mass and Enhances Their Joint Synchrony in Healthy Men," J Endocrinol and Metab., Sep. 2011, 96(9):2882-2888.
Ising M, et al., "High-Affinity CRF1 Receptor Antagonist NBI-34041: Preclinical and Clinical Data Suggest Safety and Efficacy in Attenuating Elevated Stress Response," Neuropsychopharmacology, 2007, 32:1941-1949.
Ivy AS, et al., "Hippocampal Dysfunction and Cognitive Impairments Provoked by Chronic Early-Life Stress Involve Excessive Activation of CRH Receptors," J. Neurosci., 2010, 30(39):13005-13015.
Jain et al., "Spray Drying in Pharmaceutical Industry: A review," Research Journal of Pharmaceutical Dosage Forms and Technology, Apr. 10, 2012, 4(2):74-79.
Jenkins-Jones et al., "Poor compliance and increased mortality, depression and healthcare costs in patients with congenital adrenal hyperplasia," European Journal of Endocrinology, 2018, 178(4):309-320.
Jha et al., "SUN-371 Successful Induction of Fertility with Low-Dose Dexamethasone in a Patient with Congenital Adrenal Hyperplasia and Testicular Adrenal Rest Tumor," Journal of the Endocrine Society, 2019, 3(Supplement_1):SUN-371.
Johannsen et al., "Impaired cognitive function in women with congenital adrenal hyperplasia," J Clin Endocrinol Metab., Apr. 2006, 91(4):1376-1381.
Katkade et al., "Real world data: an opportunity to supplement existing evidence for the use of long-established medicines in health care decision making," J Multidiscip Healthc., 2018, 11:295-304.
Kehne et al., "Therapeutic Utility of Non-Peptidic $CRF_1$ Receptor Antagonists in Anxiety, Depression, and Stress-Related Disorders: Evidence from Animal Models," Pharmacol Ther., Dec. 2010; 128(3):460-487.
Kiddoo DA, et al., "Impact of state of arousal and stress neuropeptides on urodynamic function in freely moving rats," Am J Physiol Regul Integr Comp Physiol, 2006, 290:R1697-R1706.
Kim et al., "Cardiovascular Disease Risk in Adult Women with Congenital Adrenal Hyperplasia Due to 21-hydroxylase Deficiency," Semin Reprod Med, 2009, 27(4):316-321.
King et al., "Long-Term Corticosteroid Replacement and Bone Mineral Density in Adult Women with Classical Congenital Adrenal Hyperplasia," The Journal of Clinical Endocrinology & Metabolism, 2006, 91(3):865-869.
Kitagawa et al., "Basic Pharmaceutical Science Textbook Series 20," Pharmaceutical Science, 2nd print, Kagaku-Dojin Publishing Co., Inc., 2012, p. 16-19.
Koelsch et al., "The Impact of Acute Stress on Hormones and Cytokines, and How Their Recovery is Affected by Music-Evoked Positive Mood," Sci Reps., Mar. 2016, 6:1-11.
Koob et al., "Update on Corticotropin-Releasing Factor Pharmacotherapy for Psychiatric Disorders: A Revisionist View," Neuropsychopharmacology Reviews, 2012, 37:308-309.
Kosoyan HP, et al., "The $CRF_1$ receptor antagonist, NBI-35965, abolished the activation of locus coeruleus neurons induced by colorectal distension and intracisternal CRF in rats," Brain Research, 2005, 1056(1):85-96.
Kulshreshtha B, et al., "Pubertal development among girls with classical congenital adrenal hyperplasia initiated on treatment at different ages," Indian J Endocrinol Metab., 2012, 16(4):599-603.
Le Bas et al., "Radioiodinated analogs of EP 00652218 for the exploration of the tachykinin NKI receptor by spect," Journal of Labelled Compounds and Radiopharmaceuticals, 2001, 44(S1):S280-S282.
Lehmacher et al., "Adaptive sample size calculations in group sequential trials," Biometrics, 1999, 55(4):1286-1290.
Lekarev et al., "Adrenal disease in pregnancy," Best Practice & Research, Clinical Endocrinology & Metabolism, Dec. 2011, 25(6):959-973.
Li et al., "The pharmacology of DMP696 and DMP904, non-peptidergic $CRF_1$ receptor antagonists," CNS Drug Reviews, 2005, 11(1):21-52.
Liapakis G, et al., "Members of CRF Family and their Receptors: From Past to Future," Current Medicinal Chemistry, 2011, 18(17):2583-2600.
Linder et al., "Cortisol production rate in childhood and adolescence," J Pediatr, Dec. 1990, 117(6):892-896.
Liu J, et al., "Corticotropin-Releasing Factor and Urocortin I Modulate Excitatory Glutamatergic Synaptic Transmission," Journal of Neuroscience, 2004, 24(16): 4020-4029.
Loechner et al., "Alternative Strategies for the Treatment of Classical Congenital Adrenal Hyperplasia: Pitfalls and Promises," International Journal of Pediatric Endocrinology, vol. 2010, No. 1, Jun. 8, 2010, Article ID 670960, 10 pages.
Logachev et al., "Congenital Adrenal Hyperplasia: Modern Problems of Terminology and Treatment," Pediatrics, Apr. 19, 2012, 91(3):130-135 pages (with English Translation).
Louis et al., "Antidepressant-like Effects of the Corticotropin-Releasing Factor 1 Receptor Antagonist, SSR125543, and the Vasopressin 1b Receptor Antagonist, SSR149415, in a DRL-72 S Schedule in the Rat," Neuropsychopharmacology, 2006, 31:2180-2187.
Lovenberg TW, et al., "Cloning and characterization of a functionally distinct corticotropin-releasing factor receptor subtype from rat brain," Proceedings of the National Academy of Sciences, 1995, 92(3): 836-840.
Lowe RF, et al., "Rational Design, Synthesis, and Structure—Activity Relationships of Aryltriazoles as Novel Corticotropin-Releasing Factor-1 Receptor Antagonists," J. Med. Chem., 2005, 48(5):1540-1549.
Maciejewski-Lenoir D, et al., "Selective Impairment of Corticotropin-Releasing Factor1 (CRF1) Receptor-Mediated Function Using CRF Coupled to Saporin," Endocrinology, 2000, 141(2):498-504.
Mackay, KB, et al., "Neuroprotective Effects of the CRF1 Antagonist R121920 after Permanent Focal Ischemia in the Rat," Journal of Cerebral Blood Flow & Metabolism, 2001, 21(10): 1208-1214.
Malouf et al., "Cognitive outcome in adult women affected by congenital adrenal hyperplasia due to 21-hydroxylase deficiency," Horm Res., 2006, 65(3):142-150.
Martínez V, et al., "Central CRF, urocortins and stress increase colonic transit via CRF1 receptors while activation of CRF2 receptors delays gastric transit in mice," J Physiol., 2004, 556.1: 221-234.
Martinez-Aguayo et al., "Testicular adrenal rest tumors and Leydig and Sertoli cell function in boys with classical congenital adrenal hyperplasia," J Clin Endocrinol Metab., Dec. 2007, 92(12):4583-9.
McCarthy JR, et al., "Chapter 2. Recent Progress in Corticotropin-Releasing Factor Receptor Agents," Annual Reports in Medicinal Chemistry, 1999, 34: 11-20.
McCarthy JR, et al., "Recent advances with the CRF1 receptor: design of small molecule inhibitors, receptor subtypes and clinical indications," Curr Pharm Des., 1999, 5(5):289-315.
Medlineplus.gov, "21-Hydroxylase Deficiency," NIH US National Library of Medicine, Updated Aug. 18, 2020 [retrieved Dec. 13, 2021], retrieved from URL<https://medlineplus.gov/genetics/condition/21-hydroxylase-deficiency/>, 6 pages.
Mehta et al., "Adaptive increase in sample size when interim results are promising: a practical guide with examples," Statistics in Medicine, 2011, 30(28):3267-3284.
Merke et al., "Congenital adrenal hyperplasia," Lancet, 2005, 365:2125-2136.

(56) References Cited

OTHER PUBLICATIONS

Merke et al., "Congenital adrenal hyperplasia: epidemiology, management and practical drug treatment," Paediatr Drugs., 2001, 3(8):599-611.
Merke et al., "Flutamide, testolactone, and reduced hydrocortisone dose maintain normal growth velocity and bone maturation despite elevated androgen levels in children with congenital adrenal hyperplasia," J Clin Endocrinol Metab., Mar. 2000, 85(3):1114-1120.
Merke et al., "Management of adolescents with congenital adrenal hyperplasia," Lancet Diabetes Endocrinol., Dec. 2013, 1(4):341-352.
Merke et al., "New ideas for medical treatment of congenital adrenal hyperplasia," Endocrinol. Metab. Clin. North. Am., 2001, 30(1):121-135.
Merke et al., "NIH conference: Future directions in the study and management of congenital adrenal hyperplasia due to 21-hydroxylase deficiency," Ann. Intern. Med., 2002, 136:320-334.
Merke et al., "Congenital Adrenal Hyperplasia Due to 21-Hydroxylase Deficiency," N Engl J Med., Sep. 24, 2020, 383(13):1248-1261.
Meslamani et al., "Computational profiling of bioactive compounds using a target-dependent composite workflow," J. Chem. Inf. Model., 2013, 2322-2333.
Migeon et al., "Congenital Adrenal Hyperplasia Owing to 21-Hydroxylase Deficiency," Endocrinology and Metabolism Clinics of North America, 2001, 30(1):193-206.
Miller et al., "Emergency management of adrenal insufficiency in children: advocating for treatment options in outpatient and field settings," Journal of Investigative Medicine, 2020, 68(1):16-25.
Million et al., "The newly developed CRF1-receptor antagonists, NGD 98-2 and NGD 9002, suppress acute stress-induced stimulation of colonic motor function and visceral hypersensitivity in rats, " PLOS One, 2013, 8(9):e73749.
Million M, et al., "A novel water-soluble selective CRF1 receptor antagonist, NBI 35965, blunts stress-induced visceral hyperalgesia and colonic motor function in rats," Brain Research, 2003, 985(1): 32-42.
Mims et al., "Plasma ACTH in Rats Following Medical Adrenalectomy," Journal of the National Medical Association 69(3):145-147, 1977.
Morikawa S, et al., "Results from 28 years of Newborn Screening for Congenital Adrenal Hyperplasia in Sapporo," Clin Pediatr Endocrinol., 2014, 23(2):35-43.
Mullins et al., "Brief psychiatric rating scale for children: quantitative scoring of medical records," Psychiatry Research, 1986, 19(1):43-49.
Muthusamy et al., "Clinical review: Adult height in patients with congenital adrenal hyperplasia: a systematic review and metaanalysis," J Clin Endocrinol Metab., Sep. 2010, 95(9):4161-4172.
Nebesio TD, et al., "Growth and Reproductive Outcomes in Congenital Adrenal Hyperplasia," Int J Pediatr Endocrinol., 2010, Article ID 298937, 1-10.
Nermoen et al., "Subjective health status in men and women with congenital adrenal hyperplasia: a population-based survey in Norway," Eur J Endocrinol., Sep. 2010, 163(3):453-459.
*Neurocrine Biosciences, Inc.*, Petitioner, v. *Spruce Biosciences, Inc.*, Patent Owner, Case No. PGR2021-00088, U.S. Pat. No. 10,849,908, Declaration of Robert M. Carey, M.D., dated May 28, 2021, 154 pages.
Newfield et al., "Crinecerfont (NBI-74788), a Novel $CRF_1$ Receptor Antagonist, Lowers Adrenal Androgens and Precursors in Adolescents with Classic Congenital Adrenal Hyperplasia," Abstract submitted to ECE for consideration at 2023 annual meeting, 2 pages.
Newfield et al., "Crinecerfont (NBI-74788), a novel $CRF_1$ receptor antagonist, lowers adrenal androgens and precursors in adolescents with classic congenital adrenal hyperplasia," Presentation Slides presented at the 104th annual meeting and expo of the Endocrine Society (ENDO 2022), Atlanta, GA, Jun. 2022, 13 pages.
Newfield R.S., "Acth receptor blockade: A novel approach to treat congenital adrenal hyperplasia, or Cushing's disease," Medical Hypotheses, 2010, 74:705-706.
Nieves-Remacha et al., "Scale-up of N-alkylation reaction using phase-transfer catalysis with integrated separation in flow," Reaction Chemistry & Engineering, 2019, 4(2):334-345.
Nokoff et al., "Sex differences in effects of obesity on reproductive hormones and glucose metabolism in early puberty," The Journal of Clinical Endocrinology & Metabolism, 2019, 104(10):4390-4397.
Okuyama et al., "Receptor Binding, Behavioral, and Electrophysiological Profiles of Nonpeptide Corticotropin-Releasing Factor Subtype 1 Receptor Antagonists CRA1000 and CRA1001," Journal of Pharmacology and Experimental Therapeutics, 1999, 289(2):926-935.
Oray et al., "Long-term effect of glucocorticoids," Expert Opinion on Drug Safety, 2016, 15(4):457-465.
Oster et al., "The functional and clinical significance of the 24-hour rhythm of circulating glucocorticoids," Endocrine Reviews, 2017, 38(1):3-45.
Overall et al., "The Brief Psychiatric Rating Scale (BPRS): recent developments in ascertainment and scaling," Psychopharmacology Bulletin, 1988, 24(1):97-99.
Overall et al., "The brief psychiatric rating scale," Psychological Reports, 1962, 10(3):799-812.
Overstreet et al., "Antidepressant-like effects of $CRF_1$ receptor antagonist SSR125543 in an animal model of depression," European Journal of Pharmacology, 2004, 497:49- 53.
Owens et al., "Physiology and pharmacology of corticotropin-releasing factor," Pharmacol Rev., Dec. 1991, 43(4):425-473.
Pang et al., "Worldwide Experience in Newborn Screening for Classical Congenital Adrenal Hyperplasia due to 21-Hydroxylase Deficiency," Pediatrics, 1988, 81(6):866-874.
Pang S, et al., "Congenital adrenal hyperplasia due to 21-hydroxylase deficiency: newborn screening and its relationship to the diagnosis and treatment of the disorder," Screening, 1993, 2:105-139.
Pelleymounter MA, et al., "Role of Corticotropin-Releasing Factor (CRF) Receptors in the Anorexic Syndrome Induced by CRF," Journal of Pharmacology and Experimental Therapeutics, 2000, 293(3): 799-806.
Peplow et al., "Blood draws up to 3% of blood vol. in clinical trials are safe in children," Acta Paediatrica, 2019, 108(5):940-944.
Perry SJ, et al., "Distinct Conformations of the Corticotropin Releasing Factor Type 1 Receptor Adopted following Agonist and Antagonist Binding Are Differentially Regulated," J. Biol. Chem., 2005, 280(12): 11560-11568.
Philbert et al., "The $CRF_1$ Receptor Antagonist SSR125543 Attenuates Long-Term Cognitive Deficit Induced by Acute Inescapable Stress in Mice, Independently From the Hypothalamic Pituitary Adrenal Axis," Pharmacology, Biochemistry, and Behavior, 2012, 10:415-422.
Philbert et al., "The $CRF_1$ Receptor Antagonist SSR125543 Prevents Stress-Induced Cognitive Deficit Associated With Hippocampal Dysfunction: Comparison With Paroxetine and D-cycloserine," Psychopharmacology, 2013, 228:97-107.
Purnell et al., "Association of 24-hour cortisol production rates, cortisol-binding globulin, and plasma-free cortisol levels with body composition, leptin levels, and aging in adult men and women," The Journal of Clinical Endocrinology & Metabolism, 2004, 89(1):281-287.
Ramos et al., "Drug-induced suppression of ACTH secretion does not promote anti-depressive or anxiolytic effects," Behavioral Brain Research, 2014, 265:69-75.
Ravens-Sieberer et al., "Feasibility, reliability, and validity of the EQ-5D-Y: results from a multinational study," Quality of Life Research, 2010, 19(6):887-897.
Reisch, "Substitution therapy in adult patients with congenital adrenal hyperplasia," Best Practice & Research Clinical Endocrinology & Metabolism, 2015, 29(1):33-45.
Rief et al., "Mechanisms involved in placebo and nocebo responses and implications for drug trials," Clinical Pharmacology & Therapeutics, 2011, 90(5):722-726.
Rivier CL, et al., "Role of Corticotropin-Releasing Factor Receptors Type 1 and 2 in Modulating the Rat Adrenocorticotropin Response to Stressors," Endocrinology, 2003, 144(6): 2396-2403.

(56) References Cited

OTHER PUBLICATIONS

Rivier JE, et al., "Constrained Corticotropin Releasing Factor Antagonists (Astressin Analogues) with Long Duration of Action in the Rat," J. Med. Chem. 1999, 42(16):3175-3182.
Rose & Hurst, "Plasma Cortisol and Growth Hormone Responses to Intravenous Catheterization," J Hum Stress., Mar. 1975, 1(1):22-36.
Ross et al., "Improved biochemical control with dose reduction in chronic glucocorticoid therapy: A phase III extension study of Chronocort (Efmody) in the treatment of Congenital Adrenal Hyperplasia (CAH)," Abstract submitted to ENDO 2023 for consideration, prepared on Dec. 2022, 2 pages.
Ross et al., "Switching patients with Congenital Adrenal Hyperplasia to Modified release hydrocortisone capsules: relative bioavailability and disease control," Abstract submitted to European Congress of Endocrinology 2023 for consideration, prepared on Jan. 2023, 2 pages.
Sarafoglou et al., "Tildacerfont in adults with classic congenital adrenal hyperplasia: results from two phase 2 studies," Manuscript, The Journal of Clinical Endocrinology & Metabolism, 2021, 106(11):e4666-79.
Sarafoglou K, et al., "Impact of Hydrocortisone on Adult Height in Congenital Adrenal Hyperplasia—The Minnesota Cohort," J Pediatr., 2014, 164(5):1141-1146.
Science.nichd.nih.gov [Online], "Pediatric Endocrinology Training Program," 2020, [Retrieved on Mar. 6, 2023], retrieved from: URL<https://science.nichd.nih.gov/confluence/display/pe/Patient+Handouts+and+Support+Groups#PatientHandoutsandSupportGroups-CAHandAdrenalInsufficiency>, 3 pages.
Scott et al., "The use of the EQ-5D-Y health related quality of life outcome measure in children in the Western Cape, South Africa: psychometric properties, feasibility and usefulness—a longitudinal, analytical study," Health and Quality of Life Outcomes, 2017, 15:12.
Seymour et al., "The pharmacology of CP-154,526, a non-peptide antagonist of the CRH1 receptor: a review," CNS Drug Reviews, 2003, 9(1):57-96.
Shargel et al., "Multiple-Dosage Regiments," Applied Biopharmaceutics & Pharmacokinetics, 2012, 6th Edition, 31 pages.
Shargel et al., "Multiple-Dosage Regiments," Applied Biopharmaceutics & Pharmacokinetics, 2016, 7th Edition, 33 pages.
Silva IN, et al., "Randomised controlled trial of growth effect of hydrocortisone in congenital adrenal hyperplasia," Archives of Disease in Childhood, 1997, 77:214-218.
Smith et al., "Measures of sleep: the insomnia severity index, medical outcomes study (MOS) sleep scale, Pittsburgh sleep diary (PSD), and Pittsburgh sleep quality index (PSQI)," Arthritis Care & Research: Official Journal of the American College of Rheumatology, 2003, 49(S5):S184-S196.
Smith et al., "The role of the hypothalamic-pituitary-adrenal axis in neuroendocrine responses to stress," Dialogues Clin Neurosci., 2006, 8:383-395.
Soliman et al., "Congenital adrenal hyperplasia complicated by central precocious puberty: linear growth during infancy and treatment with gonadotropin- releasing hormone analog," Metabolism., May 1997, 46(5):513-517.
Somajni et al., "Neuropsychological assessment in prepubertal patients with congenital adrenal hyperplasia: preliminary study," Minerva Pediatr., Feb. 2011, 63(1):1-9.
Speiser et al., "Congenital adrenal hyperplasia due to steroid 21-hydroxylase deficiency: an Endocrine Society clinical practice guideline," J Clin Endocrinol Metab., Sep. 2010, 95(9):4133-60.
Speiser et al., "A Summary of the Endocrine Society Clinical Practice Guidelines on Congenital Adrenal Hyperplasia due to Steroid 21-Hydroxylase Deficiency," International Journal of Pediatric Endocrinology 2010, 2010:494173.
Speiser et al., "Congenital Adrenal Hyperplasia Due to Steroid 21-Hydroxylase Deficiency: An Endocrine Society Clinical Practice Guideline," J Clin Endocrinol Metab., 2018, 103(11):4043-4088.
Spierling et al., "Don't stress about CRF: assessing the translational failures of $CRF_1$ antagonists," Psychopharmacology, 2017, 234(9-10):1467-1481.
Steckler, "Developing small molecule nonpeptidergic drugs for the treatment of anxiety disorders: is the challenge still ahead?" Curr. Topics in Behav. Neurosciences, 2009, 415-428.
Stewart et al., "Development of a Biorelevant, Material-Sparing Membrane Flux Test for Rapid Screening of Bioavailability-Enhancing Drug Product Formulations," Mol Pharm., 2017, 14(6):2032-2046.
Stewart et al., "Exploring inpatient hospitalizations and morbidity in patients with adrenal insufficiency," The Journal of Clinical Endocrinology & Metabolism, 2016, 101(12):4843-4850.
Stikkelbroeck et al., "High prevalence of testicular adrenal rest tumors, impaired spermatogenesis, and Leydig cell failure in adolescent and adult males with congenital adrenal hyperplasia," J Clin Endocrinol Metab., Dec. 2001, 86(12):5721-5728.
Surget et al., "Corticolimbic transcriptome changes are state-dependent and region-specific in a rodent model of depression and of antidepressant reversal," Neuropsychopharmacology, 2009, 34:1363-1380.
Surget et al., "Drug-dependent requirement of hippocampal neurogenesis in a model of depression and of antidepressant reversal," Biol. Psychiatry, 2008, 64:293-301.
Teitelbaum, "Chronic peripheral administration of corticotropin-releasing factor causes colonic barrier dysfunction similar to psychological stress," Am J Physiol Gastrointest Liver Physiol, 2008, 295: G452-G459.
Tellew et al., "Discovery ofNBI-77860/GSK561679, a potent corticotropin-releasing factor ($CRF_1$) receptor antagonist with improved pharmacokinetic properties," Bioorganic & Medicinal Chemistry Letters, 2010, 20(24):7259-7264.
Thefreedictionary.com, "Baseline," available on or before Nov. 7, 2016, via Internet Archive: Wayback Machine URL <https://web.archive.org/web/20161107132345/http:/medical-dictionary.thefreedictionary.com/baseline>, 3 pages.
Therrell BL, et al., "Newborn Screening for Congenital Adrenal Hyperplasia," Endocrinol Metab Clin North Am., 2001, 30(1):15-30.
Trakakis et al., "An update to 21-hydroxylase deficient congenital adrenal hyperplasia," Gynecol Endocrinol., Jan. 2010, 26(1):63-71.
Trapp CM, et al. "Recommendations for Treatment of Nonclassic Congenital Adrenal Hyperplasia (NCCAH): an Update," Steroids, 2012, 77(4):342-346.
Trapp et al., "Congenital adrenal hyperplasia: an update in children," Curr Opin Endocrinol Diabetes Obes., 2011, 18(3):166-170.
Turcu et al., "Novel treatment strategies in congenital adrenal hyperplasia," Curr Opin Endocrinol Diabetes Obes., 2016, 23(3):225-232.
Turcu et al., "Single-Dose Study of a Corticotropin-Releasing Factor Receptor-1 Antagonist in Women With 21-Hydroxylase Deficiency," J Clin Endocrinol Metab., Mar. 2016, 101(3):1174-1180.
Turcu et al., "The Next 150 Years of Congenital Adrenal Hyperplasia," J Steroid Biochem Mol Biol., Sep. 2015, 153:63-71.
Urani et al., "The Corticotropin-Releasing Factor 1 Receptor Antagonist, SSR125543, and the Vasopressin 1b Receptor Antagonist, SSR149415, Prevent Stress-Induced Cognitive Impairment in Mice," Pharmacology, Biochemistry, and Behavior, 2011, 98:425-431.
U.S. Appl. No. 62/545,406, Howerton et al., "Corticotropin Releasing Factor Receptor Antagonists," filed Aug. 14, 2017, 65 pages.
Vale et al., "Chemical and biological characterization of corticotropin releasing factor," Recent Prog Horm Res., 1983, 39:245-270.
Vale et al., "Characterization of a 41-Residue Ovine Hypothalamic Peptide That Stimulates Secretion of Corticotropin and β-Endorphin," Science, 1981, 213:1394-1397.
Varni et al., "PedsQL™ 4.0: Reliability and validity of the Pediatric Quality of Life Inventory™ Version 4.0 Generic Core Scales in healthy and patient populations," Medical Care, 2001, 39(8):800-812.
Varni et al., "The PedsQL™ 4.0 as a school population health measure: feasibility, reliability, and validity," Quality of Life Research, 2006, 15:203-215.

(56) References Cited

OTHER PUBLICATIONS

Varni et al., "The PedsQL™ family impact module: preliminary reliability and validity," Health and Quality of Life Outcomes, 2004, 2:55.
Vickers et al., "Why Use Placebos in Clinical Trials? A Narrative Review of the Methodological Literature," Journal of Clinical Epidemiology, 2000, 53(2):157-161.
Vijayan et al., "Metabolic profile, cardiovascular risk factors and health-related quality of life in children, adolescents and young adults with congenital adrenal hyperplasia," 2019, 32(8):871-877.
Vokl TMK, et al., "Adrenarche and Puberty in Children with Classic Congenital Adrenal Hyperplasia due to 21-Hydroxylase Deficiency," Horm Res Paediatr., 2011, 76(6):400-410.
Vokl TMK, et al., "Obesity Among Children and Adolescents with Classic Congenital Adrenal Hyperplasia due to 21-Hydroxylase Deficiency," Pediatrics, 2006, 117(1):e98-e105.
Webb et al., "Current and Novel Approaches to Children and Young People with Congenital Adrenal Hyperplasia and Adrenal Insufficiency," Best Pract Res Clin Endocrinol Metab., 2015, 29:449-468.
Webb TR, et al., "Synthesis of benzoylpyrimidines as antagonists of the corticotropin-releasing factor-1 receptor," Bioorganic & Medicinal Chemistry Letters, 2004, 14(15): 3869-3873.
Webster et al., "In Vivo and In Vitro Characterization of Antalarmin, a Nonpeptide Corticotropin-Releasing Hormone (CRH) Receptor Antagonist: Suppression of Pituitary ACTH Release and Peripheral Inflammation," Endocrinology, Jan. 1, 1996, 137(12):5747-5750.
White PC, et al., "Congenital Adrenal Hyperplasia due to 21-Hydroxylase Deficiency," Endocr Rev., 2000, 21(3):245-291.
White PC, et al., "Optimizing Newborn Screening for Congenital Adrenal Hyperplasia," J. Pediatr., 2013, 163:10-12.
Whitten JP, et al., "Rapid Microscale Synthesis, a New Method for Lead Optimization Using Robotics and Solution Phase Chemistry: Application to the Synthesis and Optimization of Corticotropin-Releasing Factor1 Receptor Antagonists," J. Med. Chem., 1996, 39(22): 4354-4357.
Wiens, "A fixed sequence Bonferroni procedure for testing multiple endpoints," Pharmaceutical Statistics: The Journal of Applied Statistics in the Pharmaceutical Industry, 2003, 2(3):211-215.
Wilcoxen K, et al., "Synthesis of 3-phenylpyrazolo[4,3-b]pyridines via a convenient synthesis of 4-amino-3-arylpyrazoles and SAR of corticotropin-Releasing factor receptor type-1 antagonists," Bioorganic & Medicinal Chemistry Letters, 2003, 13(19): 3367-3370.
Williams, "Corticotropin-releasing factor I receptor antagonists: a patent review," Expert Opin. Ther. Patents, 2013, 23(8):1057-1068.
Witchel et al., "Congenital Adrenal Hyperplasia," J. Pediatr. Adolesc. Gynecol., 2011, 24:116-126.
Witchel et al., "Congenital Adrenal Hyperplasia," J. Pediatr. Adolesc. Gynecol., 2017, 30(5):520-534.
Wong et al., "Increased hepatobiliary clearance of unconjugated thyroxine determines DMP 904-induced alterations in thyroid hormone homeostasis in rats," Toxicological Sciences, 2005, 84(2):232-242.
Wood S, et al., "Depressive and cardiovascular disease comorbidity in a rat model of social stress: a putative role for corticotropin-releasing factor," Psychopharmacology, 2012, 222(2): 325-336.
Wustrow DJ, et al., "Pyrazolo[1,5-a]pyrimidine CRF-1 receptor antagonists," Bioorganic & Medicinal Chemistry Letters, 1998, 8(16): 2067-2070.
Yuan J, et al., "3-Aryl pyrazolo[4,3-d]pyrimidine derivatives: nonpeptide CRF-1 antagonists," Bioorganic & Medicinal Chemistry Letters, 2002, 12(16): 2133-2136.
Zhu et al., "Synthesis and mode of action of $^{125}$I-and $^{3}$H-labeled thieno [2,3-c]pyridine antagonists of cell adhesion molecule expression," The Journal of Organic Chemistry, 2002, 67(3):943-948.
Zorrilla et al., "Behavioral, biological, and chemical perspectives on targeting CRF(1) receptor antagonists to treat alcoholism," Drug and Alcohol Dependence, (2013), 128(3):175-186.
Zorrilla et al., "The therapeutic potential of CRF1 antagonists for anxiety," Expert Opin. Investig. Drugs, 2004, 13(7):799-828.
Zorrilla, "Progress in corticotropin-releasing factor-1 antagonist development," Drug Discov Today, 2010, 15:371-383.
Zoumakis et al., "Corticotropin-releasing hormone receptor antagonists," European Journal of Endocrinology, 2006, 155(1):S85-S91.
Zoumakis et al., "Corticotropin-releasing hormone receptor antagonists: an update," Pediatric Neuroendocrinology Endocr Dev., 2010, 17:36-43.
[No Author Listed], "Search Results for CAS No. 121548-04-7," American Chemical Society CAS SciFinder, search performed on Apr. 7, 2025 at www.cas.org, 2 pages.
[No Author], "Guidance for Industry: Q3A Impurities in New Drug Substances," U.S. Department of Health and Human Services, Jun. 2008, 17 pages.
Accessdata.fda.gov [online], "FDA, Center for Drug Evaluation and Research, 218808Orig1s000, 218820Orig1s000, Product Quality Review(S)," Oct. 7, 2024, retrieved on Apr. 10, 2025, retrieved from URL <https://www.accessdata.fda.gov/drugsatfda_docs/nda/2025/218808Orig1s000,218820Orig1s000ChemR.pdf>, 90 pages.
Auchus et al., "Crinecerfont Lowers Elevated Biomarkers of Disease Control in Adults with Congenital Adrenal Hyperplasia Due to 21-Hydroxylase Deficiency," submitted to Lancet Apr. 30, 2021, 33 pages.
Auchus et al., "Phase 3 Trial of Crinecerfont in Adult Congenital Adrenal Hyperplasia," The New England Journal of Medicine, Jun. 1, 2024, 11 pages.
Bastin et al., "Salt Selection and Optimisation Procedures for Pharmaceutical New Chemical Entities," Organic Process Research & Development, 2000, 4:427-435.
Boston University, "InterQuartile Range (IQR)," available on or before Oct. 31, 2013, via Internet Archive: Wayback Machine URL<https://web.archive.org/web/20131031075431/https://sphweb.bumc.bu.edu/otlt/mph-modules/bs/bs704_summarizingdata/bs704_summarizingdata7.html>, retrieved on Feb. 17, 2024, retrieved from URL<https://sphweb.bumc.bu.edu/otlt/mph-modules/bs/bs704 summarizingdata/bs704_summarizingdata7.html>, 3 pages.
Byrn et al., "Pharmaceutical Solids: A Strategic Approach to Regulatory Considerations," Pharmaceutical Research, 1995, 12(7):945-954.
Ceramella et al., "A Look at the Importance of Chirality in Drug Activity: Some Significative Examples," Applied Sciences, Oct. 27, 2022, 12:10909, 22 pages.
Claahsen-van der Grinten et al., "Challenges in Adolescent and Adult Males With Classic Congenital Adrenal Hyperplasia Due to 21-Hydroxylase Deficiency," J Clinical Endocrinology & Metabolism, Feb. 2025, 110 (Supplement_1):S25-36.
Croce et al., "A Simple Procedure for N-Propenylation and N-Propynylation of Secondary Amines," Gazetta Chimica Italiana, 1996, 126(2):107-109.
De Villiers, "Pharmaceutical solvents and solubilizing agents," Pharmaceutical Excipients, Part 4, 2009, 15 pages.
De Villiers, "Vehicles for Liquid Preparations," A Practical Guide to Contemporary Pharmacy Practice, 3rd Editions, Jan. 2009, 22:267-276 pages.
Do Thi et al., "Formulate-ability of ten compounds with different physicochemical profiles in SMEDDS," European journal of pharmaceutical sciences, Dec. 8, 2009, 38(5):479-88.
Dwivedi et al., "Evergreening: a deceptive device in patent rights," Technology in Society, Nov. 1, 2010, 32(4):324-30.
Eitel et al., "Barriers to the Management of Classic Congenital Adrenal Hyperplasia Due to 21-Hydroxylase Deficiency," J Clinical Endocrinology & Metabolism, Feb. 2025, 110 (Supplement_1):S67-73.
Engberg et al., "Clinical Manifestations and Challenges in Adolescent and Adult Females With Classic Congenital Adrenal Hyperplasia Due to 21-Hydroxylase Deficiency," J Clinical Endocrinology & Metabolism, Feb. 2025, 110 (Supplement_1):S37-45.
Feldman, "Understanding 'Evergreening': Making Minor Modifications of Existing Medications to Extend Protections, " Health Affairs, Jun. 1, 2022, 41(6):801-4.
Foster, "Deuterium isotope effects in the metabolism of drugs and xenobiotics: implications for drug design," Advances in Drug Research, 1985, 14:1-40.

(56) References Cited

OTHER PUBLICATIONS

Gattefosse.com [online], "Gelucire® 44/14," available on or before Nov. 30, 2023 via Internet Archive: Wayback Machine URL<https://web.archive.org/web/20231130013520/https://www.gattefosse.com/pharmaceuticals/product-finder/gelucire-4414>, retrieved on Apr. 10, 2025, retrieved from URL <https://www.gattefosse.com/pharmaceuticals/product-finder/gelucire-4414>, 6 pages.
Gattefosse.com [online], "Labrafac™M Lipophile WL 1349," available on or before Nov. 30, 2023 via Internet Archive: Wayback Machine URL<https://web.archive.org/web/20231130120205/https://www.gattefosse.com/pharmaceuticals/product-finder/labrafac-lipophile-wl-1349>, retrieved on Apr. 10, 2025, retrieved from URL <https://www.gattefosse.com/pharmaceuticals/product-finder/labrafac-lipophile-wl-1349>, 6 pages.
Gattefosse.com [online], "LabrafacTM PG," available on or before Nov. 30, 2023 via Internet Archive: Wayback Machine URL<https://web.archive.org/web/20231130184227/https://www.gattefosse.com/pharmaceuticals/product-finder/labrafac-pg>, retrieved on Apr. 10, 2025, retrieved from URL <https://www.gattefosse.com/pharmaceuticals/product-finder/labrafac-pg>, 5 pages.
Gupta et al., "Formulation strategies to improve the bioavailability of poorly absorbed drugs with special emphasis on self-emulsifying systems," ISRN Pharmaceutics, 2013, pp. 1-16.
Gupta et al., "Salts of therapeutic agents: chemical, physicochemical, and biological considerations, " Molecules, Jul. 14, 2018, 23(7):1719.
Habibzadeh, "Statistical Data Editing in Scientific Articles," Journal of Korean Medical Science, Jul. 2017, 32(7):1072-1076.
Hirayama, "[Handbook for manufacturing crystal of organic compound—principle and know-how]," Maruzen, Jul. 2008, 57-84 (with English translation).
Kamrath et al., "CRH receptor antagonist crinecerfont—a promising new treatment option for patients with congenital adrenal hyperplasia due to 21-hydroxylase deficiency," Journal of Pediatric Endocrinology and Metabolism, Nov. 25, 2024, 38(1):16-21.
Kojima, "[Effective solid form selection for the pharmaceutical development," Journal of Pharmaceutical Science and Technology, Sep. 1, 2008, 68(5):344-349 (with English translation).
Kumbhar et al., "D-α-tocopheryl polyethylene glycol succinate: A review of multifarious applications in nanomedicines," OpenNano, Mar. 2022, 6:100036, 13 pages.
Kushner et al., "Pharmacological uses and perspectives of heavy water and deuterated compounds," Canadian journal of physiology and pharmacology, Feb. 1, 1999, 77(2):79-88.
Lee et al., "Standard deviation and standard error of the mean," Korean Journal of Anesthesiology, Jun. 2015, 68(3):220-223.
Li et al., "Use of Spray-Dried Dispersions in Early Pharmaceutical Development: Theoretical and Practical Challenges," Aaps J, Mar. 2017, 19:321-333.
Mercado-Asis et al., "Acute Effects of Bromocriptine, Cyproheptadine, and Valproic Acid on Plasma Adrenocorticotropin Secretion in Nelson's Syndrome," Journal of Clinical Endocrinology & Metabolism, 1997, 82(2):514-517.
Nahm et al., "N-Methoxy-N-methylamides as effective acylating agents," Tetrahedron Letters, Jan. 1, 1981, 22(39):3815-8.
*Neurocrine Biosciences, Inc*., Petitioner, v. *Spruce Biosciences, Inc*., Patent Owner, Case No. PGR2021-00088, U.S. Pat. No. 10,849,908, Decision Denying Institution of Post-Grant Review 35 U.S.C. § 324, filed Dec. 10, 2021, 36 pages.
*Neurocrine Biosciences, Inc*., Petitioner, v. *Spruce Biosciences, Inc*., Patent Owner, Case No. PGR2021-00088, U.S. Pat. No. 10,849,908, Decision Granting Institution of Post-Grant Review 35 U.S.C. § 324, filed Dec. 1, 2023, 57 pages.
*Neurocrine Biosciences, Inc*., Petitioner, v. *Spruce Biosciences, Inc*., Patent Owner, Case No. PGR2021-00088, U.S. Pat. No. 10,849,908, Decision Vacating the Decision Denying Institution and Remanding to the Patent Trial and Appeal Board Panel for Further Proceedings, filed Aug. 4, 2023, 16 pages.
*Neurocrine Biosciences, Inc*., Petitioner, v. *Spruce Biosciences, Inc*., Patent Owner, Case No. PGR2021-00088, U.S. Pat. No. 10,849,908, Declaration of Adrian Dobs, M.D., M.H.S., filed Mar. 12, 2024, 68 pages.
*Neurocrine Biosciences, Inc*., Petitioner, v. *Spruce Biosciences, Inc*., Patent Owner, Case No. PGR2021-00088, U.S. Pat. No. 10,849,908, Declaration of Gordon B. Cutler, Jr., M.D. in Support of Petition for Post Grant Review of U.S. Pat. No. 10,849,908, filed Jan. 5, 2024, 228 pages.
*Neurocrine Biosciences, Inc*., Petitioner, v. *Spruce Biosciences, Inc*., Patent Owner, Case No. PGR2021-00088, U.S. Pat. No. 10,849,908, Deposition of Dr. Gordon B. Cutler, Jr., Washington, D.C., Thursday, Jul. 25, 2024, 207 pages.
*Neurocrine Biosciences, Inc*., Petitioner, v. *Spruce Biosciences, Inc*., Patent Owner, Case No. PGR2021-00088, U.S. Pat. No. 10,849,908, filed Mar. 12, 2024, 91 pages.
*Neurocrine Biosciences, Inc*., Petitioner, v. *Spruce Biosciences, Inc*., Patent Owner, Case No. PGR2021-00088, U.S. Pat. No. 10,849,908, filed on Jun. 20, 2024, 38 pages.
*Neurocrine Biosciences, Inc*., Petitioner, v. *Spruce Biosciences, Inc*., Patent Owner, Case No. PGR2021-00088, U.S. Pat. No. 10,849,908, filed on Jun. 27, 2024, 9 pages.
*Neurocrine Biosciences, Inc*., Petitioner, v. *Spruce Biosciences, Inc*., Patent Owner, Case No. PGR2021-00088, U.S. Pat. No. 10,849,908, Patent Owner Spruce Biosciences' Motion To Exclude 37 C.F.R. §42.64(c), filed Aug. 14, 2024, 10 pages.
*Neurocrine Biosciences, Inc*., Petitioner, v. *Spruce Biosciences, Inc*., Patent Owner, Case No. PGR2021-00088, U.S. Pat. No. 10,849,908, Patent Owner's Opposition To Petitioner's Motion To Exclude Evidence 37 C.F.R. §42.64, filed Aug. 20, 2024, 15 pages.
*Neurocrine Biosciences, Inc*., Petitioner, v. *Spruce Biosciences, Inc*., Patent Owner, Case No. PGR2021-00088, U.S. Pat. No. 10,849,908, Patent Owner's Opposition To Petitioner's Motion To Strike, filed Aug. 28, 2024, 8 pages.
*Neurocrine Biosciences, Inc*., Petitioner, v. *Spruce Biosciences, Inc*., Patent Owner, Case No. PGR2021-00088, U.S. Pat. No. 10,849,908, Patent Owner's Preliminary Response, filed Sep. 15, 2021, 57 pages.
*Neurocrine Biosciences, Inc*., Petitioner, v. *Spruce Biosciences, Inc*., Patent Owner, Case No. PGR2021-00088, U.S. Pat. No. 10,849,908, Patent Owner's Reply in Support of Its Motion To Exclude, filed Aug. 23, 2024, 8 pages.
*Neurocrine Biosciences, Inc*., Petitioner, v. *Spruce Biosciences, Inc*., Patent Owner, Case No. PGR2021-00088, U.S. Pat. No. 10,849,908, Patent Owner's Sur-Reply, filed Aug. 12, 2024, 36 pages.
*Neurocrine Biosciences, Inc*., Petitioner, v. *Spruce Biosciences, Inc*., Patent Owner, Case No. PGR2021-00088, U.S. Pat. No. 10,849,908, Petition for Post Grant Review of U.S. Pat. No. 10,849,908, filed May 28, 2021, 90 pages.
*Neurocrine Biosciences, Inc*., Petitioner, v. *Spruce Biosciences, Inc*., Patent Owner, Case No. PGR2021-00088, U.S. Pat. No. 10,849,908, Petitioner's Motion to Exclude Evidence, filed Aug. 14, 2024, 16 pages.
*Neurocrine Biosciences, Inc*., Petitioner, v. *Spruce Biosciences, Inc*., Patent Owner, Case No. PGR2021-00088, U.S. Pat. No. 10,849,908, Petitioner's Motion to Strike, filed Aug. 22, 2024, 13 pages.
*Neurocrine Biosciences, Inc*., Petitioner, v. *Spruce Biosciences, Inc*., Patent Owner, Case No. PGR2021-00088, U.S. Pat. No. 10,849,908, Petitioner's Opposition to Patent Owner's Motion To Exclude Evidence, filed Aug. 20, 2024, 19 pages.
*Neurocrine Biosciences, Inc*., Petitioner, v. *Spruce Biosciences, Inc*., Patent Owner, Case No. PGR2021-00088, U.S. Pat. No. 10,849,908, Petitioner's Reply in Support of Its Motion To Exclude Evidence, filed Aug. 23, 2024, 9 pages.
*Neurocrine Biosciences, Inc*., Petitioner, v. *Spruce Biosciences, Inc*., Patent Owner, Case No. PGR2021-00088, U.S. Pat. No. 10,849,908, Petitioner's Request for Rehearing, filed Jan. 10, 2022, 18 pages.
*Neurocrine Biosciences, Inc*., Petitioner, v. *Spruce Biosciences, Inc*., Patent Owner, Case No. PGR2021-00088, U.S. Pat. No. 10,849,908, Reply Declaration of Gordon B. Cutler, Jr., M.D., filed Jun. 20, 2024, 64 pages.
*Neurocrine Biosciences, Inc*., Petitioner, v. *Spruce Biosciences, Inc*., Patent Owner, Case No. PGR2022-00025, U.S. Pat. No. 11,007,201,

(56) References Cited

OTHER PUBLICATIONS

Decision Denying Institution of Post-Grant Review 35 U.S.C. § 324(a), filed Sep. 15, 2022, 35 pages.
*Neurocrine Biosciences, Inc*., Petitioner, v. *Spruce Biosciences, Inc*., Patent Owner, Case No. PGR2022-00025, U.S. Pat. No. 11,007,201, Decision Granting Institution of Post-Grant Review 35 U.S.C. § 324(a), filed Dec. 1, 2023, 38 pages.
*Neurocrine Biosciences, Inc*., Petitioner, v. *Spruce Biosciences, Inc*., Patent Owner, Case No. PGR2022-00025, U.S. Pat. No. 11,007,201, Declaration of Adrian Dobs, M.D., M.H.S., filed Mar. 12, 2024, 63 pages.
*Neurocrine Biosciences, Inc*., Petitioner, v. *Spruce Biosciences, Inc*., Patent Owner, Case No. PGR2022-00025, U.S. Pat. No. 11,007,201, Declaration of Gordon B. Cutler, Jr., M.D. in Support of Petition for Post Grant Review of U.S. Pat. No. 11,007,201, filed Jan. 5, 2024, 224 pages.
*Neurocrine Biosciences, Inc*., Petitioner, v. *Spruce Biosciences, Inc*., Patent Owner, Case No. PGR2022-00025, U.S. Pat. No. 11,007,201, Patent Owner Spruce Biosciences' Motion to Exclude 37 C.F.R. §42.64(c), filed Aug. 14, 2024, 9 pages.
*Neurocrine Biosciences, Inc*., Petitioner, v. *Spruce Biosciences, Inc*., Patent Owner, Case No. PGR2022-00025, U.S. Pat. No. 11,007,201, Patent Owner's Objections to Evidence, filed Jun. 27, 2024, 8 pages.
*Neurocrine Biosciences, Inc*., Petitioner, v. *Spruce Biosciences, Inc*., Patent Owner, Case No. PGR2022-00025, U.S. Pat. No. 11,007,201, Patent Owner's Objections to Evidence, filed on Dec. 15, 2023, 7 pages.
*Neurocrine Biosciences, Inc*., Petitioner, v. *Spruce Biosciences, Inc*., Patent Owner, Case No. PGR2022-00025, U.S. Pat. No. 11,007,201, Patent Owner's Opposition to Petitioner's Motion To Exclude Evidence 37 C.F.R. §42.64, filed Aug. 20, 2024, 15 pages.
*Neurocrine Biosciences, Inc*., Petitioner, v. *Spruce Biosciences, Inc*., Patent Owner, Case No. PGR2022-00025, U.S. Pat. No. 11,007,201, Patent Owner's Opposition to Petitioner's Motion To Strike, filed Aug. 28, 2024, 8 pages.
*Neurocrine Biosciences, Inc*., Petitioner, v. *Spruce Biosciences, Inc*., Patent Owner, Case No. PGR2022-00025, U.S. Pat. No. 11,007,201, Patent Owner's Pre-Institution Sur-Reply, filed Jul. 28, 2022, 8 pages.
*Neurocrine Biosciences, Inc*., Petitioner, v. *Spruce Biosciences, Inc*., Patent Owner, Case No. PGR2022-00025, U.S. Pat. No. 11,007,201, Patent Owner's Preliminary Response, filed Jun. 17, 2022, 72 pages.
*Neurocrine Biosciences, Inc*., Petitioner, v. *Spruce Biosciences, Inc*., Patent Owner, Case No. PGR2022-00025, U.S. Pat. No. 11,007,201, Patent Owner's Reply in Support of Its Motion to Exclude, filed Aug. 23, 2024, 7 pages.
*Neurocrine Biosciences, Inc*., Petitioner, v. *Spruce Biosciences, Inc*., Patent Owner, Case No. PGR2022-00025, U.S. Pat. No. 11,007,201, Patent Owner's Response, filed Mar. 12, 2024, 93 pages.
*Neurocrine Biosciences, Inc*., Petitioner, v. *Spruce Biosciences, Inc*., Patent Owner, Case No. PGR2022-00025, U.S. Pat. No. 11,007,201, Patent Owner's Sur-Reply, filed Aug. 12, 2024, 33 pages.
*Neurocrine Biosciences, Inc*., Petitioner, v. *Spruce Biosciences, Inc*., Patent Owner, Case No. PGR2022-00025, U.S. Pat. No. 11,007,201, Petition for Post Grant Review of U.S. Pat. No. 11,007,201, filed Feb. 18, 2022, 92 pages.
*Neurocrine Biosciences, Inc*., Petitioner, v. *Spruce Biosciences, Inc*., Patent Owner, Case No. PGR2022-00025, U.S. Pat. No. 11,007,201, Petitioner's Motion to Exclude Evidence, filed Aug. 14, 2024, 16 pages.
*Neurocrine Biosciences, Inc*., Petitioner, v. *Spruce Biosciences, Inc*., Patent Owner, Case No. PGR2022-00025, U.S. Pat. No. 11,007,201, Petitioner's Motion to Strike, filed Aug. 22, 2024, 14 pages.
*Neurocrine Biosciences, Inc*., Petitioner, v. *Spruce Biosciences, Inc*., Patent Owner, Case No. PGR2022-00025, U.S. Pat. No. 11,007,201, Petitioner's Objections to Evidence, filed Aug. 19, 2024, 4 pages.
*Neurocrine Biosciences, Inc*., Petitioner, v. *Spruce Biosciences, Inc*., Patent Owner, Case No. PGR2022-00025, U.S. Pat. No. 11,007,201, Petitioner's Objections to Evidence, filed Mar. 19, 2024, 6 pages.
*Neurocrine Biosciences, Inc*., Petitioner, v. *Spruce Biosciences, Inc*., Patent Owner, Case No. PGR2022-00025, U.S. Pat. No. 11,007,201, Petitioner's Opposition to Patent Owner's Motion to Exclude Evidence, filed Aug. 20, 2024, 15 pages.
*Neurocrine Biosciences, Inc*., Petitioner, v. *Spruce Biosciences, Inc*., Patent Owner, Case No. PGR2022-00025, U.S. Pat. No. 11,007,201, Petitioner's Reply in Support of Its Motion to Exclude Evidence, filed Aug. 23, 2024, 9 pages.
*Neurocrine Biosciences, Inc*., Petitioner, v. *Spruce Biosciences, Inc*., Patent Owner, Case No. PGR2022-00025, U.S. Pat. No. 11,007,201, Petitioner's Reply to Patent Owner's Preliminary Response, filed Jul. 14, 2022, 9 pages.
*Neurocrine Biosciences, Inc*., Petitioner, v. *Spruce Biosciences, Inc*., Patent Owner, Case No. PGR2022-00025, U.S. Pat. No. 11,007,201, Petitioner's Reply to Patent Owner's Response, filed Jun. 20, 2024, 36 pages.
*Neurocrine Biosciences, Inc*., Petitioner, v. *Spruce Biosciences, Inc*., Patent Owner, Case No. PGR2022-00025, U.S. Pat. No. 11,007,201, Petitioner's Request for Rehearing, filed Oct. 13, 2022, 17 pages.
*Neurocrine Biosciences, Inc*., Petitioner, v. *Spruce Biosciences, Inc*., Patent Owner, Case No. PGR2022-00025, U.S. Pat. No. 11,007,201, Reply Declaration of Gordon B. Cutler, Jr., M.D., filed Jun. 20, 2024, 60 pages.
*Neurocrine Biosciences, Inc*., Petitioner, v. *Spruce Biosciences, Inc*., Patent Owner, Case Nos. PGR2021-00088 and PGR2022-00025, U.S. Pat. Nos. 10,849,908 and 11,007,201, "Transcript of Feb. 29, 2024 Deposition of Gordon B. Cutler, Jr., M.D.," filed on Mar. 12, 2024, 147 pages.
*Neurocrine Biosciences, Inc*., Petitioner, v. *Spruce Biosciences, Inc*., Patent Owner, Case Nos. PGR2021-00088 and PGR2022-00025, U.S. Pat. Nos. 10,849,908 and 11,007,201, "Transcript of Jun. 5, 2024 Deposition of Dr. Adrian Dobs, " filed on Jun. 20, 2024, 169 pages.
Newfield et al., "ACTH receptor blockade: A novel approach to treat congenital adrenal hyperplasia, or Cushing's disease," Medical Hypotheses, Apr. 2010, 74(4):705-706.
Nokoff et al., "Clinical Manifestations and Treatment Challenges in Infants and Children With Classic Congenital Adrenal Hyperplasia Due to 21-Hydroxylase Deficiency," J Clinical Endocrinology & Metabolism, Feb. 2025, 110 (Supplement_1):S13-24.
Online.Uspnf.com [online], "Medium-Chain Triglycerides," Nov. 1, 2020, retrieved on Mar. 26, 2025, retrieved from URL <https://online.uspnf.com/uspnf/document/1_GUID-995A5AEA-A8B8-473A-BE2C-94DA0912145B_5_en-US?source-Activity>, 4 pages.
Online.Uspnf.com [online], "Propylene Glycol Dicaprylate/Dicaprate," May 1, 2020, retrieved on Mar. 27, 2025, retrieved from URL <https://online.uspnf.com/uspnf/document/1_GUID-8CD288A0-4573-4B12-9F29-87144943C326_2_en-US?source=Search Results &highlight=Pro . . . >, 2 pages.
Peter, "Congenital adrenal hyperplasia: 11β-hydroxylase deficiency," Seminars in reproductive medicine, Aug. 2002, 20(3):249-254, abstract.
Pouton, "Lipid formulations for oral administration of drugs: non-emulsifying, self-emulsifying and 'self-microemulsifying' drug delivery systems," European journal of pharmaceutical sciences, Oct. 1, 2000, 11:S93-8.
Recto II et al., "Comparison of the Efficacy and Tolerability of Simvastatin and Atorvastatin in the Treatment of Hypercholesterolemia," Clinical Cardiology, 2000, 23(9):682-688.
Saal et al., "Pharmaceutical salts: A summary on doses of salt formers from the Orange Book," European Journal of Pharmaceutical Sciences, Jul. 16, 2013, 49(4):614-623.
Sandberg et al., "Mental Health Issues Associated With Classic Congenital Adrenal Hyperplasia Due to 21-Hydroxylase Deficiency," J Clinical Endocrinology & Metabolism, Feb. 2025, 110 (Supplement_1):S46-55.
Sarafoglou et al., "Future Directions in the Management of Classic Congenital Adrenal Hyperplasia Due to 21-Hydroxylase Deficiency," J Clinical Endocrinology & Metabolism, Feb. 2025, 110 (Supplement_1):S74-87.
Sarafoglou et al., "Phase 3 Trial of Crinecerfont in Pediatric Congenital Adrenal Hyperplasia," New England Journal of Medicine, Jun. 2, 2024, 1-11.

(56) References Cited

OTHER PUBLICATIONS

Souron, "New Introduction of Pharmacology," Nanzando Co., 3rd edition, 1987, p. 414-416 (with English translation).
Spernath et al., "Microemulsions as carriers for drugs and nutraceuticals," Advances in colloid and interface science, Dec. 21, 2006, 128:47-64.
Wikipedia.org [online], "Medium-chain triglyceride," last updated on Dec. 28, 2024, retrieved on Apr. 10, 2025, retrieved from URL<https://en.wikipedia.org/w/index.php?title=Medium-chain_triglyceride&oldid=1265809727>, 4 pages.
Wikipedia.org [online], "Molecular mass," last updated on Nov. 2, 2024, retrieved on Apr. 10, 2025, retrieved from URL<https://en.wikipedia.org/w/index.php?title=Molecular_mass&oldid=1254996685>, 4 pages.
Witchel et al., "Life With Classic Congenital Adrenal Hyperplasia Due to 21-Hydroxylase Deficiency: Challenges and Burdens," J Clinical Endocrinology & Metabolism, Feb. 2025, 110 (Supplement_1):S56-66.
Yang et al., "Genetics and Pathophysiology of Classic Congenital Adrenal Hyperplasia Due to 21-Hydroxylase Deficiency," J Clinical Endocrinology & Metabolism, Feb. 2025, 110 (Supplement 1):S1-2.
Yanovski et al., "Etiology of the Differences in Corticotropin-Releasing Hormone-Induced Adrenocorticotropin Secretion of Black and White Women," Journal of Clinical Endocrinology & Metabolism, 1996, 81(9):3307-3311.
[No Author Listed], "EU/3/19/2194—orphan designation for treatment of congenital adrenal hyperplasia," European Medicines Agency, Aug. 21, 2019, 4 pages.
[No Author Listed], "Highlights of Prescribing Information: RAYOS," Horizon Therapeutics, Mar. 2024, 22 pages.
[No Author Listed], "Proposed INN: List 119," WHO Drug Information, Jul. 2018, 32(2):369-370.
[No Author Listed], "Public summary of opinion on orphan designation: Verucerfont for the treatment of congenital adrenal hyperplasia," European Medicines Agency, Sep. 30, 2015, 5 pages.
[No Author Listed], "Recommended INN: List 81," WHO Drug Information, Apr. 2019, 33(1):122.
[No Author Listed], "Regulation (EC) No. 141/2000 of the European Parliament and of the Council of Dec. 16, 1999 on orphan medicinal products," Official Journal of the European Communities, Jan. 22, 2000, L18/1-L18/5.
Application to Amend Claims of EP 3784233 B1 in Claim No. HP-2025-000005 against EP Patent No. 378423, filed on Nov. 11, 2025, 8 pages.
Application to Stay Proceedings in UPC Proceeding No. 34386/2025, filed on Sep. 18, 2025, 18 pages.
Auchus et al., "Phase 3 Trial of Crinecerfont in Adult Congenital Adrenal Hyperplasia," N. Engl. J. Med., Aug. 8, 2024, 391(6):504-514.
Auchus et al., "Phase 3 Trial of Crinecerfont in Adult Congenital Adrenal Hyperplasia," N. Engl. J. Med., Aug. 8, 2024, 391(6):504-514; Supplementary Appendix, 30 pages.
Auchus, "Clinical Study Protocol: A Phase 2, Multiple-Dose, Dose-Escalation Study to Evaluate the Safety and Efficacy of SPR001 in Adults with Classic Congenital Adrenal Hyperplasia (CAH)," Spruce Biosciences, Inc., Aug. 23, 2018, 80 pages.
Auchus, "Management considerations for the adult with congenital adrenal hyperplasia," Mol. Cell Endocrinol., Jun. 15, 2015, 408:190-197.
Avila et al., "Testicular adrenal rest tissue in congenital adrenal hyperplasia: serial sonographic and clinical findings," Am. J. Roentgenol., May 1999, 172(5):1235-1238.
Aycan et al., "Prevalence and long-term follow-up outcomes of testicular adrenal rest tumours in children and adolescent males with congenital adrenal hyperplasia," Clin. Endocrinol., May 2013, 78(5):667-672.
Bacon et al., "Effect of Cortisol Treatment on Hormonal Relationships in Congenital Adrenal Hyperplasia," Clin. Endocrinol., Feb. 1977, 6(2):113-126.
Benvenga et al., "Testicular adrenal rests: evidence for luteinizing hormone receptors and for distinct types of testicular nodules differing for their autonomization," Eur. J. Endocrinol., Sep. 1999, 141(3):231-237.
Bhatt et al., "A Controlled Trial of Renal Denervation for Resistant Hypertension," N. Engl. J. Med., Apr. 10, 2014, 370(15):1393-1401.
Brown et al., "Medication Adherence: WHO Cares?," Mayo Clin. Proc., Apr. 2011, 86(4):304-314.
Cakir et al., "Testicular Adrenal Rest Tumors in Patients with Congenital Adrenal Hyperplasia," J. Clin. Res. Pediatr. Endocrinol., Jun. 2012, 4(2):94-100.
Campinos, "G 1/24 ("Heated aerosol"): Comments by the President of the EPO," European Patent Office, dated Nov. 7, 2024, 50 pages.
Chen et al., "Ovarian Adrenal Rest Tumors Undetected by Imaging Studies and Identified at Surgery in Three Females with Congenital Adrenal Hyperplasia Unresponsive to Increased Hormone Therapy Dosage," Endocr. Pathol., Dec. 28, 2016, 28(2):146-151.
Claahsen-van der Grinten et al., "Repeated successful induction of fertility after replacing hydrocortisone with dexamethasone in a patient with congenital adrenal hyperplasia and testicular adrenal rest tumors," Fertil. Steril., Sep. 2007, 88(3):705.e5-e8.
Claahsen-van der Grinten et al., "Testicular adrenal rest tumours in congenital adrenal hyperplasia," Int. J. Pediatr. Endocrinol., Feb. 2009, 2009:624823, 8 pages.
Claahsen-van der Grinten et al., "Testicular Tumors in Patients with Congenital Adrenal Hyperplasia due to 21-Hydroxylase Deficiency Show Functional Features of Adrenocortical Tissue," J. Clin. Endocrinol. Metab.,Jun. 26, 2007, 92(9):3674-3680.
Claim Form in Claim No. HP-2025-000005 against EP Patent No. 3784233, filed on Jan. 30, 2025, 5 pages.
Claimant's Initial Disclosure List in Claim No. HP-2025-000005 against EP Patent No. 378423, filed on Jan. 31, 2025, 2 pages.
ClinicalTrials.gov [online], "A Ph2b to Evaluate Clinical Efficacy and Safety of Tildacerfont in Adult CAH," NCT04457336, last updated Jun. 10, 2024, retrieved on Jul. 18, 2025, retrieved from URL<https://clinicaltrials.gov/study/NCT04457336?term=NCT04457336&rank=1>, 14 pages.
Communication of Notices of Opposition against European Patent No. 3784233, mailed on Mar. 18, 2025, 2 pages.
Congenital Adrenal Hyperplasia, 1st ed., Hindmarsh et al. (eds)., May 2017, pp. 263-264 and 319-320.
Congenital Adrenal Hyperplasia, 1st ed., Hindmarsh et al. (eds)., May 2017, pp. 24, 42, 165, 170, 171, 212, 264, 319, 320, 413 and 417.
Curriculum Vitae of Associate Professor Dr. Henrik Falhammar, produced Nov. 17, 2025, 2 pages.
Curriculum Vitae of Vivian H Lin, MD, produced Nov. 14, 2025, 2 pages.
Decision of the Enlarged Board of Appeal in Case No. G 0001/24, dated Jun. 18, 2025, 12 pages.
Decision of the Enlarged Board of Appeal in Case No. G 0002/21, dated Mar. 23, 2023, 75 pages.
Decision of the Technical Board of Appeal in Case No. T 0184/16—3.3.02, dated Dec. 12, 2019, 33 pages.
Decision of the Technical Board of Appeal in Case No. T 0429/96—3.3.4, dated May 31, 2001, 23 pages.
Decision of the Technical Board of Appeal in Case No. T 0609/02—3.3.8, dated Oct. 27, 2004, 18 pages.
Decision of the Technical Board of Appeal in Case No. T 0728/21—3.3.07, dated Nov. 16, 2023, 25 pages.
Decision of the Technical Board of Appeal in Case No. T 0799/16—3.3.01, dated Sep. 4, 2019, 42 pages.
Decision of the Technical Board of Appeal in Case No. T 0816/22—3.3.04, dated Nov. 19, 2024, 17 pages.
Decision of the Technical Board of Appeal in Case No. T 0852/09—3.3.04, dated Sep. 6, 2013, 10 pages.
Decision of the Technical Board of Appeal in Case No. T 0979/23—3.3.04, dated Oct. 1, 2024, 26 pages.
Decision of the Technical Board of Appeal in Case No. T 1045/13—3.3.01, dated Oct. 23, 2017, 13 pages.
Decision of the Technical Board of Appeal in Case No. T 1229/03—3.3.02, dated Nov. 23, 2006, 21 pages.

(56) References Cited

OTHER PUBLICATIONS

Decision of the Technical Board of Appeal in Case No. T 1437/07—3.3.04, dated Oct. 26, 2009, 42 pages.
Decision of the Technical Board of Appeal in Case No. T 1863/21—3.3.09, dated Apr. 29, 2024, 29 pages.
Decision of the Technical Board of Appeal in Case No. T 19/90—3.3.2, dated Oct. 3, 1990 (with correction dated Oct. 22, 1990), 26 pages.
Decision of the Technical Board of Appeal in Case No. T 1959/15—3.3.01, dated Apr. 2, 2020, 14 pages.
Decision of the Technical Board of Appeal in Case No. T 2443/18—3.3.01, dated Apr. 9, 2021, 14 pages.
Declaration of Associate Professor Dr. Henrik Falhammar in Opposition against European Patent No. 3784233, dated Nov. 17, 2025, 9 pages.
Declaration of Dr. Chris N. Barnes under 37 C.F.R. § 1.132 in U.S. Appl. No. 17/081,694, filed Dec. 13, 2021, 4 pages.
Declaration of Professor Peter Hindmarsh in Opposition against European Patent No. 3784233, dated Oct. 23, 2025, 5 pages.
Declaration of Vivian H Lin, MD, in Opposition against European Patent No. 3784233, dated Nov. 14, 2025, 7 pages.
Defendant's Defense in Claim No. HP-2025-000005 against EP Patent No. 378423, filed on Mar. 13, 2025, 3 pages.
Delfino et al., "Testicular adrenal rest tumors in patients with congenital adrenal hyperplasia: prevalence and sonographic, hormonal, and seminal characteristics," J. Ultrasound Med., Mar. 2012, 31(3):383-388.
Engels et al., "Testicular Adrenal Rest Tumors: Current Insights on Prevalence, Characteristics, Origin, and Treatment," Endocr. Rev., Aug. 2019, 40(4):973-987.
EP Patent Application No. 19793181.9 as filed on Apr. 26, 2019, 134 pages.
Essentials of Cell Biology, 1st ed., O'Connor (ed.), 2010, Units 4.2 and 4.4, 7 pages.
FDA.gov [online], "FDA Approves New Treatment for Congenital Adrenal Hyperplasia," Dec. 13, 2024, retrieved on Jul. 24, 2025, retrieved from URL<https://www.fda.gov/news-events/pressannouncements/fda-approves-new-treatment-congenital-adrenal-hyperplasia>, 2 pages.
FierceBiotech.com [online], "Spruce saws off only drug after 2nd hyperplasia fail, leaving biotech's direction in doubt," Dec. 11, 2024, retrieved on Feb. 28, 2025, retrieved from URL<https://www.fiercebiotech.com/biotech/spruce-drops-only-drug-after-2nd-hyperplasia-fail-leaving-biotechs-direction-doubt>, 2 pages.
Gjerstad et al., "Role of glucocorticoid negative feedback in the regulation of HPA axis pulsatility, " Stress, May 15, 2018, 21(5):403-416.
Greenspan's Basic & Clinical Endocrinology, 10th ed., Gardner et al. (eds)., Sep. 19, 2017, pp. 413 and 440-441.
Greenspan's Basic & Clinical Endocrinology, 10th ed., Gardner et al. (eds)., Sep. 19, 2017, excerpt from Chapter 9, 4 pages.
Grounds of Invalidity in Claim No. HP-2025-000005 against EP Patent No. 378423, filed on Jan. 31, 2025, 10 pages.
Gupta et al., "Corticosteroid Physiology and Principles of Therapy," Indian J. Pediatr., Oct. 2008, 75(10):1039-1044.
Gwathmey et al., "Glucocorticoid-Induced Fetal Programming Alters the Functional Complement of Angiotensin Receptor Subtypes Within the Kidney," Hypertension, Mar. 2011, 57(3):620-626.
Hillhouse et al., "The Molecular Mechanisms Underlying the Regulation of the Biological Activity of Corticotropin-Releasing Hormone Receptors: Implications for Physiology and Pathophysiology," Endocr. Rev.,Feb. 16, 2006, 27(3):260-286.
Joseph et al., "Stress and the HPA Axis: Balancing Homeostasis and Fertility," Int. J. Mol. Sci., Oct. 24, 2017, 18(10):2224, 15 pages.
Letter to the European Patent Office in European Appln. No. 19793181.9, filed on Jul. 21, 2021, 2 pages.
Ma et al., "Sonographic features of the testicular adrenal rests tumors in patients with congenital adrenal hyperplasia: a single-center experience and literature review," Orphanet J. Rare Dis., Nov. 6, 2019, 14(1):242, 8 pages.
Matsubara, "Pathophysiological Role of Angiotensin II Type 2 Receptor in Cardiovascular and Renal Diseases," Circ. Res., Dec. 14, 1998, 83(12):1182-1191.
Meena et al., "Growth Pattern and Clinical Profile of Indian Children with Classical 21-Hydroxylase Deficiency Congenital Adrenal Hyperplasia on Treatment," Indian J. Pediatr., Jan. 30, 2019, 86(6):496-502.
Memorandum in United States District Court Case No. 1:25-cv-00059-JDW, issued on Jun. 9, 2025, 10 pages.
Mendes-dos-Santos et al., "Prevalence of Testicular Adrenal Rest Tumor and Factors Associated with Its Development in Congenital Adrenal Hyperplasia," Horm. Res. Paediatr., Aug. 27, 2018, 90(3):161-168.
Mesa et al., "Immunophenotypic differences between neoplastic and non-neoplastic androgen-producing cells containing and lacking Reinke crystals," Virchows Arch., Oct. 1, 2016, 469:679-686.
Nagurney et al., "The Accuracy and Completeness of Data Collected by Prospective and Retrospective Methods," Acad. Emerg. Med., Sep. 2005, 12(9):884-895.
Neurocrine Biosciences, Inc., "Form 10-Q: Quarterly Report Pursuant to Section 13 or 15(d) of the Securities Exchange Act of 1934 for the quarterly period ended Jun. 30, 2025," United States Securities and Exchange Commission, filed Jul. 30, 2025, 63 pages.
Nissen et al., "The clinical case report: a review of its merits and limitations," BMC Research Notes, Apr. 23, 2014, 7(1):264, 7 pages.
Notice of Opposition against European Patent No. 3096756, filed on Mar. 7, 2025, 17 pages.
Notice of Opposition against European Patent No. 3784233, filed on Feb. 28, 2025, 36 pages.
Notice of Opposition against European Patent No. 3784233, filed on Dec. 10, 2024, 3 pages.
Opinion of the Enlarged Board of Appeal in Case No. G 10/91, dated Mar. 31, 1993, 17 pages.
Opponents Response to Patentees Submissions under Rule 116 EPC in Opposition against European Patent No. 3784233, filed on Nov. 17, 2025, 10 pages.
Opponents Submission under Rule 116 EPC in Opposition against European Patent No. 3784233, filed on Oct. 24, 2025, 7 pages.
Order in Claim No. HP-2025-000005 against EP Patent No. 378423, issued on May 2, 2025, 6 pages.
OUP.com [online], "JCEM Author Guidelines, " available on or before Jan. 27, 2017 via Internet Archive: Wayback Machine URL<https://web.archive.org/web/20170127125012/https://academic.oup.com/jcem/pages/author_guidelines>, retrieved on Jun. 9, 2025, retrieved from URL<https://academic.oup.com/jcem/pages/author_guidelines>, 1 page.
Paragliola, "Treatment with Synthetic Glucocorticoids and the Hypothalamus-Pituitary-Adrenal Axis," Int. J. Mol. Sci., Oct. 20, 2017, 18(10):2201, 18 pages.
Particulars of Claim in Claim No. HP-2025-000005 against EP Patent No. 378423, filed on Jan. 31, 2025, 2 pages.
Patentees Response to Opponents Submission under Rule 116 EPC in Opposition against European Patent No. 3784233, filed on Nov. 14, 2025, 14 pages.
Patentees Submission under Rule 116 EPC in Opposition against European Patent No. 3784233, filed on Oct. 24, 2025, 48 pages.
Poyrazoglu et al., "Prevalence of Testicular Microlithiasis in Males with Congenital Adrenal Hyperplasia and Its Association with Testicular Adrenal Rest Tumors," Horm. Res. Paediatr., Apr. 20, 2010, 73:443-448.
Preliminary Order in UPC Proceeding No. 34386/2025, issued on Sep. 25, 2025, 2 pages.
Preliminary Order in UPC Proceeding No. 34386/2025, issued on Sep. 30, 2025, 4 pages.
Reisch et al., "High prevalence of reduced fecundity in men with congenital adrenal hyperplasia," J. Clin. Endocrinol. Metab., Mar. 3, 2009, 94(5): 1665-1670.
Reisch et al., "Testicular adrenal rest tumors develop independently of long-term disease control: a longitudinal analysis of 50 adult men with congenital adrenal hyperplasia due to classic 21- hydroxylase deficiency," J. Clin. Endocrinol. Metab., Aug. 22, 2013, 98(11):E1820-E1826.

(56) References Cited

OTHER PUBLICATIONS

Reply to Response to Notice of Opposition against European Patent No. 3784233, filed on Jul. 18, 2025, 7 pages.
Reply to the Notice of Opposition against European Patent No. 3096756, filed on Jul. 24, 2025, 36 pages.
Response to Application to Stay Proceedings in UPC Proceeding No. 34386/2025, filed on Sep. 26, 2025, 26 pages.
Response to Notice of Opposition against European Patent No. 3784233, filed on Jun. 18, 2025, 123 pages.
Response to the Reply to the Notice of Opposition against European Patent No. 3096756, filed on Oct. 24, 2025, 9 pages.
Smeets et al., "Molecular Characterization of Testicular Adrenal Rest Tumors in Congenital Adrenal Hyperplasia: Lesions With Both Adrenocortical and Leydig Cell Features," J. Clin. Endocrinol. Metab., Mar. 2015, 100(3):E524-E530.
Sowers et al., "Effect of dexamethasone on gonadotropin responsiveness to luteinizing hormone-releasing hormone and clomiphene in women with secondary amenorrhea, " Am. J. Obstet. Gynecol., Jun. 1979, 134(3):325-328.
Spruce Biosciences, Inc., "Form 10-Q: Quarterly Report Pursuant to Section 13 or 15(d) of the Securities Exchange Act of 1934 For the quarterly period ended Mar. 31, 2025," United States Securities and Exchange Commission, filed May 6, 2025, pp. 19 and 34-35.
SpruceBio.com [online], "Investors/Media, " last updated Jul. 24, 2025, retrieved on Aug. 1, 2025, retrieved from URL<https://investors.sprucebio.com>, 2 pages.
SpruceBio.com [online], "Spruce Biosciences announces topline results from CAHMELIA-203 in adult classic CAH and CAHPTAIN-205 in pediatric classic CAH," Mar. 13, 2024, retrieved on Feb. 28, 2025, retrieved from URL<https://investors.sprucebio.com/news-releases/news-release-details/spruce-biosciences-announcestopline-results-cahmelia-203-adult>, 7 pages.
SpruceBio.com [online], "Spruce Biosciences announces topline results from CAHMELIA-204 in adult CAH and CAHPTAIN-205 in adult and pediatric CAH," Dec. 10, 2024, retrieved on Feb. 28, 2025, retrieved from URL<https://investors.sprucebio.com/news-releases/news-release-details/spruce-biosciences-announcestopline-results-cahmelia-204-adult>, 4 pages.
SpruceBio.com [online], "SpruceBio: About US," available on or before Jul. 24, 2023 via Internet Archive: Wayback Machine URL<https://web.archive.org/web/20230724173717/https://sprucebio.com/>, retrieved on Oct. 15, 2025, retrieved from URL<https://sprucebio.com>, 5 pages.
Statement for Revocation of Patent EP 3784233 B1 in UPC Proceeding No. 34386/2025, filed on Aug. 8, 2025, 45 pages.
Statement of Defense and Application to Amend in UPC Proceeding No. 34386/2025, filed on Oct. 15, 2025, 168 pages.
Statement of Grounds for Amendment of EP 3784233 in Claim No. HP-2025-000005 against EP Patent No. 378423, filed on Nov. 11, 2025, 4 pages.
Summons to Attend Oral Proceedings in Opposition against European Patent No. 3784233, mailed on Aug. 5, 2025, 21 pages.
Transmission of the certificate for a European patent with unitary effect for European Patent No. 3784233, mailed on Jul. 8, 2024, 2 pages.
Turcu et al., "Adrenal steroidogenesis and congenital adrenal hyperplasia," Endocrinol. Metab. Clin. North Am., Jun. 2015, 44(2):275-296.
U.S. Appl. No. 62/663,951, filed Apr. 27, 2018, 153 pages.
U.S. Appl. No. 62/822,815, filed Mar. 23, 2019, 25 pages.
Wang et al., "Diagnosis of Testicular Adrenal Rest Tumors on Ultrasound: A retrospective Study of 15 Cases Report," Medicine, Sep. 2015, 94(36):e1471, 6 pages.
Williams Textbook of Endocrinology, 13th ed., Melmed et al. (eds.), Oct. 2016, pp. 497 and 507-510.
Withdrawal of an opt-out pursuant to RoP5.9 from the exclusive competence of the Unified Patent Court in UPC Proceeding No. 38945/2024, dated Jun. 29, 2024, 4 pages.
Xavier et al., "Gene Expression Control by Glucocorticoid Receptors during Innate Immune Responses," Front. Endocrinol., Apr. 19, 2016, 7:31, 8 pages.
Xue et al., "Glucocorticoid Modulates Angiotensin II Receptor Expression Patterns and Protects the Heart from Ischemia and Reperfusion Injury," PLOS ONE, Sep. 2014, 9(9):e106827, 10 pages.
Yamada et al., "New class of corticotropin-releasing factor (CRF) antagonists: small peptides having high binding affinity for CRF receptor," J. Med. Chem., Feb. 26, 2004, 47(5):1075-1078.
Yasir et al., "Corticosteroid Adverse Effects," StatPearls, Jul. 3, 2023, 14 pages.
Yu et al., "Clinical manifestations of testicular adrenal rest tumor in males with congenital adrenal hyperplasia," Ann. Pediatr. Endocrinol. Metab., Sep. 30, 2015, 20(3):155-161.
Zaarour et al., "Bilateral ovary adrenal rest tumor in a congenital adrenal hyperplasia following adrenalectomy," Endocr. Pract., Jan. 21, 2014, 20(4):e69-e74.
[No Author Listed], "Highlights of Prescribing Information: Crenessity," Neurocrine Biosciences Inc., Dec. 2024, 24 pages.
[No Author Listed], "Medium-chain Triglycerides," Handbook of Pharmaceutical Excipients, 6th ed., Rowe et al. (ed.), 2009, pp. 429-431.
[No Author Listed], "Regulatory data sheet (RDS)—Pharmaceutical market (human and veterinary medicines): Labrafac Lipophile WL 1349 (Code: 3139)," Gattefossé SAS, Mar. 19, 2025, 8 pages.
Al-Kasmi et al., "Mechanical microencapsulation: The best technique in taste masking for the manufacturing scale-Effect of polymer encapsulation on drug targeting, " Journal of Controlled Release, Aug. 28, 2017, 260:134-41.
Cano et al., "Direct asymmetric alkylation of ketones: still unconquered," Angewandte Chemie International Edition, May 12, 2017, 56(32):9278-90.
CAS Registry No. 57107-95-6, "Poly(oxy-1,2-ethanediyl), α,α',α"-1,2,3-propanetriyltris[ω-hydroxy-, dodecanoate (9Cl, ACl)," SciFinder, retrieved on Aug. 4, 2025, 3 pages.
CAS Registry No. 61789-25-1, "Corn oil, ethoxylated (13C, 14C)," SciFinder, retrieved on Aug. 4, 2025, 2 pages.
CAS Registry No. 68583-51-7, "Decanoic acid, mixed diesters with octanoic acid and propylene glycol," SciFinder, retrieved on Aug. 4, 2025, 4 pages.
CAS Registry No. 69071-70-1, "Ethoxylated apricot kernel oil (16C)," SciFinder, retrieved on Aug. 4, 2025, 2 pages.
CAS Registry No. 73398-61-5, "Glycerides, mixed decanoyl and octanoyl (10C)," SciFinder, retrieved on Aug. 4, 2025, 3 pages.
CAS.org [online], "CAS Registry®," available on or before Apr. 30, 2021 via Internet Archive: Wayback Machine URL<https://web.archive.org/web/20210430123159/https://www.cas.org/cas-data/cas-registry#registry-1>, retrieved on Sep. 3, 2025, retrieved from URL<https://www.cas.org/cas-data/cas-registry#registry-1>, 10 pages.
Claahsen-van der Grinten et al., "Congenital Adrenal Hyperplasia-Current Insights in Pathophysiology, Diagnostics, and Management," Endocr Rev, Jan. 12, 2022, 43(1):91-159.
Gattefosse.com [online], "Labrafac™ PG," available on or before Nov. 30, 2023 via Internet Archive: Wayback Machine URL<https://web.archive.org/web/20231130184227/https://www.gattefosse.com/pharmaceuticals/product-finder/labrafac-pg>, retrieved on Sep. 3, 2025, retrieved from URL<https://www.gattefosse.com/pharmaceuticals/product-finder/labrafac-pg>, 4 pages.
Gattefosse.com [online], "Labrafil® M 1944 CS," available on or before Dec. 5, 2023 via Internet Archive: Wayback Machine URL<https://web.archive.org/web/20231205000437/https://www.gattefosse.com/pharmaceuticals/product-finder/labrafil-m-1944-cs>, retrieved on Sep. 3, 2025, retrieved from URL<https://www.gattefosse.com/pharmaceuticals/product-finder/labrafil-m-1944-cs>, 4 pages.
Gattefosse.com [online], "Labrafil® M 2125 CS," available on or before Nov. 30, 2023 via Internet Archive: Wayback Machine URL<https://web.archive.org/web/20231130171716/https://www.gattefosse.com/pharmaceuticals/product-finder/labrafil-m-2125-cs>, retrieved on Sep. 3, 2025, retrieved from URL<https://www.gattefosse.com/pharmaceuticals/product-finder/labrafil-m-2125-cs>, 4 pages.

(56) References Cited

OTHER PUBLICATIONS

Ghadi et al., "BCS class IV drugs: Highly notorious candidates for formulation development," Journal of Controlled Release, Feb. 28, 2017, 248:71-95 (abstract only).
Kageyama et al., "Hypothalamic Regulation of Corticotropin-Releasing Factor under Stress and Stress Resilience," Int J Mol Sci, Nov. 12, 2021, 22(22):12242.
Newfield et al., "Crinecerfont, a CRF1 Receptor Antagonist, Lowers Adrenal Androgens in Adolescents With Congenital Adrenal Hyperplasia," J Clin Endocrinol Metab, Oct. 18, 2023, 108(11):2871-2878.
Nicolaides et al., "Glucocorticoid Therapy and Adrenal Suppression," Endotext, Oct. 19, 2018, retrieved on Aug. 27, 2025, retrieved from URL<https://www.ncbi.nlm.nih.gov/books/NBK279156/>, 28 pages.
PharmaExcipients.com [online], "Handbook of Pharmaceutical Excipients—9th Edition," available on or before Jan. 16, 2021 via Internet Archive: Wayback Machine URL<https://web.archive.org/web/20210116075359/https://www.pharmaexcipients.com/handbook-of-pharmaceutical-excipients-9th-edition/>, retrieved on Sep. 3, 2025, retrieved from URL<https://www.pharmaexcipients.com/handbook-of-pharmaceutical-excipients-9th-edition/>, 3 pages.
Prete et al., "Clinical advances in the pharmacotherapy of congenital adrenal hyperplasia, " Eur J Endocrinol, Nov. 30, 2021, 186(1):R1-R14.
Rentsch, "The importance of stereoselective determination of drugs in the clinical laboratory," Journal of Biochemical and Biophysical Methods, Nov. 15, 2002, 54(1-3):1-9.
Rxlist.com [online], "Definition of Body Surface Area," available on or before Jan. 21, 2021, via Internet Archive: Wayback Machine URL <https://web.archive.org/web/20210121083600/https://www.rxlist.com/body_surface area/definition.htm>, retrieved on Oct. 8, 2025, retrieved from URL <https://www.rxlist.com/body_surface_area/definition.htm>, 1 page.
Sharma et al., "Congenital Adrenal Hyperplasia," StatPearls Publishing, Jan. 27, 2025, retrieved on Aug. 27, 2025, retrieved from URL<https://www.ncbi.nlm.nih.gov/books/NBK448098/>, 16 pages.
USP.org [online], "USP Reference Standards," available on or before Feb. 5, 2012 via Internet Archive: Wayback Machine URL<https://web.archive.org/web/20120205154740/https://www.usp.org/reference-standards>, retrieved on Sep. 3, 2025, retrieved from URL<https://www.usp.org/reference-standards>, 7 pages.
Alfa-chemical.com [online], CAS Registry No. 68583-51-7, "Propylene Glycol Dicaprylate/Dicaprate," retrieved on Jan. 28, 2026, retrieved from URL <https://www.alfa-chemical.com/organic-chemistry/organic-building-blocks/cas-68583-51-7-propylene-glycol-dicaprylate.html>, 6 pages.
Bachelot et al., "Determining clinical and biological indicators for health outcomes in adult patients with childhood onset of congenital adrenal hyperplasia," European Journal of Endocrinology, Aug. 2015, 173(2):175-84.
Fedorova et al., "What is the need for adrenalectomy in patients with congenital adrenal hyperplasia in the era of CRF1/ACTH inhibitors?," Front Endocrinol (Lausanne), Nov. 5, 2025, 16(1693063):1-10.
Koziolek et al., "Intragastric pH and pressure profiles after intake of the high-caloric, high-fat meal as used for food effect studies," J. Controlled Release, 2015, 220:71-78.
Leung, "Polyethylene Glycol," Encyclopedia of Toxicology, Apr. 14, 2014, Third edition, pp. 1043-1044.
Manu et al., "Spray Drying in pharmaceutical industry: A Review," Research Journal Pharmaceutical Dosage Forms Technology, Mar. 1, 2012, 4(2):74-79.
marcordev.com [online], "Technical Data Sheet Miglyol 812 N (Excipient)," IOI Oleochemical, Apr. 2017, retrieved on Jan. 28, 2026, retrieved from URL <https://marcordev.com/wp-content/uploads/2019/08/MIGLYOL_812_N_Excipient_TDSH.pdf>, 5 pages.
MedKoo.com [online], Cat#: 522656, 2025, retrieved on Nov. 22, 2025, retrieved from URL <https://www.medkoo.com/products/8261>, 2 pages.
pharmaffiliates.com [online], CAS Registry No. 68583-51-7, "Decanoic acid, mixed diesters with octanoic acid and propylene glycol," retrieved on Jan. 28, 2026, retrieved from URL <https://www.pharmaffiliates.com/en/68583-51-7-propylene-glycol-dicaprylate-dicaprate-pa270022416.html>, 5 pages.
Rivkees, "Dexamethasone therapy of congenital adrenal hyperplasia and the myth of the" growth toxic" glucocorticoid," International journal of pediatric endocrinology, Mar. 28, 2010, 2010(569680):1-7.
who.int [online], "Weight charts for Girls and Boys 5 to 10 years old," World Health Organization, 2007, retrieved on Dec. 3, 2025, retrieved from URL https://cdn.who.int/media/docs/default-source/child-growth/growth-reference-5-19-years/weight-for-age-(5-10-years)/cht-wfa-girls-z-5-10years.pdf?sfvrsn-47c7069d 4, 2 pages.
WorldData. Info [online], "Average Sizes of Man and Woman," Nov. 2025, retrieved on Nov. 22, 2025, retrieved from URL <https://www.worlddata.info/average-bodyheight.php>, 9 pages.

SUBSTITUTED PYRAZOLO[1,5-α]PYRIMIDINES AS CRF RECEPTOR ANTAGONISTS

CROSS-REFERENCE TO RELATED APPLICATIONS

This application is a National Stage Application under 35 U.S.C. § 371 and claims the benefit of International Application No. PCT/US2020/062747, filed Dec. 1, 2020, which claims priority to U.S. Provisional Application No. 62/943,517, filed Dec. 4, 2019. The disclosures of the foregoing applications are hereby incorporated by reference in their entireties.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND

Technical Field

This disclosure relates generally to corticotropin-releasing factor (CRF) receptor 1 ($CRF_1$) antagonist compounds, compositions and methods related thereto such as methods for treating congenital adrenal hyperplasia (CAH).

Description of Related Technology

Corticotropin-releasing factor (CRF) is a hypothalamic hormone that acts as the key regulator of the hypothalamic-pituitary-adrenal (HPA) axis. CRF activates the $CRF_1$ receptor, a class B G protein-coupled receptor (GPCR). This activation ultimately leads to cortisol biosynthesis and negative feedback inhibition of hypothalamic CRH secretion. Congenital adrenal hyperplasia (CAH) is a group of autosomal recessive genetic disorders that result in little or no cortisol biosynthesis. One clinical manifestation of the absence of cortisol is the lack of feedback inhibition of CRF which causes dysregulation of the HPA axis. The most frequent form of the disease is 21-hydroxylase deficiency caused by mutations in the CYP21A2 gene located on chromosome 6p21, which accounts for approximately 95% of CAH cases, the 21-hydroxylase enzyme deficiency also causes a shunting of cortisol precursor steroids leading to excess androgen (e.g., 17-hydroxyprogesterone, androstenedione, and testosterone) product. These mutations can range from complete loss of enzyme activity required for synthesis of cortisol in the adrenal cortex to a spectrum of partial loss, which results in disease severity that is a direct consequence of a specific mutation. This continuum of 21-hydroxylase deficiency has been broadly classified into salt-wasting and simple-virilizing forms, grouped as classic (or classical) CAH, and the milder form known as non-classic (or non-classical) CAH (NCCAH) or "late-onset" CAH, which is usually diagnosed in late childhood or early adulthood. Non-classic CAH patients are either homozygous or compound heterozygotes, often with a classical CAH allele. These patients have sufficient enzyme activity (>20-50% of normal) such that they do not have salt-wasting or cortisol deficiency and have normal genitalia at birth, and many remain asymptomatic throughout life. In the less frequent form of the disease, which accounts for 5% of cases, mutation of the 11β-hydroxylase gene CYP11B1 results in CAH (11β-OH CAH). Classic CAH is a rare disease; the incidence of classic CAH is estimated to be ~1:15,000 worldwide. Approximately 75% of patients with classic CAH have the salt wasting form of the disease, characterized by severe enzyme deficiency and insufficient levels of cortisol and aldosterone. Approximately 25% of patients with classic CAH have the simple virilizing form, in which cortisol synthesis is impaired, but enzyme activity is sufficient for adequate production of aldosterone.

Currently, exogenous corticosteroids are the standard of care for treating patients with classic CAH. This treatment is used to correct the cortisol deficiency and reduce androgen excess. However, the dose of corticosteroid used is typically well above the normal physiological level used for cortisol replacement alone (as in patients with Addison's disease). This increased exposure to corticosteroids can lead to iatrogenic Cushing's syndrome, increased cardiovascular risk factors, glucose intolerance, reduced growth velocity, and decreased bone mineral density in CAH patients. Thus, there is a need for a treatment for CAH that avoids the severe complications associated with current corticosteroid therapy.

It has been demonstrated in clinical trials that certain $CRF_1$ antagonist compounds provide significant reduction in relevant steroid biomarkers (e.g., 17-hydroxyprogesterone and androstenedione) compared to placebo in patients with CAH.

There remains a need to identify new $CRF_1$ antagonists for use in the treatment of CAH. The present disclosure fulfills these and other needs, as evident in reference to the following disclosure.

BRIEF SUMMARY

Provided herein are compounds that are CRF antagonists. In particular embodiments, compounds are provided that are $CRF_1$ antagonists. Accordingly, such compounds are useful in the treatment of CAH.

Some embodiments provide a compound having the structure of Formula (I):

(I)

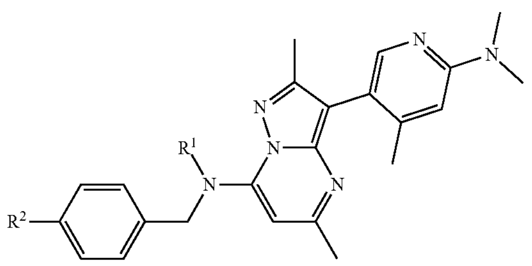

or a pharmaceutically acceptable salt thereof.

Some embodiments provide a compound having the structure of Formula (I):

(II)

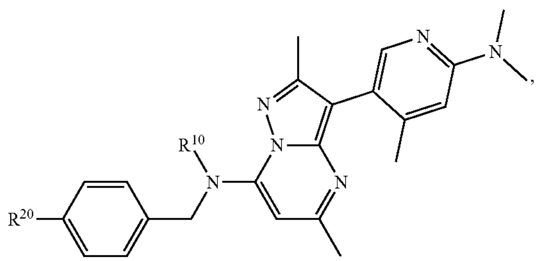

or a pharmaceutically acceptable salt thereof.

Some embodiments provide a compound of the disclosure, or a pharmaceutically acceptable salt thereof, or composition of the disclosure, for use in treating congenital adrenal hyperplasia in a subject, wherein the compound or composition is administered in an amount sufficient to reduce the level of one or more biomarkers selected from (a) 17-hydroxyprogesterone (17-OHP); (b) testosterone; and (c) androstenedione in the subject.

Some embodiments provide a compound of the disclosure, or a pharmaceutically acceptable salt thereof, or composition of the disclosure, for use in reducing the severity of one or more symptoms selected from hirsutism, precocious puberty, fertility problems, acne, and growth impairment in a subject having classic congenital adrenal hyperplasia, wherein the compound or a pharmaceutically acceptable salt thereof or composition, is administered in an amount sufficient to reduce the level of androstenedione in the subject.

Some embodiments provide a compound of the disclosure, or a pharmaceutically acceptable salt thereof, or composition of the disclosure, for use in reducing the level of one or more biomarkers in a subject having congenital adrenal hyperplasia.

Some embodiments provide a compound of the disclosure, or a pharmaceutically acceptable salt thereof, or composition of the disclosure, for use in reducing the dosage of corticosteroid administered to a subject having congenital adrenal hyperplasia.

Some embodiments provide a compound of the disclosure, or a pharmaceutically acceptable salt thereof, or composition of the disclosure, for use in reducing the severity of one or more side effects of glucocorticoid treatment in a subject having congenital adrenal hyperplasia, wherein the side effect is selected from osteoporosis, avascular necrosis of bone, myopathy, hyperglycemia, diabetes mellitus, dyslipidemia, weight gain, Cushing syndrome, Cushingoid features, growth suppression, adrenal suppression, gastritis, peptic ulcer, gastrointestinal bleeding, visceral perforation, hepatic steatosis, pancreatitis, hypertension, coronary heart disease, ischemic heart disease, heart failure, dermatoprosis, skin atrophy, ecchymosis, purpura, erosions, striae, delayed wound healing, easy bruising, acne, hirsutism, hair loss, mood changes, depression, euphoria, mood lability, irritability, akathisia, anxiety, cognitive impairment, psychosis, dementia, delirium, cataract, glaucoma, ptosis, mydriasis, opportunistic ocular infections, central serous chorioretinopathy, suppression of cell-mediated immunity, predisposition to infections, reactivation of latent infections.

Some embodiments provide a compound of the disclosure, or a pharmaceutically acceptable salt thereof, or composition of the disclosure for use in treating congenital adrenal hyperplasia in a subject comprising (i) measuring the level of one or more biomarkers selected from (a) 17-hydroxyprogesterone (17-OHP); (b) testosterone; and (c) androstenedione in a biological sample obtained from the subject; (ii) analyzing the level of the one or more biomarkers to determine if the level of the one or more biomarkers is elevated compared to a healthy subject not having congenital adrenal hyperplasia; and (iii) administering to the subject the compound or a pharmaceutically acceptable salt thereof, or composition, if the subject is determined to have elevated levels of the one or more biomarkers.

Some embodiments provide a pharmaceutical composition comprising a compound of the disclosure, or a pharmaceutically acceptable salt thereof, and at least one pharmaceutical acceptable excipient.

Some embodiments provide a pharmaceutical composition comprising a compound of the disclosure, or a pharmaceutically acceptable salt thereof.

Some embodiments provide a method of treating a subject suffering from or diagnosed with a disorder mediated by $CRF_1$ activity, comprising administering to a subject in need thereof a compound of the disclosure, or a pharmaceutically acceptable salt thereof, or composition of the disclosure.

Some embodiments provide a method of modulating $CRF_1$ activity, comprising exposing $CRF_1$ to an effective amount of a compound of the disclosure.

Some embodiments provide a method of treating congenital adrenal hyperplasia in a subject in need thereof comprising administering a compound of the disclosure, or a pharmaceutically acceptable salt thereof, or composition of the disclosure, in an amount sufficient to reduce the level of one or more biomarkers selected from (a) 17-hydroxyprogesterone (17-OHP); (b) testosterone; and (c) androstenedione in the subject.

Some embodiments provide a method for reducing the severity of one or more symptoms selected from hirsutism, precocious puberty, fertility problems, acne, and growth impairment in a subject having classic congenital adrenal hyperplasia, comprising administering a compound of the disclosure, or a pharmaceutically acceptable salt thereof, or composition of the disclosure in an amount sufficient to reduce the level of androstenedione in the subject.

Some embodiments provide a method of reducing the level of one or more biomarkers in a subject having congenital adrenal hyperplasia comprising administering to the subject a compound of the disclosure, or a pharmaceutically acceptable salt thereof, or composition of the disclosure.

Some embodiments provide a method of reducing the dosage of corticosteroid administered to a subject having congenital adrenal hyperplasia for controlling congenital adrenal hyperplasia comprising administering to the subject a compound of the disclosure, or a pharmaceutically acceptable salt thereof, or composition of the disclosure.

Some embodiments provide a method of reducing the severity of one or more side effects of glucocorticoid treatment in a subject having congenital adrenal hyperplasia comprising administering to the subject a compound of the disclosure, or a pharmaceutically acceptable salt thereof, or composition of the disclosure, wherein the side effect is selected from osteoporosis, avascular necrosis of bone, myopathy, hyperglycemia, diabetes mellitus, dyslipidemia, weight gain, Cushing syndrome, Cushingoid features, growth suppression, adrenal suppression, gastritis, peptic ulcer, gastrointestinal bleeding, visceral perforation, hepatic steatosis, pancreatitis, hypertension, coronary heart disease, ischemic heart disease, heart failure, dermatoprosis, skin atrophy, ecchymosis, purpura, erosions, striae, delayed wound healing, easy bruising, acne, hirsutism, hair loss, mood changes, depression, euphoria, mood lability, irritability, akathisia, anxiety, cognitive impairment, psychosis, dementia, delirium, cataract, glaucoma, ptosis, mydriasis, opportunistic ocular infections, central serous chorioretinopathy, suppression of cell-mediated immunity, predisposition to infections, reactivation of latent infections.

Some embodiments provide a method of treating congenital adrenal hyperplasia in a subject comprising (i) measuring the level of one or more biomarkers selected from (a) 17-hydroxyprogesterone (17-OHP); (b) testosterone; and (c) androstenedione in a biological sample obtained from the subject; (ii) analyzing the level of the one or more biomarkers to determine if the level of the one or more biomarkers is elevated compared to a healthy subject not having congenital adrenal hyperplasia; and (iii) administering to the subject a compound of the disclosure, or a pharmaceutically acceptable salt thereof, or composition of the disclosure, if the subject is determined to have elevated levels of the one or more biomarkers.

Also provided herein are solid forms of Compound 1 and pharmaceutically acceptable salts thereof. In some embodiments, the solid forms are crystalline.

Some embodiments provide a process of preparing Compound 1:

Compound 1

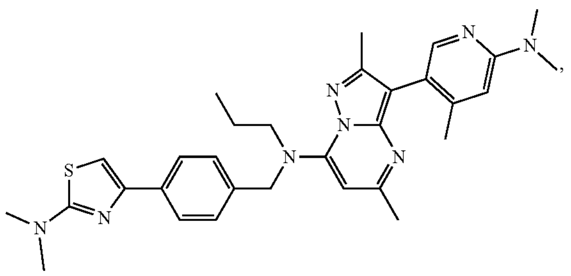

comprising reacting Compound 8-D:

8-D

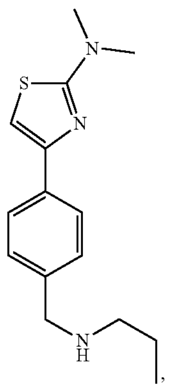

or a salt thereof, with Compound 3-D:

3-D

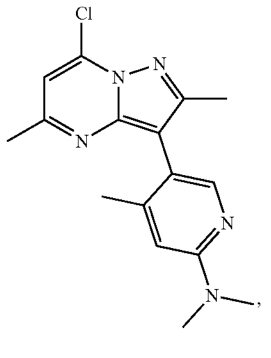

or a salt thereof, optionally in the presence of B1, wherein B1 is a base, to afford Compound 1.

Some embodiments provide a process for preparing a pharmaceutical composition comprising: preparing Compound 1 as described herein, and combining Compound 1 with a pharmaceutically acceptable carrier and/or diluent.

DETAILED DESCRIPTION

Compounds

Figure 1:
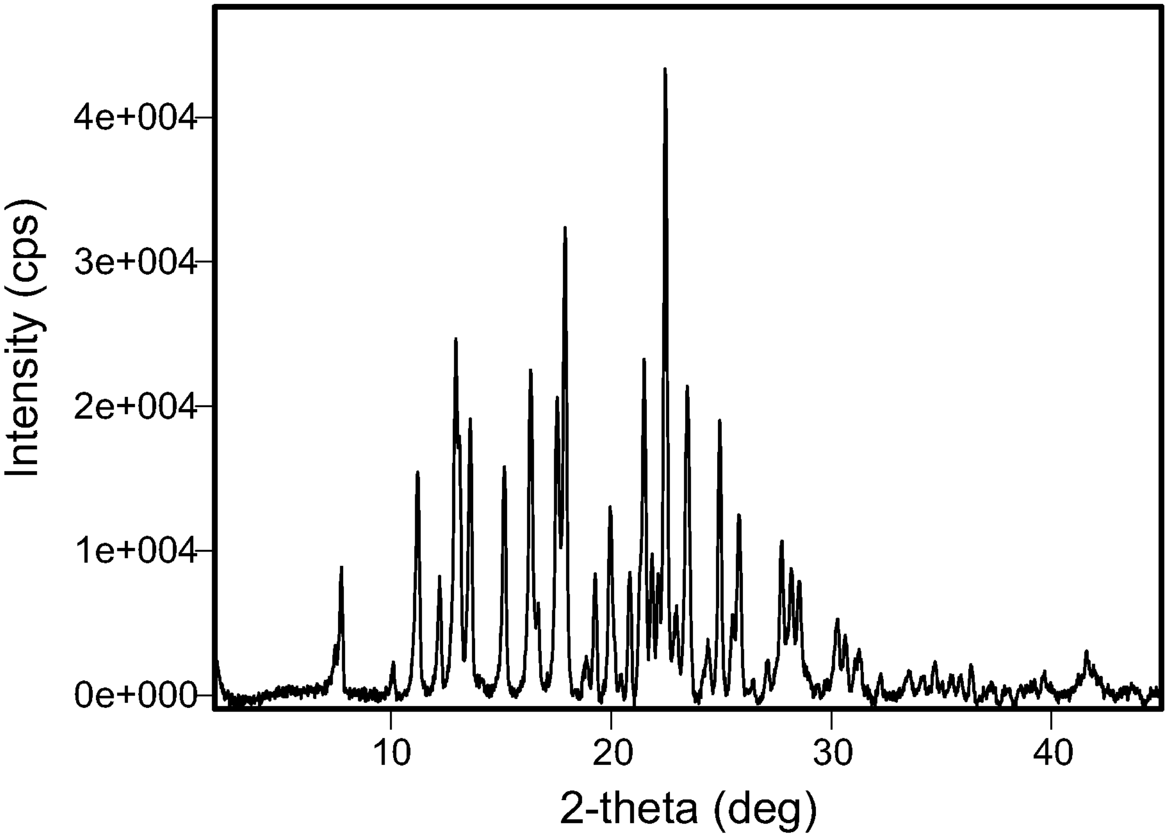
FIG. 1 depicts an exemplary X-ray powder diffraction pattern (XRPD) of a sample of 5-{7-[({4-[2-(dimethylamino)-1,3-thiazol-4-yl]phenyl}methyl)(propyl)amino]-2,5-dimethylpyrazolo[1,5-a]pyrimidin-3-yl}-N,N,4-trimethylpyridin-2-amine (Compound 1) in crystalline Form I.

Provided herein are compounds useful for treating diseases and/or disorders treatable by modulating $CRF_1$.

In some embodiments, provided herein is a compound of Formula (I):

(I)

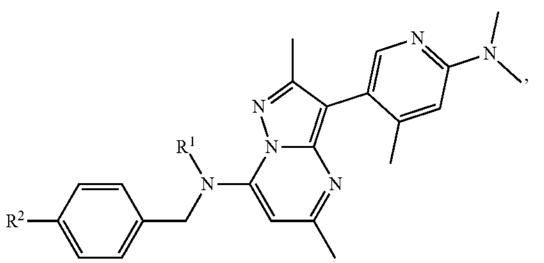

or a pharmaceutically acceptable salt thereof, wherein:

$R^1$ is H or $C_{1-6}$ alkyl;

$R^2$ is $C_{6-10}$ aryl, 5-10 membered heteroaryl, $C_{3-10}$ cycloalkyl, or 4-14 membered heterocycloalkyl, each optionally substituted by 1, 2, 3, 4, or 5 substituents independently selected from Cy, Cy-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$, wherein said $C_{1-6}$ alkyl, $C_{2-6}$ alkenyl, and $C_{2-6}$ alkynyl are each optionally substituted by 1, 2, or 3 substitutents independently selected from halo, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

each Cy is independently selected from $C_{6-10}$ aryl, $C_{3-7}$ cycloalkyl, 5-10 membered heteroaryl, and 4-10 membered heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

each $R^a$, $R^b$, $R^c$, $R^d$, $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R^a$, $R^b$, $R^c$, $R^d$, $R^{a1}$, $R^{b1}$, $R^{c1}$, and $R^{d1}$ is optionally substituted with 1, 2, 3, 4, or 5 substituents independently selected from halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{c2})NR^{c2}R^{d2}$, $NR^{c2}C(=NR^{c2})NR^{c2}R^{d2}$ $S(O)R^{b2}$ $S(O)NR^{c2}R^{d2}$, $S(O)_2R^{b2}$, $NR^{c2}S(O)_2R^{b2}$, $NR^{c2}S(O)_2NR^{c2}R^{d2}$ and $S(O)_2NR^{c2}R^{d2}$; and or $R^c$ and $R^d$ together with the N atom to which they are attached form a 4-7 membered heterocycloalkyl group optionally substituted with 1, 2, or 3 substituents independently selected from halo, $C_{1-4}$ alkyl, $C_{1-4}$ haloalkyl, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{c2})NR^{c2}R^{d2}$, $NR^{c2}C(=NR^{c2})NR^{c2}R^{d2}$ $S(O)R^{b2}$, $S(O)NR^{c2}R^{d2}$, $S(O)_2R^{b2}$, $NR^{c2}S(O)_2R^{b2}$, $NR^{c2}S(O)_2NR^{c2}R^{d2}$ and $S(O)_2NR^{c2}R^{d2}$.

or $R^{c1}$ and $R^{d1}$ together with the N atom to which they are attached form a 4-7 membered heterocycloalkyl group optionally substituted with 1, 2, or 3 substituents independently selected from halo, $C_{1-4}$ alkyl, $C_{1-4}$ haloalkyl, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{c2})NR^{c2}R^{d2}$, $NR^{c2}C(=NR^{c2})NR^{c2}R^{d2}$ $S(O)R^{b2}$, $S(O)NR^{c2}R^{d2}$, $S(O)_2R^{b2}$, $NR^{c2}S(O)_2R^{b2}$, $NR^{c2}S(O)_2NR^{c2}R^{d2}$ and $S(O)_2NR^{c2}R^{d2}$;

each $R^{a2}$, $R^{b2}$, $R^{e2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl are each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy; and each $R^e$, $R^{e1}$, and $R^{e2}$ is independently selected from H, $C_{1-4}$ alkyl, and CN;

wherein one or more ring-forming C or N atoms of any aforementioned heterocycloalkyl group is optionally substituted by an oxo (=O) group; and wherein one or more ring-forming S atoms of any aforementioned heterocycloalkyl group is optionally substituted by one or two oxo (=O) groups.

In some embodiments, $R^1$ is $C_{1-6}$ alkyl.

In some embodiments, $R^1$ is n-propyl.

In some embodiments, $R^2$ is $C_{6-10}$ aryl or 5-10 membered heteroaryl, each optionally substituted by 1, 2, 3, 4, or 5 substituents independently selected from Cy, Cy-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$, wherein said $C_{1-6}$ alkyl, $C_{2-6}$ alkenyl, and $C_{2-6}$ alkynyl are each optionally substituted by 1, 2, or 3 substituents independently selected from halo, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments, $R^2$ is phenyl or 5-6 membered heteroaryl, each optionally substituted by 1, 2, 3, 4, or 5 substituents independently selected from Cy, Cy-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$, wherein said $C_{1-6}$ alkyl, $C_{2-6}$ alkenyl, and $C_{2-6}$ alkynyl are each optionally substituted by 1, 2, or 3 substituents independently selected from halo, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments, $R^2$ is 5-6 membered heteroaryl optionally substituted by 1, 2, 3, 4, or 5 substituents independently selected from Cy, Cy-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$, wherein said $C_{1-6}$ alkyl, $C_{2-6}$ alkenyl, and $C_{2-6}$ alkynyl are each optionally substituted by 1, 2, or 3 substituents independently selected from halo, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments, $R^2$ is $C_{1-4}$ 5 membered heteroaryl optionally substituted by 1, 2, 3, 4, or 5 substituents independently selected from Cy, Cy-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^aOC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$, wherein said $C_{1-6}$ alkyl, $C_{2-6}$ alkenyl, and $C_{2-6}$ alkynyl are each optionally substituted by 1, 2, or 3 substituents independently selected from halo, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$. In some embodiments, $R^2$ is $C_{24}$ 5 membered heteroaryl optionally substituted by 1, or 2 substituents independently selected from phenyl, halo, $C_{1-6}$ alkyl, $C_{2-6}$ alkenyl, $C_{2-6}$ alkynyl, $C_{1-6}$ haloalkyl, CN, $NO_2$, $OR^a$, and $SR^a$, wherein said $C_{1-6}$ alkyl, $C_{2-6}$ alkenyl, and $C_{2-6}$ alkynyl are each optionally substituted by 1, 2, or 3 substituents independently selected from halo, $C_{1-6}$ haloalkyl, CN, $NO_2$, $OR^a$, and $SR^a$; and each $R^a$ is independently selected from H, $C_{1-6}$ alkyl, $C_{1-6}$ haloalkyl, phenyl, and $C_{3-7}$ cycloalkyl. In some embodiments, $R^2$ is $C_{2-5}$ 6 membered heteroaryl optionally substituted by 1, 2, 3, 4, or 5 substituents independently selected from Cy, Cy-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$ $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$, wherein said $C_{1-6}$ alkyl, $C_{2-6}$ alkenyl, and $C_{2-6}$ alkynyl are each optionally substituted by 1, 2, or 3 substituents independently selected from halo, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$. In some embodiments, $R^2$ is $C_{3-5}$ 6 membered heteroaryl optionally substituted by 1, 2, or 3 substituents independently selected from phenyl, halo, $C_{1-6}$ alkyl, $C_{2-6}$ alkenyl, $C_{2-6}$ alkynyl, $C_{1-6}$ haloalkyl, CN, $NO_2$, $OR^a$, and $SR^a$, wherein said $C_{1-6}$ alkyl, $C_{2-6}$ alkenyl, and $C_{2-6}$ alkynyl are each optionally substituted by 1, 2, or 3 substituents independently selected from halo, $C_{1-6}$ haloalkyl, CN, $NO_2$, $OR^a$, and $SR^a$; and each $R^a$ is independently selected from H, $C_{1-6}$ alkyl, $C_{1-6}$ haloalkyl, phenyl, and $C_{3-7}$ cycloalkyl.

In some embodiments, $R^2$ is phenyl, pyridyl, pyrimidinyl, pyrazolyl, triazolyl, thiazolyl, thiadiazolyl, or isoxazolyl, each optionally substituted by 1, 2, 3, 4, or 5 substituents independently selected from Cy, Cy-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$, wherein said $C_{1-6}$ alkyl, $C_{2-6}$ alkenyl, and $C_{2-6}$ alkynyl are each optionally substituted by 1, 2, or 3 substituents independently selected from halo, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments, $R^2$ is phenyl, pyridyl, pyrimidinyl, or pyrazolyl, each optionally substituted by 1, 2, or 3 substituents independently selected from phenyl, $C_{3-7}$ cycloalkyl, halo, $C_{1-6}$ alkyl, $C_{2-6}$ alkenyl, $C_{2-6}$ alkynyl, $C_{1-6}$ haloalkyl, CN, $NO_2$, $OR^a$, and $SR^a$, wherein said $C_{1-6}$ alkyl, $C_{2-6}$ alkenyl, and $C_{2-6}$ alkynyl are each optionally substituted by 1, 2, or 3 substituents independently selected from halo, $C_{1-6}$ haloalkyl, CN, $NO_2$, $OR^a$, and $SR^a$; and each $R^a$ is independently selected from H, $C_{1-6}$ alkyl, $C_{1-6}$ haloalkyl, phenyl, and $C_{3-7}$ cycloalkyl. In some embodiments, $R^2$ is thiazolyl, thiadiazolyl, or isoxazolyl, each optionally substituted by 1, or 2 substituents independently selected from phenyl, $C_{3-7}$ cycloalkyl, halo, $C_{1-6}$ alkyl, $C_{2-6}$ alkenyl, $C_{2-6}$ alkynyl, $C_{1-6}$ haloalkyl, CN, $NO_2$, $OR^a$, and $SR^a$, wherein said $C_{1-6}$ alkyl, $C_{2-6}$ alkenyl, and $C_{2-6}$ alkynyl are each optionally substituted by 1, 2, or 3 substituents independently selected from halo, $C_{1-6}$ haloalkyl, CN, $NO_2$, $OR^a$, and $SR^a$; and each $R^a$ is independently selected from H, $C_{1-6}$ alkyl, $C_{1-6}$ haloalkyl, phenyl, and $C_{3-7}$ cycloalkyl.

In some embodiments, $R^2$ is selected from:

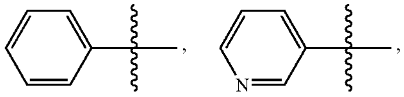

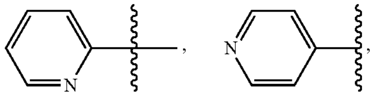

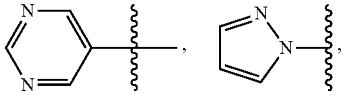

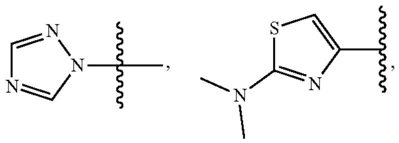

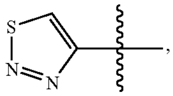, and 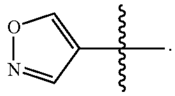.

In some embodiments, $R^2$ is selected from:

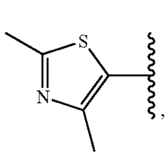, 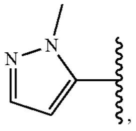, 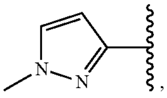,

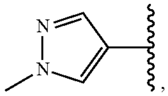, 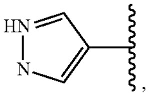, 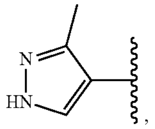,

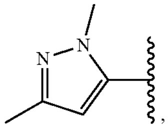, 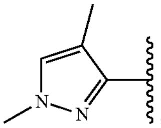, 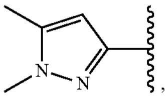,

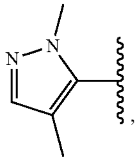, 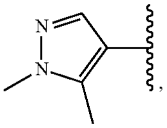, 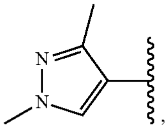,

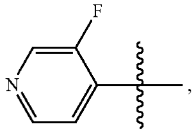, 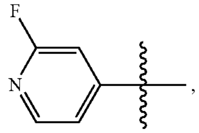,

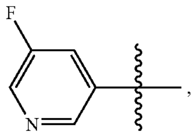, 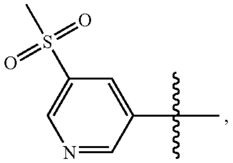,

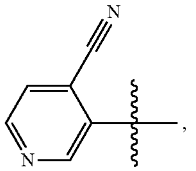, 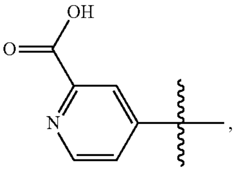,

-continued

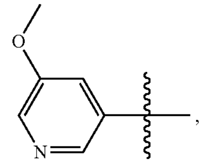, 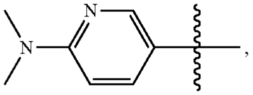,

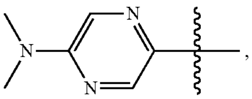, 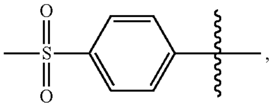,

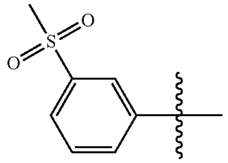, 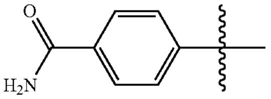,

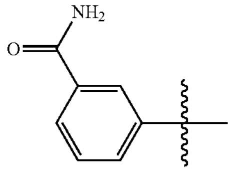, 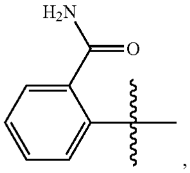,

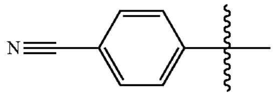,

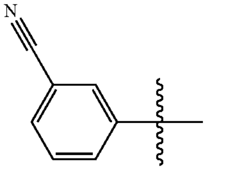 and 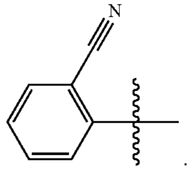.

In some embodiments, $R^2$ is

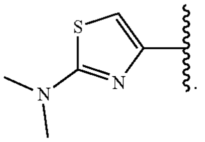 [SMILES: *c1csc(N(C)C)n1].

Also provided herein is a compound of Formula (I), or a pharmaceutically acceptable salt thereof, wherein:

$R^1$ is $C_{1-6}$ alkyl;

$R^2$ is $C_{6-10}$ aryl or 5-10 membered heteroaryl, each optionally substituted by 1 or 2 substituents independently selected from halo, $C_{1-6}$ alkyl, $C_{1-6}$ haloalkyl, CN, $NO_2$, $OR^a$, $C(O)R^b$, $C(O)NR^cR^d$, $C(O)OR^a$, $OC(O)R^b$, $NR^cR^d$, $NR^cC(O)R^b$, $NR^cC(O)OR^a$, $NR^cC(O)NR^cR^d$, $NR^cS(O)_2R^b$, $NR^cS(O)_2NR^cR^d$, $S(O)_2R^b$, and $S(O)_2NR^cR^d$;

each $R^a$, $R^b$, $R^c$, and $R^d$ is independently selected from H, $C_{1-6}$ alkyl, $C_{1-6}$ haloalkyl, wherein said $C_{1-6}$ alkyl of $R^a$, $R^b$, $R^C$, and $R^d$ is optionally substituted with 1 or 2 substituents independently selected from halo, $C_{1-4}$ alkyl, CN, $OR^{a2}$, $SR^{a2}$, $C(O)R^{b2}$, $C(O)NR^{c2}R^{d2}$, $C(O)OR^{a2}$, $OC(O)R^{b2}$, $NR^{c2}R^{d2}$, $NR^{c2}C(O)R^{b2}$, $NR^{c2}C(O)NR^{c2}R^{d2}$, $NR^{c2}C(O)OR^{a2}$ $S(O)_2R^{b2}$, $NR^{c2}S(O)_2R^{b2}$, $NR^{c2}S(O)_2NR^{c2}R^{d2}$ and $S(O)_2NR^{c2}R^{d2}$;

or $R^c$ and $R^d$ together with the N atom to which they are attached form a 4-7 membered heterocycloalkyl group optionally substituted with 1, 2, or 3 substituents independently selected from halo, $C_{1-4}$ alkyl, CN, $OR^{a2}$, $SR^{a2}$, $C(O)R^{b2}$, $C(O)NR^{c2}R^{d2}$, $C(O)OR^{a2}$, $OC(O)R^{b2}$, $NR^{c2}R^{d2}$, $NR^{c2}C(O)R^{b2}$, $NR^{c2}C(O)NR^{c2}R^{d2}$, $NR^{c2}C(O)OR^{a2}$, $S(O)_2R^{b2}$, $NR^{c2}S(O)_2R^{b2}$, $NR^{c2}S(O)_2NR^{c2}R^{d2}$ and $S(O)_2NR^{c2}R^{d2}$;

each $R^{a2}$, $R^{b2}$, $R^{e2}$, and $R^{d2}$ is independently selected from H, $C_{1-6}$ alkyl, and $C_{1-6}$ haloalkyl, wherein the $C_{1-6}$ alkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy; and wherein one or more ring-forming C or N atoms of any aforementioned heterocycloalkyl group is optionally substituted by an oxo (=O) group; and wherein one or more ring-forming S atoms of any aforementioned heterocycloalkyl group is optionally substituted by one or two oxo (=O) groups.

Also provided herein is a compound of Formula (II):

(II)

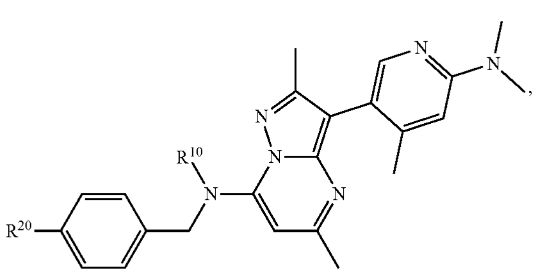

or a pharmaceutically acceptable salt thereof, wherein:

$R^{10}$ is $C_{1-6}$ alkyl optionally substituted by 1, 2, or 3 substitutents independently selected from halo, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

$R^{20}$ is $C_{6-10}$ aryl, 5-10 membered heteroaryl, $C_{3-10}$ cycloalkyl, or 4-14 membered heterocycloalkyl, each optionally substituted by 1, 2, 3, 4, or 5 substituents independently selected from Cy, Cy-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$, wherein said $C_{1-6}$ alkyl, $C_{2-6}$ alkenyl, and $C_{2-6}$ alkynyl are each optionally substituted by 1, 2, or 3 substitutents independently selected from halo, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

each Cy is independently selected from $C_{6-10}$ aryl, $C_{3-7}$ cycloalkyl, 5-10 membered heteroaryl, and 4-10 membered heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d}$, $NR^{c1}S(O)R^{b1}$, $NR^{c1}S(O)_2R^b$, $NR^{c1}S(O)_2NR^{c1}R^{d1}$, $S(O)R^{b1}$, $S(O)NR^{c1}R^{d1}$, $S(O)_2R^b$, and $S(O)_2NR^{c1}R^{d1}$;

each $R^a$, $R^b$, $R^c$, $R^d$, $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R^a$, $R^b$, $R^c$, $R^d$, $R^{a1}$, $R^{b1}$, $R^{c1}$, and $R^{d1}$ is optionally substituted with 1, 2, 3, 4, or 5 substituents independently selected from halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$ $NR^{c2}C(O)NR^{c2}R^{d2}$, $NR^{c2}C(O)OR^{a2}$, $C(=NR^{c2})NR^{c2}R^{d2}$, $NR^{c2}C(=NR^{c2})NR^{c2}R^{d2}$ $S(O)R^{b2}$ $S(O)NR^{c2}R^{d2}$, $S(O)_2R^{b2}$, $NR^{c2}S(O)_2R^{b2}$, $NR^{c2}S(O)_2NR^{c2}R^{d2}$ and $S(O)_2NR^{c2}R^{d2}$; and or $R^c$ and $R^d$ together with the N atom to which they are attached form a 4-7 membered heterocycloalkyl group optionally substituted with 1, 2, or 3 substituents independently selected from halo, $C_{1-4}$ alkyl, $C_{1-4}$ haloalkyl, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{c2})NR^{c2}R^{d2}$, $NR^{c2}C(=NR^{c2})NR^{c2}R^{d2}$, $S(O)R^{b2}$, $S(O)NR^{c2}R^{d2}$, $S(O)_2R^{b2}$, $NR^{c2}S(O)_2R^{b2}$, $NR^{c2}S(O)_2NR^{c2}R^{d2}$ and $S(O)_2NR^{c2}R^{d2}$;

or $R^{c1}$ and $R^{d1}$ together with the N atom to which they are attached form a 4-7 membered heterocycloalkyl group optionally substituted with 1, 2, or 3 substituents independently selected from halo, $C_{1-4}$ alkyl, $C_{1-4}$ haloalkyl, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{c2})NR^{c2}R^{d2}$, $NR^{c2}C(=NR^{c2})NR^{c2}R^{d2}$, $S(O)R^{b2}$, $S(O)NR^{c2}R^{d2}$, $S(O)_2R^{b2}$, $NR^{c2}S(O)_2R^{b2}$, $NR^{c2}S(O)_2NR^{c2}R^{d2}$ and $S(O)_2NR^{c2}R^{d2}$;

each $R^{a2}$, $R^{b2}$, $R^{e2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl are each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy; and each $R^e$, $R^{e1}$, and $R^{e2}$ is independently selected from H, $C_{1-4}$ alkyl, and CN;

wherein one or more ring-forming C or N atoms of any aforementioned heterocycloalkyl group is optionally substituted by an oxo (=O) group; and wherein one or more ring-forming S atoms of any aforementioned heterocycloalkyl group is optionally substituted by one or two oxo (=O) groups.

In some embodiments, $R^{10}$ is $C_{1-6}$ alkyl optionally substituted by 1, 2, or 3 substitutents independently selected from halo, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$. In some embodiments, $R^{10}$ is $C_{1-6}$ alkyl optionally substituted by 1, 2, or 3 substituents independently selected from halo, $C_{1-6}$ haloalkyl, CN, $NO_2$, $OR^a$, and $SR^a$ where each $R^a$ is independently selected from H, $C_{1-6}$ alkyl, and $C_{1-6}$ haloalkyl. In some embodiments, $R^{10}$ is $C_{1-6}$ alkyl optionally substituted by 1, 2, or 3 substitutents independently selected from halo, CN, and $OR^a$ where each $R^a$ is independently selected from H, $C_{1-6}$ alkyl, and $C_{1-6}$ haloalkyl. In some embodiments, $R^{10}$ is $C_{1-6}$ alkyl substituted by 1, 2, or 3 substitutents independently selected from halo, CN, and $OR^a$ where each $R^a$ is independently selected from H, $C_{1-6}$ alkyl, and $C_{1-6}$ haloalkyl. In some embodiments, $R^{10}$ is $C_{1-6}$ alkyl substituted by $OR^a$ where $R^a$ is $C_{1-6}$ alkyl. In some embodiments, $R^{10}$ is $CH_2CH_2OCH_3$.

In some embodiments, $R^{20}$ is $C_{6-10}$ aryl or 5-10 membered heteroaryl, each optionally substituted by 1, 2, 3, 4, or 5 substituents independently selected from Cy, Cy-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$, wherein said $C_{1-6}$ alkyl, $C_{2-6}$ alkenyl, and $C_{2-6}$ alkynyl are each optionally substituted by 1, 2, or 3 substituents independently selected from halo, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments, $R^{20}$ is phenyl or 5-6 membered heteroaryl, each optionally substituted by 1, 2, 3, 4, or 5 substituents independently selected from Cy, Cy-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$, wherein said $C_{1-6}$ alkyl, $C_{2-6}$ alkenyl, and $C_{2-6}$ alkynyl are each optionally substituted by 1, 2, or 3 substitutents independently selected from halo, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments, $R^{20}$ is phenyl, pyridyl, pyrimidinyl, pyrazinyl, pyrazolyl, triazolyl, thiazolyl, thiadiazolyl, or isoxazolyl, each optionally substituted by 1, 2, 3, 4, or 5 substituents independently selected from Cy, Cy-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$, wherein said $C_{1-6}$ alkyl, $C_{2-6}$ alkenyl, and $C_{2-6}$ alkynyl are each optionally substituted by 1, 2, or 3 substituents independently selected from halo, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, NWRS$(O)_2NR^cR^d$, $S(O)R^b$, $S(O)NR^cR^d$, $S(O)_2R^b$, and $S(O)_2NR^cR^d$.

In some embodiments, $R^{20}$ is selected from:

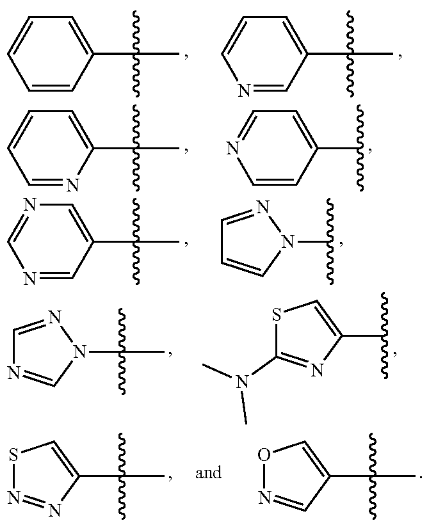

In some embodiments, $R^{20}$ is selected from:

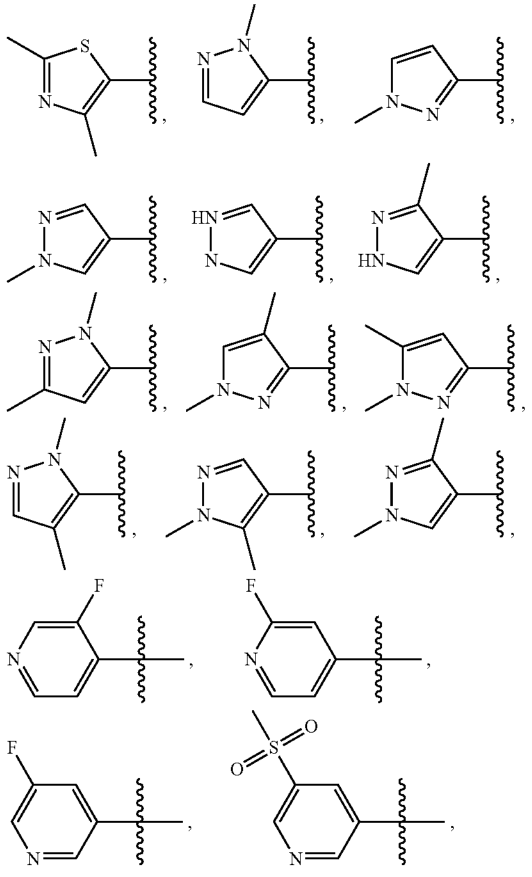

-continued

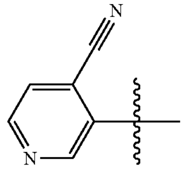, 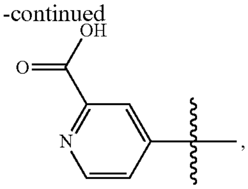, 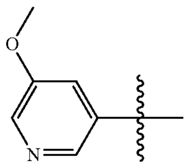, 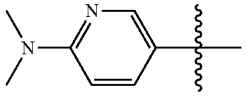, 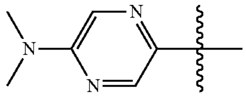, 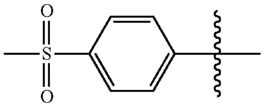, 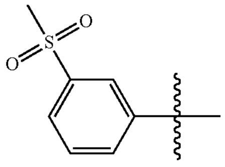, 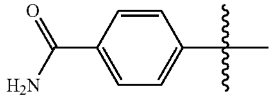, 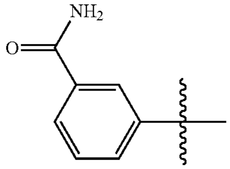, 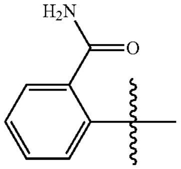, 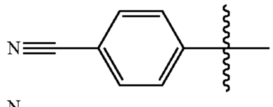, 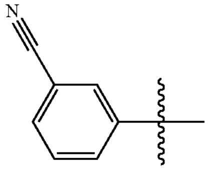 and 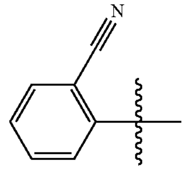.

Also provided herein is a compound selected from:

5-{7-[({4-[2-(dimethylamino)-1,3-thiazol-4-yl]phenyl}methyl)(propyl)amino]-2,5-dimethylpyrazolo[1,5-a]pyrimidin-3-yl}-N,N,4-trimethylpyridin-2-amine (1);

5-{2,5-dimethyl-7-[propyl({[4-(pyridin-3-yl)phenyl]methyl})amino]pyrazolo[1,5-a]pyrimidin-3-yl}-N,N,4-trimethylpyridin-2-amine (2);

5-{2,5-dimethyl-7-[propyl({[4-(pyridin-2-yl)phenyl]methyl})amino]pyrazolo[1,5-a]pyrimidin-3-yl}-N,N,4-trimethylpyridin-2-amine (3);

5-{2,5-dimethyl-7-[propyl({[4-(pyrimidin-5-yl)phenyl]methyl})amino]pyrazolo[1,5-a]pyrimidin-3-yl}-N,N,4-trimethylpyridin-2-amine (4);

5-{2,5-dimethyl-7-[propyl({[4-(1,2,3-thiadiazol-4-yl)phenyl]methyl})amino]pyrazolo[1,5-a]pyrimidin-3-yl}-N,N,4-trimethylpyridin-2-amine (5);

5-{2,5-dimethyl-7-[propyl({[4-(pyridin-4-yl)phenyl]methyl})amino]pyrazolo[1,5-a]pyrimidin-3-yl}-N,N,4-trimethylpyridin-2-amine (6);

5-[2,5-dimethyl-7-({[4-(1,2-oxazol-4-yl)phenyl]methyl}(propyl)amino)pyrazolo[1,5-a]pyrimidin-3-yl]-N,N,4-trimethylpyridin-2-amine (7);

5-(2,5-dimethyl-7-{[(4-phenylphenyl)methyl](propyl)amino}pyrazolo[1,5-a]pyrimidin-3-yl)-N,N,4-trimethylpyridin-2-amine (8);

5-{2,5-dimethyl-7-[propyl({[4-(1H-pyrazol-1-yl)phenyl]methyl})amino]pyrazolo[1,5-a]pyrimidin-3-yl}-N,N,4-trimethylpyridin-2-amine (9); and 5-{2,5-dimethyl-7-[propyl({[4-(1H-1,2,4-triazol-1-yl)phenyl]methyl})amino]pyrazolo[1,5-a]pyrimidin-3-yl}-N,N,4-trimethylpyridin-2-amine (10), or a pharmaceutically acceptable salt thereof.

In other embodiments, the present invention provides a pharmaceutical composition comprising a compound of Formula (I), including one or more of the specific compounds described herein (see, e.g., Table 1), and at least one pharmaceutically acceptable excipient.

Some embodiments provide a compound of the disclosure, or a pharmaceutically acceptable salt thereof, or composition of the disclosure, for use in treating congenital adrenal hyperplasia in a subject, wherein the compound or composition is administered in an amount sufficient to reduce the level of one or more biomarkers selected from (a) 17-hydroxyprogesterone (17-OHP); (b) testosterone; and (c) androstenedione in the subject. In some embodiments, the compound, or a pharmaceutically acceptable salt thereof, is administered in an amount sufficient to reduce the level of two or more biomarkers selected from (a) 17-hydroxyprogesterone (17-OHP); (b) adrenocorticotropic hormone (ACTH); and (c) androstenedione in the subject. In some embodiments, the compound, or a pharmaceutically acceptable salt thereof, is administered in an amount sufficient to reduce the level of (a) 17-hydroxyprogesterone (17-OHP); (b) adrenocorticotropic hormone (ACTH); and (c) androstenedione in the subject. In some embodiments, the level of 17-OHP is reduced by at least 10%, at least 15%, at least 20%, at least 25%, at least 30%, at least 35%, at least 40%, at least 50%, at least 55% or at least 60% from pre-administration levels. In some embodiments, the level of 17-OHP is reduced by at least 25%. In some embodiments, the level of 17-OHP is reduced by at least 50%. In some embodiments, the level of 17-OHP is reduced by an amount of from about 10% to about 90%, about 15% to about 90%, about 20% to about 90%, about 25% to about 90%, about 30% to about 90%, about 35% to about 90%, about 40% to about 90%, about 50% to about 90%, about 55% to about 90%, or about 60% to about 90% from pre-administration levels. In some embodiments, the level of 17-OHP is reduced to a level within the range of 17-hydroxyprogesterone expected for a subject without CAH, i.e., less than 1,000 ng/dL or less than 200 ng/dL. In some embodiments, the level of adrenocorticotropic hormone is reduced by at least 10%, at least 15%, at least 20%, at least 25%, at least 30%, at least 35%, at least 40%, at least 50%, at least 55% or at least 60% from pre-administration levels. In some embodiments, the level of adrenocorticotropic hormone is reduced by at least 25%. In some embodiments, the level of adrenocorticotropic hormone is reduced by at least 40%. In some embodiments, the level of adrenocorticotropic hormone is reduced by at least 50%. In some embodiments, the level of adrenocorticotropic hormone is reduced by an amount of from about 10% to about 90%, about 15% to about 90%, about 20% to about 90%, about 25% to about 90%, about 30% to about 90%, about 35% to about 90%, about 40% to about 90%, about 50% to about 90%, about 55% to about 90%, or about 60% to about 90% from pre-administration levels. In some embodiments, the level of adrenocorticotropic hormone is reduced to a level within the range of adrenocorticotropic hormone expected for a subject without CAH. In some embodiments, the level of androstenedione is reduced by at least 10%, at least 15%, at least 20%, at least 25%, at least 30%, at least 35%, at least 40%, at least 50%, at least 55% or at least 60% from pre-administration levels. In some embodiments, the level of androstenedione is reduced by at least 25%. In some embodiments, the level of androstenedione is reduced by at least 30%. In some embodiments, the level of androstenedione is reduced by at least 50%. In some embodiments, the level of androstenedione is reduced by an amount of from about 10% to about 90%, about 15% to about 90%, about 20% to about 90%, about 25% to about 90%, about 30% to about 90%, about 35% to about 90%, about 40% to about 90%, about 50% to about 90%, about 55% to about 90%, or about 60% to about 90% from pre-administration levels. In some embodiments, the level of androstenedione is reduced to a level within the range of androstenedione expected for a subject without CAH, i.e., less than 200 ng/dL.

Some embodiments provide a compound of the disclosure, or a pharmaceutically acceptable salt thereof, or composition of the disclosure, for use in reducing the severity of one or more symptoms selected from hirsutism, precocious puberty, fertility problems, acne, and growth impairment in a subject having classic congenital adrenal hyperplasia, wherein the compound or a pharmaceutically acceptable salt thereof or composition, is administered in an amount sufficient to reduce the level of androstenedione in the subject. In some embodiments, the level of androstenedione is reduced by at least 10%, at least 15%, at least 20%, at least 25%, at least 30%, at least 35%, at least 40%, at least 50%, at least 55% or at least 60% from pre-administration levels. In some embodiments, the level of androstenedione is reduced by at least 25%. In some embodiments, the level of androstenedione is reduced by at least 30%. In some embodiments, the level of androstenedione is reduced by at least 50%. In some embodiments, the level of androstenedione is reduced by an amount of from about 10% to about 90%, about 15% to about 90%, about 20% to about 90%, about 25% to about 90%, about 30% to about 90%, about 35% to about 90%, about 40% to about 90%, about 50% to about 90%, about 55% to about 90%, or about 60% to about 90% from pre-administration levels. In some embodiments, the level of androstenedione is reduced to a level within the range of androstenedione expected for a subject without CAH, i.e., less than 200 ng/dL. In some embodiments, the growth impairment is selected from one or more of accelerated height velocity, accelerated weight velocity, or accelerated bone age. In some embodiments, the congenital adrenal hyperplasia (CAH) is classic CAH. In some embodiments, the compound is suitable for administration in combination with glucocorticoid treatment. In some embodiments, the glucocorticoid is hydrocortisone, prednisone, prednisolone or dexamethasone. In some embodiments, the classic congenital adrenal hyperplasia is due to 21-hydroxylase deficiency. In some embodiments, the subject has a mutation in the CYP21A2 gene located on chromosome 6p21. In some embodiments, the subject does not have a mutation of the 11β-hydroxylase gene CYP11B1 (11β-OH CAH).

Some embodiments provide a compound of the disclosure, or a pharmaceutically acceptable salt thereof, or composition of the disclosure, for use in reducing the level of one or more biomarkers in a subject having congenital adrenal hyperplasia. In some embodiments, the one or more biomarkers is selected from (a) 17-hydroxyprogesterone (17-OHP); (b) testosterone; and (c) androstenedione. In some embodiments, the compound, or a pharmaceutically acceptable salt thereof, is administered in an amount sufficient to reduce the level of (a) 17-hydroxyprogesterone (17-OHP); (b) adrenocorticotropic hormone (ACTH); and (c) androstenedione in the subject. In some embodiments, the level of 17-OHP is reduced by at least 10%, at least 15%, at least 20%, at least 25%, at least 30%, at least 35%, at least 40%, at least 50%, at least 55% or at least 60% from pre-administration levels. In some embodiments, the level of 17-OHP is reduced by at least 25%. In some embodiments, the level of 17-OHP is reduced by at least 50%. In some embodiments, the level of 17-OHP is reduced by an amount of from about 10% to about 90%, about 15% to about 90%, about 20% to about 90%, about 25% to about 90%, about 30% to about 90%, about 35% to about 90%, about 40% to about 90%, about 50% to about 90%, about 55% to about 90%, or about 60% to about 90% from pre-administration levels. In some embodiments, the level of 17-OHP is reduced to a level within the range of 17-hydroxyprogesterone expected for a subject without CAH, i.e., less than 1,000 ng/dL or less than 200 ng/dL. In some embodiments, the level of adrenocorticotropic hormone is reduced by at least 10%, at least 15%, at least 20%, at least 25%, at least 30%, at least 35%, at least 40%, at least 50%, at least 55% or at least 60% from pre-administration levels. In some embodiments, the level of adrenocorticotropic hormone is reduced by at least 25%. In some embodiments, the level of adrenocorticotropic hormone is reduced by at least 40%. In some embodiments, the level of adrenocorticotropic hormone is reduced by at least 50%. In some embodiments, the level of adrenocorticotropic hormone is reduced by an amount of from about 10% to about 90%, about 15% to about 90%, about 20% to about 90%, about 25% to about 90%, about 30% to about 90%, about 35% to about 90%, about 40% to about 90%, about 50% to about 90%, about 55% to about 90%, or about 60% to about 90% from pre-administration levels. In some embodiments, the level of adrenocorticotropic hormone is reduced to a level within the range of adrenocorticotropic hormone expected for a subject without CAH. In some embodiments, the level of androstenedione is reduced by at least 10%, at least 15%, at least 20%, at least 25%, at least 30%, at least 35%, at least 40%, at least 50%, at least 55% or at least 60% from pre-administration levels. In some embodiments, the level of androstenedione is reduced by at least 25%. In some embodiments, the level of androstenedione is reduced by at least 30%. In some embodiments, the level of androstenedione is reduced by at least 50%. In some embodiments, the level of androstenedione is reduced by an amount of from about 10% to about 90%, about 15% to about 90%, about 20% to about 90%, about 25% to about 90%, about 30% to about 90%, about 35% to about 90%, about 40% to about 90%, about 50% to about 90%, about 55% to about 90%, or about 60% to about 90% from pre-administration levels. In some embodiments, the level of androstenedione is reduced to a level within the range of androstenedione expected for a subject without CAH, i.e., less than 200 ng/dL. In some embodiments, the congenital adrenal hyperplasia (CAH) is classic CAH. In some embodiments, the compound is suitable for administration in combination with glucocorticoid treatment. In some embodiments, the glucocorticoid is hydrocortisone, prednisone, prednisolone or dexamethasone. In some embodiments, the classic congenital adrenal hyperplasia is due to 21-hydroxylase deficiency. In some embodiments, the subject has a mutation in the CYP21A2 gene located on chromosome 6p21. In some embodiments, the subject does not have a mutation of the 11β-hydroxylase gene CYP11B1 (11β-OH CAH).

Some embodiments provide a compound of the disclosure, or a pharmaceutically acceptable salt thereof, or composition of the disclosure, for use in reducing the dosage of corticosteroid administered to a subject having congenital adrenal hyperplasia. In some embodiments, the congenital adrenal hyperplasia (CAH) is classic CAH. In some embodiments, the corticosteroid is a glucocorticoid. In some embodiments, the glucocorticoid is hydrocortisone, prednisone, prednisolone or dexamethasone. In some embodiments, the classic congenital adrenal hyperplasia is due to 21-hydroxylase deficiency. In some embodiments, the subject has a mutation in the CYP21A2 gene located on chromosome 6p21. In some embodiments, the subject does not have a mutation of the 11β-hydroxylase gene CYP11B1 (11β-OH CAH).

Some embodiments provide a compound of the disclosure, or a pharmaceutically acceptable salt thereof, or composition of the disclosure, for use in reducing the severity of one or more side effects of glucocorticoid treatment in a subject having congenital adrenal hyperplasia, wherein the side effect is selected from osteoporosis, avascular necrosis of bone, myopathy, hyperglycemia, diabetes mellitus, dyslipidemia, weight gain, Cushing syndrome, Cushingoid features, growth suppression, adrenal suppression, gastritis, peptic ulcer, gastrointestinal bleeding, visceral perforation, hepatic steatosis, pancreatitis, hypertension, coronary heart disease, ischemic heart disease, heart failure, dermatoprosis, skin atrophy, ecchymosis, purpura, erosions, striae, delayed wound healing, easy bruising, acne, hirsutism, hair loss, mood changes, depression, euphoria, mood lability, irritability, akathisia, anxiety, cognitive impairment, psychosis, dementia, delirium, cataract, glaucoma, ptosis, mydriasis, opportunistic ocular infections, central serous chorioretinopathy, suppression of cell-mediated immunity, predisposition to infections, reactivation of latent infections, wherein the compound, or a pharmaceutically acceptable salt thereof, is administered in an amount sufficient to reduce the severity of one or more side effects of the glucocorticoid treatment. In some embodiments, the congenital adrenal hyperplasia (CAH) is classic CAH. In some embodiments, the glucocorticoid is hydrocortisone, prednisone, prednisolone or dexamethasone. In some embodiments, the classic congenital adrenal hyperplasia is due to 21-hydroxylase deficiency. In some embodiments, the subject has a mutation in the CYP21A2 gene located on chromosome 6p21. In some embodiments, the subject does not have a mutation of the 11β-hydroxylase gene CYP11B1 (11β-OH CAH).

Some embodiments provide a compound of the disclosure, or a pharmaceutically acceptable salt thereof, or composition of the disclosure for use in treating congenital adrenal hyperplasia in a subject comprising (i) measuring the level of one or more biomarkers selected from (a) 17-hydroxyprogesterone (17-OHP); (b) testosterone; and (c) androstenedione in a biological sample obtained from the subject; (ii) analyzing the level of the one or more biomarkers to determine if the level of the one or more biomarkers is elevated compared to a healthy subject not having congenital adrenal hyperplasia; and (iii) administering to the subject the compound or a pharmaceutically acceptable salt thereof, or composition, if the subject is determined to have elevated levels of the one or more biomarkers. In some embodiments, the use further comprises (iv) measuring the level of the one or more biomarkers after administering a compound of Formula (I), or a pharmaceutically acceptable salt thereof, in a biological sample obtained from the subject to determine whether the subject has reduced levels of the one or more biomarkers as compared with the measurement of step (i). In some embodiments, the use further comprises (v) continuing the administration of the compound of Formula (I), or a pharmaceutically acceptable salt thereof if the subject has reduced levels of the one or more biomarkers. In some embodiments, steps (i) and (iv) are performed on biological samples taken from the subject in a similar manner and within a same time of day window. In some embodiments, steps (i) and (iv) are performed on biological samples taken from the subject within the time of day window from 2 a.m. to 10 a.m. In some embodiments, steps (i) and (iv) are performed on biological samples taken from the subject within the time of day window from 6 a.m. to 10 a.m. In some embodiments, steps (i) and (iv) comprise measuring the levels of at least two biomarkers selected from (a) 17-hydroxyprogesterone (17-OHP); (b) testosterone; and (c) androstenedione. In some embodiments, steps (i) and (iv) comprise measuring the levels of (a) 17-hydroxyprogesterone (17-OHP); (b) testosterone; and (c) androstenedione. In some embodiments, step (i) comprises measuring the level of 17-hydroxyprogesterone (17-OHP), wherein the level of 17-hydroxyprogesterone (17-OHP) is elevated when it is greater than or equal to 1,000 ng/dL. In some embodiments, step (i) comprises measuring the level of androstenedione, wherein the level of androstenedione is elevated when it is greater than 200 ng/dL. In some embodiments, the congenital adrenal hyperplasia is classic congenital adrenal hyperplasia (CAH). In some embodiments, the compound is suitable for administration in combination with glucocorticoid treatment. In some embodiments, the glucocorticoid is hydrocortisone, prednisone, prednisolone or dexamethasone. In some embodiments, the classic CAH is due to 21-hydroxylase deficiency. In some embodiments, the subject has a mutation in the CYP21A2 gene located on chromosome 6p21. In some embodiments, the subject does not have a mutation of the 11β-hydroxylase gene CYP11B1 (11β-OH CAH).

It is further appreciated that certain features, which are, for clarity, described in the context of separate embodiments, can also be provided in combination in a single embodiment. Conversely, various features which are, for brevity, described in the context of a single embodiment, can also be provided separately or in any suitable subcombination.

The compounds described herein can be asymmetric (e.g., having one or more stereocenters). All stereoisomers, such as enantiomers and diastereomers, are intended unless otherwise indicated. It is understood that, in any compound described herein having one or more chiral centers, if an absolute stereochemistry is not expressly indicated, then each center can independently be of R-configuration or S-configuration or a mixture thereof. Thus, the compounds provided herein can be enantiomerically pure, enantiomerically enriched, a racemic mixture, diastereomerically pure, diastereomerically enriched, or a stereoisomeric mixture. Preparation of enantiomerically pure or enantiomerically enriched forms can be accomplished by resolution of racemic mixtures or by using enantiomerically pure or enriched starting materials or by stereoselective or stereospecific synthesis. Stereochemical definitions are available in E.L. Eliel, S. H. Wilen & L. N. Mander "Stereochemistry of Organic Compounds" John Wiley & Sons, Inc., New York, NY, 1994 which is incorporated herein by reference in its entirety. In some embodiments, where the compound of the invention is chiral or otherwise includes one or more stereocenters, the compound can be prepared with an enantiomeric excess or diastereomeric excess of greater than about 75%, greater than about 80%, greater than about 85%, greater than about 90%, greater than about 95%, or greater than about 99%.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Other resolving agents suitable for fractional crystallization methods include stereoisomerically pure forms of methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

The compounds described herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

The compounds described herein, and their pharmaceutically acceptable salts, can be found together with other substances such as water and solvents, for example, in the form of hydrates or solvates. When in the solid state, the compounds described herein and salts thereof can occur in various forms and can, e.g., take the form of solvates, including hydrates. The compounds can be in any solid state form, such as a crystalline form, amorphous form, solvated form, etc. so unless clearly indicated otherwise, reference in the specification to compounds and salts thereof should be understood as reading on any solid state form of the compound.

In addition, it is understood that, when the compounds described herein contain one or more double bond(s) (e.g., C═C, C═N, and the like) or other centers of geometric asymmetry, and unless specified otherwise, it is intended that the compounds include both E and Z geometric isomers (e.g., cis or trans). Cis and trans geometric isomers of the compounds described herein can be isolated as a mixture of isomers or as separated isomeric form.

Isotopes

The compounds disclosed and described herein allow atoms at each position of the compound independently to have an isotopic distribution for a chemical element in proportional amounts to those usually found in nature or an isotopic distribution in proportional amounts different to those usually found in nature unless the context clearly dictates otherwise. A particular chemical element has an atomic number defined by the number of protons within the atom's nucleus. Each atomic number identifies a specific element, but not the isotope; an atom of a given element can have a wide range in its number of neutrons. The number of both protons and neutrons in the nucleus is the atom's mass number, and each isotope of a given element has a different mass number. A compound wherein one or more atoms have an isotopic distribution for a chemical element in proportional amounts different to those usually found in nature is commonly referred to as being an isotopically-labeled compound. Each chemical element as represented in a compound structure may include any isotopic distribution of said element. For example, in a compound structure a hydrogen atom may be explicitly disclosed or understood to be present in the compound. At any position of the compound that a hydrogen atom may be present, the hydrogen atom can be an isotopic distribution of hydrogen, including but not limited to protium ($^1H$) and deuterium ($^2H$) in proportional amounts to those usually found in nature and in proportional amounts different to those usually found in nature. Thus, reference herein to a compound encompasses all potential isotopic distributions for each atom unless the context clearly dictates otherwise. Examples of isotopes include isotopes of hydrogen, carbon, nitrogen, oxygen, phosphorous, sulfur, fluorine, chlorine, bromine and iodine. As one of skill in the art would appreciate, any of the compounds as disclosed and described herein can include radioactive isotopes. Accordingly, also contemplated is use of compounds as disclosed and described herein, wherein one or more atoms have an isotopic distribution different to those usually found in nature, such as having $^2H$ or $^3H$ in greater proportion, or $^{11}C$, $^{13}C$, or $^{14}C$ in greater proportion than found in nature. By way of general example, and without limitation, isotopes of hydrogen include protium ($^1H$), deuterium ($^2H$) and tritium ($^3H$). Isotopes of carbon include carbon-11 ($^{11}C$), carbon-12 ($^{12}C$), carbon-13 ($^{13}C$), and carbon-14 ($^{14}C$). Isotopes of nitrogen include nitrogen-13 ($^{13}N$), nitrogen-14 ($^{14}N$) and nitrogen-15 ($^{15}N$). Isotopes of oxygen include oxygen-14 ($^{14}O$), oxygen-15 ($^{15}O$), oxygen-16 ($^{16}O$), oxygen-17 ($^{17}O$), and oxygen-18 ($^{18}O$). Isotope of fluorine include fluorine-17 ($^{17}F$), fluorine-18 ($^{18}F$) and fluorine-19 ($^{19}F$). Isotopes of phosphorous include phosphorus-31 ($^{31}P$), phosphorus-32 ($^{32}P$), phosphorus-33 ($^{33}P$) phosphorus-34 ($^{34}P$), phosphorus-35 ($^{35}P$) and phosphorus-36 ($^{36}P$). Isotopes of sulfur include sulfur-32 ($^{32}S$), sulfur-33 ($^{33}S$), sulfur-34 ($^{34}S$), sulfur-35 ($^{35}S$), sulfur-36 ($^{36}S$) and sulfur-38 ($^{38}S$). Isotopes of chlorine include chlorine-35 ($^{35}Cl$), chlorine-36 ($^{36}Cl$) and chlorine-37 $^3$(7Cl). Isotopes of bromine include bromine-75 ($^{75}Br$), bromine-76 ($^{76}Br$), bromine-77 ($^{77}Br$), bromine-79 ($^{79}Br$), bromine-81 ($^{81}Br$) and bromine-82 ($^{82}Br$). Isotopes of iodine include iodine-123 ($^{123}I$), iodine-124 ($^{124}I$), iodine-125 ($^{125}I$), iodine-131 ($^{131}I$) and iodine-135 ($^{135}I$). In some embodiments, atoms at every position of the compound have an isotopic distribution for each chemical element in proportional amounts to those usually found in nature. In some embodiments, an atoms in one position of the compound has an isotopic distribution for a chemical element in proportional amounts different to those usually found in nature (remainder atoms having an isotopic distribution for a chemical element in proportional amounts to those usually found in nature). In some embodiments, atoms in at least two positions of the compound independently have an isotopic distribution for a chemical element in proportional amounts different to those usually found in nature (remainder atoms having an isotopic distribution for a chemical element in proportional amounts to those usually found in nature). In some embodiments, atoms in at least three positions of the compound independently have an isotopic distribution for a chemical element in proportional amounts different to those usually found in nature (remainder atoms having an isotopic distribution for a chemical element in proportional amounts to those usually found in nature). In some embodiments, atoms in at least four positions of the compound independently have an isotopic distribution for a chemical element in proportional amounts different to those usually found in nature (remainder atoms having an isotopic distribution for a chemical element in proportional amounts to those usually found in nature). In some embodiments, atoms in at least five positions of the compound independently have an isotopic distribution for a chemical element in proportional amounts different to those usually found in nature (remainder atoms having an isotopic distribution for a chemical element in proportional amounts to those usually found in nature). In some embodiments, atoms in at least six positions of the compound independently have an isotopic distribution for a chemical element in proportional amounts different to those usually found in nature (remainder atoms having an isotopic distribution for a chemical element in proportional amounts to those usually found in nature).

Certain compounds, for example those having radioactive isotopes such as $^{3}H$ and $^{14}C$ incorporated, are also useful in drug or substrate tissue distribution assays. Tritium ($^{3}H$) and carbon-14 ($^{14}C$) isotopes are particularly preferred for their ease of preparation and detectability. Compounds with isotopes such as deuterium ($^{2}H$) in proportional amounts greater than is usually found in nature can afford certain therapeutic advantages resulting from greater metabolic stability, such as, for example, increased in vivo half-life or reduced dosage requirements. Isotopically-labeled compounds can generally be prepared by performing procedures routinely practiced in the art. Methods are readily available to measure such isotope perturbations or enrichments, such as, mass spectrometry, and for isotopes that are radioisotopes additional methods are available, such as, radiodetectors used in connection with HPLC or GC.

As used herein, "isotopic variant" means a compound that contains an unnatural proportion of an isotope at one or more of the atoms that constitute such a compound. In certain embodiments, an "isotopic variant" of a compound contains unnatural proportions of one or more isotopes, including, but not limited to, protium ($^{1}H$), deuterium ($^{2}H$), tritium ($^{3}H$), carbon-11 ($^{11}C$), carbon-12 ($^{12}C$), carbon-13 ($^{13}C$), carbon-14 ($^{14}C$), nitrogen-13 ($^{13}N$), nitrogen-14 ($^{14}N$), nitrogen-15 ($^{15}N$), oxygen-14 ($^{14}O$), oxygen-15 ($^{15}O$), oxygen-16 ($^{16}O$), oxygen-17 ($^{17}O$), oxygen-18 ($^{18}O$), fluorine-17 ($^{17}F$), fluorine-18 ($^{18}F$), phosphorus-31 ($^{31}P$), phosphorus-32 ($^{32}P$), phosphorus-33 ($^{33}P$), sulfur-32 ($^{32}S$), sulfur-33 ($^{33}S$), sulfur-34 ($^{34}S$), sulfur-35 ($^{35}S$), sulfur-36 ($^{36}S$), chlorine-35 ($^{35}Cl$), chlorine-36 ($^{36}Cl$), chlorine-37 ($^{37}Cl$), bromine-79 ($^{79}Br$), bromine-81 ($^{81}Br$), iodine-123 ($^{123}I$), iodine-125 ($^{125}I$), iodine-127 ($^{127}I$), iodine-129 ($^{129}I$), and iodine-131 ($^{131}I$). In certain embodiments, an "isotopic variant" of a compound is in a stable form, that is, non-radioactive. In certain embodiments, an "isotopic variant" of a compound contains unnatural proportions of one or more isotopes, including, but not limited to, hydrogen ($^{1}H$), deuterium ($^{2}H$), carbon-12 ($^{12}C$), carbon-13 ($^{13}C$), nitrogen-14 ($^{14}N$), nitrogen-15 ($^{15}N$), oxygen-16 ($^{16}O$), oxygen-17 ($^{17}O$), and oxygen-18 ($^{18}O$). In certain embodiments, an "isotopic variant" of a compound is in an unstable form, that is, radioactive. In certain embodiments, an "isotopic variant" of a compound of the invention contains unnatural proportions of one or more isotopes, including, but not limited to, tritium ($^{3}H$), carbon-11 ($^{11}C$), carbon-14 ($^{14}C$), nitrogen-13 ($^{13}N$), oxygen-14 ($^{14}O$), and oxygen-15 ($^{15}O$). It will be understood that, in a compound as provided herein, any hydrogen can include $^{2}H$ as the major isotopic form, as example, or any carbon include be $^{13}C$ as the major isotopic form, as example, or any nitrogen can include $^{15}N$ as the major isotopic form, as example, and any oxygen can include $^{18}O$ as the major isotopic form, as example. In certain embodiments, an "isotopic variant" of a compound contains an unnatural proportion of deuterium ($^{2}H$).

With regard to the compounds provided herein, when a particular atomic position is designated as having deuterium or "D" or "d", it is understood that the abundance of deuterium at that position is substantially greater than the natural abundance of deuterium, which is about 0.015%. A position designated as having deuterium typically has a minimum isotopic enrichment factor of, in certain embodiments, at least 3500 (52.5% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation) at each designated deuterium position.

Synthetic methods for incorporating radio-isotopes into organic compounds are applicable to compounds of the invention and are well known in the art. These synthetic methods, for example, incorporating activity levels of tritium into target molecules, are as follows:

A. Catalytic Reduction with Tritium Gas: This procedure normally yields high specific activity products and requires halogenated or unsaturated precursors.
B. Reduction with Sodium Borohydride [$^{3}H$]: This procedure is rather inexpensive and requires precursors containing reducible functional groups such as aldehydes, ketones, lactones, esters and the like.
C. Reduction with Lithium Aluminum Hydride [$^{3}H$]: This procedure offers products at almost theoretical specific activities. It also requires precursors containing reducible functional groups such as aldehydes, ketones, lactones, esters and the like.
D. Tritium Gas Exposure Labeling: This procedure involves exposing precursors containing exchangeable protons to tritium gas in the presence of a suitable catalyst.
E. N-Methylation using Methyl Iodide [$^{3}H$]: This procedure is usually employed to prepare O-methyl or N-methyl ($^{3}H$) products by treating appropriate precursors with high specific activity methyl iodide ($^{3}H$). This method in general allows for higher specific activity, such as for example, about 70-90 Ci/mmol.

Synthetic methods for incorporating activity levels of $^{125}I$ into target molecules include:

A. Sandmeyer and like reactions: This procedure transforms an aryl amine or a heteroaryl amine into a diazonium salt, such as a diazonium tetrafluoroborate salt and subsequently to $^{125}I$ labeled compound using $Na^{125}I$. A representative procedure was reported by Zhu, G-D. and co-workers in J. Org. Chem., 2002, 67, 943-948.
B. Ortho $^{125}$Iodination of phenols: This procedure allows for the incorporation of $^{125}I$ at the ortho position of a phenol as reported by Collier, T. L. and co-workers in J. Labelled Compd. Radiopharm., 1999, 42, S264-S266.
C. Aryl and heteroaryl bromide exchange with $^{125}I$: This method is generally a two step process. The first step is the conversion of the aryl or heteroaryl bromide to the corresponding tri-alkyltin intermediate using for example, a Pd catalyzed reaction [i.e., $Pd(Ph_3P)_4$] or through an aryl or heteroaryl lithium, in the presence of a tri-alkyltinhalide or hexaalkylditin [e.g., $(CH_3)_3SnSn(CH_3)_3$]. A representative procedure was reported by Le Bas, M.-D. and co-workers in J. Labelled Compd. Radiopharm. 2001, 44, S280-S282.

A radiolabeled form of a compound of the invention can be used in a screening assay to identify/evaluate compounds. In general terms, a newly synthesized or identified compound (i.e., test compound) can be evaluated for its ability to reduce binding of a radiolabeled form of a compound disclosed herein to $CRF_1$. The ability of a test compound to compete with a radiolabeled form of a compound of the invention for the binding to a $CRF_1$ correlates to its binding affinity.

Solid Forms

The present disclosure is further directed to solid forms, including crystalline forms and amorphous forms, of Compound 1 and pharmaceutically acceptable salts thereof. The solid forms (e.g., crystalline forms) described herein can have certain advantages, for example, they can have desirable properties, such as ease of handling, ease of processing, storage stability, and ease of purification. Moreover, the crystalline forms can be useful for improving the performance characteristics of a pharmaceutical product such as dissolution profile, shelf-life and bioavailability.

Some embodiments provide a process of preparing a crystal form of a compound of the disclosure, or a pharmaceutically acceptable salt thereof, comprising a) dissolving the compound in a solvent mixture including an organic solvent and aqueous solution; and b) crystallizing the compound of the disclosure, or a pharmaceutically acceptable salt thereof. In some embodiments, the solvent mixture includes an organic solvent and an aqueous counter-ion solution.

Compound 1 Form I

Provided herein is a solid form of Compound 1 which is crystalline, referred to as Form I, which is described below in the Examples.

In some embodiments, Form I has an X-ray powder diffraction (XRPD) pattern having one or more characteristic XRPD peaks selected from 11.2, 13.1, 15.1, 19.9 and 22.5 degrees two-theta±0.2 theta. In some embodiments, Form I has an X-ray powder diffraction pattern having two or more characteristic XRPD peaks selected from 11.2, 13.1, 15.1, 19.9 and 22.5 degrees two-theta±0.2 theta. In some embodiments, Form I has an X-ray powder diffraction pattern having three or more characteristic XRPD peaks selected from 11.2, 13.1, 15.1, 19.9 and 22.5 degrees two-theta±0.2 theta. In some embodiments, Form I has an X-ray powder diffraction pattern having four or more characteristic XRPD peaks selected from 11.2, 13.1, 15.1, 19.9 and 22.5 degrees two-theta±0.2 theta. In some embodiments, Form I has an X-ray powder diffraction pattern having characteristic XRPD peaks of 11.2, 13.1, 15.1, 19.9 and 22.5 degrees two-theta±0.2 theta. In some embodiments, Form I has an XRPD pattern substantially as shown in FIG. 1.

Figure 2:
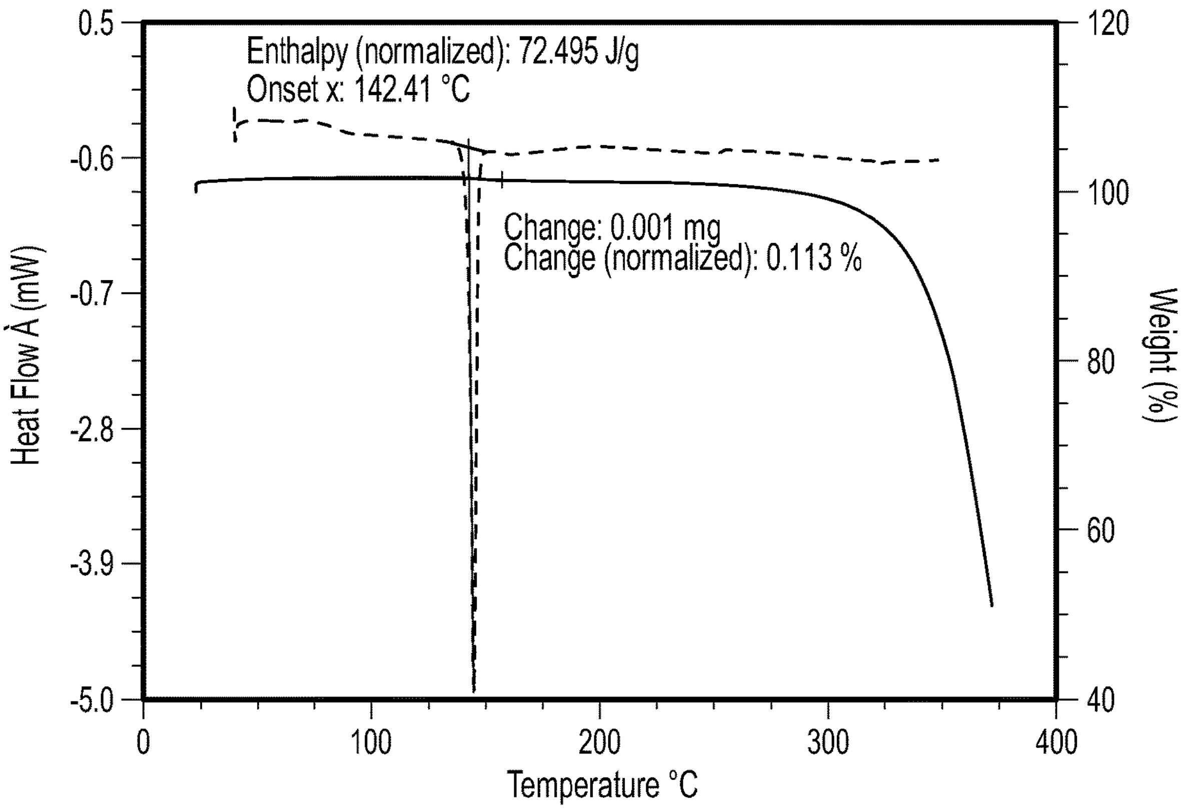
FIG. 2 depicts exemplary Differential Scanning Calorimetry (DSC) diffractogram and Thermogravimetric Analysis (TGA) thermogram of a sample of Compound 1 in crystalline Form I.

In some embodiments, Form I has a differential scanning calorimetry thermogram comprising an endothermic event with an onset temperature of about 142° C. In some embodiments, Form I has a differential scanning calorimetry thermogram substantially as shown in FIG. 2.

In some embodiments, Form I has a thermal gravimetric analysis plot comprising a mass loss of less than about 1% when heated from about 25° C. to about 140° C.

Compound 1 Form II

Provided herein is a solid form of Compound 1 which is crystalline, referred to as Form II, which is described below in the Examples.

Figure 3:
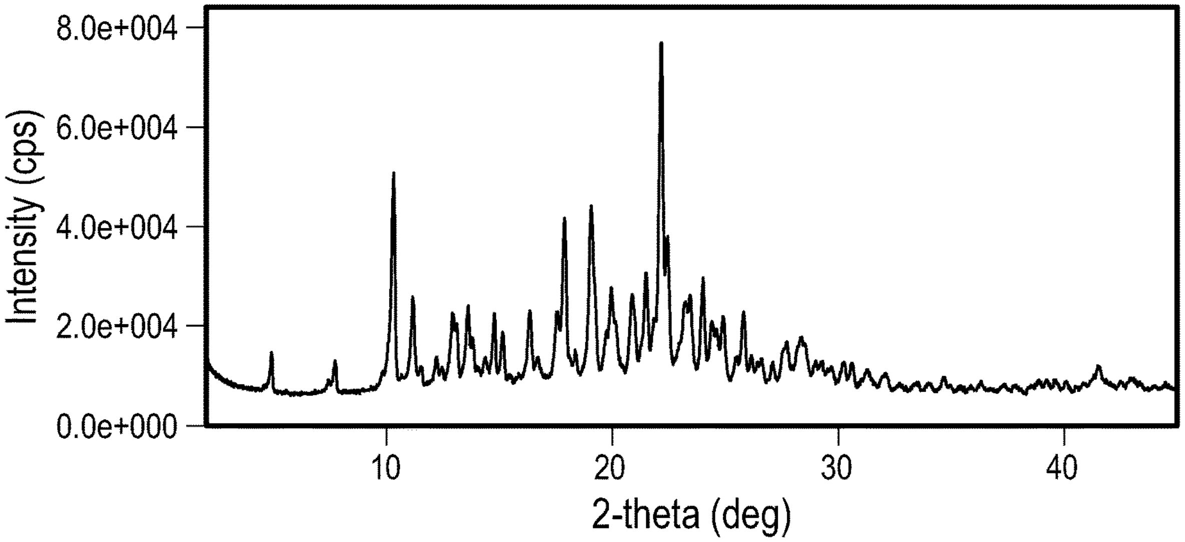
FIG. 3 depicts an exemplary XRPD of a sample of Compound 1 in crystalline Form II.

In some embodiments, Form II has an XRPD pattern substantially as shown in FIG. 3.

Figure 4:
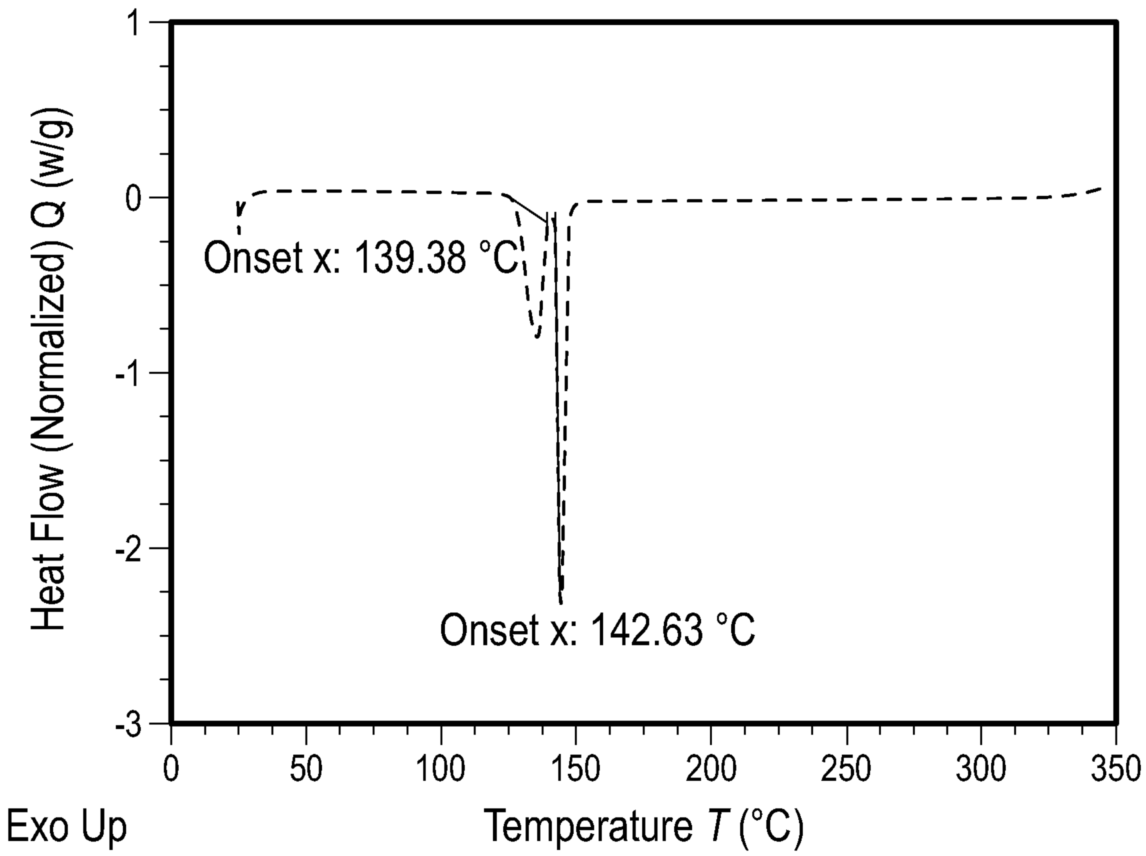
FIG. 4 depicts exemplary DSC diffractogram of a sample of Compound 1 in crystalline Form II.

In some embodiments, Form II has a differential scanning calorimetry thermogram substantially as shown in FIG. 4.

Compound 1 Form III

Provided herein is a solid form of Compound 1 which is crystalline, referred to as Form III, which is described below in the Examples.

Figure 5:
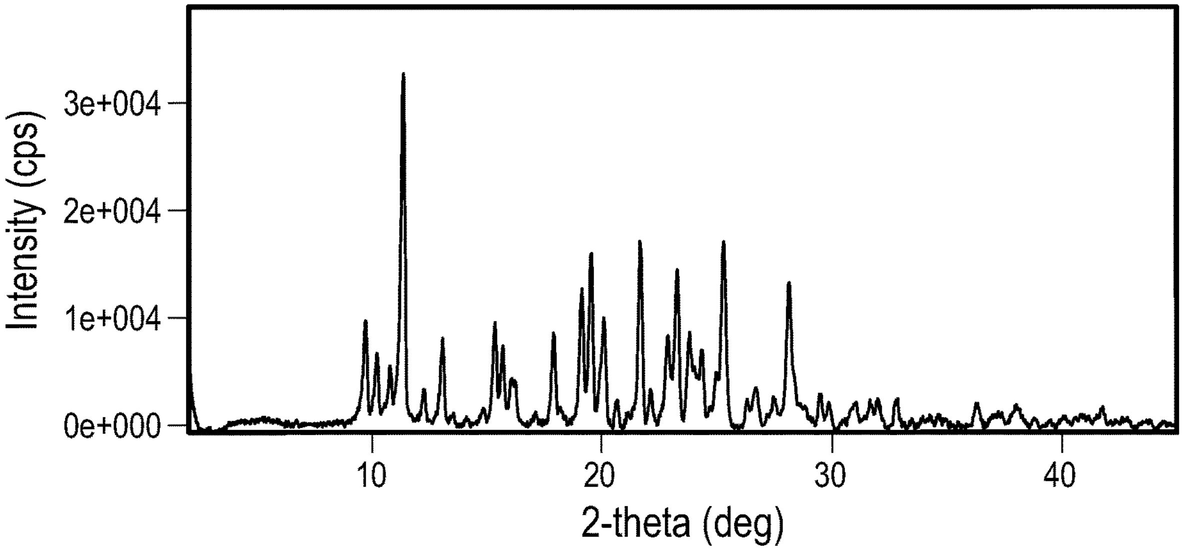
FIG. 5 depicts an exemplary XRPD diffractogram of a sample of Compound 1 in crystalline Form III.

In some embodiments, Form III has an XRPD pattern substantially as shown in FIG. 5.

Figure 6:
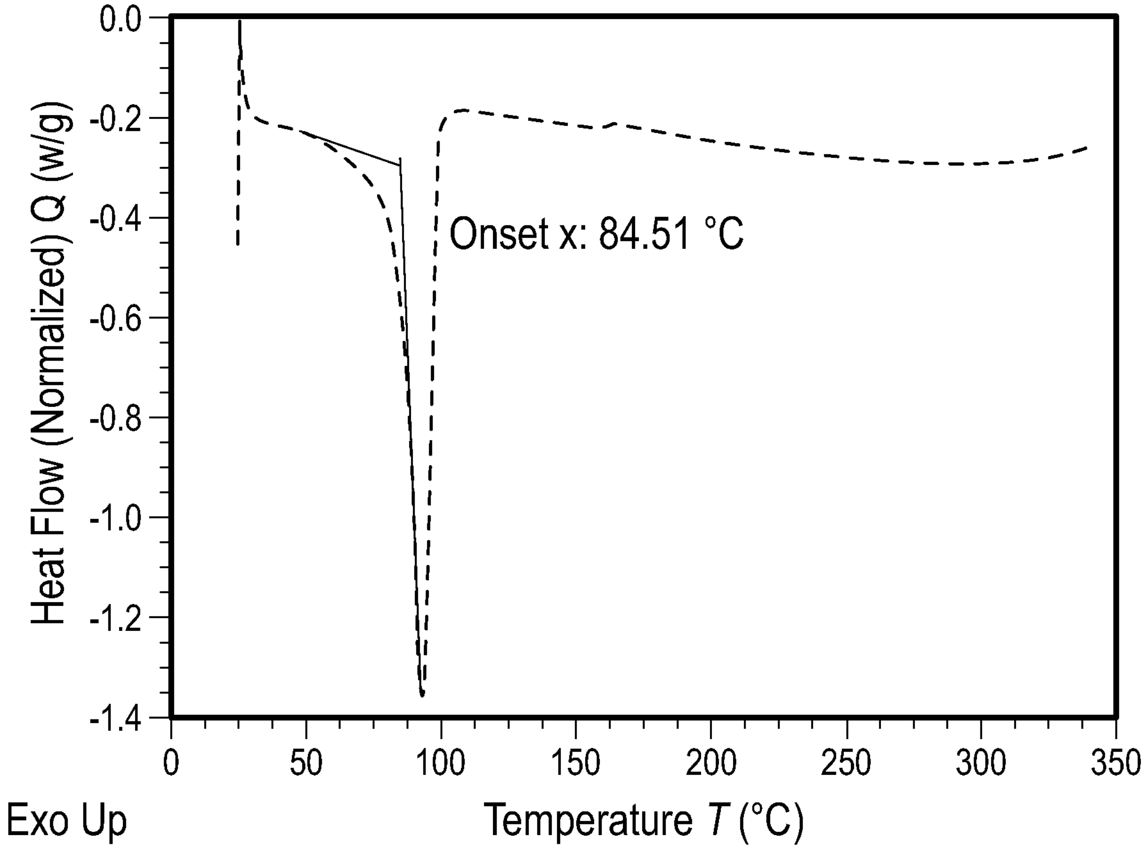
FIG. 6 depicts exemplary DSC diffractogram of a sample of Compound 1 in crystalline Form III.

In some embodiments, Form III has a differential scanning calorimetry thermogram substantially as shown in FIG. 6.

HCl Salt Compound 1 Form I

Provided herein is a solid form of the HCl salt of Compound 1 which is crystalline, referred to as HCl Salt Form I, which is described below in the Examples.

Figure 7:
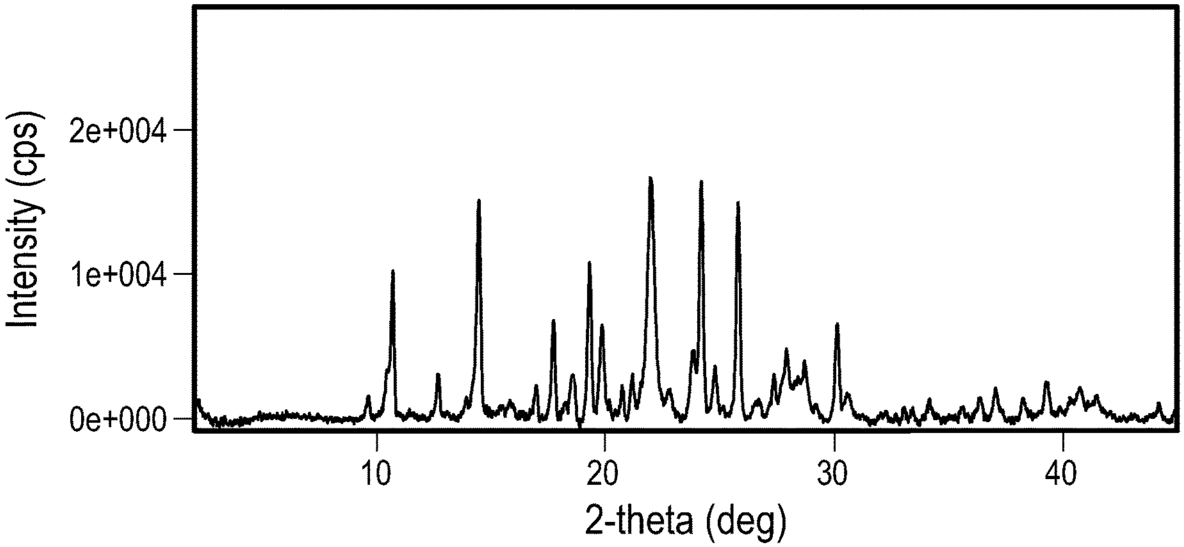
FIG. 7 depicts an exemplary XRPD of a sample of the HCl salt of Compound 1.

In some embodiments, HCl Salt Form I has an X-ray powder diffraction pattern having one or more characteristic XRPD peaks selected from 10.6, 14.4, 22.0, 24.2 and 25.8 degrees two-theta±0.2 theta. In some embodiments, HCl Salt Form I has an X-ray powder diffraction pattern having two or more characteristic XRPD peaks selected from 10.6, 14.4, 22.0, 24.2 and 25.8 degrees two-theta±0.2 theta. In some embodiments, HCl Salt Form I has an X-ray powder diffraction pattern having three or more characteristic XRPD peaks selected from 10.6, 14.4, 22.0, 24.2 and 25.8 degrees two-theta±0.2 theta. In some embodiments, HCl Salt Form I has an X-ray powder diffraction pattern having four or more characteristic XRPD peaks selected from 10.6, 14.4, 22.0, 24.2 and 25.8 degrees two-theta±0.2 theta. In some embodiments, HCl Salt Form I has an X-ray powder diffraction pattern having characteristic XRPD peaks of 10.6, 14.4, 22.0, 24.2 and 25.8 degrees two-theta±0.2 theta. In some embodiments, HCl Salt Form I has an XRPD pattern substantially as shown in FIG. 7.

Figure 8:
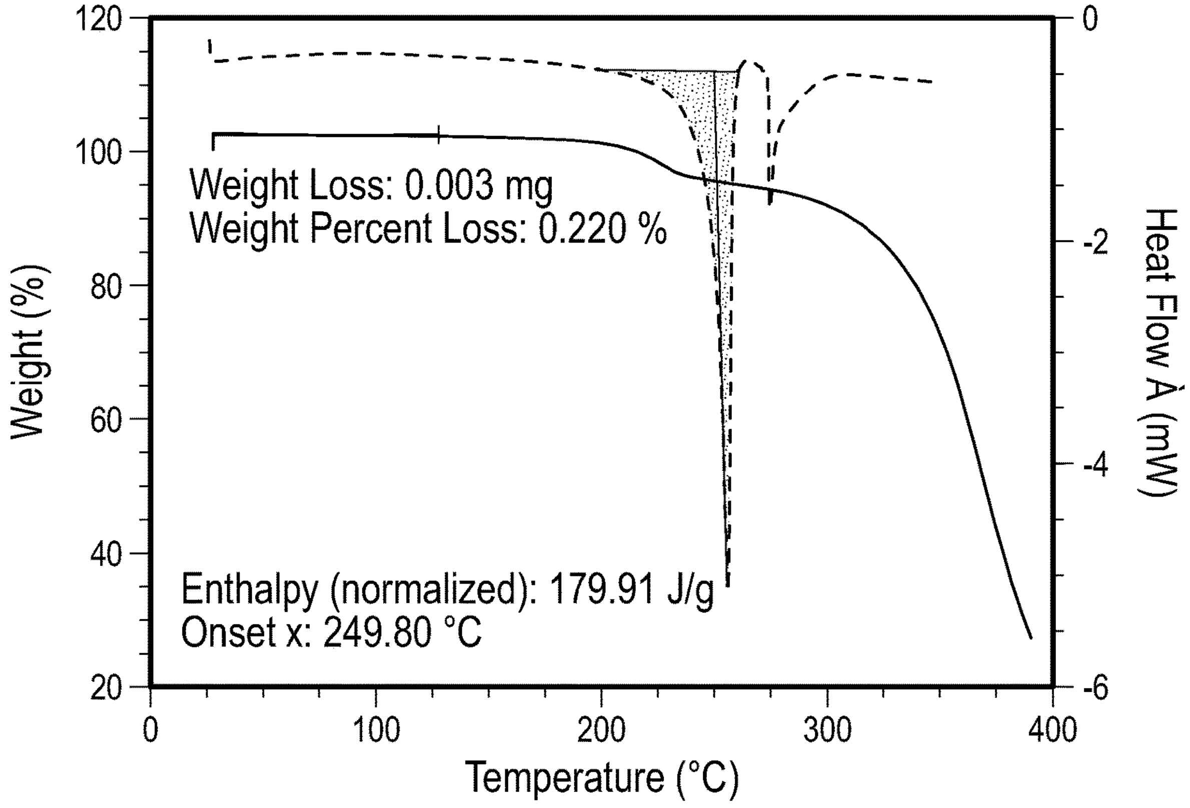
FIG. 8 depicts exemplary DSC diffractogram and TGA thermogram of a sample of the HCl salt of Compound 1.

In some embodiments, HCl Salt Form I has a differential scanning calorimetry thermogram comprising an endothermic event with an onset temperature of about 250° C. In some embodiments, HCl Salt Form I has a differential scanning calorimetry thermogram substantially as shown in FIG. 8.

In some embodiments, HCl Salt Form I has a thermal gravimetric analysis plot comprising a mass loss of less than about 1% when heated from about 25° C. to about 140° C.

HCl Salt Form I can be prepared by a process comprising a) dissolving Compound 1 in a mixture including an organic solvent and HCl; and b) precipitating the HCl salt of Compound 1 from the mixture. In some embodiments, the dissolving in step a) comprises heating the solvent mixture. In some embodiments, the precipitating in step b) comprises (i) cooling the heated mixture, or (ii) removing about 10% to about 99% of the organic solvent by weight or volume of the organic solvent, based on an initial amount of the organic solvent.

Maleate Salt Compound 1 Form I

Provided herein is a solid form of the maleic acid salt of Compound 1 which is crystalline, referred to as Maleate Salt Form I, which is described below in the Examples.

Figure 9:
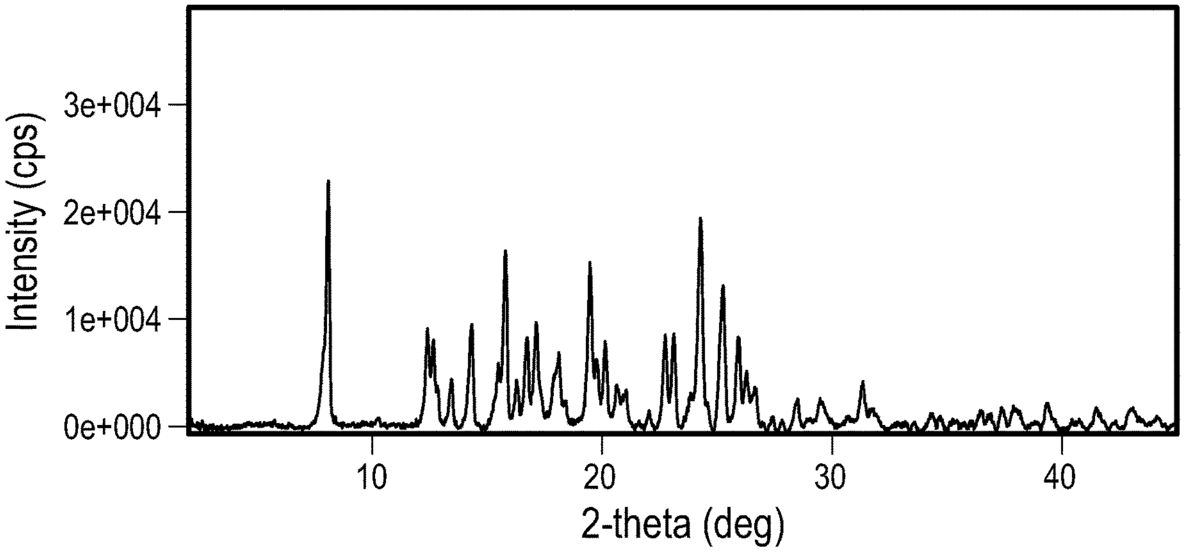
FIG. 9 depicts an exemplary XRPD diffractogram of a sample of the maleic acid salt of Compound 1.

In some embodiments, Maleate Salt Form I has an X-ray powder diffraction pattern having one or more characteristic XRPD peaks selected from 8.1, 14.3, 15.8, 19.5 and 24.3 degrees two-theta±0.2 theta. In some embodiments, Maleate Salt Form I has an X-ray powder diffraction pattern having two or more characteristic XRPD peaks selected from 8.1, 14.3, 15.8, 19.5 and 24.3 degrees two-theta±0.2 theta. In some embodiments, Maleate Salt Form I has an X-ray powder diffraction pattern having three or more characteristic XRPD peaks selected from 8.1, 14.3, 15.8, 19.5 and 24.3 degrees two-theta±0.2 theta. In some embodiments, Maleate Salt Form I has an X-ray powder diffraction pattern having four or more characteristic XRPD peaks selected from 8.1, 14.3, 15.8, 19.5 and 24.3 degrees two-theta±0.2 theta. In some embodiments, Maleate Salt Form I has an X-ray powder diffraction pattern having characteristic XRPD peaks of 8.1, 14.3, 15.8, 19.5 and 24.3 degrees two-theta±0.2 theta. In some embodiments, Maleate Salt Form I has an XRPD pattern substantially as shown in FIG. 9.

Figure 10:
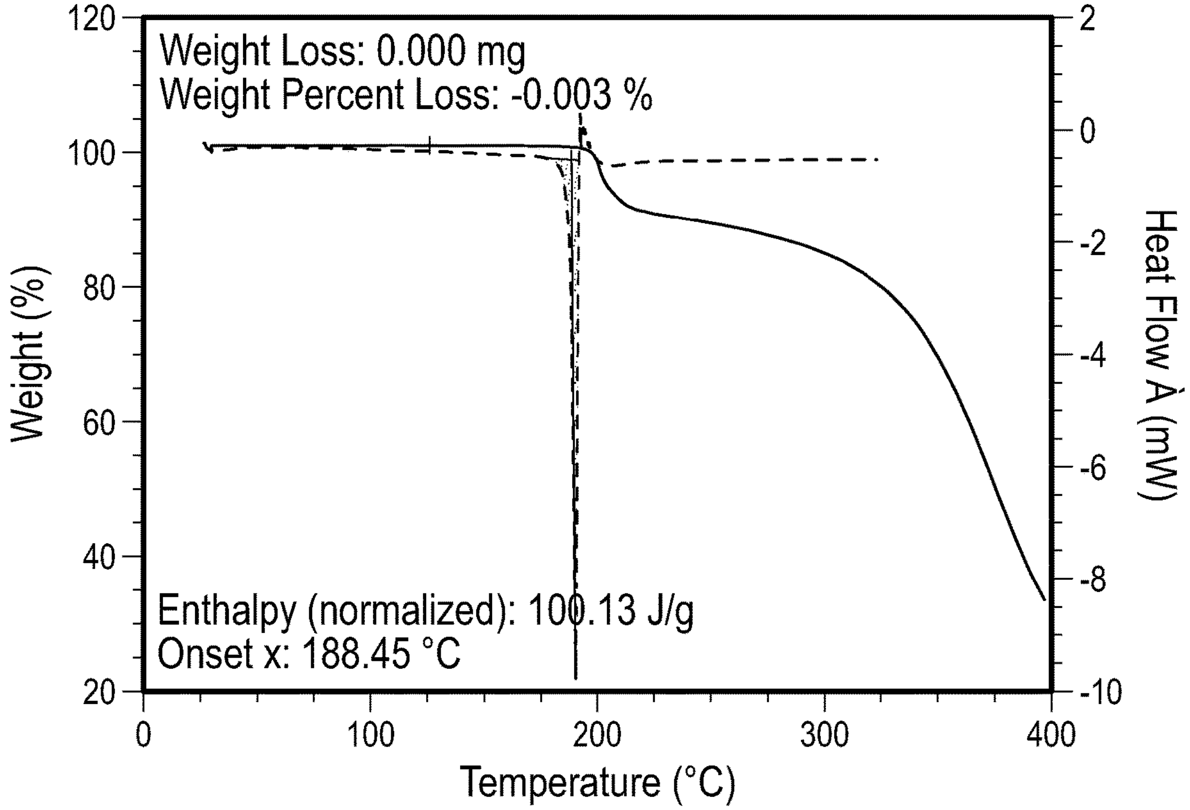
FIG. 10 depicts exemplary DSC diffractogram and TGA thermogram of a sample of the maleic acid salt of Compound 1.

In some embodiments, Maleate Salt Form I has a differential scanning calorimetry thermogram comprising an endothermic event with an onset temperature of about 188° C. In some embodiments, Maleate Salt Form I has a differential scanning calorimetry thermogram substantially as shown in FIG. 10.

In some embodiments, Maleate Salt Form I has a thermal gravimetric analysis plot comprising a mass loss of less than about 1% when heated from about 25° C. to about 140° C.

Maleate Salt Form I can be prepared by a process comprising a) dissolving Compound 1 in a mixture including an organic solvent and maleic acid; and b) precipitating the maleic acid salt of Compound 1 from the mixture. In some embodiments, the dissolving in step a) comprises heating the solvent mixture. In some embodiments, the precipitating in step b) comprises (i) cooling the heated mixture, or (ii) removing about 10% to about 99% of the organic solvent by weight or volume of the organic solvent, based on an initial amount of the organic solvent.

Mesylate Salt Compound 1 Form I

Provided herein is a solid form of the methanesulfonic acid salt of Compound 1 which is crystalline, referred to as Mesylate Salt Form I, which is described below in the Examples.

Figure 11:
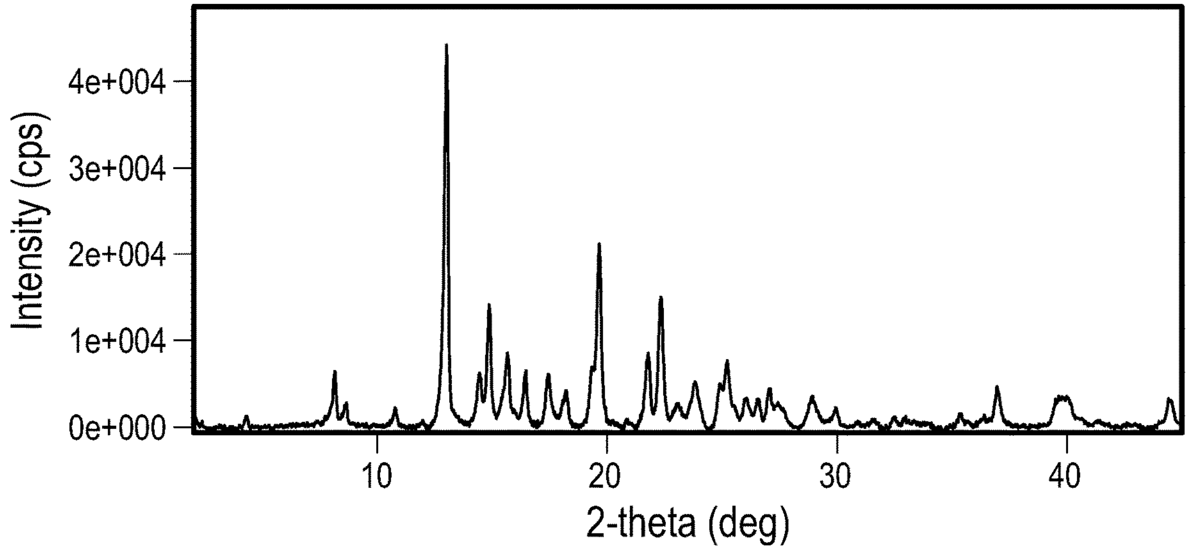
FIG. 11 depicts an exemplary XRPD diffractogram of a sample of the methanesulfonic acid salt of Compound 1.

In some embodiments, Mesylate Salt Form I has an X-ray powder diffraction pattern having one or more characteristic XRPD peaks selected from 8.2, 13.0, 14.9, 19.7, and 22.3 degrees two-theta±0.2 theta. In some embodiments, Mesylate Salt Form I has an X-ray powder diffraction pattern having two or more characteristic XRPD peaks selected from 8.2, 13.0, 14.9, 19.7, and 22.3 degrees two-theta±0.2 theta. In some embodiments, Mesylate Salt Form I has an X-ray powder diffraction pattern having three or more characteristic XRPD peaks selected from 8.2, 13.0, 14.9, 19.7, and 22.3 degrees two-theta±0.2 theta. In some embodiments, Mesylate Salt Form I has an X-ray powder diffraction pattern having four or more characteristic XRPD peaks selected from 8.2, 13.0, 14.9, 19.7, and 22.3 degrees two-theta±0.2 theta. In some embodiments, Mesylate Salt Form I has an X-ray powder diffraction pattern having characteristic XRPD peaks of 8.2, 13.0, 14.9, 19.7, and 22.3 degrees two-theta±0.2 theta. In some embodiments, Mesylate Salt Form I has an X-ray powder diffraction pattern having characteristic XRPD peaks of 8.2 and 13.0 degrees two-theta±0.2 theta. In some embodiments, Mesylate Salt Form I has an X-ray powder diffraction pattern having characteristic XRPD peaks of 8.2 and 14.9 degrees two-theta±0.2 theta. In some embodiments, Mesylate Salt Form I has an X-ray powder diffraction pattern having characteristic XRPD peaks of 8.2 and 19.7 degrees two-theta±0.2 theta. In some embodiments, Mesylate Salt Form I has an X-ray powder diffraction pattern having characteristic XRPD peaks of 8.2 and 22.3 degrees two-theta±0.2 theta. In some embodiments, Mesylate Salt Form I has an X-ray powder diffraction pattern having characteristic XRPD peaks of 13.0, and 14.9 degrees two-theta±0.2 theta. In some embodiments, Mesylate Salt Form I has an X-ray powder diffraction pattern having characteristic XRPD peaks of 13.0 and 19.7 degrees two-theta±0.2 theta. In some embodiments, Mesylate Salt Form I has an X-ray powder diffraction pattern having characteristic XRPD peaks of 13.0 and 22.3 degrees two-theta±0.2 theta. In some embodiments, Mesylate Salt Form I has an X-ray powder diffraction pattern having characteristic XRPD peaks of 14.9 and 19.7 degrees two-theta±0.2 theta. In some embodiments, Mesylate Salt Form I has an X-ray powder diffraction pattern having characteristic XRPD peaks of 14.9 and 22.3 degrees two-theta±0.2 theta. In some embodiments, Mesylate Salt Form I has an X-ray powder diffraction pattern having characteristic XRPD peaks of 19.7, and 22.3 degrees two-theta±0.2 theta. In some embodiments, Mesylate Salt Form I has an XRPD pattern substantially as shown in FIG. 11.

Figure 12:
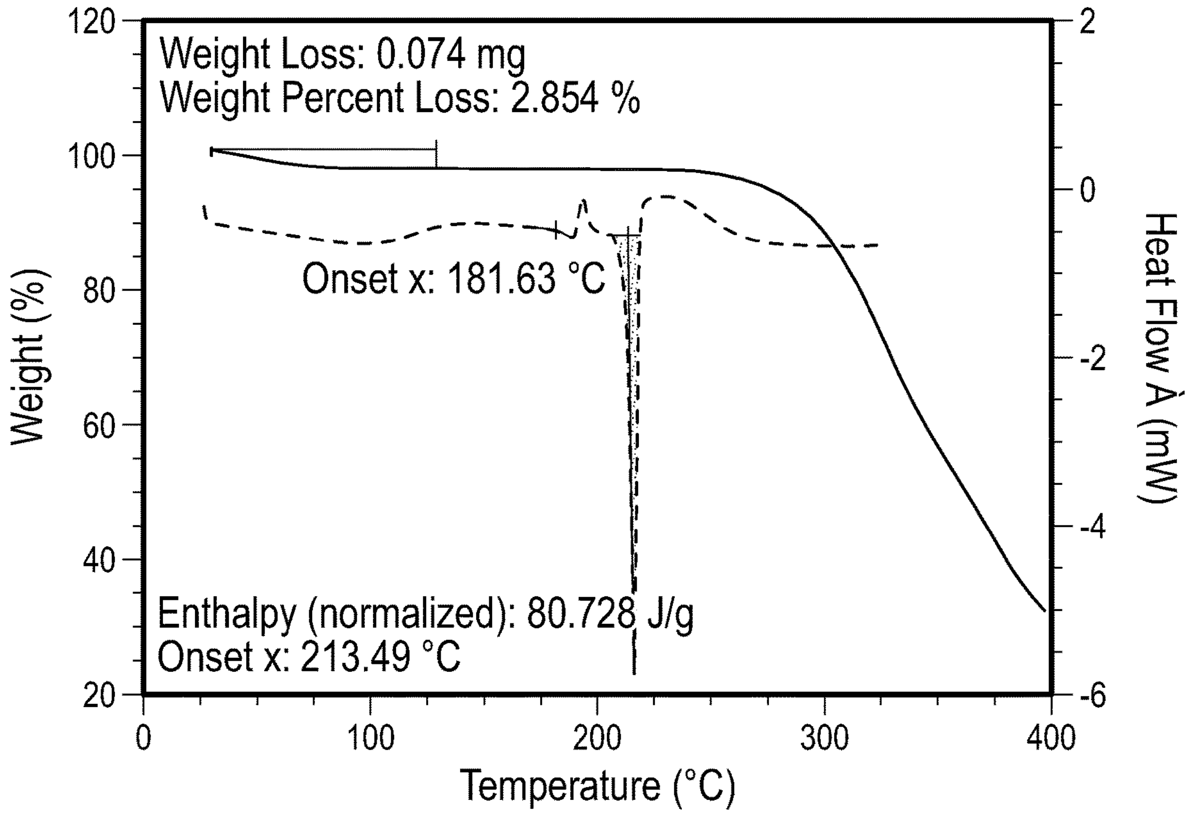
FIG. 12 depicts exemplary DSC diffractogram and TGA thermogram of a sample of the methanesulfonic acid salt of Compound 1.

In some embodiments, Mesylate Salt Form I has a differential scanning calorimetry thermogram comprising an endothermic event with an onset temperature of about 182° C. In some embodiments, Mesylate Salt Form I has a differential scanning calorimetry thermogram substantially as shown in FIG. 12.

In some embodiments, Mesylate Salt Form I has a thermal gravimetric analysis plot comprising a mass loss of about 3% when heated from about 25° C. to about 140° C.

In some embodiments, Mesylate Salt Form I can be prepared by a process comprising a) dissolving Compound 1 in a mixture including an organic solvent and methanesulfonic acid; and b) precipitating the methanesulfonic acid salt of Compound 1 from the mixture. In some embodiments, the dissolving in step a) comprises heating the solvent mixture. In some embodiments, the precipitating in step b) comprises (i) cooling the heated mixture, or (ii) removing about 10% to about 99% of the organic solvent by weight or volume of the organic solvent, based on an initial amount of the organic solvent. In some embodiments, Mesylate Salt Form I can be prepared by a process comprising a) dissolving Compound 1 in acetone to form a solution; b) combining the solution in step a) with an aqueous solution of methanesulfonic acid; and c) precipitating the methanesulfonic salt of Compound 1 from the mixture. In some embodiments, the dissolving in step a) comprises heating the solvent mixture. In some embodiments, the precipitating in step b) comprises cooling the heated mixture. In some embodiments, the combining in step c) further comprises seeding with Mesylate Salt Form I using a 0.1% to 2% seed load. In some embodiments, the combining in step c) further comprises seeding with Mesylate Salt Form I using a 1% seed load.

Esylate Salt Compound 1 Form I

Provided herein is a solid form of the ethanesulfonic acid salt of Compound 1 which is crystalline, referred to as Esylate Salt Form I, which is described below in the Examples.

Figure 13:
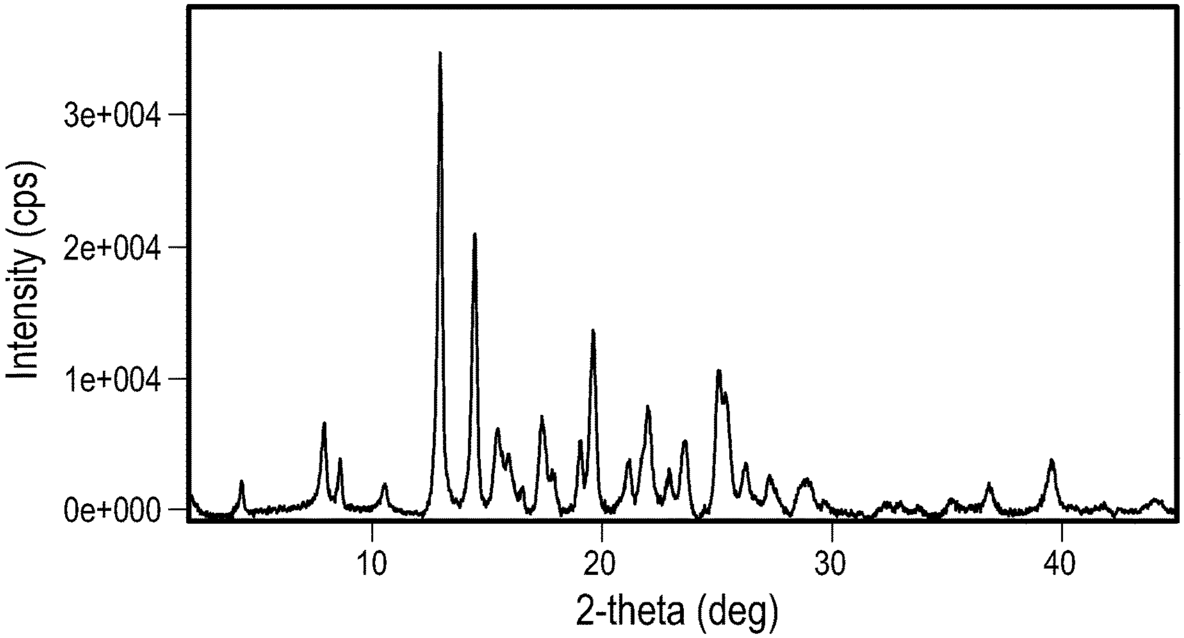
FIG. 13 depicts an exemplary XRPD diffractogram of a sample of the ethanesulfonic acid salt of Compound 1.

In some embodiments, Esylate Salt Form I has an X-ray powder diffraction pattern having one or more characteristic XRPD peaks selected from 8.6, 13.0, 14.4, 17.4, and 19.6 degrees two-theta±0.2 theta. In some embodiments, Esylate Salt Form I has an X-ray powder diffraction pattern having two or more characteristic XRPD peaks selected from 8.6, 13.0, 14.4, 17.4, and 19.6 degrees two-theta±0.2 theta. In some embodiments, Esylate Salt Form I has an X-ray powder diffraction pattern having three or more characteristic XRPD peaks selected from 8.6, 13.0, 14.4, 17.4, and 19.6 degrees two-theta±0.2 theta. In some embodiments, Esylate Salt Form I has an X-ray powder diffraction pattern having four or more characteristic XRPD peaks selected from 8.6, 13.0, 14.4, 17.4, and 19.6 degrees two-theta±0.2 theta. In some embodiments, Esylate Salt Form I has an X-ray powder diffraction pattern having characteristic XRPD peaks of 8.6, 13.0, 14.4, 17.4, and 19.6 degrees two-theta±0.2 theta. In some embodiments, Esylate Salt Form I has an XRPD pattern substantially as shown in FIG. 13.

Figure 14:
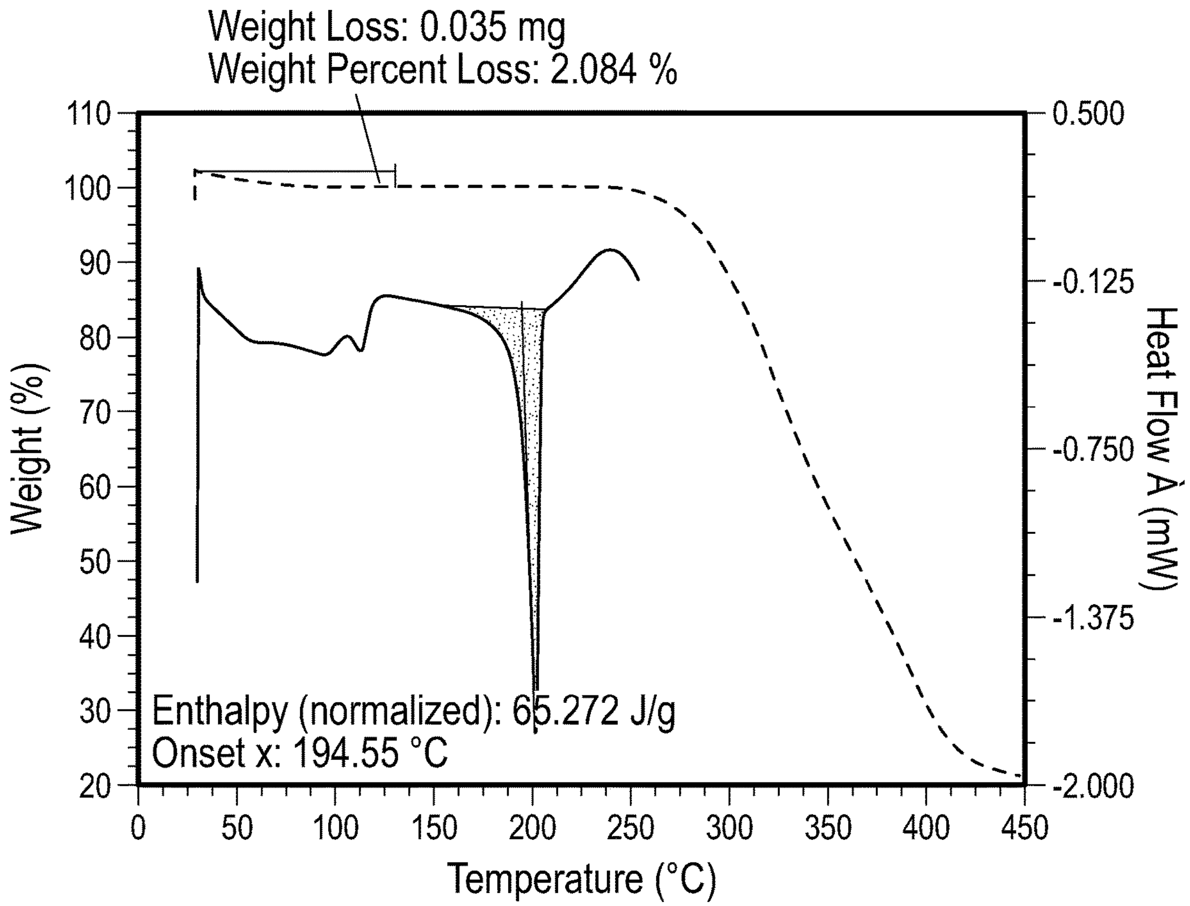
FIG. 14 depicts exemplary DSC diffractogram and TGA thermogram of a sample of the ethanesulfonic acid salt of Compound 1.

In some embodiments, Esylate Salt Form I has a differential scanning calorimetry thermogram comprising an endothermic event with an onset temperature of about 195° C. In some embodiments, Esylate Salt Form I has a differential scanning calorimetry thermogram substantially as shown in FIG. 14.

In some embodiments, Esylate Salt Form I has a thermal gravimetric analysis plot comprising a mass loss of about 2% when heated from about 25° C. to about 125° C.

Esylate Salt Form I can be prepared by a process comprising a) dissolving Compound 1 in a mixture including an organic solvent and ethanesulfonic acid; and b) precipitating the ethanesulfonic acid salt of Compound 1 from the mixture. In some embodiments, the dissolving in step a) comprises heating the solvent mixture. In some embodiments, the precipitating in step b) comprises (i) cooling the heated mixture, or (ii) removing about 10% to about 99% of the organic solvent by weight or volume of the organic solvent, based on an initial amount of the organic solvent.

Aspartate Salt Compound 1 Form I

Provided herein is a solid form of the aspartic acid salt of Compound 1 which is crystalline, referred to as Aspartate Salt Form I, which is described below in the Examples.

Figure 15:
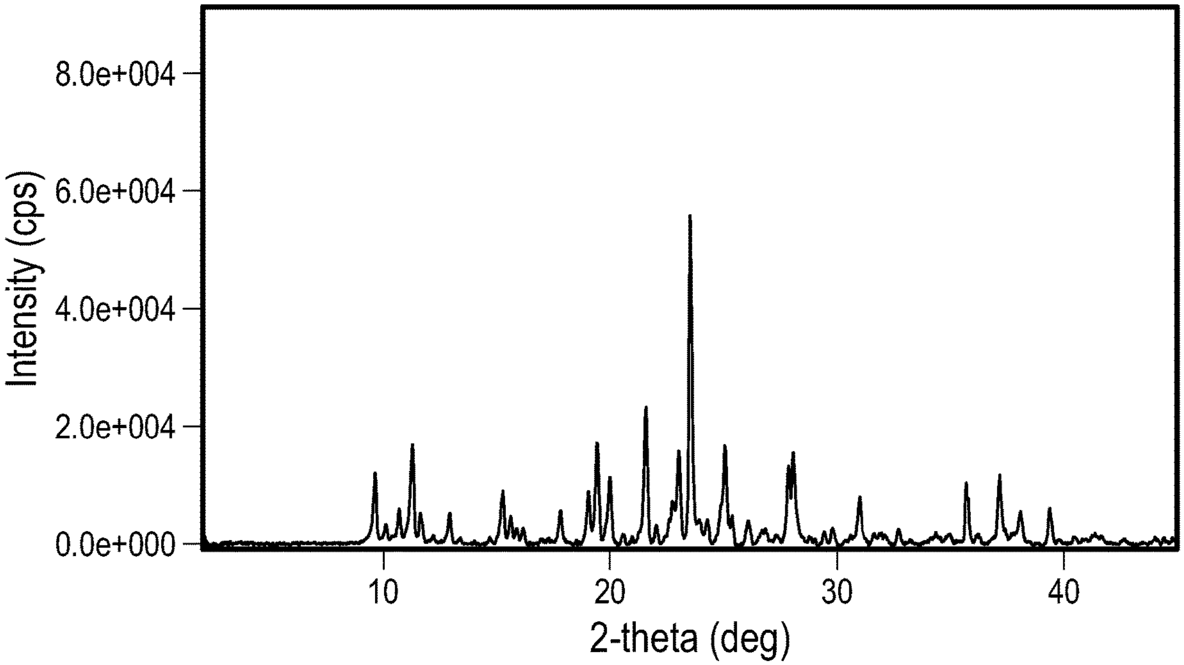
FIG. 15 depicts an exemplary XRPD diffractogram of a sample of the aspartic acid salt of Compound 1.

In some embodiments, Aspartate Salt Form I has an X-ray powder diffraction pattern having one or more characteristic XRPD peaks selected from 9.6, 11.6, 19.4, 23.5, and 35.7 degrees two-theta±0.2 theta. In some embodiments, Aspartate Salt Form I has an X-ray powder diffraction pattern having two or more characteristic XRPD peaks selected from 9.6, 11.6, 19.4, 23.5, and 35.7 degrees two-theta±0.2 theta. In some embodiments, Aspartate Salt Form I has an X-ray powder diffraction pattern having three or more characteristic XRPD peaks selected from 9.6, 11.6, 19.4, 23.5, and 35.7 degrees two-theta±0.2 theta. In some embodiments, Aspartate Salt Form I has an X-ray powder diffraction pattern having four or more characteristic XRPD peaks selected from 9.6, 11.6, 19.4, 23.5, and 35.7 degrees two-theta±0.2 theta. In some embodiments, Aspartate Salt Form I has an X-ray powder diffraction pattern having characteristic XRPD peaks of 9.6, 11.6, 19.4, 23.5, and 35.7 degrees two-theta±0.2 theta. In some embodiments, Aspartate Salt Form I has an XRPD pattern substantially as shown in FIG. 15.

Figure 16:
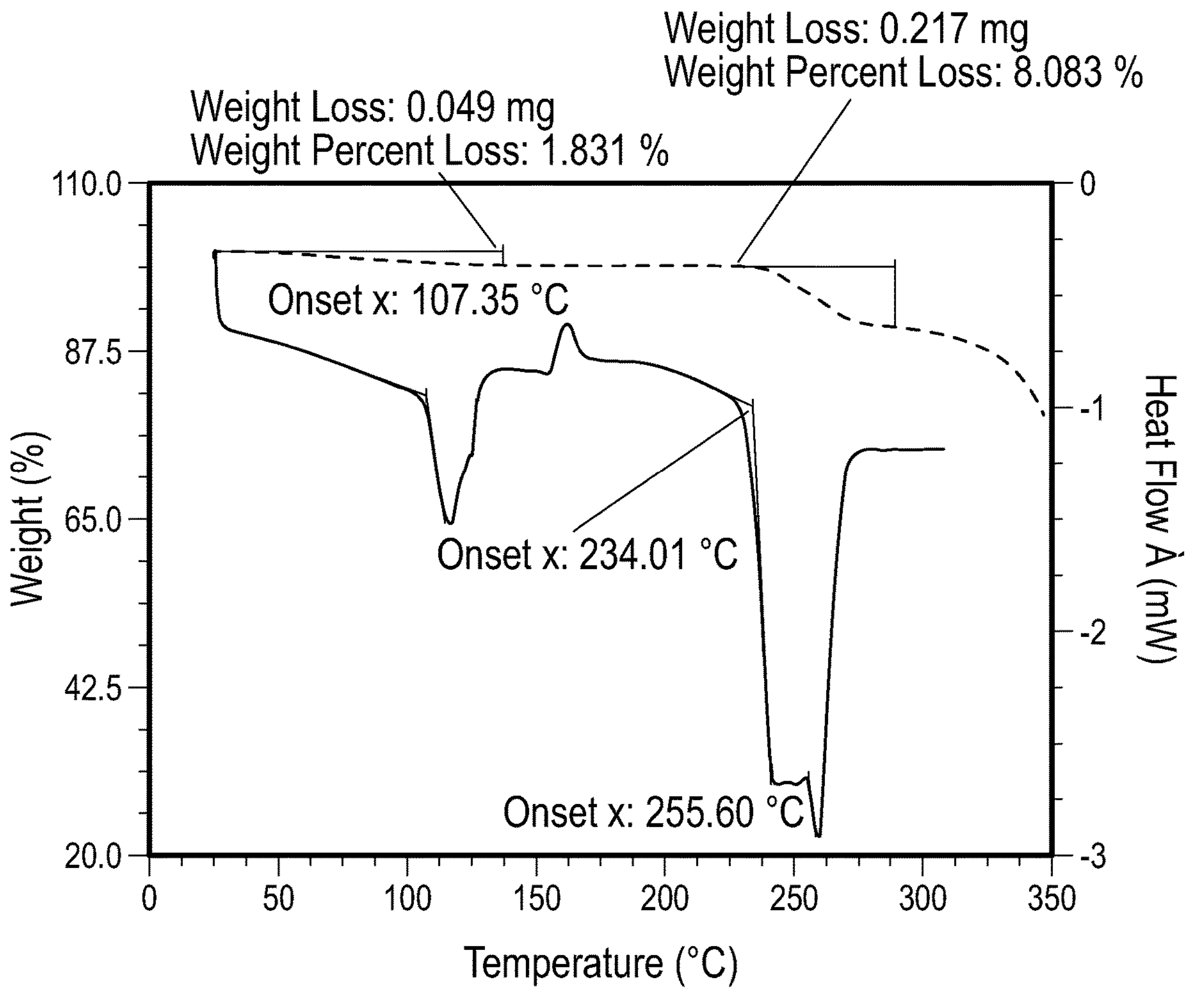
FIG. 16 depicts exemplary DSC diffractogram and TGA thermogram of a sample of the aspartic acid salt of Compound 1.

In some embodiments, Aspartate Salt Form I has a differential scanning calorimetry thermogram substantially as shown in FIG. 16.

In some embodiments, Aspartate Salt Form I has a thermal gravimetric analysis plot comprising a mass loss of less than about 2% when heated from about 25° C. to about 140° C.

Aspartate Salt Form I can be prepared by a process comprising a) dissolving Compound 1 in a mixture including an organic solvent and aspartic acid; and b) precipitating the aspartic acid salt of Compound 1 from the mixture. In some embodiments, the dissolving in step a) comprises heating the solvent mixture. In some embodiments, the precipitating in step b) comprises (i) cooling the heated mixture, or (ii) removing about 10% to about 99% of the organic solvent by weight or volume of the organic solvent, based on an initial amount of the organic solvent.

diHCl Salt Compound 8-E Form I

Provided herein is a solid form of N,N-dimethyl-4-(4-((propylamino)methyl)phenyl)thiazol-2-amine 2HCl (Compound 8-E), which is described below in the Examples.

Figure 17:
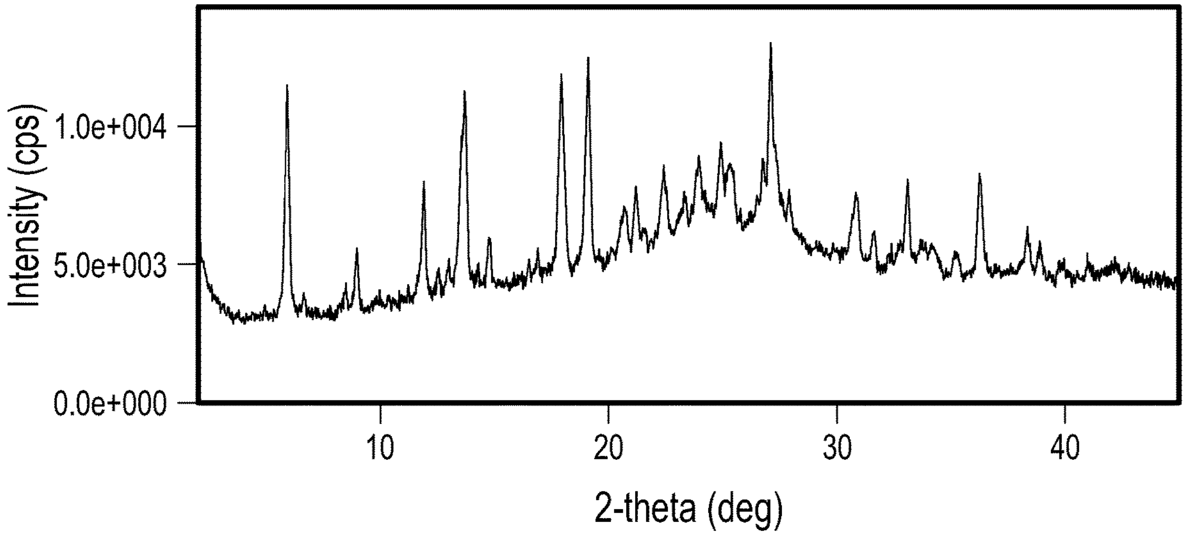
FIG. 17 depicts an exemplary XRPD diffractogram of a sample of Compound 8-E.

In some embodiments, diHCl Salt Form I has an X-ray powder diffraction pattern having one or more characteristic XRPD peaks selected from the peaks listed in Table A±0.2 theta. In some embodiments, diHCl Salt Form I has an X-ray powder diffraction pattern having two or more characteristic XRPD peaks selected from the peaks listed in Table A±0.2 theta. In some embodiments, diHCl Salt Form I has an X-ray powder diffraction pattern having three or more characteristic XRPD peaks selected from the peaks listed in Table A±0.2 theta. In some embodiments, diHCl Salt Form I has an X-ray powder diffraction pattern having four or more characteristic XRPD peaks selected from the peaks listed in Table A±0.2 theta. In some embodiments, diHCl Salt Form I has an X-ray powder diffraction pattern having four or more characteristic XRPD peaks selected from the peaks listed in Table A±0.2 theta. In some embodiments, diHCl Salt Form I has an XRPD pattern substantially as shown in FIG. 17.

Figure 18:
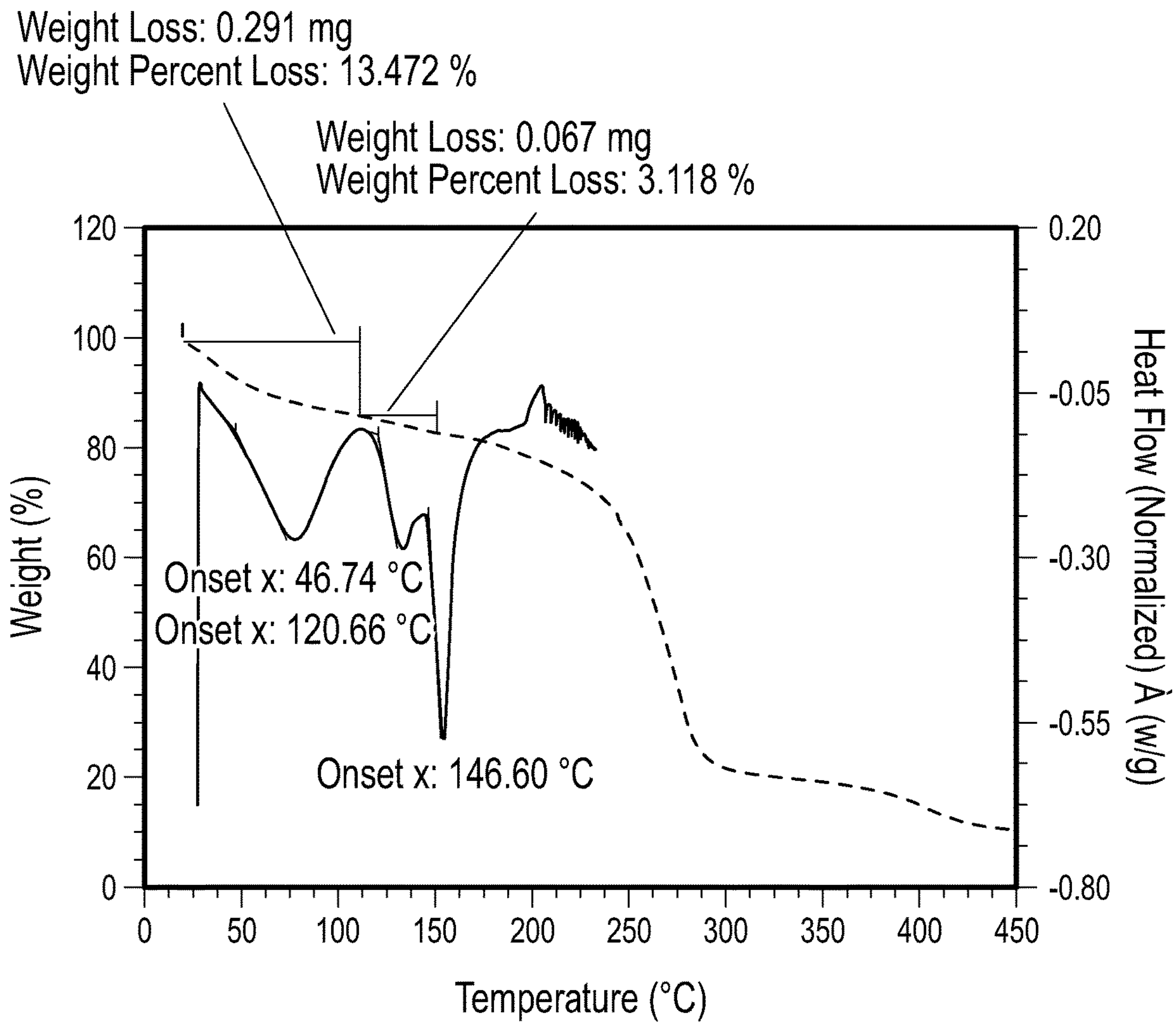
FIG. 18 depicts exemplary DSC diffractogram and TGA thermogram of a sample of Compound 8-E.

In some embodiments, diHCl Salt Form I has a differential scanning calorimetry thermogram substantially as shown in FIG. 18.

In some embodiments, diHCl Salt Form I has a thermal gravimetric analysis plot comprising a mass loss of greater than 15% and less than about 18% when heated from about 25° C. to about 150° C.

In some embodiments, diHCl Salt Form I can be prepared as described in Example 4.

As used herein, the phrase "solid form" refers to a compound provided herein in either an amorphous state or a crystalline state ("crystalline form" or "crystalline solid" or "crystalline solid form"), whereby a compound provided herein in a crystalline state may optionally include solvent or water within the crystalline lattice, for example, to form a solvated or hydrated crystalline form. In some embodiments, the compound provided herein is in a crystalline state as described herein. Solid forms can be identified by the unique solid state signatures with respect to, for example, Differential Scanning Calorimetry (DSC), X-ray Powder Diffraction (XRPD), and other solid state methods. Further characterization with respect to water or solvent content of the crystalline forms can be gauged by any of the following methods for example, Thermogravimetric Analysis (TGA), DSC and the like.

As used herein, the term "peak" or "characteristic peak" refers to an XRPD reflection having a relative height/intensity of at least about 3% of the maximum peak height/intensity.

As used herein, the term "crystalline" or "crystalline form" refers to a crystalline solid form of a chemical compound, including, but not limited to, a single-component or multiple-component crystal form, e.g., including solvates, hydrates, clathrates, and a co-crystal. For example, crystalline means having a regularly repeating and/or ordered arrangement of molecules, and possessing a distinguishable crystal lattice. The term "crystalline form" is meant to refer to a certain lattice configuration of a crystalline substance. Different crystalline forms of the same substance typically have different crystalline lattices (e.g., unit cells), typically have different physical properties attributed to their different crystalline lattices, and in some instances, have different water or solvent content. The different crystalline lattices can be identified by solid state characterization methods such as by XRPD. Other characterization methods such as differential scanning calorimetry (DSC), thermogravimetric analysis (TGA), dynamic vapor sorption (DVS), and the like further help identify the crystalline form as well as help determine stability and solvent/water content.

For DSC, it is known that the temperatures observed for thermal events will depend upon sample purity and can also depend on the rate of temperature change, as well as sample preparation technique, and the instrument employed. Thus, the values reported herein relating to DSC thermograms can vary by plus or minus about 5° C. (i.e., ±about 5° C.). The values reported herein relating to DSC thermograms can also vary by plus or minus about 20 joules per gram (i.e., ±about 20 joules per gram).

For XRPD, the relative intensities of the peaks can vary, depending upon the sample preparation technique, the sample mounting procedure and the instrument employed. Moreover, instrument variation and other factors can often affect the 2θ values. Therefore, the peak assignments of diffraction patterns can vary by plus or minus about 0.2° (i.e., ±about 0.2°). For TGA, the temperature features reported herein can vary by plus or minus about 5° C. (i.e., ±about 5° C.). The TGA % weight changes reported herein over a specified temperature range can vary by plus or minus about 2% weight change (i.e., ±about 2% weight change) due to, for example, variations in sample quality and sample size. All X-ray powder diffraction patterns (diffractograms) were obtained using Cu-Kα radiation.

Further characterization with respect to hygroscopicity of the crystalline form can be gauged by, for example, Gravimetric Vapor Sorption (GVS). The GVS features can vary by plus or minus about 5% relative humidity (i.e., ±about 5% relative humidity). The GVS features can also vary by plus or minus about 2% weight change (i.e., ±about 2% weight change). One aspect of the present disclosure relates to a novel crystalline form of 5-{7-[({4-[2-(dimethylamino)-1,3-thiazol-4-yl]phenyl}methyl)(propyl)amino]-2,5-dimethylpyrazolo[1,5-a]pyrimidin-3-yl}-N,N,4-trimethylpyridin-2-amine (i.e., Compound 1) and processes related thereto. It is understood that peak intensities can vary from one diffractogram to another for the same crystalline form based on any number of factors that are known to those skilled in the art, such as, preferred orientation effects, preparation technique, the sample mounting procedure, the instrument employed, etc. In some instances, peak intensities can be rather dramatical. Accordingly, the diffraction peak intensities shown herein are illustrative and identical diffraction peak intensities are not necessarily required. Further, it is understood that those skilled in the art would readily be capable of comparing the diffractogram provided herein with a diffractogram generated for an unknown crystal form and confirm whether the diffractogram is characterizing the same crystal form as provided herein or a different form, or a mixture thereof.

Different crystalline forms of a particular substance, such as Compound 1 as described herein, can include both anhydrous forms of that substance and solvated/hydrated forms of that substance, where each of the anhydrous forms and solvated/hydrated forms are distinguished from each other by different XRPD patterns, or other solid state characterization methods, thereby signifying different crystalline lattices. In some instances, a single crystalline form (e.g., identified by a unique XRPD pattern) can have variable water or solvent content, where the lattice remains substantially unchanged (as does the XRPD pattern) despite the compositional variation with respect to water and/or solvent.

An XRPD pattern of reflections (peaks) is typically considered a fingerprint of a particular crystalline form. It is well known that the relative intensities of the XRPD peaks can widely vary depending on, inter alia, the sample preparation technique, crystal size distribution, filters used, the sample mounting procedure, and the particular instrument employed. In some instances, new peaks can be observed or existing peaks can disappear, depending on the type of the machine or the settings (for example, whether a Ni filter is used or not). As used herein, the term "peak" refers to a reflection having a relative height/intensity of at least about 3% or at least about 4% of the maximum peak height/intensity. Moreover, instrument variation and other factors can affect the 2-theta values. Thus, peak assignments, such as those reported herein, can vary by plus or minus about 0.2° (2-theta) and the term "substantially" as used in the context of XRPD herein is meant to encompass the above-mentioned variations.

In the same way, temperature readings in connection with DSC, TGA, or other thermal experiments can vary about ±3° C. depending on the instrument, particular settings, sample preparation, etc. Accordingly, a crystalline form reported herein having a DSC thermogram "substantially" as shown in any of the Figures is understood to accommodate such variation.

Crystalline forms of a substance can be obtained by a number of methods, as known in the art. Such methods include, but are not limited to, melt recrystallization, melt cooling, solvent recrystallization, recrystallization in confined spaces such as, e.g., in nanopores or capillaries, recrystallization on surfaces or templates such as, e.g., on polymers, recrystallization in the presence of additives, such as, e.g., co-crystal counter-molecules, desolvation, dehydration, rapid evaporation, rapid cooling, slow cooling, vapor diffusion, sublimation, exposure to moisture, grinding and solvent-drop grinding.

As used herein, the term "amorphous" or "amorphous form" is intended to mean that the substance, component, or product in question is not crystalline as determined, for instance, by XRPD or where the substance, component, or product in question, for example is not birefringent when viewed microscopically. For example, amorphous means essentially without regularly repeating arrangement of molecules or lacks the long range order of a crystal, i.e., amorphous form is non-crystalline. An amorphous form does not display a defined x-ray diffraction pattern with sharp maxima. In certain embodiments, a sample comprising an amorphous form of a substance can be substantially free of other amorphous forms and/or crystalline forms. For example, an amorphous substance can be identified by an XRPD spectrum having an absence of reflections.

As used herein, the term "substantially amorphous" means a majority of the weight of a sample or preparation of Compound 1 is amorphous and the remainder of the sample is a crystalline form of the same compound. In some embodiments, a substantially amorphous sample has less than about 5% crystallinity (e.g., about 95% of the non-crystalline form of the same compound), less than about 4% crystallinity (e.g., about 96% of the non-crystalline form of the same compound), less than about 3% crystallinity (e.g., about 97% of the non-crystalline form of the same compound), less than about 2% crystallinity (e.g., about 98% of the non-crystalline form of the same compound), less than about 1% crystallinity (e.g., about 99% of the non-crystalline form of the same compound), or about 0% crystallinity (e.g., about 100% of the non-crystalline form of the same compound). In some embodiments, the term "fully amorphous" means less than about 99% or about 0% crystallinity.

The compounds described herein, and their pharmaceutically acceptable salts, can be found together with other substances such as water and solvents, for example, in the form of hydrates or solvates. When in the solid state, the compounds described herein and salts thereof can occur in various forms and can, e.g., take the form of solvates, including hydrates. The compounds can be in any solid state form, such as a crystalline form, amorphous form, solvated form, etc. so unless clearly indicated otherwise, reference in the specification to compounds and salts thereof should be understood as reading on any solid state form of the compound.

As used herein, the term "solvate" refers to a solid form of a compound of the present invention (or a pharmaceutically acceptable salt thereof), which includes one or more molecules of a solvent in stoichiometric or non-stoichiometric amount. Where the solvent is water, the solvate is a hydrate. In some embodiments, the solid forms of the invention include hemihydrates, monohydrates, and dihydrates. In some embodiments, the solid form is anhydrous.

In some embodiments, the compounds described herein, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds disclosed herein.

As used herein, "about" means ±20% of the stated value, and includes more specifically values of ±10%, +5%, +2% and +1% of the stated value.

Chemical Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

As used herein, any "R" group(s) such as, without limitation, $R^1$ and $R^2$ represent substituents that can be attached to the indicated atom.

At various places in the present disclosure, rings are described (e.g., "a piperidine ring"). Unless otherwise specified, these rings can be attached to the rest of the molecule at any ring member as permitted by valency. For example, the term "a piperidine ring" may refer to a piperidin-1-yl, a pipieridin-2-yl, a piperidin-3-yl, or a piperidin-4-yl ring.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

For compounds of Formula (I), and pharmaceutically acceptable salts thereof, in which a variable appears more than once, each variable can be a different moiety independently selected from the group defining the variable. For example, where a structure is described having two R groups that are simultaneously present on the same compound, the two R groups can represent different moieties independently selected from the group defined for R.

Whenever a group is described as being "optionally substituted" that group may be unsubstituted, or may be substituted with one or more of the indicated substituents. Likewise, when a group is described as being "unsubstituted or substituted" if substituted, the substituent(s) may be selected from one or more of the indicated substituents. It is to be understood that substitution at a given atom is limited by valency. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, aryl, heteroaryl, heterocycloalkyl, aralkyl, heteroaralkyl, heterocycloalkyl(alkyl), hydroxy, alkoxy, acyl, cyano, halogen, C-amido, N-amido, S-sulfonamido, N-sulfonamido, C-carboxy, O-carboxy, isocyanato, thiocyanato, isothiocyanato, azido, nitro, sulfenyl, sulfinyl, sulfonyl, haloalkyl, haloalkoxy, trihalomethanesulfonyl, trihalomethanesulfonamido, amino, alkylamino, and dialkylamino, as defined herein.

As used herein, "$C_a$ to $C_b$" or "$C_{a-b}$" in which "a" and "b" are integers refer to the number of carbon atoms in an alkyl, alkylene, alkenyl, or alkynyl group, or the number of carbon atoms in the ring of a cycloalkyl, cycloalkenyl, or aryl group. That is, these groups can contain from "a" to "b", inclusive, carbon atoms. Thus, for example, a "$C_1$ to $C_4$ alkyl" or a "$C_{1-4}$" group refers to all alkyl groups having from 1 to 4 carbons, that is, $CH_3$—, $CH_3CH_2$—, $CH_3CH_2CH_2$, $(CH_3)_2CH$—, $CH_3CH_2CH_2CH_2$—, $CH_3CH_2CH(CH_3)$ and $(CH_3)_3C$—. If no "a" and "b" are designated with regard to an alkyl, alkenyl, alkynyl, cycloalkyl, cycloalkenyl, or aryl group, the broadest range described in these definitions is to be assumed.

In addition to the foregoing, as used in the specification and appended claims, unless specified to the contrary, the following terms have the meaning indicated:

As used herein, "alkyl" refers to a straight chain or branched hydrocarbon chain that comprises a fully saturated (no double or triple bonds) hydrocarbon group. The alkyl group can have 1 to 20 carbon atoms (whenever it appears herein, a numerical range such as "1 to 20" refers to each integer in the given range; e.g., "1 to 20 carbon atoms" means that the alkyl group can consist of 1 carbon atom, 2 carbon atoms, 3 carbon atoms, etc., up to and including 20 carbon atoms, although the present definition also covers the occurrence of the term "alkyl" where no numerical range is designated). In some embodiments, the alkyl group can have 1 to 10 carbon atoms. In some embodiments, the alkyl group can have 1 to 6 carbon atoms. The alkyl group of the compounds can be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, and hexyl. In some embodiments, an alkyl group can be substituted or unsubstituted.

As used herein, "alkenyl" refers to an alkyl group that contains in the straight or branched hydrocarbon chain one or more double bonds. Examples of alkenyl groups include allenyl, vinylmethyl, and ethenyl. In some embodiments, an alkenyl group can be unsubstituted or substituted.

As used herein, "alkynyl" refers to an alkyl group that contains in the straight or branched hydrocarbon chain one or more triple bonds. Examples of alkynyls include ethynyl and propynyl. An alkynyl group can be unsubstituted or substituted.

As used herein, "cycloalkyl" refers to a completely saturated (no double or triple bonds) mono- or multi-cyclic hydrocarbon ring system. When composed of two or more rings, the rings can be joined together in a fused, bridged, or spiro fashion. Cycloalkyl groups can contain 3 to 12 atoms in the ring(s) or 3 to 8 atoms in the ring(s). Typical cycloalkyl groups include, but are in no way limited to, cyclopropyl, cyclobutyl, cyclopentyl, cyclohexyl, cycloheptyl, cyclooctyl, and decahydronaphthalene. In some embodiments, a cycloalkyl group can be unsubstituted or substituted.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (i.e., an aromatic system), otherwise the group would be "aryl," as defined herein. When composed of two or more rings, the rings can be connected together in a fused, bridged, or spiro fashion. A cycloalkenyl can contain 3 to 12 atoms in the ring(s) or 3 to 8 atoms in the ring(s). An example is cyclohexenyl. In some embodiments, a cycloalkenyl group can be unsubstituted or substituted.

As used herein, "aryl" refers to a carbocyclic (all carbon) monocyclic or multicyclic aromatic ring system, including fused ring systems where two carbocyclic rings share a chemical bond, that has a fully delocalized pi-electron system throughout all the rings. The number of carbon atoms in an aryl group can vary. For example, the aryl group can be a $C_6$-$C_{14}$ aryl group, a $C_6$ or $C_{10}$ aryl group, or a $C_6$ aryl group. Examples of aryl groups include, but are not limited to, phenyl, 1-naphthyl, 2-naphthyl, anthracenyl, phenanthrenyl, and the like. In some embodiments, an aryl group can be substituted or unsubstituted. In some embodiments, aryl is phenyl or naphthyl. In some embodiments, aryl is phenyl.

As used herein, "heteroaryl" refers to a monocyclic or multicyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, pyridyl, pyrimidinyl, pyrazinyl, pyridazinyl, triazinyl, furyl, quinolyl, isoquinolyl, thienyl, imidazolyl, thiazolyl, indolyl, isoindolyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, dibenzo[b,d]furan, dibenzo[b,d]thiophene, phenanthridinyl, benzimidazolyl, pyrrolyl, quinolinyl, isoquinolinyl, benzisoxazolyl, imidazo[1,2-b]thiazolyl, and the like. A heteroaryl group can be substituted or unsubstituted. In some embodiments, the heteroaryl group has 5 to 10 ring members or 5 to 7 ring members. The heteroaryl group can be designated as "5-7 membered heteroaryl," "5-10 membered heteroaryl," or similar designations. In some embodiments, the heteroaryl can be a substituted or unsubstituted $C_1$-$C_{13}$ five-, six-, seven, eight-, nine-, ten-, up to 14-membered monocyclic, bicyclic, or tricyclic ring system including 1 to 5 heteroatoms selected from nitrogen, oxygen and sulfur. In some embodiments, the heteroaryl can be a substituted or unsubstituted $C_1$-$C_5$ five- or six-membered monocyclic ring including 1 to 5 heteroatoms selected from nitrogen, oxygen and sulfur. In some embodiments, the heteroaryl can be a substituted or unsubstituted $C_5$-$C_9$ eight-, nine- or ten-membered bicyclic ring system including 1 to 5 heteroatoms selected from nitrogen, oxygen and sulfur. In some embodiments, the heteroaryl can be a substituted or unsubstituted $C_8$-$C_{13}$ 13- or 14-membered tricyclic ring system including 1 to 5 heteroatoms selected from nitrogen, oxygen and sulfur. In some embodiments, the heteroaryl can be an azolyl such as imidazolyl, pyrazolyl, 1,2,3-triazolyl, 1,2,4-triazolyl, tetrazolyl, 1,2,4-thiadiazolyl, thiazolyl, isothiazolyl, oxazolyl, or isoxazolyl, each of which can be substituted or unsubstituted.

As used herein, "heterocycloalkyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system and optionally containing one or more unsaturated bonds situated in such a way, however, that a fully delocalized pi-electron system (aromatic system) does not occur in the monocyclic ring or in at least one ring of the bicyclic or tricyclic ring system. The heteroatom(s) is an element other than carbon including, but not limited to, oxygen, sulfur, and nitrogen. When composed of two or more rings, the rings can be joined together in a fused, bridged, or spiro fashion where the heteroatom(s) can be present in either a non-aromatic or aromatic ring in the ring system. Additionally, any nitrogen atoms in a heterocycloalkyl can be quaternized. Heterocycloalkyl groups can be connected to the rest of the molecule via a carbon atom (i.e., a C-linked heterocycloalkyl group) or via a heteroatom such as nitrogen (i.e., an N-linked heterocycloalkyl group), where valency allows. Heterocycloalkyl groups can be unsubstituted or substituted. In some embodiments, a heterocycloalkyl can be substituted with an oxygen or sulfur on a carbon adjacent to a hetero atom where the substituted ring system is a lactam, lactone, cyclic imide, cyclic thioimide or cyclic carbamate. Examples of such unsubstituted or substituted "heterocycloalkyl" groups include but are not limited to, aziridinyl, azetidinyl, tetrahydrofuranyl, 1,3-dioxinyl, 1,3-dioxanyl, 1,4-dioxanyl, 1,2-dioxolanyl, 1,3-dioxolanyl, 1,4-dioxolanyl, 1,3-oxathianyl, 1,4-oxathiinyl, 1,3-oxathiolanyl, 1,3-dithiolyl, 1,3-dithiolanyl, 1,4-oxathianyl, tetrahydro-1,4-thiazinyl, 2H-1,2-oxazinyl, maleimidyl, succinimidyl, dioxopiperazinyl, hydantoinyl, imidazolinyl, imidazolidinyl, isoxazolinyl, isoxazolidinyl, isoindolinyl, indolinyl, oxazolinyl, oxazolidinyl, oxazolidinonyl, thiazolinyl, thiazolidinyl, morpholinyl, oxiranyl, piperidinyl N-oxide, piperidinyl, piperazinyl, pyrrolidinyl, pyrrolidonyl, pyrrolidionyl, 4-piperidonyl, pyrazolinyl, pyrazolidinyl, 2-oxopyrrolidinyl, tetrahydropyranyl, 4H-pyranyl, tetrahydrothiopyranyl, 1,4-diazabicyclo[2.2.2]octane, 1,4-diazabicyclo[3.1.1]heptane, 2-azaspiro[3,3]heptane, 2,6-diazaspiro[3,3]heptane, 2-oxa-6-azaspiro[3,3]heptane, and their benzo-fused analogs (e.g., benzimidazolidinonyl, tetrahydroquinolinyl, and 3,4-methylenedioxyphenyl). The heterocycloalkyl group can be designated as "3-10 membered heterocycloalkyl" or similar designations. In some embodiments, the heterocycloalkyl can be a $C_2$-$C_{12}$ three-, four-, five-, six-, seven-, eight-, nine-, ten-, up to 13-membered monocyclic, bicyclic, or tricyclic ring system including 1 to 5 heteroatoms selected from nitrogen, oxygen and sulfur. In some embodiments, the heterocycloalkyl can be a substituted or unsubstituted $C_{2-6}$ three-, four-, five-, six-, or seven-membered monocyclic ring including 1 to 5 heteroatoms selected from nitrogen, oxygen and sulfur. In some embodiments, the heterocycloalkyl can be a substituted or unsubstituted $C_2$-$C_{10}$ four-, five-, six-, seven-, eight-, nine-, ten- or eleven-membered bicyclic ring system including 1 to 5 heteroatoms selected from nitrogen, oxygen and sulfur. In some embodiments, the heterocycloalkyl can be a substituted or unsubstituted $C_7$-$C_{12}$ 12- or 13-membered tricyclic ring system including 1 to 5 heteroatoms selected from nitrogen, oxygen and sulfur. In preferred six membered monocyclic heterocycloalkyls, the heteroatom(s) are selected from one up to three of O (oxygen), N (nitrogen) or S (sulfur), and in preferred five membered monocyclic heterocycloalkyls, the heteroatom(s) are selected from one or two heteroatoms selected from O (oxygen), N (nitrogen) or S (sulfur). In some embodiments, the heterocycloalkyl can be aziridinyl, azetidinyl, tetrahydrofuranyl, 1,3-dioxinyl, 1,3-dioxanyl, 1,4-dioxanyl, 1,2-dioxolanyl, 1,3-dioxolanyl, 1,3-oxathianyl, 1,4-oxathianyl, 1,3-oxathiolanyl, 1,3-dithiolyl, 1,3-dithiolanyl, 1,4-oxathianyl, tetrahydro-1,4-thiazinyl, imidazolinyl, imidazolidinyl, isoxazolinyl, isoxazolidinyl, isoindolinyl, indolinyl, oxazolinyl, oxazolidinyl, thiazolinyl, thiazolidinyl, morpholinyl, oxiranyl, piperidinyl, piperazinyl, pyrrolidinyl, pyrazolinyl, pyrazolidinyl, tetrahydropyranyl, tetrahydrothiopyranyl, 1,4-diazabicyclo[2.2.2]octane, 1,4-diazabicyclo[3.1.1]heptane, 2-azaspiro[3,3]heptane, 2,6-diazaspiro[3,3]heptane, tetrahydroquinolinyl, 1,2,3,4-tetrahydroisoquinolinyl, 1,2,3,4-tetrahydro-2,6-naphthyridinyl, 1,2,3,4-tetrahydro-2,7-naphthyridinyl, 1,2,3,4-tetrahydro-1,7-naphthyridinyl, 1,2,3,4-tetrahydro-1,6-naphthyridinyl, 5,6,7,8-tetrahydropyrido[2,3-d]pyrimidinyl, 5,6,7,8-tetrahydropyrido[3,4-d]pyrimidinyl, [1,3]dioxolo[4,5-c]pyridinyl, [1,3]dioxolo[4,5-b]pyridinyl, [1,3]dioxolo[4,5-d]pyrimidinyl or 3,4-methylenedioxyphenyl.

As used herein, "heteroaralkyl" refers to a heteroaryl group connected, as a substituent, via an alkylene group. The alkylene and heteroaryl group of heteroaralkyl can be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl) and their benzo-fused analogs.

"Alkylene groups" are straight-chained $—CH_2—$ tethering groups, forming bonds to connect molecular fragments via their terminal carbon atoms. Alkylene groups can have, for example, from 1 to 10 carbon atoms, from 1 to 6 carbon atoms, or from 1 to 3 carbon atoms. Examples of alkylene groups include but are not limited to methylene ($—CH_2—$), ethylene ($CH_2CH_2—$), propylene ($—CH_2CH_2CH_2—$), and butylene ($—CH_2CH_2CH_2CH_2—$). An alkylene group can be unsubstituted, or can be substituted by replacing one or more hydrogen of the alkylene group with a substituent(s) listed under the definition of "substituted."

As used herein, "alkoxy" refers to the formula OR wherein R is an alkyl defined herein. A non-limiting list of alkoxys are methoxy, ethoxy, n-propoxy, 1-methylethoxy (iso-propoxy), n-butoxy, iso-butoxy, sec-butoxy, and tert-butoxy. An alkoxy can be substituted or unsubstituted.

As used herein, "acyl" refers to $—C(=O)R$, wherein R is a hydrogen, an $C_1$-$C_{14}$ alkyl, an $C_2$-$C_{14}$ alkenyl, an $C_2$-$C_{14}$ alkynyl, a $C_3$-$C_{14}$ cycloalkyl, a $C_3$-$C_{14}$ cycloalkenyl, $C_6$ or $C_{10}$ aryl, heteroaryl, heterocycloalkyl, aralkyl, heteroaralkyl, or heterocycloalkyl(alkyl). Examples include formyl, acetyl, propanoyl, benzoyl, and acryl. When R is methyl, the acyl group is also referred to as acetyl. An acyl can be substituted or unsubstituted.

As used herein, "haloalkyl" refers to an alkyl group in which one or more of the hydrogen atoms are replaced by a halogen (e.g., mono-haloalkyl, di-haloalkyl, and tri-haloalkyl). Such groups include but are not limited to, chloromethyl, fluoromethyl, difluoromethyl, trifluoromethyl, 1-chloro-2-fluoromethyl, and 2-fluoroisobutyl.

As used herein, "amino" refers to a $—NH_2$ group.

As used herein, "cyano" refers to a —CN group.

As used herein, "hydroxy" refers to a —OH group.

A "carbonyl" refers to a C=O group.

As used herein, "nitro" refers to a $—NO_2$ group.

As used herein, "oxo refers to the =O substituent.

As used herein, "trifluoromethyl" refers to the $—CF_3$ group.

As used herein, "trifluoromethoxy" refers to the $—OCF_3$ radical.

The term "halogen atom," "halogen" or "halo" as used herein, means a fluorine, chlorine, bromine or iodine atom (i.e., bromo, chloro, fluoro or iodo).

Where the number of substituents is not specified (e.g., haloalkyl), there may be one or more substituents present. For example "haloalkyl" may include one or more of the same or different halogens.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, Protective Groups in Organic Synthesis, 3. Ed. John Wiley & Sons, 1999, and in J. F. W. McOmie, Protective Groups in Organic Chemistry Plenum Press, 1973, both of which are hereby incorporated by reference for the limited purpose of disclosing suitable protecting groups. The protecting group moiety can be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g., methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl, or t-butyldiphenylsilyl); esters (e.g., benzoate ester); carbonates (e.g., methoxymethylcarbonate); sulfonates (e.g., tosylate or mesylate); acyclic ketal (e.g., dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4"-trimethoxytrityl (TMTr); and those described herein).

The phrase "pharmaceutically acceptable" is employed herein to refer to those compounds, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds described herein can be used in neutral form such as a free acid or free base form. Alternatively, the compounds can be used in the form of acid or base addition salts. The term "pharmaceutically acceptable salt" refers to salts of a compound having an acidic or basic moiety which are not biologically or otherwise undesirable for use in a pharmaceutical. In many cases, the compounds disclosed herein are capable of forming acid and/or base salts by virtue of the presence of an acidic or basic moiety (e.g., amino and/or carboxyl groups or groups similar thereto). Pharmaceutically acceptable acid addition salts can be formed by combining a compound having a basic moiety with inorganic acids and organic acids. Lists of suitable salts are found in WO 87/05297, Johnston et al., published Sep. 11, 1987; Remington's Pharmaceutical Sciences, 17th ed., Mack Publishing Company, Easton, Pa., 1985, p. 1418; and *J. Pharm. Sci.,* 66, 2 (1977), each of which is incorporated herein by reference in its entirety. A reference for the preparation and selection of pharmaceutical salts of the present disclosure is P. H. Stahl & C. G. Wermuth "Handbook of Pharmaceutical Salts," *Verlag Helvetica Chimica Acta,* Zurich, 2002 which is incorporated herein by reference in its entirety.

Methods of Use

Provided herein are methods of treating congenital adrenal hyperplasia (CAH) comprising administering a compound of Formula (I) or pharmaceutically acceptable salt thereof, to normalize or partially normalize levels of biomarkers associated with congenital adrenal hyperplasia. In some embodiments, normalizing or partially normalizing levels of biomarkers comprises reducing levels of elevated biomarkers or increasing levels of depressed biomarkers as compared to subject without CAH. In some embodiments, the congenital adrenal hyperplasia (CAH) is classic congenital adrenal hyperplasia (CAH). In some embodiments, the method further comprises administering a glucocorticoid to the subject. In some embodiments, the glucocorticoid is hydrocortisone, prednisone, prednisolone or dexamethasone. In some embodiments, the classic CAH is due to 21-hydroxylase deficiency. In some embodiments, the subject has a mutation in the CYP21A2 gene located on chromosome 6p21. In some embodiments, the subject does not have a mutation of the 11β-hydroxylase gene CYP11B1 (11β-OH CAH).

Provided herein is a method of treating congenital adrenal hyperplasia in a subject in need thereof comprising administering a compound of Formula (I), or a pharmaceutically acceptable salt thereof, in an amount sufficient to reduce the level of one or more biomarkers associated with congenital adrenal hyperplasia. In some embodiments, the biomarkers are selected from (a) 17-hydroxyprogesterone (17-OHP); (b) testosterone; and (c) androstenedione in the subject. In some embodiments, the congenital adrenal hyperplasia (CAH) is classic congenital adrenal hyperplasia (CAH). In some embodiments, the method further comprises administering a glucocorticoid to the subject. In some embodiments, the glucocorticoid is hydrocortisone, prednisone, prednisolone or dexamethasone. In some embodiments, the classic CAH is due to 21-hydroxylase deficiency. In some embodiments, the subject has a mutation in the CYP21A2 gene located on chromosome 6p21. In some embodiments, the subject does not have a mutation of the 11β-hydroxylase gene CYP11B1 (11β-OH CAH).

In some embodiments, the reduction in level of any of the biomarkers (e.g., any of 17-OHP, testosterone, and androstenedione) is determined by comparing the level of the biomarker as measured during the circadian release on a day prior to administering the compound of Formula (I), or a pharmaceutically acceptable salt thereof and the level of the biomarker as measured during the circadian release on the day after administering the compound of Formula (I), or a pharmaceutically acceptable salt thereof. A day prior to administering the compound of Formula (I) applies to a subject that has not previously been administered the compound of Formula (I) within at least the past 24 hours.

In some embodiments, the circadian release of biomarkers associated with CAH occurs between the hours of 2 a.m. and 10 a.m. In other embodiments, the circadian release of biomarkers associated with CAH occurs between the hours of 6 a.m. and 10 a.m. In some embodiments, the CAH is classic CAH.

In some embodiments of any of the methods disclosed herein, the compound of Formula (I), or a pharmaceutically acceptable salt, is administered to the subject at nighttime or administration prior to sleep (i.e., bedtime administration). In some embodiments, the compound of Formula (I), or a pharmaceutically acceptable salt thereof, is administered three to eight hours prior to the circadian release of the biomarker. In some embodiments, the compound of Formula (I), or a pharmaceutically acceptable salt thereof, is administered six to eight hours prior to the circadian release of the biomarker. Administration prior to the circadian release can be adapted for shift workers (e.g., those who work at night and sleep during the day), in which case administration will not necessarily occur at nighttime. Administration is therefore dependent upon the expected circadian release of the biomarker, and can vary depending upon the individual's (i.e., subject, patient) particular work and sleep patterns.

In some embodiments of the methods provided herein, the level of 17-hydroxyprogesterone is reduced by at least 10%, at least 15%, at least 20%, at least 25%, at least 30%, at least 35%, at least 40%, at least 50%, at least 55% or at least 60% from pre-administration levels. In some embodiments, the level of 17-hydroxyprogesterone is reduced by at least 25%. In some embodiments, the level of 17-hydroxyprogesterone is reduced by at least 50%. In some embodiments of the methods provided herein, the level of 17-hydroxyprogesterone is reduced by an amount of from about 10% to about 90%, about 15% to about 90%, about 20% to about 90%, about 25% to about 90%, about 30% to about 90%, about 35% to about 90%, about 40% to about 90%, about 50% to about 90%, about 55% to about 90%, or about 60% to about 90% from pre-administration levels.

In some embodiments, the level of 17-hydroxyprogesterone is reduced to a level within the range of 17-hydroxyprogesterone expected for a subject without CAH, i.e., less than 1,000 ng/dL or less than 200 ng/dL.

In some embodiments of the methods provided herein, the level of adrenocorticotropic hormone is reduced by at least 10%, at least 15%, at least 20%, at least 25%, at least 30%, at least 35%, at least 40%, at least 50%, at least 55% or at least 60% from pre-administration levels. In some embodiments, the level of adrenocorticotropic hormone is reduced by at least 25%. In some embodiments, the level of adrenocorticotropic hormone is reduced by at least 40%. In some embodiments, the level of adrenocorticotropic hormone is reduced by at least 50%.

In some embodiments of the methods provided herein, the level of adrenocorticotropic hormone is reduced by an amount of from about 10% to about 90%, about 15% to about 90%, about 20% to about 90%, about 25% to about 90%, about 30% to about 90%, about 35% to about 90%, about 40% to about 90%, about 50% to about 90%, about 55% to about 90%, or about 60% to about 90% from pre-administration levels.

In some embodiments, the level of adrenocorticotropic hormone is reduced to a level within the range of adrenocorticotropic hormone expected for a subject without CAH.

In some embodiments of the methods provided herein, the level of androstenedione is reduced by at least 10%, at least 15%, at least 20%, at least 25%, at least 30%, at least 35%, at least 40%, at least 50%, at least 55% or at least 60% from pre-administration levels. In some embodiments, the level of androstenedione is reduced by at least 25%. In some embodiments, the level of androstenedione is reduced by at least 30%. In some embodiments, the level of androstenedione is reduced by at least 50%.

In some embodiments of the methods provided herein, the level of androstenedione is reduced by an amount of from about 10% to about 90%, about 15% to about 90%, about 20% to about 90%, about 25% to about 90%, about 30% to about 90%, about 35% to about 90%, about 40% to about 90%, about 50% to about 90%, about 55% to about 90%, or about 60% to about 90% from pre-administration levels.

In some embodiments, the level of androstenedione is reduced to a level within the range of androstenedione expected for a subject without CAH, i.e., less than 200 ng/dL.

Also provided herein are methods for reducing the severity of one or more symptoms selected from hirsutism, precocious puberty, fertility problems, acne, and growth impairment in a subject having classic congenital adrenal hyperplasia, comprising administering a compound of Formula (I), or a pharmaceutically acceptable salt thereof, in an amount sufficient to reduce one or more biomarker of CAH in a subject, e.g., reduce the androstenedione in the subject. Growth impairment can refer to, e.g., accelerated height velocity, accelerated weight velocity, and/or accelerated bone age. In some embodiments, the method further comprises administering a glucocorticoid to the subject. In some embodiments, the glucocorticoid is hydrocortisone, prednisone, prednisolone or dexamethasone. In some embodiments, the classic congenital adrenal hyperplasia is due to 21-hydroxylase deficiency. In some embodiments, the subject has a mutation in the CYP21A2 gene located on chromosome 6p21. In some embodiments, the subject does not have a mutation of the 11β-hydroxylase gene CYP11B1 (11β-OH CAH).

Provided herein are methods for reducing the level of one or more biomarkers in a subject having congenital adrenal hyperplasia comprising administering to the subject a compound of Formula (I), or a pharmaceutically acceptable salt thereof. In some embodiments, the one or more biomarkers are selected from (a) 17-hydroxyprogesterone (17-OHP); (b) testosterone; and (c) androstenedione. In some embodiments, the congenital adrenal hyperplasia (CAH) is classic congenital adrenal hyperplasia (CAH). In some embodiments, the method further comprises administering a glucocorticoid to the subject. In some embodiments, the glucocorticoid is hydrocortisone, prednisone, prednisolone or dexamethasone. In some embodiments, the classic CAH is due to 21-hydroxylase deficiency. In some embodiments, the subject has a mutation in the CYP21A2 gene located on chromosome 6p21. In some embodiments, the subject does not have a mutation of the 11β-hydroxylase gene CYP11B1 (11β-OH CAH).

Provided herein are methods for reducing the dosage of corticosteroid administered to a subject having congenital adrenal hyperplasia for controlling congenital adrenal hyperplasia comprising administering to the subject a compound of Formula (I), or a pharmaceutically acceptable salt thereof. In some embodiments, the corticosteroid is a glucocorticoid. In some embodiments, the glucocorticoid is hydrocortisone, prednisone, prednisolone or dexamethasone.

Also provided herein is a method of reducing the severity of one or more side effects of glucocorticoid treatment in a subject having congenital adrenal hyperplasia comprising administering to the subject a compound of Formula (I), or a pharmaceutically acceptable salt thereof. The long-term effects of glucocorticoid treatment are well documented in the art (see, e.g., Oray, M. et al. (2016): Long-term effect of glucocorticoids, Expert Opinion on Drug Safety. DOI: 10.1517/14740338.2016.1140743). Such side effects are associated with every biological system, e.g., musculoskeletal (e.g., osteoporosis, avascular necrosis of bone, and myopathy), endocrine and metabolic (e.g., hyperglycemia, diabetes mellitus, dyslipidemia, weight gain, Cushing syndrome, Cushingoid features, growth suppression, adrenal suppression), gastrointestinal (e.g., gastritis, peptic ulcer, gastrointestinal bleeding, visceral perforation, hepatic steatosis, pancreatitis), cardiovascular (e.g., hypertension, coronary heart disease, ischemic heart disease, heart failure), dermatologic (e.g., dermatoprosis, skin atrophy, ecchymosis, purpura, erosions, striae, delayed wound healing, easy bruising, acne, hirsutism, and hair loss), neuropsychiatric (e.g., mood changes, depression, euphoria, mood lability, irritability, akathisia, anxiety, cognitive impairment, psychosis, dementia, and delirium), ophthalmologic (e.g., cataract, glaucoma, ptosis, mydriasis, opportunistic ocular infections, and central serous chorioretinopathy), and immunologic (e.g., suppression of cell-mediated immunity, predisposition to infections, and reactivation of latent infections). In some embodiments, the congenital adrenal hyperplasia is classic congenital adrenal hyperplasia (CAH). In some embodiments, the method further comprises administering a glucocorticoid to the subject. In some embodiments, the glucocorticoid is hydrocortisone, prednisone, prednisolone or dexamethasone. In some embodiments, the classic CAH is due to 21-hydroxylase deficiency. In some embodiments, the subject has a mutation in the CYP21A2 gene located on chromosome 6p21. In some embodiments, the subject does not have a mutation of the 11β-hydroxylase gene CYP11B1 (11β-OH CAH).

Accordingly, in some embodiments, the side effects of glucocorticoid treatment are selected from osteoporosis, avascular necrosis of bone, myopathy, hyperglycemia, diabetes mellitus, dyslipidemia, weight gain, Cushing syndrome, Cushingoid features, growth suppression, adrenal suppression, gastritis, peptic ulcer, gastrointestinal bleeding, visceral perforation, hepatic steatosis, pancreatitis, hypertension, coronary heart disease, ischemic heart disease, heart failure, dermatoprosis, skin atrophy, ecchymosis, purpura, erosions, striae, delayed wound healing, easy bruising, acne, hirsutism, hair loss, mood changes, depression, euphoria, mood lability, irritability, akathisia, anxiety, cognitive impairment, psychosis, dementia, delirium, cataract, glaucoma, ptosis, mydriasis, opportunistic ocular infections, central serous chorioretinopathy, suppression of cell-mediated immunity, predisposition to infections, reactivation of latent infections, and any combination thereof.

Provided herein are methods of treating congenital adrenal hyperplasia in a subject comprising (i) measuring the level of one or more biomarkers selected from (a) 17-hydroxyprogesterone (17-OHP); (b) testosterone; and (c) androstenedione in a biological sample obtained from the subject; (ii) analyzing the level of the one or more biomarkers to determine if the level of the one or more biomarkers is elevated compared to a healthy subject not having congenital adrenal hyperplasia; and (iii) administering to the subject a compound of Formula (I), or a pharmaceutically acceptable salt thereof if the subject is determined to have elevated levels of the one or more biomarkers. In some embodiments, the method further comprises (iv) measuring the level of the one or more biomarkers after administering a compound of Formula (I), or a pharmaceutically acceptable salt thereof, in a biological sample obtained from the subject to determine whether the subject has reduced levels of the one or more biomarkers as compared with the measurement of step (i). In some embodiments, the method further comprises (v) continuing the administration of the compound of Formula (I), or a pharmaceutically acceptable salt thereof if the subject has reduced levels of the one or more biomarkers. In some embodiments, steps (i) and (iv) are performed on biological samples taken from the subject in a similar manner and within a same time of day window. In some embodiments, steps (i) and (iv) are performed on biological samples taken from the subject within the time of day window from 2 a.m. to 10 a.m. In some embodiments, steps (i) and (iv) are performed on biological samples taken from the subject within the time of day window from 6 a.m. to 10 a.m. In some embodiments, steps (i) and (iv) comprise measuring the levels of at least two biomarkers selected from (a) 17-hydroxyprogesterone (17-OHP); (b) testosterone; and (c) androstenedione. In some embodiments, steps (i) and (iv) comprise measuring the levels of (a) 17-hydroxyprogesterone (17-OHP); (b) testosterone; and (c) androstenedione. In some embodiments, step (i) comprises measuring the level of 17-hydroxyprogesterone (17-OHP), wherein the level of 17-hydroxyprogesterone (17-OHP) is elevated when it is greater than or equal to 1,000 ng/dL. In some embodiments, step (i) comprises measuring the level of androstenedione, wherein the level of androstenedione is elevated when it is greater than 200 ng/dL. In some embodiments, the congenital adrenal hyperplasia is classic congenital adrenal hyperplasia (CAH). In some embodiments, the method further comprises administering a glucocorticoid to the subject. In some embodiments, the glucocorticoid is hydrocortisone, prednisone, prednisolone or dexamethasone. In some embodiments, the classic CAH is due to 21-hydroxylase deficiency. In some embodiments, the subject has a mutation in the CYP21A2 gene located on chromosome 6p21. In some embodiments, the subject does not have a mutation of the 11β-hydroxylase gene CYP11B1 (11β-OH CAH).

As used herein, the term "contacting" refers to the bringing together of indicated moieties in an in vitro system or an in vivo system. For example, "contacting" $CRF_1$ with a compound of Formula (I) includes the administration of the compound to a subject, such as a human, as well as, for example, introducing the compound into a sample containing a cellular or purified preparation containing $CRF_1$.

As used herein, the term "subject" refers to any animal, including mammals, preferably mice, rats, other rodents, rabbits, dogs, cats, swine, cattle, sheep, horses, or primates, and most preferably humans. In the context of a clinical trial or screening or activity experiment the subject can be a healthy volunteer or healthy participant without an underlying $CRF_1$ mediated disorder or condition or a volunteer or participant that has received a diagnosis for a disorder or condition in need of medical treatment as determined by a health care professional. In the context outside of a clinical trial a subject under the care of a health care professional who has received a diagnosis for a disorder or condition is typically described as a patient. In some embodiments, the subject has experienced and/or exhibited at least one symptom of the disease or disorder to be treated and/or prevented. In some embodiments, the subject has been identified or diagnosed as having congenital adrenal hyperplasia (CAH). In some embodiments, the subject is suspected of having CAH. In some embodiments, the subject has a clinical record indicating that the subject has CAH (and optionally the clinical record indicates that the subject should be treated with any of the compositions provided herein). In some embodiments, the subject is a pediatric subject.

The term "pediatric subject" as used herein refers to a subject under the age of 21 years at the time of diagnosis or treatment. The term "pediatric" can be further divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman et al., *Textbook of Pediatrics,* 15th Ed. Philadelphia: W.B. Saunders Company, 1996; Rudolph et al., *Rudolph's Pediatrics,* 21st Ed. New York: McGraw-Hill, 2002; and Avery et al., *Pediatric Medicine,* 2nd Ed. Baltimore: Williams & Wilkins; 1994. In some embodiments, a pediatric subject is from birth through the first 28 days of life, from 29 days of age to less than two years of age, from two years of age to less than 12 years of age, or 12 years of age through 21 years of age (up to, but not including, the twenty-second birthday). In some embodiments, a pediatric subject is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from 6 years of age to less than 13 years of age, from 10 years of age to less than 15 years of age, or from 15 years of age to less than 22 years of age.

As used herein, the terms, "treat" and "treatment," refer to medical management of a disease, disorder, or condition of a subject (i.e., patient) (see, e.g., Stedman's Medical Dictionary). In general, an appropriate dose and treatment regimen provide the $CRF_1$ antagonist in an amount sufficient to provide therapeutic and/or prophylactic benefit. Therapeutic benefit for subjects to whom the $CRF_1$ antagonist compound(s) described herein are administered, includes, for example, an improved clinical outcome, wherein the object is to prevent or slow or retard (lessen) an undesired physiological change associated with the disease, or to prevent or slow or retard (lessen) the expansion or severity of such disease. As discussed herein, effectiveness of the one or more $CRF_1$ antagonists can include beneficial or desired clinical results that comprise, but are not limited to, abatement, lessening, or alleviation of symptoms that result from or are associated with the disease to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; and/or overall survival.

"Treatment" can also mean prolonging survival when compared to expected survival if a subject were not receiving treatment. Subjects in need of treatment include those who already have the disease or disorder as well as subjects prone to have or at risk of developing the disease or disorder, and those in which the disease, condition, or disorder is to be prevented (i.e., decreasing the likelihood of occurrence or recurrence of the disease or disorder).

As used herein, the term "preventing" or "prevention" refers to preventing the onset of the indicated disease; for example, preventing a disease, condition or disorder in a subject who can be predisposed to the disease, condition or disorder but does not yet experience or display the pathology and/or symptomatology of the disease.

As used herein, "therapeutically effective amount" is an amount of the compound of the invention, or a pharmaceutically acceptable salt thereof, or an amount of a pharmaceutical composition comprising the compound of the invention, or a pharmaceutically acceptable salt thereof, which is sufficient to achieve the desired effect and can vary according to the nature and severity of the disease condition, and the potency of the compound. A therapeutic effect is the relief, to some extent, of one or more of the symptoms of the disease, and can include curing a disease. "Curing" means that the symptoms of active disease are eliminated. However, certain long-term or permanent effects of the disease can exist even after a cure is obtained (such as, e.g., extensive tissue damage).

As used herein, "time of day window" refers to a period of time defined by a window start time and a window stop time. These times all refer to local times where a sample was taken. The phrase "same time of day window" when referring to samples taken from the subject mean, e.g., that a sample taken at 8:15 a.m. and a sample taken at 9:15 a.m. are considered to be taken in the same time of day window of, e.g., 2 a.m. to 10 a.m. or 6 a.m. to 10 a.m.

Various indicators for determining the effectiveness of a method for treating CAH are known to those skilled in the art. Example of suitable indicators include, but are not limited to, a reduction in 17-OHP, and androstenedione compared to non-treatment or reduction of amount of glucocorticoid (e.g., hydrocortisone) administered per day.

In some embodiments, a compound of Formula (I), or a pharmaceutically acceptable salt thereof, can result in at least a 1, 2, 3, 4, 5, 10, 15, 20, 25, 50, 75, 100-fold or more decrease in 17-OHP plasma levels during 6.00 to 10.00 relative to pre-treatment levels in a subject, as determined after completion of the treatment regime (for example, 1 week after completion). In some embodiments, a compound of Formula (I), or a pharmaceutically acceptable salt thereof, can result in a decrease in androstenedione plasma levels during 6.00 to 10.00 relative to pre-treatment levels in the range of about 2 to about 5 fold, about 10 to about 20 fold, about 15 to about 40 fold, or about 50 to about 100 fold. In some embodiments, a compound of Formula (I), or a pharmaceutically acceptable salt thereof, can result in a decrease in testosterone plasma levels during 6.00 to 10.00 relative to pre-treatment levels in the range of 2 to 5 fold, 10 to 20 fold, 15 to 40 fold, or 50 to 100 fold. In some embodiments, administration of a compound of Formula (I), or a pharmaceutically acceptable salt thereof, can result in decrease in glucocorticoid (e.g., hydrocortisone) administered per day compared to the current standard of care for CAH, or can achieve the same plasma levels of at least one selected from 17-OHP, androstenedione and testosterone plasma levels during 6.00 to 10.00 as that of glucocorticoid (e.g., hydrocortisone) monotherapy, as determined after completion of the treatment regime (for example, 1, 2, 3, 4, 5, 6, or 7 weeks after completion).

In some embodiments, a compound of Formula (I), or a pharmaceutically acceptable salt thereof, can decrease the percentage of subjects that experience complications from CAH compared to the percentage of subjects that experience complication being treated with glucocorticoids (e.g., hydrocortisone) monotherapy. For example, the percentage of subjects being treated with a compound of Formula (I), or a pharmaceutically acceptable salt thereof, that experience complications can be 10%, 25%, 40%, 50%, 60%, 70%, 80% and 90% less compared to subjects being treated with glucocorticoids (e.g., hydrocortisone).

In another embodiment, a method is provided for antagonizing $CRF_1$ in a cell comprising contacting the cell and a compound of Formula (I), including specific compounds described herein, for a time sufficient and under appropriate conditions to permit interaction between the cell and the compound. In certain embodiments, the cell is in a subject who is in need of treatment with a compound disclosed herein.

Combination Therapies

The compounds of Formula (I), and pharmaceutically acceptable salts thereof, can be used in combination treatments where the compound of Formula (I), or a pharmaceutically acceptable salt thereof, is administered in conjunction with other treatments such as the administration of one or more additional therapeutic agents. The additional therapeutic agents are typically those which are normally used to treat the particular condition to be treated. The additional therapeutic agents can include, glucocorticoids (e.g., hydrocortisone) or mineralocorticoids (e.g., fludrocortisone). Examples of additional therapeutic agents that can be administered in combination with compounds of Formula (I), or a pharmaceutically acceptable salt thereof, include, but are not limited to glucocorticoids (e.g., hydrocortisone) and mineralocorticoids (e.g., fludrocortisone). Other treatments that can be administered in conjunction with compounds of Formula (I), or pharmaceutically acceptable salts thereof, include, but are not limited to surgical intervention.

A compound of Formula (I), or a pharmaceutically acceptable salt thereof, can be administered with one or more additional agent(s) together in a single pharmaceutical composition, or as two or more separate pharmaceutical compositions.

The order of administration of a compound of Formula (I), or a pharmaceutically acceptable salt thereof, can be administered concurrently with any/all additional agents, or sequentially with any/all additional agents, in either order (e.g., a compound of Formula (I), or a pharmaceutically acceptable salt thereof, can be administered before, or after, any/all additional agents).

Pharmaceutical Compositions, Formulation, and Dosage Forms

The present disclosure further provides for compositions comprising any one of the compounds as disclosed and described herein (a compound of Formula (I), including specific compounds described herein) and pharmaceutically acceptable salts thereof, and an excipient such as a pharmaceutically acceptable excipient for use in the methods for treating CAH. A pharmaceutically acceptable excipient is a physiologically and pharmaceutically suitable non-toxic and inactive material or ingredient that does not interfere with the activity of the drug substance; an excipient also can be called a carrier. The formulation methods and excipients described herein are exemplary and are in no way limiting. Pharmaceutically acceptable excipients are well known in the pharmaceutical art and described, for example, in Rowe et al., Handbook of Pharmaceutical Excipients: A Comprehensive Guide to Uses, Properties, and Safety, $5^{th}$ Ed., 2006, and in *Remington: The Science and Practice of Pharmacy* (Gennaro, $21^{st}$ Ed. Mack Pub. Co., Easton, PA (2005)). Exemplary pharmaceutically acceptable excipients include sterile saline and phosphate buffered saline at physiological pH. Preservatives, stabilizers, dyes, buffers, and the like can be provided in the pharmaceutical composition. In addition, antioxidants and suspending agents can also be used.

For compositions formulated as liquid solutions, acceptable carriers and/or diluents include saline and sterile water, and can optionally include antioxidants, buffers, bacteriostats and other common additives. The compositions can also be formulated as pills, capsules, granules, or tablets which contain, in addition to $CRF_1$ antagonist, diluents, dispersing and surface active agents, binders, and lubricants. One skilled in this art can further formulate the $CRF_1$ antagonist in an appropriate manner, and in accordance with accepted practices, such as those disclosed in Remington, supra.

Methods of administration include systemic administration of a $CRF_1$ antagonist described herein, preferably in the form of a pharmaceutical composition as discussed above. As used herein, systemic administration includes oral and parenteral methods of administration. For oral administration, suitable pharmaceutical compositions include powders, granules, pills, tablets, and capsules as well as liquids, syrups, suspensions, and emulsions. These compositions can also include flavorants, preservatives, suspending, thickening and emulsifying agents, and other pharmaceutically acceptable additives. For parental administration, the compounds as disclosed herein can be prepared in aqueous injection solutions which can contain, in addition to the $CRF_1$ antagonist, buffers, antioxidants, bacteriostats, and other additives commonly employed in such solutions.

As described herein optimal doses are generally determined using experimental models and/or clinical trials. The optimal dose of the $CRF_1$ antagonist can depend upon the body mass, weight, blood volume, or other individual characteristics of the subject. For example, a person skilled in the medical art can consider the subject's condition, that is, stage of the disease, severity of symptoms caused by the disease, general health status, as well as age, gender, and weight, and other factors apparent to a person skilled in the medical art. The use of the minimum dose that is sufficient to provide effective therapy is usually preferred. Subjects can generally be monitored for therapeutic effectiveness by clinical evaluation and using assays suitable for the condition being treated or prevented, which methods will be familiar to those having ordinary skill in the art and are described herein. The level of a compound that is administered to a subject can be monitored by determining the level of the compound in a biological fluid, for example, in the blood, blood fraction (e.g., plasma, serum), and/or in the urine, and/or other biological sample from the subject. Any method practiced in the art to detect the compound can be used to measure the level of compound during the course of a therapeutic regimen.

The pharmaceutical compositions described herein that comprise at least one of the $CRF_1$ antagonist compounds described herein can be administered to a subject in need by any one of several routes that effectively deliver an effective amount of the compound. Such administrative routes include, for example, oral, parenteral (e.g., subcutaneous, intravenous, intramuscular, intrasternal, intracavernous), enteral, rectal, intranasal, buccal, sublingual, intramuscular, and transdermal.

Pharmaceutical compositions for oral administration can be obtained by any suitable method, typically by uniformly mixing the compound(s) with liquids or finely divided solid carriers, or both, in the required proportions and then, if necessary, processing the mixture, after adding suitable auxiliaries, if desired, forming the resulting mixture into a desired shape to obtain tablets or dragee cores.

Conventional excipients, such as binding agents, fillers, adjuvant, carrier, acceptable wetting agents, tabletting lubricants and disintegrants can be used in tablets and capsules for oral administration. Liquid preparations for oral administration can be in the form of solutions, emulsions, aqueous or oily suspensions and syrups. Alternatively, the oral compositions can be in the form of dry powder that can be reconstituted with water or another suitable liquid vehicle before use. Additional additives such as suspending or emulsifying agents, non-aqueous vehicles (including edible oils), preservatives and flavorings and colorants can be added to the liquid preparations. Parenteral dosage forms can be prepared by dissolving the compound of the invention in a suitable liquid vehicle and filter sterilizing the solution before lyophilization, or simply filling and sealing an appropriate vial or ampule.

As used herein, "drug substance", defined in the context of a "pharmaceutical composition", refers to a component of a pharmaceutical composition such as any one of the compounds as disclosed and described herein (a compound of Formula (I), including specific compounds described herein) and pharmaceutically acceptable salts thereof that provides the primary pharmacological effect, as opposed to an "inactive ingredient" which would generally be recognized as providing no therapeutic benefit.

As used herein, an "excipient" refers to a substance that is added to a composition to provide, without limitation, bulk, consistency, stability, binding ability, lubrication, disintegrating ability, etc., to the composition. A "diluent" is a type of excipient, and refers to an ingredient in a pharmaceutical composition that lacks pharmacological activity but may be pharmaceutically necessary or desirable. For example, a diluent can be used to increase the bulk of a potent drug whose mass is too small for manufacture and/or administration. It can also be a liquid for the dissolution of a drug to be administered by injection, ingestion, or inhalation. A pharmaceutically acceptable excipient is a physiologically and pharmaceutically suitable non-toxic and inactive material or ingredient that does not interfere with the activity of the drug substance. Pharmaceutically acceptable excipients are well known in the pharmaceutical art and described, for example, in Rowe et al., Handbook of Pharmaceutical Excipients: A Comprehensive Guide to Uses, Properties, and Safety, $5^{th}$ Ed., 2006, and in *Remington: The Science and Practice of Pharmacy* (Gennaro, $21^{st}$ Ed. Mack Pub. Co., Easton, PA (2005)). Preservatives, stabilizers, dyes, buffers, and the like can be provided in the pharmaceutical composition. In addition, antioxidants and suspending agents can also be used. For compositions formulated as liquid solutions, acceptable carriers and/or diluents include saline and sterile water, and can optionally include antioxidants, buffers, bacteriostats and other common additives. In some embodiments, the diluents can be a buffered aqueous solution such as, without limitation, phosphate buffered saline. The compositions can also be formulated as capsules, granules, or tablets which contain, in addition to a compound as disclosed and described herein, diluents, dispersing and surface active agents, binders, and lubricants. One skilled in this art can further formulate a compound as disclosed and described herein in an appropriate manner, and in accordance with accepted practices, such as those disclosed in Remington, supra.

In making pharmaceutical compositions comprising compounds of Formula (I), and pharmaceutically acceptable salts thereof, the drug substance is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier, or medium for the drug substance. Thus, the compositions can be in the form of tablets, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

For preparing solid form pharmaceutical compositions such as powders, tablets, capsules, cachets, suppositories and dispersible granules an excipient can be one or more substances which can also act as diluents, flavoring agents, solubilizers, lubricants, suspending agents, binders, preservatives, tablet disintegrating agents, or an encapsulating material. Also included are solid form compositions which are intended to be converted, shortly before use, to liquid form compositions for oral administration. Such liquid forms include solutions, suspensions and emulsions. These compositions can contain, in addition to the drug substance, colorants, flavors, stabilizers, buffers, artificial and natural sweeteners, dispersants, thickeners, solubilizing agents and the like.

For preparing suppositories, a low melting wax, such as an admixture of fatty acid glycerides or cocoa butter, is first melted and the drug substance is dispersed homogeneously therein, as by stirring. The molten homogenous mixture is then poured into convenient sized molds, allowed to cool and thereby to solidify.

Formulations suitable for vaginal administration can be presented as pessaries, tampons, creams, gels, pastes, foams or sprays containing in addition to the drug substance such carriers as are known in the art to be appropriate.

Liquid form compositions include solutions, suspensions and emulsions, for example, water or water-propylene glycol solutions. For example, parenteral injection liquid compositions can be formulated as solutions in aqueous polyethylene glycol solution. Injectable compositions, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

The pharmaceutical compositions can take such forms as suspensions, solutions, or emulsions in oily or aqueous vehicles and can contain formulatory agents such as suspending, stabilizing and/or dispersing agents. Alternatively, the pharmaceutical compositions can be in powder form, obtained by aseptic isolation of sterile solid or by lyophilization from solution, for constitution with a suitable vehicle, e.g., sterile, pyrogen-free water, before use.

The pharmaceutical compositions can be formulated as an aqueous solution, an aqua-alcoholic solution, a solid suspension, an emulsion, a liposomal suspension, or a freeze-dried powder for reconstitution. Such pharmaceutical compositions can be administered directly or as an admixture for further dilution/reconstitution. Route of administration includes intravenous bolus, intravenous infusion, irrigation, and instillation.

Aqueous formulations suitable for oral use can be prepared by dissolving or suspending the drug substance in water and adding suitable colorants, flavors, stabilizing and thickening agents, as desired.

Aqueous suspensions suitable for oral use can be made by dispersing the finely divided drug substance in water with viscous material, such as natural or synthetic gums, resins, methylcellulose, sodium carboxymethylcellulose, or other well-known suspending agents.

For topical administration to the epidermis the compounds of Formula (I), and pharmaceutically acceptable salts thereof can be formulated as gels, ointments, creams or lotions, or as a transdermal patch. Also, formulations suitable for topical administration in the mouth include lozenges comprising drug substance in a flavored base, usually sucrose and acacia or tragacanth; pastilles comprising the drug substance in an inert base such as gelatin and glycerin or sucrose and acacia; and mouthwashes comprising the drug substance in a suitable liquid carrier. Ointments and creams can, for example, be formulated with an aqueous or oily base with the addition of suitable thickening and/or gelling agents. Lotions can be formulated with an aqueous or oily base and will in general also contain one or more emulsifying agents, stabilizing agents, dispersing agents, suspending agents, thickening agents, or coloring agents. In some embodiments, topical formulations can contain one or more conventional carriers. In some embodiments, ointments can contain water and one or more hydrophobic carriers.

Solutions or suspensions can be applied directly to the nasal cavity by conventional means, for example with a dropper, pipette or spray. The formulations can be provided in single or multi-dose form. In the latter case of a dropper or pipette, this can be achieved by the patient administering an appropriate, predetermined volume of the solution or suspension. In the case of a spray, this can be achieved for example by means of a metering atomizing spray pump.

Administration to the respiratory tract can also be achieved by means of an aerosol formulation in which the drug substance is provided in a pressurized pack with a suitable propellant. If the compounds of Formula (I), and pharmaceutically acceptable salts thereof or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler.

Alternatively the pharmaceutical composition can be provided in the form of a dry powder, for example, a powder mix that will form a gel in the nasal cavity. The powder composition can be presented in unit dose form for example in capsules or cartridges of, e.g., gelatin, or blister packs from which the powder can be administered by means of an inhaler.

The compounds of Formula (I), and pharmaceutically acceptable salts thereof can also be administered via a rapid dissolving or a slow release composition, wherein the composition includes a biodegradable rapid dissolving or slow release carrier (such as a polymer carrier and the like) and a compound of the invention. Rapid dissolving or slow release carriers are well known in the art and are used to form complexes that capture therein a drug substance and either rapidly or slowly degrade/dissolve in a suitable environment (e.g., aqueous, acidic, basic, etc.).

The pharmaceutical compositions are preferably in unit dosage forms. In such form, the preparation is subdivided into unit doses containing appropriate quantities of the drug substance. The unit dosage form can be a packaged preparation, the package containing discrete quantities of preparation, such as packeted tablets, capsules and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

The compositions can be formulated in a unit dosage form, each dosage containing the drug substance or equivalent mass of the drug substance. The term "unit dosage forms" refers to physically discrete units of a formulation suitable as unitary dosages for human subjects and other mammals, each unit containing a predetermined quantity of active material calculated to produce the desired therapeutic effect, in association with a suitable excipient, as described herein.

The compositions described herein can be formulated to provide immediate and/or timed release (also called extended release, sustained release, controlled release, or slow release) of the drug substance after administration to a subject by employing procedures known in the art. For example, the tablets including compounds of Formula (I), or pharmaceutically acceptable salts thereof, can be coated or otherwise compounded to provide a dosage form affording the advantage of prolonged action. For example, the tablet can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Pharmaceutical composition comprising drug substance can formulated for timed release. Such compositions can generally be prepared using well known technology and administered by, for example, oral, rectal or subcutaneous implantation, or by implantation at the desired target site. Sustained-release formulations can contain the compound dispersed in a carrier matrix and/or contained within a reservoir surrounded by a rate controlling membrane. Excipients for use within such formulations are biocompatible, and can also be biodegradable. The amount of drug substance contained within a sustained release formulation depends upon the site of implantation, the rate and expected duration of release, and the nature of the condition to be treated or prevented.

The liquid forms including the drug substance can be incorporated for administration orally or by injection include aqueous solutions, suitably flavored syrups, aqueous or oil suspensions, and flavored emulsions with edible oils such as cottonseed oil, sesame oil, coconut oil, or peanut oil, and similar excipients.

The pharmaceutical compositions described herein can be sterilized by conventional sterilization techniques, or can be sterile filtered. Aqueous solutions can be packaged for use as is, or lyophilized, the lyophilized preparation being combined with a sterile aqueous carrier prior to administration.

Compositions for inhalation or insufflation include solutions and suspensions in pharmaceutically acceptable, aqueous or organic solvents, or mixtures thereof, and powders. The liquid or solid compositions can contain suitable excipients as described herein. In some embodiments, the compositions are administered by the oral or nasal respiratory route for local or systemic effect. Compositions can be nebulized by use of inert gases. Nebulized solutions can be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The compositions can, if desired, be presented in a pack or dispenser device which can contain one or more unit dosage forms containing the drug substance. The pack can for example comprise metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions that can include a compound described herein formulated in a compatible pharmaceutical carrier can also be prepared, placed in an appropriate container, and labeled for treatment of an indicated condition.

As used herein, a "dose" or "dosage" means the measured quantity of drug substance to be taken at one time by a patient. In certain embodiments, wherein the drug substance is not a free base or free acid of compound of Formula (I) such as a salt or hydrate, the quantity is the molar equivalent to the corresponding amount of free base or free acid of compound of Formula (I).

For preparing solid compositions such as tablets, the drug substance can be mixed with an excipient to form a solid preformulation composition containing a homogeneous mixture of components. When referring to these preformulation compositions as homogeneous, the drug substance is typically dispersed evenly throughout the composition so that the composition can be readily subdivided into equally effective unit dosage forms such as tablets and capsules. This solid preformulation is then subdivided into unit dosage forms of the type described above containing a desired amount of the drug substance.

Some embodiments provide a process for preparing a pharmaceutical composition comprising: preparing a compound of Formula (I) as described herein, and formulating the compound of Formula (I) with a pharmaceutically acceptable carrier and/or diluent.

The amount of drug substance required for use in treatment can vary depending on the route of administration, the nature of the condition being treated and the age and condition of the patient and will ultimately be at the discretion of the attendant physician or clinician. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated or prophylaxis conducted or on whether further active compounds are administered in addition to the compounds described herein and as part of a drug combination. The dosage regimen for treating a disease condition with the compounds and/or compositions described herein is selected in accordance with a variety factors as cited above. Thus, the actual dosage regimen employed can vary widely and therefore can deviate from a preferred dosage regimen and one skilled in the art will recognize that dosage and dosage regimen outside these typical ranges can be tested and, where appropriate, can be used in the methods described herein.

Kits with unit doses of one or more of the compounds described herein, usually in oral or injectable doses, are provided. Such kits can include a container containing the unit dose, an informational package insert describing the use and attendant benefits of the drugs in treating pathological condition of interest, and optionally an appliance or device for delivery of the composition.

It is understood that embodiments referring to a compound of Formula (I), or a pharmaceutically acceptable salt thereof, can also apply to a compound of Formula (II), or a pharmaceutically acceptable salt thereof.

Compound Synthesis

Detailed compound synthesis methods are described herein in the Examples. A person having ordinary skill in the chemical art would be able to make a compound of Formula (I), including specific compounds described herein, by these methods or similar methods or other methods practiced by a person skilled in the art.

In general, the compounds used in the reactions described herein can be made according to organic synthesis techniques known to those skilled in this art, starting from commercially available chemicals and/or from compounds described in the chemical literature. "Commercially available chemicals" can be obtained from standard commercial sources including Acros Organics (Pittsburgh PA), Aldrich Chemical (Milwaukee WI, including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester PA), Crescent Chemical Co. (Hauppauge NY), Eastman Organic Chemicals, Eastman Kodak Company (Rochester NY), Fisher Scientific Co. (Pittsburgh PA), Fisons Chemicals (Leicestershire UK), Frontier Scientific (Logan UT), ICN Biomedicals, Inc. (Costa Mesa CA), Key Organics (Cornwall U.K.), Lancaster Synthesis (Windham NH), Maybridge Chemical Co. Ltd. (Cornwall U.K.), Parish Chemical Co. (Orem UT), Pfaltz & Bauer, Inc. (Waterbury CN), Polyorganix (Houston TX), Pierce Chemical Co. (Rockford IL), Riedel de Haen AG (Hanover, Germany), Spectrum Quality Product, Inc. (New Brunswick, NJ), TCI America (Portland OR), Trans World Chemicals, Inc. (Rockville MD), and Wako Chemicals USA, Inc. (Richmond VA).

Methods known to one of ordinary skill in the art can be identified through various reference books and databases. Suitable reference books and treatise that detail the synthesis of reactants useful in the preparation of compounds of the present disclosure, or provide references to articles that describe the preparation, include for example, *Synthetic Organic Chemistry*, John Wiley & Sons, Inc., New York; S. R. Sandler et al., *Organic Functional Group Preparations,* 2nd Ed., Academic Press, New York, 1983; H. O. House, *Modern Synthetic Reactions,* 2nd Ed., W. A. Benjamin, Inc. Menlo Park, Calif. 1972; T. L. Gilchrist, *Heterocyclic Chemistry,* 2nd Ed., John Wiley & Sons, New York, 1992; J. March, *Advanced Organic Chemistry: Reactions, Mechanisms and Structure,* 4th Ed., Wiley Interscience, New York, 1992. Additional suitable reference books and treatise that detail the synthesis of reactants useful in the preparation of compounds of the present disclosure, or provide references to articles that describe the preparation, include for example, Fuhrhop, J. and Penzlin G. *Organic Synthesis: Concepts, Methods, Starting Materials*, Second, Revised and Enlarged Edition (1994) John Wiley & Sons ISBN: 3 527-29074-5; Hoffman, R. V. *Organic Chemistry, An Intermediate Text* (1996) Oxford University Press, ISBN 0-19-509618-5; Larock, R. C. *Comprehensive Organic Transformations: A Guide to Functional Group Preparations,* 2nd Edition (1999) Wiley-VCH, ISBN: 0-471-19031-4; March, J. *Advanced Organic Chemistry: Reactions, Mechanisms, and Structure,* 4th Edition (1992) John Wiley & Sons, ISBN: 0-471-60180-2; Otera, J. (editor) *Modern Carbonyl Chemistry,* (2000) Wiley-VCH, ISBN: 3-527-29871-1; Patai, S., *Patai's* 1992 *Guide to the Chemistry of Functional Groups*, (1992) Interscience ISBN: 0-471-93022-9; Quin, L. D. et al. *A Guide to Organophosphorus Chemistry*, (2000) Wiley-Interscience, ISBN: 0-471-31824-8; Solomons, T. W. G. *Organic Chemistry,* 7th Edition (2000) John Wiley & Sons, ISBN: 0-471-19095-0; Stowell, J. C., *Intermediate Organic Chemistry,* 2nd Edition (1993) Wiley-Interscience, ISBN: 0-471-57456-2; *Industrial Organic Chemicals: Starting Materials and Intermediates: An Ullmann's Encyclopedia*, (1999) John Wiley & Sons, ISBN: 3-527-29645-X, in 8 volumes; *Organic Reactions*, (1942-2019) John Wiley & Sons, in over 95 volumes; and *Chemistry of Functional Groups*, John Wiley & Sons, in hardcover volumes (86) and electronic volumes (26).

Specific and analogous reactants can also be identified through the indices of known chemicals prepared by the Chemical Abstract Service of the American Chemical Society, which are available in most public and university libraries, as well as through on-line databases (the American Chemical Society, Washington, D.C., can be contacted for more details). Chemicals that are known but not commercially available in catalogs can be prepared by custom chemical synthesis houses according to known methods, where many of the standard chemical supply houses (e.g., those listed above) provide custom synthesis services.

The specification can include abbreviations, select definitions of which are listed in the following Table:

| Abbreviation | Definition |
|---|---|
| ACN or $CH_3CN$ | Acetonitrile |
| AcOH or HOAc | Acetic acid |
| AcOEt or EtOAc | Ethyl acetate |
| AMPHOS Pd G3 | [4-(Di-tert-butylphosphino)-N,N-dimethyl-aniline-2-(2'-aminobiphenyl)]palladium(II) methanesulfonate |
| $Boc_2O$ | Di-tert-butyl dicarbonate |
| $B(OiPr)_3$ | Triisopropyl borate |
| CDI | 1,1'-Carbonyldiimidazole |

-continued

| Abbreviation | Definition |
|---|---|
| CELITE ® | Diatomaceous earth |
| CPME | Cyclopentyl methyl ether |
| DABCO | 1,4-Diazabicyclo-[2.2.2]octane |
| DBN | 1,5-Diazabicyclo[4.3.0]non-5-ene |
| DBU | 1,8-Diazabicyclo[5.4.0]undec-7-ene |
| DCC | Dicyclohexylcarbodiimide |
| DCM or $CH_2Cl_2$ | Dichloromethane or methylene chloride |
| de | Diastereomeric excess |
| DIBAL-H | Diisobutylaluminum hydride |
| DIPEA | N,N-Diisopropylethylamine |
| DMAP | 4-Dimethylaminopyridine |
| DME | Dimethoxyethane |
| DMF | N,N-Dimethylformamide |
| DMSO | Dimethylsulfoxide |
| DMSO-$d_6$ | Dimethylsulfoxide-$d_6$ |
| d.r. | Diastereomeric ratio |
| EDCI or EDC | 1-Ethyl-3-(3'-dimethylaminopropyl)carbodiimide (commercially available as hydrochloride) |
| ee | Enantiomeric excess |
| EtOH | Ethanol |
| $Et_2O$ | Diethyl ether |
| H or hr | Hour(s) |
| HATU | (1-[Bis(dimethylamino)methylene]-1H-1,2,3-triazolo[4,5-b]pyridinium |
| Hex | Hexane(s) |
| HPLC | High-performance liquid chromatography |
| HOBt | 1-Hydroxybenzotriazole |
| IPA | Isopropyl alcohol |
| LAH or $LiAlH_4$ | Lithium aluminum hydride |
| LCMS | Liquid chromatography-mass spectrometry |
| $LiAl(OCH_3)_3H$ | Lithium trimethoxyaluminum hydride |
| MeOH or $CH_3OH$ | Methanol |
| min. | Minute(s) |
| MOM | Methoxymethyl |
| MOMCl | Methoxymethyl chloride |
| MTBE | Methyl tert-butyl ether |
| n-BuLi or BuLi | n-Butyllithium |
| $NaBH(OAc)_3$ | Sodium triacetoxyborohydride |
| $NaB(CN)H_3$ | Sodium cyanoborohydride |
| $NH_4Cl$ | Ammonium chloride |
| $NH_4OAc$ | Ammonium acetate |
| NMM | N-methylmorpholine |
| NMP | N-Methyl-2-pyrrolidone |
| NMR | Nuclear Magnetic Resonance |
| Pd/C | Palladium on activated carbon |
| $Pd(acac)_2$ | Palladium(II) acetylacetonate |
| $[Pd(allyl)Cl]_2$ | Allylpalladium(II) chloride dimer |
| $Pd(amphos)Cl_2$ | Bis(di-tert-butyl(4-dimethylamino-phenyl)phosphine)dichloropalladium (II) |
| $Pd_2(dba)2$ | Bis(dibenzylideneacetone)palladium(0) |
| $Pd_2(dba)_3$ | Tris(dibenzylideneacetone)dipalladium (0) |
| $Pd(dppf)_2Cl_2$•DCM | [1,1'-Bis(diphenylphosphino)ferrocene]di-chloropalladium(II), dichloromethane adduct |
| $Pd(dppf)_2Cl_2$ | [1,1'-Bis(diphenylphosphino)ferrocene]di-chloropalladium(II) |
| $Pd(dtbpf)Cl_2$ | [1,1'-Bis(di-tert-butylphosphino)ferrocene]di-chloropalladium(II) |
| $Pd(PPh_3)_4$ | Palladium-tetrakis(triphenylphosphine) |
| $Pd(PPh_3)_2Cl_2$ | Bis(triphenylphosphine)palladium dichloride |
| $Pd[P(o-tol)_3]_2Cl_2$ | Dichlorobis(tri-o-tolylphosphine)palladium(II) |
| Ph | Phenyl |
| $PhCH_3$ | Toluene |
| PTSA | p-Toluenesulfonic acid |
| PyBroP | Bromotripyrrolidinophosphonium hexafluorophosphate |

-continued

| Abbreviation | Definition |
|---|---|
| rt | Room temperature |
| TBAB | Tetra-n-butyl ammonium bromide |
| TBAF | Tetra-n-butylammonium fluoride |
| TBDMS | tert-Butyldimethylsilyl |
| t-$Bu_2AlH$ | Di-tert-butylaluminum hydride |
| $tBu_3P$ | Tri-tert-butylphosphine |
| TEA | Triethylamine |
| TFA | Trifluoroacetic acid |
| TTBP | Tri-tert-butylpyrimidine |
| THF | Tetrahydrofuran |

Some embodiments provide a process of preparing Compound 1, comprising reacting Compound 8-D:

8-D

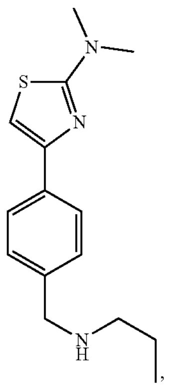

or a salt thereof, with Compound 3-D:

3-D

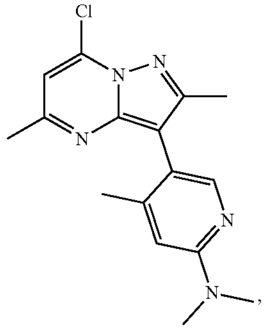

or a salt thereof, in the presence of a solvent and optionally in the presence of B1, wherein B1 is a base. In some embodiments, the reacting of Compound 8-D with Compound 3-D is performed in the presence of S1, wherein S1 is a solvent. In some embodiments, S1 is a polar protic solvent. In some embodiments, S1 is butyl alcohol. In some embodiments, B1 is an amine base. In some embodiments, B1 is DIPEA. In some embodiments, B1 is trimethylamine, triethylamine, N,N-diisopropylethylamine, diisopropylamine, piperidine, 2,2,6,6-tetramethylpiperidine, pyridine, 2,6-lutidine, 4-methylmorpholine, 4-ethylmorpholine, 1,5-diazabicyclo[4.3.0]non-5-ene, 1,8-diazabicyclo[5.4.0]undec-7-ene, 1,8-diazabicyclo[5.4.0]undec-7-ene, 1,4-diazabicyclo[2.2.2]octane, 1,8-bis(dimethylamino)naphthalene, or 4-(dimethylamino)pyridine.

Compound 3-D can be prepared by a process comprising reacting Compound 3-C:

3-C

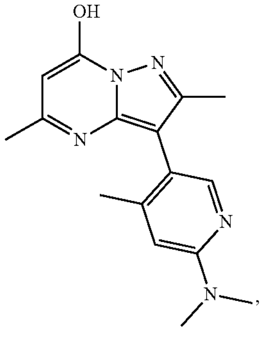

with a halogenating reagent. In some embodiments, the reacting of Compound 3-C with the halogenating reagent is performed in the presence of S2, wherein S2 is a solvent. In some embodiments, S2 is a polar aprotic solvent. In some embodiments, S2 is acetonitrile. In some embodiments, the halogenating reagent is $POCl_3$. In some embodiments, the halogenating reagent is thionyl chloride, oxalyl chloride, phosphorus oxychloride, phosphorus pentachloride, phosphorus trichloride, methanesulfonyl chloride, or p-toluenesulfonyl chloride.

Compound 3-C can be prepared by a process comprising reacting Compound 1-C:

1-C

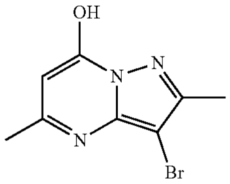

with Compound 2-C:

2-C

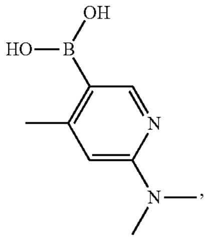

in the presence of at least one catalyst. In some embodiments, the reacting of Compound 1-C with Compound 2-C can be performed in the presence of S3, wherein S3 is a solvent. In some embodiments, S3 is a polar aprotic solvent. In some embodiments, S3 is dioxane. In some embodiments, the at least one catalyst is a Pd catalyst. In some embodiments, the at least one catalyst is $Pd_2(dba)_3$. In some embodiments, the at least one catalyst is $Pd_2(dba)_3$, $Pd(dppf)_2Cl_2DCM$, or tetrakis(triphenylphosphine) palladium (0) ($Pd(PPh_3)_4$). In some embodiments, the at least one catalyst is [1,3-bis(2,6-bi-3-pentylphenyl)imidazol-2-ylidene](3-chloropyridyl)dichloropalladium(II), (1,3-bis(2,6-diisopropylphenyl)imidazolidene)(3-chloropyridyl)palladium(II) dichloride, [1,3-bis(2,6-diisopropylphenyl) imidazol-2-ylidene](3-chloropyridyl)palladium(II) dichloride, (2-dicyclohexylphosphino-2',4',6'-triisopropyl-1, 1'-biphenyl)[2-(2'-amino-1,1'-biphenyl)]palladium(II) methanesulfonate, tetrakis(acetonitrile)palladium(II) tetrafluoroborate, dichlorobis(tricyclohexylphosphine)palladium(II), tris(dibenzylideneacetone)dipalladium(0)-chloroform adduct, palladium(II) acetate, palladium(II) trifluoroacetate, bis(acetonitrile)dichloropalladium(II), $PdCl_2$, $Pd(PPh_3)_2Cl_2$, $Pd[P(o\text{-}tol)_3]_2Cl_2$, $Pd(amphos)Cl_2$, $[Pd(allyl)Cl]_2$, $Pd(dba)_2$, $Pd_2(dba)_3$, $Pd(acac)_2$, $Pd(dtbpf)Cl_2$, $Pd(dppf)Cl_2$, $Pd(dppf)Cl_2{\cdot}CH_2{\cdot}Cl_2$ or $Pd(PPh_3)_4$. In some embodiments, the reacting of Compound 1-C and Compound 2-C can be performed in the presence of B2, wherein B2 is a base. In some embodiments, B2 is a metal hydroxide base. In some embodiments, B2 is NaOH.

Compound 1-C can be prepared by a process comprising reacting a compound having the formula:

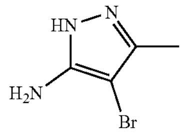

with ethyl 3-oxobutanoate, optionally in the presence of S4, wherein S4 is a solvent. In some embodiments, S4 is an organic acid. In some embodiments, S4 is acetic acid.

Compound 2-C can be prepared by a process comprising reacting a compound having the formula:

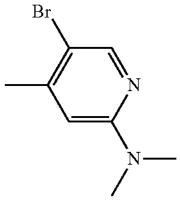

with triisopropyl borate and an organolithium compound. In some embodiments, the organolithium compound is n-butyllithium. In some embodiments, the organolithium compound is sec-butyllithium, tert-butyllithium, ethyllithium, hexyllithium, isobutyllithium, isopropyllithium, methyllithium, hexyllithium, or phenyllithium.

Protocol A:

General Procedure for Preparation of Compounds of Formula (I)

Scheme 1

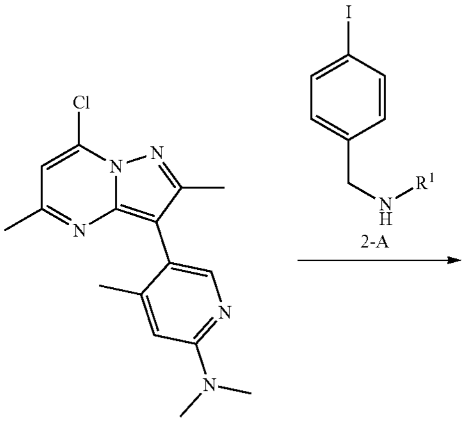

2-A

1-A

-continued

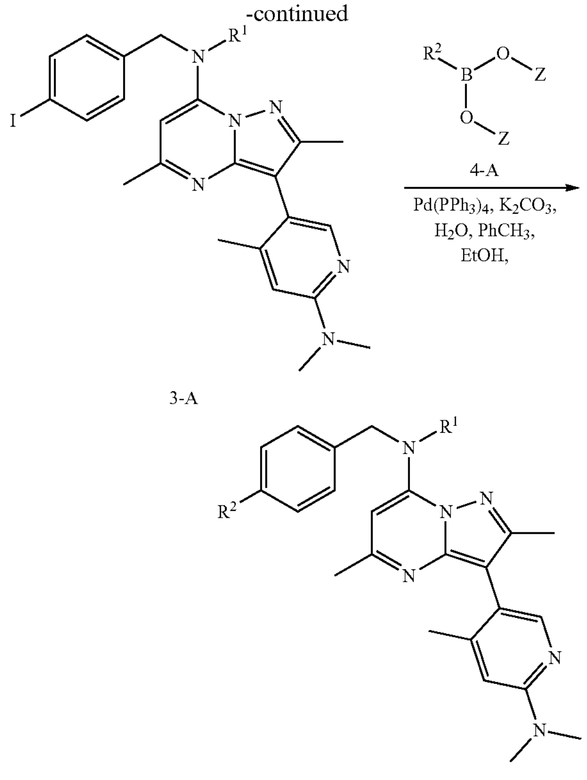

3-A (I)

According to Scheme 1, compounds of general Formula (I) can be synthesized in two steps starting from compounds of general formula 1-A. Briefly, a compound of general formula 1-A, such as 5-(7-chloro-2,5-dimethylpyrazolo[1,5-a]pyrimidin-3-yl)-N,N,4-trimethylpyridin-2-amine which can be prepared as described in Chen et al., "Design of 2,5-Dimethyl-3-(6-dimethyl-4-methylpyridin-3-yl)-7-dipropylaminopyrazolo[1,5-a]pyrimidine (NBI 30775/R121919) and Structure-Activity Relationships of a Series of Potent and Orally Active Corticotropin-Releasing Factor Receptor Antagonists," J. Med. Chem, 2004, 47(19): 4787-4798, is reacted with a compound of general formula 2-A or salt thereof, (synthesized according to Protocol 1-A), such as N-(4-iodobenzyl)propan-1-amine HCl salt, to provide compounds of general formula 3-A using appropriate coupling methodologies. Coupling reactions are achieved by conventional heteroaromatic nucleophilic substitution methodologies. Compounds of general formula 1-A are reacted with compounds of general formula 2-A or salt thereof, in a heteroaromatic nucleophilic substitution reaction. For example, compounds of general formula 1-A are reacted with compounds of general formula 2-A or salt thereof, in a suitable solvent such as ethyl alcohol, butyl alcohol, THF, dioxane, DMF, NMP and the like, in the presence of an excess of an amine base, such as triethylamine (TEA), N,N-diisopropylethylamine (DIPEA), N-methylmorpholine (NMM), tri-tert-butylpyrimidine (TTBP), 1,4-diazabicyclo-[2.2.2]octane (DABCO), 1,8-diazabicyclo[5.4.0]undec-7-ene (DBU), 1,5-Diazabicyclo[4.3.0]non-5-ene (DBN), N,N-diethylaniline, pyridine, 2,6-lutidine, 2,4,6-collidine, 4-dimethylaminopyridine (DMAP), quinuclidine, 2,6-di-tert-butylpyridine or pyridine, and the like, at temperatures ranging from 100 to 145° C., for a period of 1 to 24 h, to provide compounds of general formula 3-A. In some embodiments, the amine base can be trimethylamine, triethylamine (TEA), N,N-diisopropylethylamine (DIPEA), diisopropylamine, piperidine, 2,2,6,6-tetramethylpiperidine, pyridine, 2,6-lutidine, N-methylmorpholine (NMM), 4-ethylmorpholine, 1,5-diazabicyclo[4.3.0]non-5-ene (DBN), 1,8-diazabicyclo[5.4.0]undec-7-ene (DBU), 1,4-diazabicyclo[2.2.2]octane (DABCO), 1,8-bis(dimethylamino)naphthalene, or 4-dimethylaminopyridine (DMAP). For example, a mixture of 5-(7-chloro-2,5-dimethylpyrazolo[1,5-a]pyrimidin-3-yl)-N,N,4-trimethylpyridin-2-amine, N-(4-iodobenzyl)propan-1-amine HCl salt and DIPEA in butyl alcohol can be heated for 2 h at 120° C. to provide 5-{7-[({4-iodophenyl}methyl)(propyl)amino]-2,5-dimethylpyrazolo[1,5-a]pyrimidin-3-yl}-N,N,4-trimethylpyridin-2-amine. Subsequent coupling of the formed compounds of general formula 3-A with boronic acids or boronic esters, such as compounds of general formula 4-A under Suzuki reaction conditions and the like provides compounds of general formula (I). For example, reaction of compounds of general formula 3-A, with commercially available or synthetically accessible boronic acids or boronic esters in a solvent such as dimethoxyethane (DME), acetonitrile, toluene, EtOH, water, or a mixture thereof, in the presence of a base such as, $NaHCO_3$, $Na_2CO_3$, $K_2CO_3$, $K_3PO_4$, $Cs_2CO_3$, and the like, and an organotransition metal catalyst such as $Pd_2(dba)_3$, $Pd(dppf)_2Cl_2\cdot DCM$, tetrakis(triphenylphosphine) palladium (0) ($Pd(PPh_3)_4$), and the like, employing conventional or microwave heating, at temperatures ranging from 80 to 120° C., to provide compounds of general formula (I). In a specific example, a mixture of 5-{7-[({4-iodophenyl}methyl)(propyl)amino]-2,5-dimethylpyrazolo[1,5-a]pyrimidin-3-yl}-N,N,4-trimethylpyridin-2-amine, N,N-dimethyl-4-(tetramethyl-1,3,2-dioxaborolan-2-yl)-1,3-thiazol-2-amine, $Pd(PPh_3)_4$ and potassium carbonate in a mixture of toluene, ethyl alcohol and water can be heated under $N_2$ at 90° C. for a period of time and then cooled to rt and isolated affording 5-{7-[({4-[2-(dimethylamino)-1,3-thiazol-4-yl]phenyl}methyl)(propyl)amino]-2,5-dimethylpyrazolo[1,5-a]pyrimidin-3-yl}-N,N,4-trimethylpyridin-2-amine. In some embodiments, the organotransition metal catalyst is $Pd_2(dba)_3$, $Pd(dppf)_2Cl_2\cdot DCM$, or tetrakis(triphenylphosphine) palladium (0) ($Pd(PPh_3)_4$). In some embodiments, the organotransition metal catalyst is [1,3-bis(2,6-bi-3-pentylphenyl)imidazol-2-ylidene](3-chloropyridyl) dichloropalladium(II), (1,3-bis(2,6-diisopropylphenyl) imidazolidene)(3-chloropyridyl)palladium(II) dichloride, [1,3-bis(2,6-diisopropylphenyl)imidazol-2-ylidene](3-chloropyridyl)palladium(II) dichloride, (2-dicyclohexylphosphino-2',4',6'-triisopropyl-1,1'-biphenyl)[2-(2'-amino-1,1'-biphenyl)]palladium(II) methanesulfonate, tetrakis (acetonitrile)palladium(II) tetrafluoroborate, dichlorobis (tricyclohexylphosphine)palladium(II), tris (dibenzylideneacetone)dipalladium(0)-chloroform adduct, palladium(II) acetate, palladium(II) trifluoroacetate, bis(acetonitrile)dichloropalladium(II), $PdCl_2$, $Pd(PPh_3)_2Cl_2$, $Pd[P(o\text{-}tol)_3]_2Cl_2$, $Pd(amphos)Cl_2$, $[Pd(allyl)Cl]_2$, $Pd(dba)_2$, $Pd_2(dba)_3$, $Pd(acac)_2$, $Pd(dtbpf)Cl_2$, $Pd(dppf)Cl_2$, $Pd(dppf)Cl_2\cdot CH_2Cl_2$ or $Pd(PPh_3)_4$. In some embodiments, the base is barium carbonate, calcium carbonate, cesium carbonate, lithium carbonate, magnesium carbonate, potassium carbonate, sodium carbonate, cesium hydrogen carbonate, potassium hydrogen carbonate, sodium hydrogen carbonate, barium hydroxide, calcium hydroxide, cesium hydroxide, lithium hydroxide, magnesium hydroxide, potassium hydroxide, or sodium hydroxide. Compounds of general Formula (II) can be synthesized in two steps in a similar manner to compounds of general Formula (II) as shown in Scheme 1 where variable $R^1$ in the compound of general formula 2-A and the compound of general formula 3-A is replaced with variable $R^{10}$ and variable $R^2$ in the compound of general formula 4-A is replaced with variable $R^{20}$.

Protocol 1-A:

Scheme 1-A

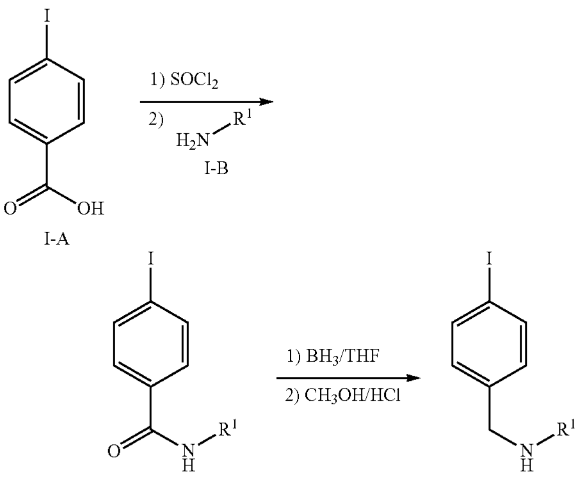

I-A I-B I-C 2-A

According to Scheme 1-A, an alkylamine of general formula 2-A can be synthesized from compounds of general formula I-A. Briefly, a carboxylic acid, such as compounds of general formula I-A, can be converted to an amide using appropriate coupling methodologies. Coupling reactions are achieved by conventional amide bond forming techniques. For example, a carboxylic acid of general formula I-A is converted to an active intermediate, such as an acyl chloride, using an activating agent, such as thionyl chloride, and after removal of excess activating agent the acyl chloride is reacted with an amine, such as such as compounds of general formula I-B, optionally in the presence of an excess of a tertiary amine, such as TEA or pyridine, optionally in the presence of a suitable catalyst, such as DMAP, in a suitable solvent such as DCM or THF and the like, at a temperature of about 0° C. to room temperature, to provide amide compounds of general formula I-C. In a specific example using an activating agent, 4-iodo benzoic acid was heated with thionyl chloride at 80° C. for 3 h and then the excess thionyl chloride removed under vacuum to afford N-(4-iodobenzyl)propan-1-amine. Subsequently, the N-(4-iodobenzyl)propan-1-amine was combined with DCM and then treated with n-propylamine (excess) by dropwise addition to form a mixture which was stirred at rt for 1 h affording 4-iodo-N-propylbenzamide as a white solid after isolation. A variety of other coupling methodologies can be used to couple compounds of general formula I-A with the compounds of general formula I-B. For example, a carboxylic acid of general formula I-A or a suitable salt thereof (e.g., sodium salt) is activated with an appropriate activating reagent, for example a carbodiimide, such as DCC or EDCI optionally in the presence of HOBt and the like, and/or a catalyst such as DMAP; a halotrisaminophosphonium salt such as PyBroP; a suitable pyridinium salt such as 2-chloro-1-methyl pyridinium chloride; or another suitable coupling agent such as HATU. In some embodiments, the coupling agent can be thionyl chloride, oxalyl chloride, phosphorus oxychloride, Vilsmeier reagent, propylphosphonic anhydride, ethylmethylphosphinic anhydride (EMPA), $Ac_2O$, pivaloyl chloride, ethyl chloroformate (ECF), isobutyl chloroformate (IBCF), 2-ethoxy-1-ethoxycarbonyl-1,2-dihydroquinoline (EEDQ), methanesulfonyl chloride (MsCl),p-toluenesulfonyl chloride (TsCl), pentafluorophenyl trifluoroacetate, cyanuric chloride, 2-chloro-4,6-dimethoxy-1,3,5-triazine (CDMT), 4-(4,6-dimethoxy-1,3,5-triazin-2-yl)-4-methyl morpholinium chloride (DMTMM), 1-tert-butyl-3-ethylcarbodiimide, 1,1'-carbonyldiimidazole (CDI), N,N'-dicyclohexylcarbodiimide (DCC), N,N'-diisopropylcarbodiimide (DIC), N-(3-dimethylaminopropyl)-N'-ethylcarbodiimide (EDC), 1,3-di-p-tolylcarbodiimide, benzotriazole-1-yl-oxy-tris-(dimethylamino)-phosphonium hexafluorophosphate (BOP), benzotriazole-1-yl-oxy-tris-pyrrolidino-phosphonium hexafluorophosphate (PyBOP), 6-chloro-benzotriazole-1-yloxy-tris-pyrrolidinophosphonium hexafluorophosphate (PyClock), (7-azabenzotriazol-1-yloxy)trispyrrolidinophosphonium hexafluorophosphate (PyAOP), 1-cyano-2-ethoxy-2-oxoethylideneaminooxy-tris-pyrrolidino-phosphonium hexafluorophosphate (PyOxim), 1-[(1-(cyano-2-ethoxy-2-oxoethylideneaminooxy) dimethylaminomorpholino)]uronium hexafluorophosphate (COMU), 3-(diethoxy-phosphoryloxy)-1,2,3-benzo[d]triazin-4(3H)-one (DEPBT), O-[(ethoxycarbonyl) cyanomethylenamino]-N,N,N'N'-tetramethyluronium tetrafluoroborate (TOTU), O-(2-Oxo-1(2H)pyridyl)-N,N,N'N'-tetramethyluronium tetrafluoroborate (TPTU), 2-(1H-benzotriazole-1-yl)-1,1,3,3-tetramethylaminium tetrafluoroborate (TBTU), N,N,N',N'-tetramethyl-O—(N-succinimidyl)uronium hexafluorophosphate (HSTU), 2-(1H-benzotriazole-1-yl)-1,1,3,3-tetramethyluronium hexafluorophosphate (HBTU), 2-(6-Chloro-1H-benzotriazole-1-yl)-1,1,3,3-tetramethylaminium hexafluorophosphate (HCTU), or 1-[bis(dimethylamino)methylene]-1H-1,2,3-triazolo[4,5-b]pyridinium 3-oxide hexafluorophosphate (HATU). Coupling reactions are conducted in a suitable solvent such as DCM, THF, DMF and the like, optionally in the presence of a tertiary amine such as DABCO, DBU, DBN, NMM, DIPEA, and the like, at from about 0° C. to room temperature, to provide an amide compound of general formula I-C. Reduction of an amide compound of general formula I-C with a reducing agent, such as borane tetrahydrofuran complex reagent ($BH_3$·THF), $BH_3$·TEA, $BH_3·S(CH_3)_2$, $BH_3$·pyridine, $BH_3$·4-methylmorpholine, $BH_3$·morpholine, $LiAlH_4$, $NaBH_4$—$TiCl_4$, $AlH_3$, $NaBH_4$—$AlCl_3$, $NaAlH_4$, t-$Bu_2AlH$, $LiBH_3CN$, $NaBH(OAc)_3$, $LiBH_4$, DIBAL-H, $LiAl(OCH_3)_3H$, sodium bis(2-methoxyethoxy)aluminum hydride, lithium tri-tert-butoxyaluminum hydride, and the like, optionally in a solvent such as THF, 1,4-dioxane, $Et_2O$ and the like, at temperatures ranging from 0° C. to 100° C., for a period of 0.2 to 24 h, affords an alkylamine of general formula 2-A. For example, an amide compound of general formula I-C can be treated with a borane reducing agent at rt and then refluxed overnight with stirring to afford an alkylamine of general formula 2-A after isolation. In a specific example using a borane reducing agent, 4-iodo-N-propylbenzamide was combined with $BH_3$·THF (1 M, 3 equiv.) and the resulting mixture was refluxed overnight. Subsequently, the refluxing mixture was slowly and carefully treated with methyl alcohol followed 5 mins later by treatment with 4 M HCl in dioxane (30 mL) where refluxing was continued for 2 h. The mixture was cooled and most of the solvent removed under vacuum allowing N-(4-iodobenzyl)propan-1-amine to precipitate out as the HCl salt. In some embodiments, the reducing agent can be diborane, borane (e.g., borane tetrahydrofuran complex), 9-borabicyclo[3.3.1]nonane, lithium aluminum hydride, diisobutylaluminum hydride, lithium diisobutyltert-butoxyaluminum hydride, lithium tri-tert-butoxyaluminum hydride, lithium tris[(3-ethyl-3-pentyl)oxy]aluminohydride, sodium bis(2-methoxyethoxy)aluminum dihydride, sodium aluminum hydride, calcium borohydride, lithium borohydride, magnesium borohydride, potassium borohydride, tetrabutylammonium borohydride, tetraethylammonium borohydride, tetramethylammonium borohydride, bis(triphenylphosphine)copper(I) borohydride, lithium 9-borabicyclo[3.3.1]nonane hydride, sodium triacetoxyborohydride, potassium tri-sec-butylborohydride, sodium tri-sec-butylborohydride, potassium trisiamylborohydride, lithium triethylborohydride, potassium triethylborohydride, sodium triethylborohydride, potassium triphenylborohydride, lithium dimethylaminoborohydride, lithium pyrrolidinoborohydride, sodium cyanoborohydride, sodium trimethoxyborohydride, or sodium borohydride. Compounds of general Formula (II) can be synthesized in two steps in a similar manner to compounds of general Formula (I) as shown in Scheme 1 where variable $R^1$ in the compound of general formula 2-A and the compound of general formula 3-A is replaced with variable $R^{10}$ and variable $R^2$ in the compound of general formula 4-A is replaced with variable $R^{20}$.

Protocol B:

Alternative General Procedure for Preparation of Compounds of Formula (I)

Scheme 2

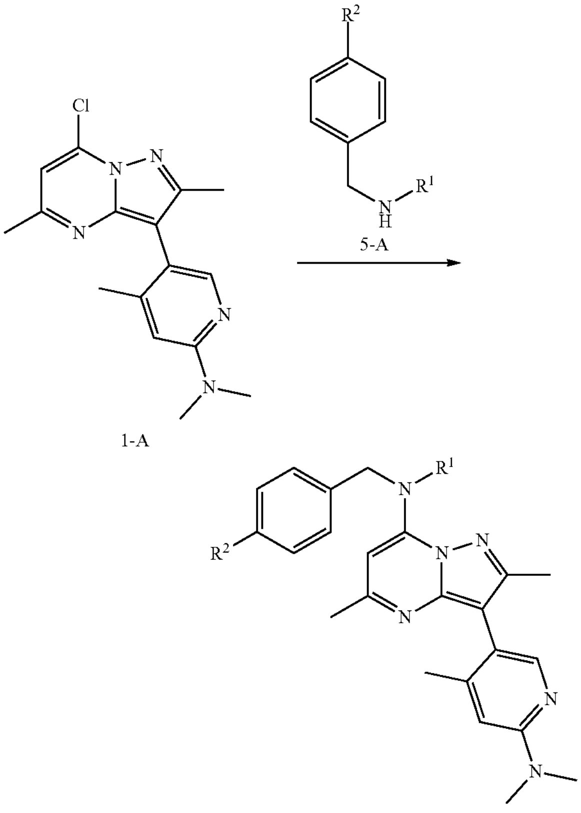

1-A

5-A (I)

According to Scheme 2, compounds of general formula (I) can be synthesized in one step starting from compounds of general formula 1-A. Briefly, a compound of general formula 1-A, such as 5-(7-chloro-2,5-dimethylpyrazolo[1,5-a]pyrimidin-3-yl)-N,N,4-trimethylpyridin-2-amine, is reacted with a compound of general formula 5-A or salt thereof, (synthesized according to Protocol 2-A), such as N-(4-(1H-pyrazol-1-yl)benzyl)propan-1-amine, to provide a compound of general formula (I), such as 5-{2,5-dimethyl-7-[propyl({[4-(1H-pyrazol-1-yl)phenyl]methyl})amino]pyrazolo[1,5-a]pyrimidin-3-yl}-N,N,4-trimethylpyridin-2-amine using appropriate coupling methodologies. Coupling reactions are achieved by conventional heteroaromatic nucleophilic substitution methodologies. Compounds of general formula 1-A are reacted with commercially available or synthetically accessible amine compounds of general formula 5-A or salt thereof, in a heteroaromatic nucleophilic substitution reaction. For example, compounds of general formula 1-A are reacted with compounds of general formula 5-A or salt thereof, in a suitable solvent such as $CH_3CN$, IPA, ethyl alcohol, butyl alcohol, THF, dioxane, DMF, NMP and the like, in the presence of an excess of an amine base, such as triethylamine (TEA), N,N-diisopropylethylamine (DIPEA), N-methylmorpholine (NMM), tri-tert-butylpyrimidine (TTBP), 1,4-diazabicyclo-[2.2.2]octane (DABCO), 1,8-diazabicyclo[5.4.0]undec-7-ene (DBU), 1,5-Diazabicyclo[4.3.0]non-5-ene (DBN), N,N-diethylaniline, pyridine, 2,6-lutidine, 2,4,6-collidine, 4-dimethylaminopyridine (DMAP), quinuclidine, 2,6-di-tert-butylpyridine or pyridine, and the like, at temperatures ranging from 100 to 145° C., for a period of 1 to 24 h, to provide compounds of general formula (I). In some embodiments, the amine base is trimethylamine, triethylamine (TEA), N,N-diisopropylethylamine (DIPEA), diisopropylamine, piperidine, 2,2,6,6-tetramethylpiperidine, pyridine, 2,6-lutidine, N-methylmorpholine (NMM), 4-ethylmorpholine, 1,5-diazabicyclo[4.3.0]non-5-ene (DBN), 1,8-diazabicyclo[5.4.0]undec-7-ene (DBU), 1,4-diazabicyclo[2.2.2]octane (DABCO), 1,8-bis(dimethylamino)naphthalene, or 4-dimethylaminopyridine (DMAP). Compounds of general Formula (II) can be synthesized in one step in a similar manner to compounds of general Formula (I) as shown in Scheme 2 where variables $R^1$ and $R^2$ in the compound of general formula 5-A are replaced with variables $R^{10}$ and $R^{20}$, respectively.

Protocol 1-B:

Scheme 2-A

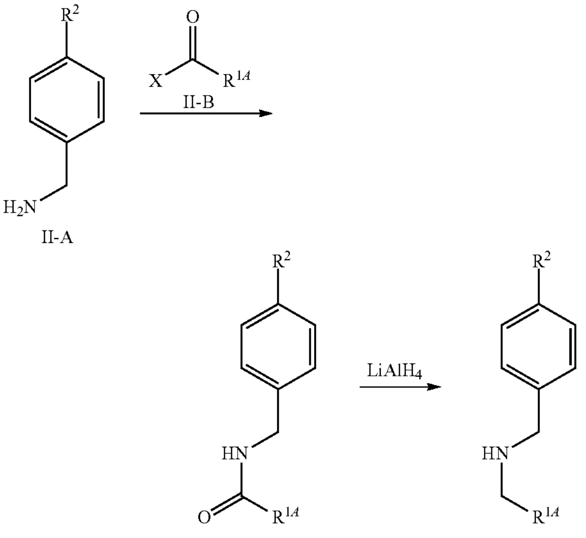

II-A

II-C

5-A

According to Scheme 2-A, an alkylamine of general formula 5-A can be synthesized from compounds of general formula II-A. Briefly, compounds of general formula II-A can be reacted with compounds of general formula II-B using appropriate coupling methodologies. Coupling reactions are achieved by conventional amide bond forming techniques. For example, an acyl halide (general formula II-B, X=halo; e.g., chloride) can be reacted with a compound of general formula II-A, in the presence of an excess of a tertiary amine, such as TEA or pyridine, optionally in the presence of a suitable catalyst, such as DMAP, in a suitable solvent such as DCM or THF, at a temperature of about 0° C. to room temperature, to provide amide compounds of general formula II-C. A variety of other coupling methodologies can be used to couple carboxylic acid (general formula II-B, X═OH) with the compound of general formula II-A. For example, a carboxylic acid (general formula II-B, X═OH) or a suitable salt thereof (e.g., sodium salt) is activated with an appropriate activating reagent, for example a carbodiimide, such as DCC or EDCI optionally in the presence of HOBt and the like, and/or a catalyst such as DMAP; a halotrisaminophosphonium salt such as PyBroP; a suitable pyridinium salt such as 2-chloro-1-methyl pyridinium chloride; or another suitable coupling agent such as HATU. In some embodiments, the coupling agent can be thionyl chloride, oxalyl chloride, phosphorus oxychloride, Vilsmeier reagent, propylphosphonic anhydride, ethylmethylphosphinic anhydride (EMPA), $Ac_2O$, pivaloyl chloride, ethyl chloroformate (ECF), isobutyl chloroformate (IBCF), 2-ethoxy-1-ethoxycarbonyl-1,2-dihydroquinoline (EEDQ), methanesulfonyl chloride (MsCl),p-toluenesulfonyl chloride (TsCl), pentafluorophenyl trifluoroacetate, cyanuric chloride, 2-chloro-4,6-dimethoxy-1,3,5-triazine (CDMT), 4-(4,6-dimethoxy-1,3,5-triazin-2-yl)-4-methyl morpholinium chloride (DMTMM), 1-tert-butyl-3-ethylcarbodiimide, 1,1'-carbonyldiimidazole (CDI), N,N'-dicyclohexylcarbodiimide (DCC), N,N'-diisopropylcarbodiimide (DIC), N-(3-dimethylaminopropyl)-N'-ethylcarbodiimide (EDC), 1,3-di-p-tolylcarbodiimide, benzotriazole-1-yl-oxy-tris-(dimethylamino)-phosphonium hexafluorophosphate (BOP), benzotriazole-1-yl-oxy-tris-pyrrolidino-phosphonium hexafluorophosphate (PyBOP), 6-chloro-benzotriazole-1-yloxy-tris-pyrrolidinophosphonium hexafluorophosphate (PyClock), (7-azabenzotriazol-1-yloxy)trispyrrolidinophosphonium hexafluorophosphate (PyAOP), 1-cyano-2-ethoxy-2-oxoethylideneaminooxy-tris-pyrrolidino-phosphonium hexafluorophosphate (PyOxim), 1-[(1-(cyano-2-ethoxy-2-oxoethylideneaminooxy) dimethylaminomorpholino)]uronium hexafluorophosphate (COMU), 3-(diethoxy-phosphoryloxy)-1,2,3-benzo[d]triazin-4(3H)-one (DEPBT), O-[(ethoxycarbonyl)cyanomethylenamino]-N,N,N'N'-tetramethyluronium tetrafluoroborate (TOTU), 0-(2-Oxo-1 (2H)pyridyl)-N,N,N'N'-tetramethyluronium tetrafluoroborate (TPTU), 2-(1H-benzotriazole-1-yl)-1,1,3,3-tetramethylaminium tetrafluoroborate (TBTU), N,N,N',N'-tetramethyl-O—(N-succinimidyl)uronium hexafluorophosphate (HSTU), 2-(1H-benzotriazole-1-yl)-1,1,3,3-tetramethyluronium hexafluorophosphate (HBTU), 2-(6-Chloro-1H-benzotriazole-1-yl)-1,1,3,3-tetramethylaminium hexafluorophosphate (HCTU), or 1-[bis(dimethylamino)methylene]-1H-1,2,3-triazolo[4,5-b]pyridinium 3-oxide hexafluorophosphate (HATU). Coupling reactions are conducted in a suitable solvent such as DCM, THF, DMF and the like, optionally in the presence of a tertiary amine such as DABCO, DBU, DBN, NMM, DIPEA, and the like, at from about 0° C. to room temperature, to provide an amide compound of general formula II-C. Reduction of an amide compound of general formula II-C with a reducing agent, such as $LiAlH_4$, $NaBH_4$—$TiCl_4$, $NaBH_4$—$AlCl_3$, $NaAlH_4$, $AlH_3$, t-$Bu_2AlH$, $LiBH_3CN$, $NaBH(OAc)_3$, $LiBH_4$, DIBAL-H, $LiAl(OCH_3)_3H$, sodium bis(2-methoxyethoxy) aluminum hydride, lithium tri-tert-butoxyaluminum hydride, $BH_3$·THF, $BH_3$·TEA, $BH_3·S(CH_3)_2$, $BH_3$ pyridine, $BH_3$·4-methylmorpholine, $BH_3$·morpholine, and the like, in a solvent such as THF, 1,4-dioxane, $Et_2O$ and the like, at temperatures ranging from 0° C. to room temperature, for a period of 0.2 to 2 h, affords an alkylamine of general formula 5-A. For example, an amide compound of general formula II-C in THF can be treated with $LiAlH_4$ at rt and stirred for a period of time and then treated with $LiAlH_4$ and stirred for another period of time. The mixture can then be treated with potassium sodium tartrate tetrahydrate (sat. aq.) and stirred at rt for a period of time affording an alkylamine of general formula 5-A after isolation. In some embodiments, the reducing agent can be diborane, borane (e.g., borane tetrahydrofuran complex), 9-borabicyclo[3.3.1]nonane, lithium aluminum hydride, diisobutylaluminum hydride, lithium diisobutyl-tert-butoxyaluminum hydride, lithium tri-tert-butoxyaluminum hydride, lithium tris[(3-ethyl-3-pentyl)oxy] aluminohydride, sodium bis(2-methoxyethoxy)aluminum dihydride, sodium aluminum hydride, calcium borohydride, lithium borohydride, magnesium borohydride, potassium borohydride, tetrabutylammonium borohydride, tetraethylammonium borohydride, tetramethylammonium borohydride, bis(triphenylphosphine)copper(I) borohydride, lithium 9-borabicyclo[3.3.1]nonane hydride, sodium triacetoxyborohydride, potassium tri-sec-butylborohydride, sodium tri-sec-butylborohydride, potassium trisiamylborohydride, lithium triethylborohydride, potassium triethylborohydride, sodium triethylborohydride, potassium triphenylborohydride, lithium dimethylaminoborohydride, lithium pyrrolidinoborohydride, sodium cyanoborohydride, sodium trimethoxyborohydride, or sodium borohydride.

EXAMPLES

The following examples are included to demonstrate embodiments of the disclosure. However, those of skill in the art should, in light of the present disclosure, appreciate that many changes can be made in the specific embodiments which are disclosed and still obtain a like or similar result without departing from the spirit and scope of the disclosure.

LC-MS analyses and/or purifications were conducted using the following methods:

Method: A

Platform: Agilent 1100 HPLC with an Agilent MSD mass detector and Agilent DAD (220 and 254 nm). HPLC column: Phenomenex Synergi MAX-RP, 4 μM, 50×2.0 mm. HPLC Gradient: 1.0 mL/min, 5% acetonitrile (with 0.035% TFA) in water (with 0.05% TFA) for 30 seconds, then increase to 95% acetonitrile over 13.0 minutes. Return to 5% acetonitrile over 6 seconds and hold at 5% for 1 minute.

Method: B

Platform: Agilent 1100 HPLC with an Agilent MSD mass detector and Agilent DAD (220 and 254 nm); HPLC column: Phenomenex Synergi MAX-RP, 4 μM, 50×2.0 mm; and HPLC Gradient: 1.0 mL/min, 5% acetonitrile (with 0.035% TFA) in water (with 0.05% TFA) for 30 seconds, then increase to 95% acetonitrile over 2.0 minutes. Return to 5% acetonitrile over 6 seconds and hold at 5% for 1 minute.

Method: C

Platform: Shimadzu LC-8A HPLC pumps equipped with a Dionex Ultimate 3000 RS autosampler, a Dionex UVD 170 UV Detector, and a Thermo Scientific MSQ mass spectrometer; HPLC column: Waters XBridge C18, 5 μM, 100A, 10.0 mm×100 mm; and HPLC Gradient: 17 mL/min, hold at 25% acetonitrile (0.04% $NH_4OH$) in 85% water (0.04% $NH_4OH$) for 1.3 minutes, increase to 35% acetonitrile in 6 seconds, then increase to 95% acetonitrile over 7.1 minutes; hold at 99% acetonitrile for 30 seconds, then drop back to 25% acetonitrile. Dual column regeneration at 25% acetonitrile in water.

Method: D

Platform: Shimadzu LC-8A HPLC pumps equipped with a Dionex Ultimate 3000 RS autosampler, a Dionex UVD 170 UV Detector, and a Thermo Scientific MSQ mass spectrometer; HPLC column: Phenomenex Kinetix C18, 5 μM, 100 A, 21.2 mm×150 mm; and HPLC Gradient: 28 ml/min, hold at 15% acetonitrile (0.035% TFA) in 85% water (0.05% TFA) for 2 minutes, increase to 20% acetonitrile in 6 seconds, then increase to 80% acetonitrile over 7.63 minutes; hold at 95% acetonitrile for 30 seconds, then drop back to 15% acetonitrile. Dual column regeneration at 15% acetonitrile in water.

Method: E

Platform: Dionex Ultimate 3000 UPLC with a Thermo MSQ mass spectrometer, Thermo Scientific Coronal Ultra RS charged aerosol detector, and a Dionex Ultimate 3000 DAD; HPLC column: Waters XBridge BEH C18, 2.5 μM, 3.0×50 mm Column XP; and HPLC Gradient: 2.0 mL/min, hold at 5% acetonitrile (with 0.025% TFA) in water (with 0.025% TFA) for 30 seconds, then increase to 95% acetonitrile over 3.4 minutes. Return to 5% acetonitrile over 6 seconds and hold at 5% for 1 minute. Dual column regeneration at 5% acetonitrile in water.

Method: F

Platform: Shimadzu LC-8A HPLC pumps equipped with a Dionex Ultimate 3000 RS autosampler, a Dionex UVD 170 UV Detector, and a Thermo Scientific MSQ mass spectrometer; HPLC column: Phenomenex Kinetix C18, 5 μM, 100 A, 10 mm×150 mm; and HPLC Gradient: 28 mL/min, hold at 31.4% acetonitrile (0.035% TFA) in 68.6% water (0.05% TFA) for 1.25 minutes, increase to 63.9% acetonitrile in 2.25 minutes, then increase to 96.4% acetonitrile over 6 seconds; hold at 96.4% acetonitrile for 1.25 minutes, then drop back to 31.4% acetonitrile. Dual column regeneration at 5% acetonitrile in water.

Method: G

Platform: Shimadzu LC-8A HPLC pumps equipped with a Dionex Ultimate 3000 RS autosampler, a Dionex UVD 170 UV Detector, and a Thermo Scientific MSQ mass spectrometer; HPLC column: Phenomenex Kinetix C18, 5 μM, 100 A, 10 mm×150 mm; and HPLC Gradient: 28 ml/min, hold at 8.2% acetonitrile (0.035% TFA) in 91.8% water (0.05% TFA) for 1.25 minutes, increase to 40.7% acetonitrile in 2.25 minutes, hold at 40.7% acetonitrile for 6 seconds, then increase to 96.4% acetonitrile over 1.25 minutes, then drop back to 8.2% acetonitrile. Dual column regeneration at 5% acetonitrile in water.

Method: H

Platform: Shimadzu LC-8A HPLC pumps equipped with a Dionex Ultimate 3000 RS autosampler, a Dionex UVD 170 UV Detector, and a Thermo Scientific MSQ mass spectrometer; HPLC column: Phenomenex Kinetix C18, 5 μM, 100 A, 10 mm×100 mm; and HPLC Gradient: 12 ml/min, hold at 20.3% acetonitrile (0.035% TFA) in 79.7% water (0.05% TFA) for 1.35 minutes, increase to 67.9% acetonitrile in 5.32 minutes, then increase to % acetonitrile in 6 seconds, hold at 99% acetonitrile for 1.06 minutes, then drop back to 20.3% acetonitrile. Dual column regeneration at 13% acetonitrile in water.

Examples 1 to 50 illustrate, without limitation, the synthesis of particular compounds of general formula (I) or general formula (II).

PREPARATION OF COMPOUNDS

Example 1: Scheme 3-A: Preparation of 5-{7-[({4-[2-(dimethylamino)-1,3-thiazol-4-yl]phenyl}methyl)(propyl)amino]-2,5-dimethylpyrazolo[1,5-a]pyrimidin-3-yl}-N,N,4-trimethylpyridin-2-amine (Compound 1)

The title compound was prepared as shown in Scheme 3-A below.

Scheme 3-A

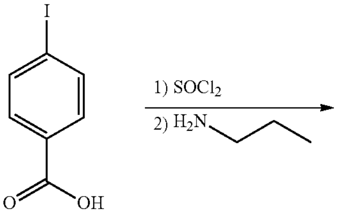

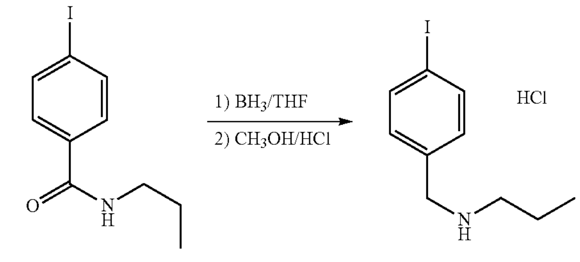

1-D

2-D

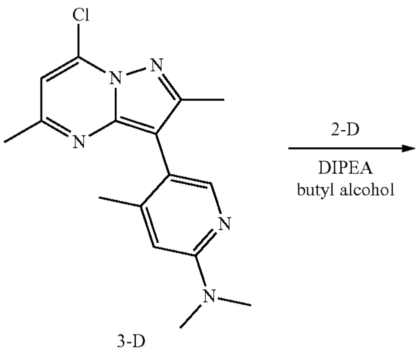

3-D

-continued

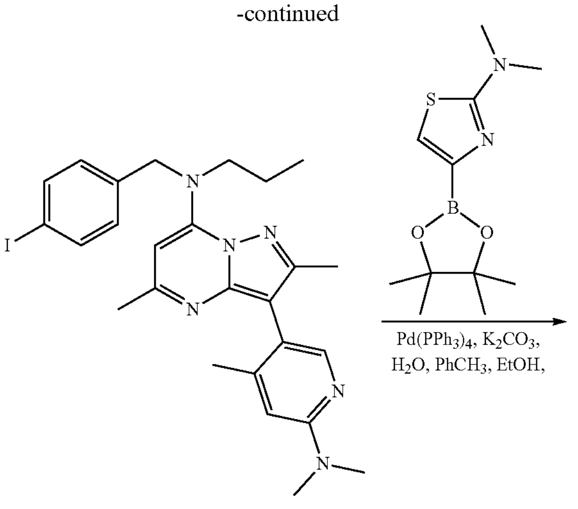

4-D

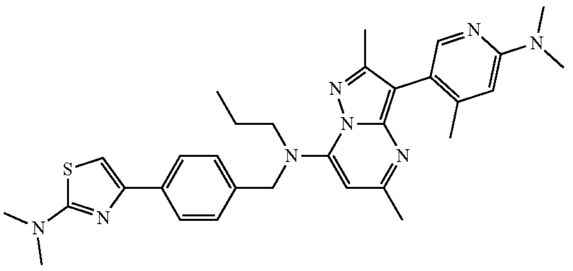

1

Step 1: Preparation of N-(4-iodobenzyl)propan-1-amine HCl (Compound 2-D)

4-Iodo benzoic acid (5.0 g, 20.2 mmol) was heated with thionyl chloride (10 mL) at 80° C. for 3 h and then the excess thionyl chloride removed under vacuum to afford crude 4-iodobenzoyl chloride. The crude acid chloride was dissolved in DCM (200 mL) and then excess n-propylamine (5 mL) was added dropwise to afford a mixture that was stirred at r.t for 1h. The organic phase was washed with citric acid solution and dried to give 4-iodo-N-propylbenzamide (1-D) as a white solid. $^1$H NMR [400 MHz, DMSO-$d_6$]δ 8.50 (t, J=6 Hz, 1H), 7.85 (d, J=8 Hz, 2H), 7.62 (d, J=8 Hz, 2H), 3.20 (q, J=6.3 Hz, 2H), 1.52 (app sextet, J=7.2 Hz, 2H), 0.89 (t, J=8 Hz). LCMS: (Method: A) (ESI+) m/z 289.9 [MH+], tR=3.37 min.

A portion (3 g) was combined with 1 M Borane-THF complex (3 eq) and the resulting mixture refluxed overnight. Methanol (20 mL) was added slowly and carefully at reflux followed 5 mins later by 4 M HCl in dioxane (30 mL) and refluxing continued for 2 h. The mixture was cooled and most of the solvent removed under vacuum affording the N-(4-iodobenzyl)propan-1-amine (2-D) precipitated as the HCl salt. A portion was basified with aq NaOH and extracted with DCM, dried over $MgSO_4$ and concentrated to give the free amine used for analysis. $^1$H NMR [400 MHz, DMSO-$d_6$]δ 7.63 (d, J=8 Hz, 2H), 7.12 (d, J=8 Hz, 2H), 3.62 (s, 2H), 2.41 (t, J=7 Hz, 2H), 1.41 (app sextet, J=7.2 Hz, 2H), 0.85 (t, J=7.5 Hz, 3H). LCMS: (Method: A) (ESI+) m/z 275.9 [MH+], tR=2.13 min.

Step 2: Preparation of 5-(7-{[(4-iodophenyl)methyl](propyl)amino}-2,5-dimethylpyrazolo[1,5-a]pyrimidin-3-yl)-N,N,4-trimethylpyridin-2-amine (Compound 4-D)

A mixture of 5-(7-chloro-2,5-dimethylpyrazolo[1,5-a]pyrimidin-3-yl)-N,N,4-trimethylpyridin-2-amine (3-D), N-(4-iodobenzyl)propan-1-amine (2-D) HCl (1.3 eq) and DIPEA (3 eq) in butyl alcohol was heated at 120° C. for 2 h. The solvent was removed under vacuum and the residue purified by chromatography on silica gel eluting with EtOAc/Hex to afford 5-(7-{[(4-iodophenyl)methyl](propyl)amino}-2,5-dimethylpyrazolo[1,5-a]pyrimidin-3-yl)-N,N,4-trimethylpyridin-2-amine (4-D). $^1$H NMR [400 MHz, DMSO-$d_6$]δ 7.87 (s, 1H), 7.71 (d, J=9 Hz, 2H), 7.15 (d, J=7 Hz, 2H), 6.59 (s, 1H), 6.12 (s, 1H), 5.09 (s, 2H), 3.63 (t, J=7 Hz, 2H), 3.05 (s, 6H), 2.29 (s, 3H), 2.23 (s, 3H), 2.06 (s, 3H), 1.67 (app sextet, J=7.4 Hz, 2H), 0.85 (t, J=7.5 Hz, 3H). LCMS: (Method: A) (ESI+) m/z 555.2 [MH+], tR=3.51 min.

Step 3: Preparation of 5-{7-[({4-[2-(dimethylamino)-1,3-thiazol-4-yl]phenyl}methyl)(propyl)amino]-2,5-dimethylpyrazolo[1,5-a]pyrimidin-3-yl}-N,N,4-trimethylpyridin-2-amine (Compound 1)

A mixture of N,N-dimethyl-4-(tetramethyl-1,3,2-dioxaborolan-2-yl)-1,3-thiazol-2-amine (5.6 mg) and 5-(7-{[(4-iodophenyl)methyl](propyl)amino}-2,5-dimethylpyrazolo[1,5-a]pyrimidin-3-yl)-N,N,4-trimethylpyridin-2-amine (4-D, 10 mg) in toluene (120 μL), ethyl alcohol (60 μL) and water (20 μL) was treated with potassium carbonate (3 eq) followed by $Pd(PPh_3)_4$(5 mol %) and the resulting mixture was heated at 90° C. under $N_2$ until reaction progress ceased. The mixture was cooled, diluted with DCM, filtered and concentrated and purified by HPLC (method: C) to afford 5-{7-[({4-[2-(dimethylamino)-1,3-thiazol-4-yl]phenyl}methyl)(propyl)amino]-2,5-dimethylpyrazolo[1,5-a]pyrimidin-3-yl}-N,N,4-trimethylpyridin-2-amine (Compound 1). $^1$H NMR matches the material made by the process of Scheme 3-B (below). LCMS: (Method: A (ESI+) m/z 555.3 [MH+], tR=3.01 min.

Example 2: Scheme 3-B: Alternative preparation of 5-{7-[({4-[2-(dimethylamino)-1,3-thiazol-4-yl]phenyl}methyl)(propyl)amino]-2,5-dimethylpyrazolo[1,5-a]pyrimidin-3-yl}-N,N,4-trimethylpyridin-2-amine (Compound 1)

The title compound was prepared as shown in Scheme 3-B below.

Scheme 3-B

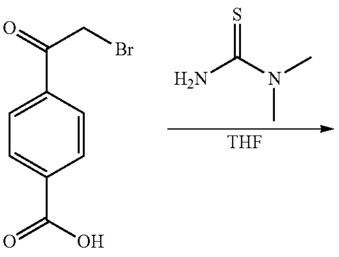

-continued

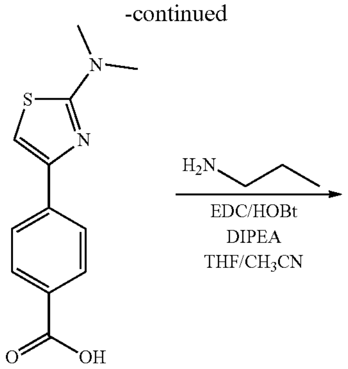

5-D

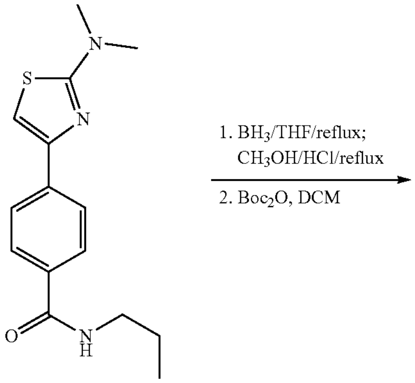

6-D

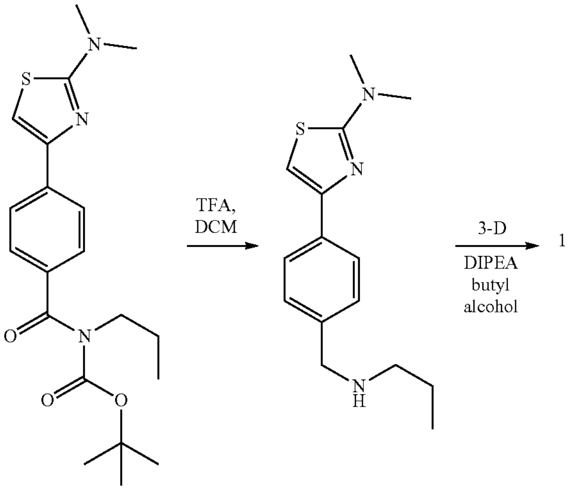

7-D 8-D

Step 1: Preparation of tert-butyl (4-(2-(dimethylamino)thiazol-4-yl)benzyl)(propyl)carbamate (Compound 7-D)

A mixture of 4-(2-bromoacetyl)benzoic acid (28.4 g) and 1,1-dimethylthiourea in THF (300 mL) was stirred at rt overnight affording 4-(2-(dimethylamino)thiazol-4-yl)benzoic acid (5-D) used directly in the next step without isolation. The mixture was then diluted with DCM (200 mL) and $CH_3CN$ (500 mL) and further combined with water (100 mL). The resulting mixture was treated with propylamine (1.1 eq), HOBt $H_2O$ (1.0 eq) and TEA (3.0 eq) followed by EDC (1.3 eq) in 2 portions and stirred at rt overnight. The majority of the solvent was removed in-vacuo and then combined with DCM. The layers were partitioned, and the DCM layer washed with 0.5 M HCl followed by sat. aq. $NaHCO_3$ and then water. The HCl phase was basified (NaOH) and re-extracted with DCM since HPLC showed remaining product in this wash. The DCM layers were combined, dried over $MgSO_4$, filtered and concentrated under reduced pressure to afford crude 4-(2-(dimethylamino)thiazol-4-yl)-N-propylbenzamide (6-D) used directly in the next step. A portion of the crude (6-D) was purified by crystallization from acetone for analysis. $^1H$ NMR [400 MHz, DMSO-$d_6$]δ 8.45 (t, J=6 Hz, 1H), 7.93 (d, J=9 Hz, 2H), 7.86 (d, J=9 Hz, 2H), 7.33 (s, 1H), 3.23 (q, J=6.7 Hz, 2H), 3.10 (s, 6H), 1.55 (app sextet, J=7 Hz, 2H), 0.91 (t, J=8 Hz, 3H). LCMS: (Method: B (ESI+) m/z 290.0 [MH+], tR=1.53 min.

The remaining crude material was dissolved in THF (300 mL) and then treated with $BH_3$·THF (1M in THF, 1.8 eq). The resulting mixture was heated at reflux overnight and then MeOH (50 mL) added carefully at reflux followed by HCl (4M in dioxane, 20 equiv.) and refluxed for 2 h. The mixture was allowed to cool to rt and the solvent was removed under reduced pressure. The crude material was taken up in DCM and basified with NaOH (2M aq) and extracted with DCM. The crude amine was combined with 1 eq $Boc_2O$ and excess 1M NaOH (aq) and stirred at rt and then additional $Boc_2O$ was added (0.1 eq) and the mixture stirred overnight. The DCM layer was separated and the solvent was removed under reduced pressure to afford a crude residue that was purified by chromatography on silica gel eluting with EtOAc/Hex to afford tert-butyl (4-(2-(dimethylamino)thiazol-4-yl)benzyl)(propyl)carbamate (7-D).

Step 2: Preparation of N,N-dimethyl-4-(4-((propylamino)methyl)phenyl)thiazol-2-amine (Compound 8-D)

A mixture of tert-butyl (4-(2-(dimethylamino)thiazol-4-yl)benzoyl)(propyl)carbamate (7-D, 12 g) in dioxane/DCM 1:1 (200 mL) was treated with 4M HCl in dioxane (80 mL) and the resulting mixture was stirred at rt for 3 h. The solvent was removed under reduced pressure the resulting residue was combined with DCM and 2M NaOH. The layers were partitioned and the aqueous layer was extracted with DCM twice and the organics combined. The combined organic was washed with water, dried over $MgSO_4$, filtered and concentrated under reduced pressure to give afford N,N-dimethyl-4-(4-((propylamino)methyl)phenyl)thiazol-2-amine (8-D). $^1H$ NMR [400 MHz, DMSO-$d_6$]δ 7.79 (d, J=8 Hz, 2H), 7.32 (d, J=8 Hz, 2H), 7.11 (s, 2H), 3.68 (s, 2H), 3.09 (s, 6H), 2.45 (t, J=7.6 Hz, 2H), 1.44 (app sextet, J=7.3 Hz, 2H), 0.87 (t, J=7.6 Hz, 3H). LCMS: Method: A (ESI+) m/z 276.0 [MH+], tR=1.76 min.

Step 3: Preparation of 5-{7-[({4-[2-(dimethylamino)-1,3-thiazol-4-yl]phenyl}methyl)(propyl)amino]-2,5-dimethylpyrazolo[1,5-a]pyrimidin-3-yl}-N,N,4-trimethylpyridin-2-amine (Compound 1)

A mixture of 5-(7-chloro-2,5-dimethylpyrazolo[1,5-a]pyrimidin-3-yl)-N,N,4-trimethylpyridin-2-amine (3-D, 0.83 g), N,N-dimethyl-4-(4-((propylamino)methyl)phenyl)thiazol-2-amine (8-D, 1.0 g) and DIPEA (2 eq) in butyl alcohol was heated at 100° C. and 120° C. for 2 h. Solvent was removed and then worked up using 1M NaOH (aq) and DCM and then dried down and columned on silica gel eluting with Acetone/Hex to give recovered compound 3-D and a first isolate (750 mg) as an oil. The first isolate was crystallized from MTBE/Heptane approx. 1:1 (~40 mL)

(dissolved in MTBE (~20 mL) and added heptane (~20 mL) and stirred at room temperature overnight; initiated by blowing with a little $N_2$ to induce solid at edges of flask and then scraping edge of flask). The mixture was filtered and washed with heptane to afford Compound 1 (500 mg) as a fine white powder (Form I of Compound 1) after drying by suction for 1h. An XRPD of this material is provided in FIG. 1. The remainder was then recrystallized again from MTBE-heptane but used seed crystal this time from first batch.

Alternatively, a mixture of 5-(7-chloro-2,5-dimethylpyrazolo[1,5-a]pyrimidin-3-yl)-N,N,4-trimethylpyridin-2-amine (3-D, 6.5 g), N,N-dimethyl-4-(4-((propylamino)methyl)phenyl)thiazol-2-amine (8-D, 7.38 g) and DIPEA (2 eq) in butyl alcohol (50 mL) was heated at 120° C. for 2 h. The solvent was removed under vacuum and DCM and 1M NaOH were added. The organic phase was separated and dried over $MgSO_4$ and concentrated under reduced pressure. The crude was purified by column chromatography on silica gel eluting with acetone/hexane (0-40%) to afford the desired compound as an oil. The reaction was repeated using 12 g of 5-(7-chloro-2,5-dimethylpyrazolo[1,5-a]pyrimidin-3-yl)-N,N,4-trimethylpyridin-2-amine (3-D) and combined with the previous material after chromatography. The combined material was crystallized from MTBE/Heptane (dissolved in the minimum amount of MTBE and a little heptane was added along with a few seed crystals and stirred overnight at rt) to give a white powder, which was collected by filtration washing with a little heptane and then drying by suction and then in a vacuum desiccator overnight over NaOH pellets. The resulting material (25 g) was pure by LCMS and NMR but was a mixture of 2 forms by X-ray powder diffraction. This material (25 g) was slurried in EtOH (500 mL) at rt over the weekend. The solid was collected by filtration and dried by suction and then dried overnight in a vacuum desiccator over NaOH pellets to give Compound 1 (20.6 g) as a single crystalline form (Form I) as shown by X-ray powder diffraction. $^1H$ NMR [400 MHz, DMSO-$d_6$]δ 7.87 (s, 1H), 7.82 (d, J=8.5 Hz, 2H), 7.33 (d, J=8 Hz, 2H), 7.15 (s, 1H), 6.59 (s, 1H), 6.13 (s, 1H), 5.12 (s, 2H), 3.67 (t, J=8 Hz, 2H), 3.08 (s, 6H), 3.05 (s, 6H), 2.30 (s, 3H), 2.26 (s, 3H), 2.07 (s, 3H), 1.69 (app sextet, J=7.6 Hz, 2H), 0.86 (t, J=7.4 Hz, 3H). LCMS: (Method: A) (ESI+) m/z 555.5 [MH+], tR=2.93 min.

Example 3: Alternative preparation of 5-{7-[({4-[2-(dimethylamino)-1,3-thiazol-4-yl]phenyl}methyl)(propyl)amino]-2,5-dimethylpyrazolo[1,5-a]pyrimidin-3-yl}-N,N,4-trimethylpyridin-2-amine (Compound 1)

A mixture of 5-(7-chloro-2,5-dimethylpyrazolo[1,5-a]pyrimidin-3-yl)-N,N,4-trimethylpyridin-2-amine (3-D, 220 g, 1.0 eq) and N,N-dimethyl-4-(4-((propylamino)methyl)phenyl)thiazol-2-amine-1.5 HCl (8-D-1.5 HCl, 1.05 eq) suspended in IPA (5 V) and DIPEA (3.2 eq, 1.76 V) was heated to reflux (82±5° C.) for at least 24 h. Upon completion, the mixture was cooled to 65±5° C. before seeding with Form I of Compound 1. The resulting mixture was stirred for at least 15 minutes to allow nucleation to occur. After 2 h, the slurry was cooled to room temperature and stirred for 1 h. The solid product was isolated by filtration, washed with IPA (1V), and then dried in a vacuum oven at 60° C. for not less than 18 h to afford Compound 1 (309.8 g, 80% yield) as a pale yellow solid.

Example 4: Preparation of N,N-dimethyl-4-(4-((propylamino)methyl)phenyl)thiazol-2-amine 2HCl (8-E)

Scheme 3-C

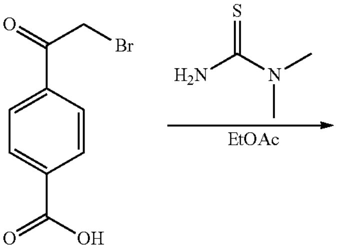

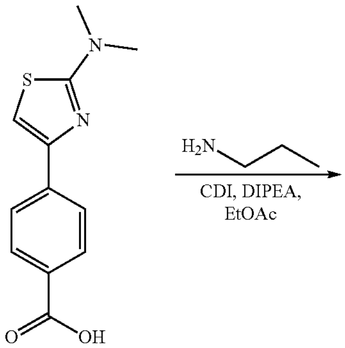

5-D

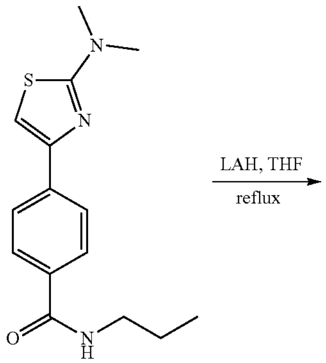

6-D

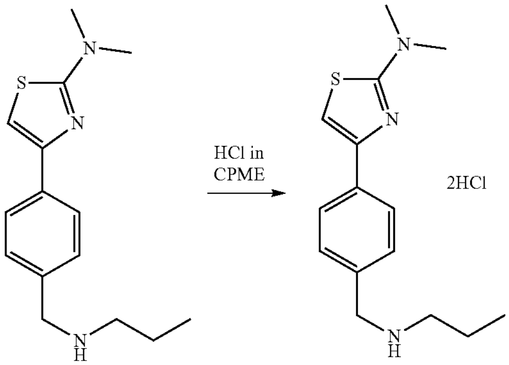

8-D 8-E

Step 1: Preparation of 4-(2-(dimethylamino)thiazol-4-yl)benzoic acid (5-D)

A mixture of 4-(2-bromoacetyl)benzoic acid (75 g) and 1,1-dimethylthiourea (33 g, 1 equiv.) in EtOAc (900 mL) was stirred 18 h at rt affording a solid. The solid was collected by filtration, washed with EtOAc (2×100 mL), and dried in a vacuum oven at 50° C. for 18 h to afford 4-(2-(dimethylamino)thiazol-4-yl)benzoic acid (5-D) (HBr salt) an off-white solid (96.1 g, 95% yield, HPLC purity 99.5%). $^1$H NMR [400 MHz, DMSO-$d_6$]δ 3.13 (s, 6H) 7.39 (s, 1H) 7.96 (s, 4H).

Step 2: Preparation of 4-(2-(dimethylamino)thiazol-4-yl)-N-propylbenzamide (6-D)

A mixture of 4-(2-(dimethylamino)thiazol-4-yl)benzoic acid (5-D) HBr (44 g, 0.213 mol.) and EtOAc (660 mL) was treated with DIPEA (24 mL, 1 eq.) and stirred for at least 15 min (an exotherm was observed: 22° C. to 27° C.). The mixture was then treated with CDI (30 g, 1.35 eq.) and the resulting mixture was stirred at room temperature for at least 4 h. The mixture was then treated with n-propylamine (12 mL, 1.1 eq.) and the resulting mixture was stirred overnight. The mixture was then treated with 10% citric acid (200 mL) and the resulting mixture was stirred for 30 min. and then transferred into a separatory funnel and THF (200 mL) was added to provide a clean phase split. The organic layer was collected and the solvent removed to afford an off-white solid. The solid was combined with MTBE (150 mL) and the mixture was stirred to dislodge solids from the flask wall. The resulting suspension was cooled in an ice-bath for at least 30 min. The solid was filtered, washed with MTBE (25 mL), and placed in vacuum oven at 50° C. for 18 h to afford 4-(2-(dimethylamino)thiazol-4-yl)-N-propylbenzamide (6-D) as an off-white solid (34.8 g, 90% yield, HPLC purity 95.4%). $^1$H NMR [400 MHz, DMSO-$d_6$]δ 0.90 (t, J=7.46 Hz, 3H), 1.54 (sxt, J=7.29 Hz, 2H), 3.10 (s, 6H), 3.19-3.26 (m, 2H), 7.32 (s, 1H), 7.81-7.98 (m, 4H), 8.43 (t, J=5.56 Hz, 1H).

Step 3: Preparation of N,N-dimethyl-4-(4-((propylamino)methyl)phenyl)thiazol-2-amine (Compound 8-D)

A mixture of 4-(2-(dimethylamino)thiazol-4-yl)-N-propylbenzamide (6-D, 57 g) in THF (855 mL) was treated with LAH (2 M in THF, 1.3 equiv., 129 mL) by dropwise addition. The resulting slurry was stirred for 4 h at 66° C. and then cooled to 10° C. The mixture was carefully treated with water (10 mL), followed by 15% NaOH (10 mL), and then additional water (30 mL). The resulting mixture was stirred overnight and then filtered through CELITE® to remove solid washing with THF (2×25 mL). The filtrate was evaporated to afford N,N-dimethyl-4-(4-((propylamino)methyl)phenyl)thiazol-2-amine (Compound 8-D) as a yellow oil (42 g, 78% isolated yield, HPLC purity 83.2%). $^1$H NMR [400 MHz, DMSO-$d_6$]δ 0.86 (t, J=7.40 Hz, 4H), 1.43 (sxt, J=7.29 Hz, 2H), 1.71-1.81 (m, 1H), 2.07-2.21 (m, 1H), 2.45 (t, J=7.15 Hz, 2H), 3.08 (s, 6H), 3.56-3.62 (m, 1H), 3.68 (s, 2H), 3.74 (s, 1H), 7.02 (s, 1H), 7.10 (s, 1H), 7.21-7.27 (m, 1H), 7.32 (d, J=8.31 Hz, 2H), 7.46 (d, J=8.31 Hz, 1H), 7.64 (s, 1H), 7.79 (d, J=8.31 Hz, 2H), 7.86-7.98 (m, 1H).

Step 4: Preparation of N,N-dimethyl-4-(4-((propylamino)methyl)phenyl)thiazol-2-amine 2HCl (Compound 8-E)

A mixture of N,N-dimethyl-4-(4-((propylamino)methyl)phenyl)thiazol-2-amine (8-D) and acetonitrile (20 mL, 5 V) was treated with 3.0 M HCl in CPME (2.5 eq, 13 mL) by dropwise addition over 15 minutes. The resulting slurry was stirred for 2 h. The solid was collected by filtration, washed with acetonitrile (5 mL), and dried in a vacuum oven at 55° C. for 18 h to afford the title compound as a tan solid (4.4 g, 83% yield, HPLC purity 93.3%). $^1$H NMR [400 MHz, DMSO-$d_6$]δ 0.90 (t, J=7.46 Hz, 3H), 1.60-1.75 (m, 2H), 2.74-2.91 (m, 2H), 3.09 (s, 6H), 4.11 (s, 2H), 7.26 (s, 1H), 7.55 (d, J=8.31 Hz, 2H), 7.91 (d, J=8.31 Hz, 2H).

Step 4A: Scale-up Preparation of N,N-dimethyl-4-(4-((propylamino)methyl)phenyl)thiazol-2-amine 2HCl (Compound 8-E)

A mixture of N,N-dimethyl-4-(4-((propylamino)methyl)phenyl)thiazol-2-amine (8-D, 190 g) and acetonitrile (950 mL, 5 V) was treated with 3.0 M HCl in CPME (2.5 eq, 575 mL) by dropwise addition until complete. The resulting mixture was stirred for 2 h with solid formation. The solid was collected by filtration, washed with acetonitrile (190 mL), and dried in a vacuum oven at 55° C. for 18 h to afford the title compound as a tan solid (165.8 g, 77% yield, HPLC purity 97.3%, X-ray powder diffraction (XRPD, see FIG. 17, and TGA and differential scanning calorimetry (DSC) thermogram, see FIG. 18). The XRPD diffractogram suggests the sample is semi-crystalline due to the presence of an amorphous halo. The thermogram has several overlapping gradual weight loss steps from room temperature, likely due to solvent/water loss and/or degradation/decomposition. Broad overlapping endothermic events are likely associated with the weight loss. There appears to be an endothermic event likely due to a melt with onset of approximately 147° C., which can be offset due to the overlapping events. Certain XRPD peaks for N,N-dimethyl-4-(4-((propylamino)methyl)phenyl)thiazol-2-amine 2HCl) (i.e., Compound 8-E) are shown in Table A below.

TABLE A

| # | 2-theta | Height (cps) |
|---|---|---|
| 1 | 5.9 | 5713 (218) |
| 2 | 6.7 | 587 (70) |
| 3 | 8.5 | 573 (69) |
| 4 | 9.0 | 1521 (113) |
| 5 | 11.9 | 2657 (149) |
| 6 | 13.0 | 596 (70) |
| 7 | 13.7 | 4434 (192) |
| 8 | 14.8 | 1060 (94) |
| 9 | 17.9 | 4493 (194) |
| 10 | 19.1 | 5484 (214) |
| 11 | 20.7 | 976 (90) |
| 12 | 21.2 | 1366 (107) |
| 13 | 21.5 | 306 (51) |
| 14 | 22.4 | 1394 (108) |
| 15 | 23.3 | 1014 (92) |
| 16 | 23.9 | 1503 (112) |
| 17 | 24.9 | 1777 (122) |
| 18 | 25.3 | 1351 (106) |
| 19 | 26.5 | 677 (75) |
| 20 | 26.7 | 1519 (112) |
| 21 | 27.1 | 4243 (188) |
| 22 | 27.9 | 978 (90) |
| 23 | 30.9 | 1575 (115) |
| 24 | 31.6 | 787 (81) |
| 25 | 33.1 | 2250 (137) |
| 26 | 35.2 | 353 (54) |
| 27 | 36.3 | 2350 (140) |
| 28 | 38.4 | 1057 (94) |
| 29 | 38.9 | 789 (81) |
| 30 | 41.0 | 392 (57) |

The PXRD analysis was performed on a Rigaku Powder X-Ray Diffractometer Miniflex 600 Serial Number BD66000190-01. For analysis, approximately 0.5-1 mg of sample was added to a PXRD zero-background sample holder. The powder was pressed down gently with a piece of weigh paper, and the sample holder was placed in the sample changer. Run Parameters: Miniflex Counter Detector, Kb Filter (x2), Scan Axis Theta/2-Theta, Mode Continuous, Start (deg) 2.0, Stop (deg) 45.0, Step (deg) 0.020, Speed (deg/min) 10.0, Spin-yes, Voltage (kV) 40, Current (mA) 15.

The DSC and TGA analysis were performed on TA Instruments Discovery DSC2500 (DSC) and TGA5500 (TGA) series. For the DSC analysis, ~1-3 mg of compound was weighed into a Tzero Pan and the Tzero lid was pressed on with tweezers. The pan was transferred to the DSC autosampler for analysis. The method for analysis was a ramp at 10° C./min to 350° C. Note: The reference pan was prepared with the same procedures, absent compound. For TGA analysis, a standard aluminum sample pan was placed into the platinum TGA pan and the blank was tared with the instrument. Approximately 1-5 mg of compound was added to the standard aluminum pan and analyzed at 10° C./min up to 375° C.

Intermediates used to synthesize compounds 11, 12, 13 and 14 to react with 4-(2-(dimethylamino)thiazol-4-yl)benzoic acid (5-D) were made via a similar method to those in scheme 3-C using the appropriate amines and thioureas, include:

TABLE B

| Compound | Intermediate | Chemical Structure | Amine | thiourea |
|---|---|---|---|---|
| 11 | 8A | 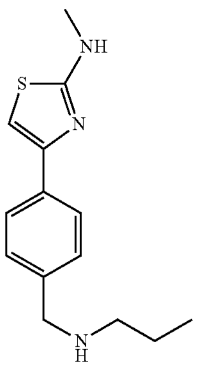 [SMILES: CCCNCc1ccc(-c2csc(NC)n2)cc1] | 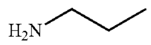 | 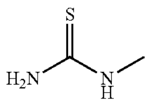 |
| 12 | 8B | 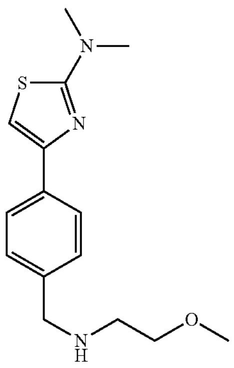 [SMILES: COCCNCc1ccc(-c2csc(N(C)C)n2)cc1] | 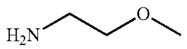 | 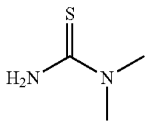 |
| 13 | 8C | 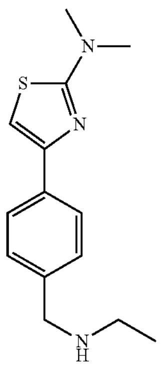 [SMILES: CCNCc1ccc(-c2csc(N(C)C)n2)cc1] | 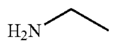 | 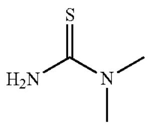 |

TABLE B-continued

| Compound | Intermediate | Chemical Structure | Amine | thiourea |
|---|---|---|---|---|
| 14 | 8D | 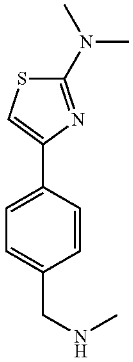 [SMILES: CNCc1ccc(-c2csc(N(C)C)n2)cc1] | 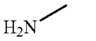 | 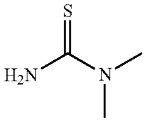 |

Example 5: Preparation of 5-(7-chloro-2,5-dimethylpyrazolo[1,5-a]pyrimidin-3-yl)-N,N,4-trimethylpyridin-2-amine (3-D)

Scheme 3-D

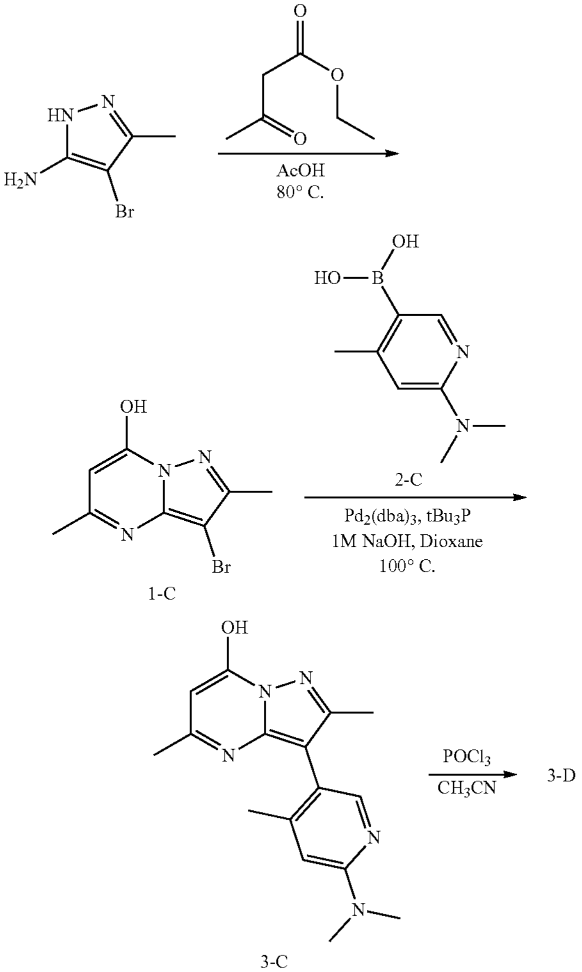

Step 1: Preparation of 3-bromo-2,5-dimethylpyrazolo[1,5-a]pyrimidin-7-ol (1-C)

A stirring slurry of 4-bromo-3-methyl-1H-pyrazol-5-amine (35.93 g, 204 mmol) in glacial acetic acid (70 mL) was treated with ethyl 3-oxobutanoate (37 mL, 306 mmol) and the resulting mixture was heated to 80° C. for 3 h. The mixture was cooled to 25° C. and treated with MTBE (175 mL) and the resulting mixture was stirred for 1 h. The solids were collected by vacuum filtration to afford 3-bromo-2,5-dimethylpyrazolo[1,5-a]pyrimidin-7-ol (1-C) as a white solid (43.6 g, 88% yield). $^1H$ NMR [400 MHz, DMSO-$d_6$]δ 2.26 (s, 3H), 2.30 (s, 3H), 12.19 (s, 1H).

Step 2: Preparation of 3-(6-(dimethylamino)-4-methylpyridin-3-yl)-2,5-dimethylpyrazolo[1,5-a]pyrimidin-7-ol (3-C)

A mixture of 3-bromo-2,5-dimethylpyrazolo[1,5-a]pyrimidin-7-ol (1-C, 1 g, 4.13 mmol), (6-(dimethylamino)-4-methylpyridin-3-yl)boronic acid (2-C, 1.12 g, 6.2 mmol), and $Pd_2(dba)_3$ (37.8 mg, 0.041 mmol) was combined in a round bottomed flask. The flask was then purged with nitrogen and the mixture was then treated with dioxane (degassed, 42 mL) followed by 1M NaOH (degassed, 12.5 mL) and tri-tert-butyl phosphine (20 μL, 0.082 mmol). The mixture was placed under vacuum and back filled with nitrogen three times. The mixture was heated to 100° C., stirred for 16 hours (98% conversion), and then allowed to cool to room temperature. The solvent was removed to afford an oil. The oil was dissolved in $CH_2Cl_2$ (ca. 100 mL) and water was added (ca. 100 mL). The pH of the aqueous phase was adjusted to 6 using conc. HCl. The heterogeneous mixture was stirred and the layers were separated. The aqueous layer was extracted with $CH_2Cl_2$ (ca. 100 mL) and the organic layers combined. The combined organic layer was dried over $MgSO_4$, the mixture was filtered to remove solid, and the filtrate concentrated. Isopropyl acetate (ca. 50 mL) was added to the oil and the mixture concentrated to a solid. Isopropyl acetate (ca. 10 mL) was added and the mixture stirred with a magnetic stir bar for 15 min. The solids were collected by vacuum filtration and washed with isopropyl acetate (ca. 5 mL) to afford 3-(6-(dimethylamino)-4-methylpyridin-3-yl)-2,5-dimethylpyrazolo[1,5-a]pyrimidin-7-ol (3-C) as a beige solid (0.95 g, 77% yield). $^1H$ NMR [400 MHz, $CDCl_3$]δ 2.12 (s, 3H), 2.19 (s, 3H), 2.35 (s, 3H), 2.94 (s, 6H), 5.61 (s, 1H), 6.28 (s, 1H), 7.67 (s, 1H), 12.78 (bs, 1H).

Example 6: Alternative preparation of 3-(6-(dimethylamino)-4-methylpyridin-3-yl)-2,5-dimethylpyrazolo[1,5-a]pyrimidin-7-ol (3-C)

A mixture of 3-bromo-2,5-dimethylpyrazolo[1,5-a]pyrimidin-7-ol (1-C, 473 g, 1.95 mol), (6-(dimethylamino)-4-methylpyridin-3-yl)boronic acid (2-C, 938.2 g, 3.91 mol, 2.0 equiv., as the AcOH salt), NaOH (390.8 g, 9.77 mol, 5.0 equiv.), dioxane (5.6 L), and $H_2O$ (1.4 L) was combined in a round bottomed flask. The flask was then purged with nitrogen (3×) and the mixture was then treated with AMPHOS Pd G3 (23.6 g, 0.037 mol, 5.0 wt % or 2 mol %) under nitrogen. The resulting mixture was heated to 100° C., stirred for 5 h, and then allowed to cool to rt. The mixture was concentrated under vacuum at 45° C. to a final volume of 4 L. The remainder was combined with water (2.5 L) and $CH_2Cl_2$ (5 L) and then the resulting mixture was treated with glacial acetic acid (352 g, 3 equiv.). The mixture was stirred for complete mixing and then the layers were allowed to separate. The aqueous layer was extracted with $CH_2Cl_2$ (5 L). The organic layer was dried over $Na_2SO_4$, the mixture was filtered to remove solid, and the filtrate concentrated to afford a brown oil (2.1 kg). The brown oil was combined with EtOAc (2 L) and the resulting mixture agitated at 40° C. for 3 h. The mixture was cooled to 20-25° C. and stirred for 16 h. The solid was collected by filtration afford a filter cake which was washed with EtOAc (500 mL) and petroleum ether (500 mL). The cake was dried under vacuum at 50° C. to afford 3-(6-(dimethylamino)-4-methylpyridin-3-yl)-2,5-dimethylpyrazolo[1,5-a]pyrimidin-7-ol (3-C) as a grey solid (467 g, 80% yield, 93.0% HPLC purity).

Example 7: Preparation of 5-(7-chloro-2,5-dimethylpyrazolo[1,5-a]pyrimidin-3-yl)-N,N,4-trimethylpyridin-2-amine (3-D)

Compound 3-D was prepared as described in Chen et al., "Design of 2,5-Dimethyl-3-(6-dimethyl-4-methylpyridin-3-yl)-7-dipropylaminopyrazolo[1,5-a]pyrimidine (NBI 30775/R121919) and Structure-Activity Relationships of a Series of Potent and Orally Active Corticotropin-Releasing Factor Receptor Antagonists," *J. Med. Chem*, 2004, 47(19): 4787-4798.

Example 8: Preparation of 2-(dimethylamino)-4-methylpyridine-5-boronic acid (2-C)

Scheme 3-E

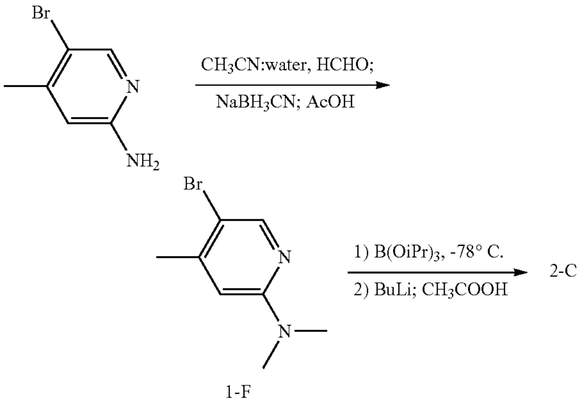

1-F

Step 1: Preparation of 5-bromo-N,N,4-trimethylpyridin-2-amine (1-F)

A mixture of 5-bromo-4-methylpyridin-2-amine (1.56 kg, 8.34 mol) in acetonitrile (25 L) and water (4.7 L) was treated with 37% aqueous formaldehyde solution (6.5 L, 306 mmol) at 0° C. The resulting mixture was allowed to warm to rt and treated with $NaBH_3CN$ (1.58 kg, 25.16 mol, 3.0 equiv.) by portion wise addition. The resulting mixture was cooled to 0-10° C. and treated with glacial acetic acid (1.71 kg) by dropwise addition. The resulting mixture was allowed to warm to rt and stirred for 72 hours. The mixture was combined with 10% NaOH (3 L) and the formed solid was removed by filtration. The mixture was extracted with petroleum ether (20 L×2). The combined organic layer was dried over $Na_2SO_4$, filtered and concentrated under reduced pressure to afford a brown oil (1.70 kg). The brown oil was dissolved in acetone (14 L) and the resulting mixture was treated with a solution of oxalic acid dihydrate (1 kg, 1 eq.) in acetone (6.5 L) by dropwise addition at rt providing a solid. The resulting mixture was stirred at 60° C. for 1.5 h and then cooled to 25-30° C. stirring for an additional 1.5 h. The solid was collected by filtration. The solid was suspended in acetone (15 L) and stirred at 60° C. for 2 h, then cooled to 25-30° C. The solid was collected by filtration. The solid was dissolved in water (10 L) and the resulting mixture combined with MTBE (15 L). The pH was adjusted to 10-11 with 10% NaOH (5 L) where a white solid formed. The solid was removed by filtration and the filtrate partitioned maintaining the MTBE layer and aqueous layer for further processing. The aqueous layer was extracted with MTBE (10 L). The combined organic layer was washed with brine (10 L), dried over $Na_2SO_4$, filtered and concentrated under reduced pressure at 35-40° C. to afford 5-bromo-N,N,4-trimethylpyridin-2-amine (1-F) as a white solid (1.1 kg, 60% yield, 99.2% by HPLC).

Step 2: Preparation of 2-(dimethylamino)-4-methylpyridine-5-boronic acid (as acetate) (2-C)

A mixture of 5-bromo-N,N,4-trimethylpyridin-2-amine (1-F, 1.2 kg, 5.58 mol) in THF (8.4 L) was treated with triisopropyl borate (1.57 kg, 8.37 mol, 1.5 eq.) at −70° C. The resulting mixture was treated with n-BuLi (2.5 M, 3.35 L, 8.37 mol, 1.5 equiv.) by dropwise addition at −70° C. under nitrogen. The resulting mixture was stirred at −65° C. to −70° C. for 1.5 h and then allowed to warm to rt and stirred overnight. The mixture was combined with glacial acetic acid (0.84 kg, 13.95 mol, 2.5 equiv.) providing a thick mixture which was then combined with water (12 L). The resulting mixture was stirred at rt for 2 h and then the formed solid was collected by filtration. The solid was slurried with petroleum ether (3 L) and the solid was collected by filtration. The solid was dried under vacuum at 45° C. to afford 2-(dimethylamino)-4-methylpyridine-5-boronic acid (as acetate) (2-C) as a white solid (1.01 kg, 75% yield).

Example 9: 5-{2,5-dimethyl-7-[propyl({[4-(pyridin-3-yl)phenyl]methyl})amino]pyrazolo[1,5-a]pyrimidin-3-yl}-N,N,4-trimethylpyridin-2-amine (Compound 2)

2

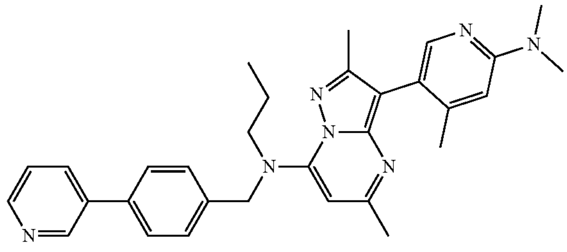

The title compound was prepared in a similar manner to Example 1 using (pyridin-3-yl)boronic acid in place of N,N-dimethyl-4-(tetramethyl-1,3,2-dioxaborolan-2-yl)-1,3-thiazol-2-amine in step 3. Purified by HPLC (method: C).

LCMS: (Method: A) (ESI+) m/z 506.3 [MH+], tR=2.18 min.

Example 10: 5-{2,5-dimethyl-7-[propyl({[4-(pyridin-2-yl)phenyl]methyl})amino]pyrazolo[1,5-a]pyrimidin-3-yl}-N,N,4-trimethylpyridin-2-amine (Compound 3)

3

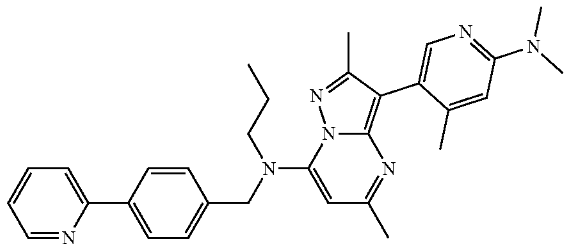

The title compound was prepared in a similar manner to Example 1 using (pyridin-2-yl)boronic acid in place of N,N-dimethyl-4-(tetramethyl-1,3,2-dioxaborolan-2-yl)-1,3-thiazol-2-amine in step 3. Purified by HPLC (method: D).

LCMS: (Method: E) (ESI+) m/z 505.2 [M+], tR=2.65 min.

Example 11: 5-{2,5-dimethyl-7-[propyl({[4-(pyrimidin-5-yl)phenyl]methyl})amino]pyrazolo[1,5-a]pyrimidin-3-yl}-N,N,4-trimethylpyridin-2-amine (Compound 4)

4

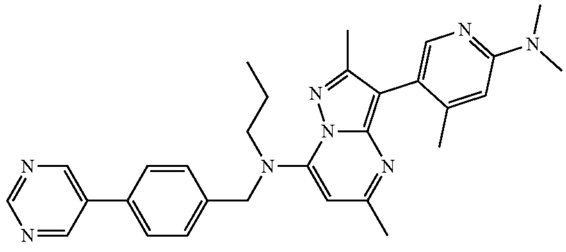

The title compound was prepared in a similar manner to Example 1 using (pyrimidin-5-yl)boronic acid in place of N,N-dimethyl-4-(tetramethyl-1,3,2-dioxaborolan-2-yl)-1,3-thiazol-2-amine in step 3. Purified by HPLC (method: C).

LCMS: (Method: A) (ESI+) m/z 507.3 [MH+], tR=2.54 min.

Example 12: 5-{2,5-dimethyl-7-[propyl({[4-(pyridin-4-yl)phenyl]methyl})amino]pyrazolo[1,5-a]pyrimidin-3-yl}-N,N,4-trimethylpyridin-2-amine (Compound 6)

6

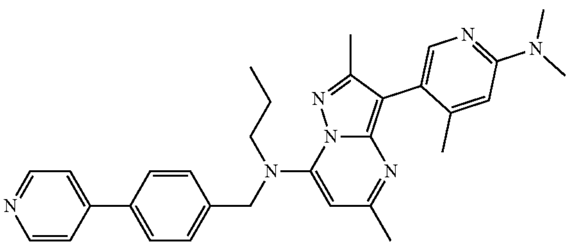

The title compound was prepared in a similar manner to Example 1 using (pyridin-4-yl)boronic acid in place of N,N-dimethyl-4-(tetramethyl-1,3,2-dioxaborolan-2-yl)-1,3-thiazol-2-amine in step 3. Purified by HPLC (Method: C).

LCMS: (Method: E) (ESI+) m/z 506.2 [MH+], tR=1.84 min.

Example 13: 5-[2,5-dimethyl-7-({[4-(1,2-oxazol-4-yl)phenyl]methyl}(propyl)amino)pyrazolo[1,5-a]pyrimidin-3-yl]-N,N,4-trimethylpyridin-2-amine (Compound 7)

7

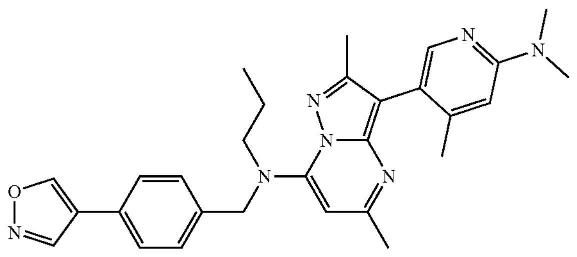

The title compound was prepared in a similar manner to Example 1 using 4-(tetramethyl-1,3,2-dioxaborolan-2-yl)-1,2-oxazole in place of N,N-dimethyl-4-(tetramethyl-1,3,2-dioxaborolan-2-yl)-1,3-thiazol-2-amine in step 3. Purified by HPLC (Method: C).

LCMS: (Method: C) (ESI+) m/z 495.3 [M+], tR=2.44 min.

Example 14: 5-(2,5-dimethyl-7-{[(4-phenylphenyl)methyl](propyl)amino}pyrazolo[1,5-a]pyrimidin-3-yl)-N,N,4-trimethylpyridin-2-amine (Compound 8)

8

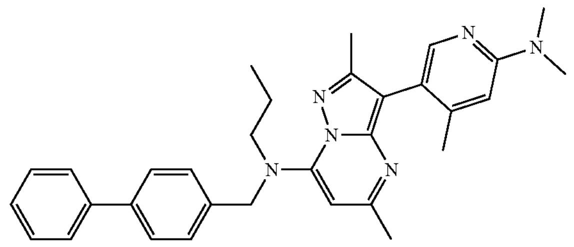

The title compound was prepared in a similar manner to Example 1 using phenylboronic acid in place of N,N-dimethyl-4-(tetramethyl-1,3,2-dioxaborolan-2-yl)-1,3-thiazol-2-amine in step 3.

LCMS: (Method: A) (ESI+) m/z 505.4 [MH+], tR=3.80 min.

Example 15: Scheme 4-A: Preparation of 5-{2,5-dimethyl-7-[propyl({[4-(1H-pyrazol-1-yl)phenyl]methyl})amino]pyrazolo[1,5-a]pyrimidin-3-yl}-N,N,4-trimethylpyridin-2-amine (Compound 9)

The title compound was prepared according to protocol B and protocol 1-B as shown in Scheme 4-A below.

Scheme 4-A

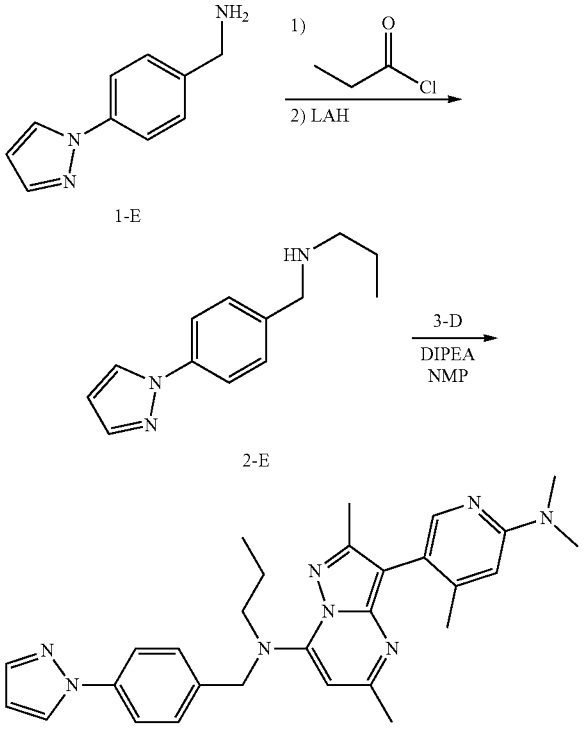

1-E

2-E

9

Step 1: Preparation of N-(4-(1H-pyrazol-1-yl)benzyl)propan-1-amine (2-E)

A mixture of [4-(1H-pyrazol-1-yl)phenyl]methanamine (1-E, 500 mg) and DIPEA (2 eq) in DCM (5 mL) was treated with propionyl chloride (320 mg) at rt and stirred 1 h. The solvent was removed under vacuum and DCM added and the organic was washed with sat. aq. $NaHCO_3$, dried over $Na_2SO_4$, filtered to remove solid and concentrated to afford N-propyl-4-(1H-pyrazol-1-yl)benzamide. Subsequently, N-propyl-4-(1H-pyrazol-1-yl)benzamide was dissolved in THF and $LiAlH_4$ (1 equiv., 2 M in THF) was added at rt and stirred and then $LiAlH_4$ (2 equiv.) was added and stirred until complete by LCMS. The mixture was treated with sat. aq. Rochelles salt and the resulting mixture was stirred at rt for 1 h and then extracted with EtOAc. The organic was dried over $Na_2SO_4$, filtered to remove solid and concentrated. Purification by chromatography on silica gel eluting with 10-50% MeOH/DCM afforded N-(4-(1H-pyrazol-1-yl)benzyl)propan-1-amine (2-E, 420 mg). $^1H$ NMR [400 MHz, DMSO-$d_6$]δ 8.46 (d, J=2.6 Hz, 1H), 7.76 (d, J=8 Hz, 2H), 7.72 (d, J=2.4 Hz, 1H), 7.45 (d, J=8 Hz, 2H), 6.52 (t, J=2 Hz, 1H), 3.70 (s, 2H), 2.45 (t, J=7 Hz, 2H), 1.43 (2H, app sextet, J=7.4 Hz, 2H), 0.97 (t, J=7.5 Hz). LCMS: (Method: A) (ESI+) m/z 216.0 [MH+], tR=1.48 min.

Step 2: Preparation of 5-{2,5-dimethyl-7-[propyl({[4-(1H-pyrazol-1-yl)phenyl]methyl})amino]pyrazolo[1,5-a]pyrimidin-3-yl}-N,N,4-trimethylpyridin-2-amine (Compound 9)

A mixture of N-(4-(1H-pyrazol-1-yl)benzyl)propan-1-amine (2-E, 3.9 mg), 5-(7-chloro-2,5-dimethylpyrazolo[1,5- a]pyrimidin-3-yl)-N,N,4-trimethylpyridin-2-amine (3-D, 5 mg), and DIPEA (3 equiv.) in NMP (0.1 mL) was heated by microwave at 140° C. The mixture was allowed to cool to rt affording 5-{2,5-dimethyl-7-[propyl({[4-(1H-pyrazol-1-yl)phenyl]methyl})amino]pyrazolo[1,5-a]pyrimidin-3-yl}-N,N,4-trimethylpyridin-2-amine (9). Purified by HPLC (Method: D). LCMS: (Method A (ESI+) m/z 495.3 [MH+], tR=2.91 min.

Example 16: 5-{2,5-dimethyl-7-[propyl({[4-(1,2,3-thiadiazol-4-yl)phenyl]methyl})amino]pyrazolo[1,5-a]pyrimidin-3-yl}-N,N,4-trimethylpyridin-2-amine (Compound 5)

5

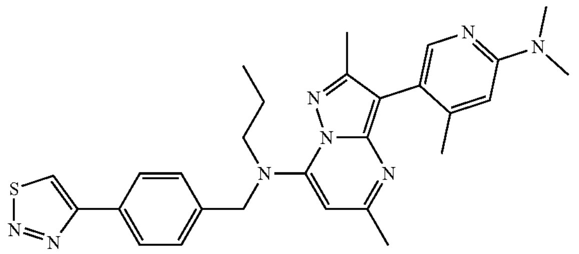

The title compound was prepared in a similar manner to Example 9 using N-(4-(1,2,3-thiadiazol-4-yl)benzyl)propan-1-amine in place of N-(4-(1H-pyrazol-1-yl)benzyl)propan-1-amine in the final step, and (4-(1,2,3-thiadiazol-4-yl)phenyl)methanamine in place of [4-(1H-pyrazol-1-yl)phenyl]methanamine (1-E).

Example 17: 5-{2,5-dimethyl-7-[propyl({[4-(1H-1,2,4-triazol-1-yl)phenyl]methyl})amino]pyrazolo[1,5-a]pyrimidin-3-yl}-N,N,4-trimethylpyridin-2-amine (Compound 10)

10

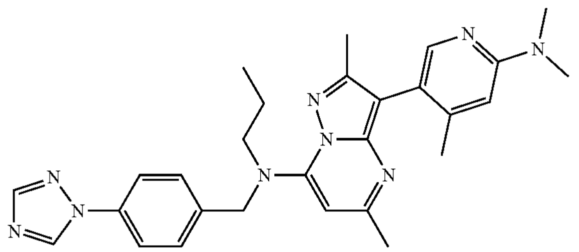

The title compound was prepared in a similar manner to Example 9 using N-(4-(1H-1,2,4-triazol-1-yl)benzyl)propan-1-amine in place of N-(4-(1H-pyrazol-1-yl)benzyl)propan-1-amine in the final step, and [4-(1H-1,2,4-triazol-1-yl)phenyl]methanamine in place of [4-(1H-pyrazol-1-yl)phenyl]methanamine (1-E). Purified by HPLC (Method: D). LCMS: (Method: A (ESI+) m/z 496.3 [MH+], tR=2.48 min.

N-(4-(1H-1,2,4-triazol-1-yl)benzyl)propan-1-amine. $^1$H NMR [DMSO-$d_6$]δ 9.25 (s, 1H), 8.22 (s, 1H), 7.79 (d, J=8.7 Hz, 2H), 7.50 (d, J=8.7 Hz, 2H), 3.72 (s, 2H), 2.45 (t, J=7.2 Hz, 2H), 2.14 (br s, 1H), 1.44 (app sextet, J=7.2 Hz, 2H) 0.87 (t, J=7.2 Hz, 3H). LCMS: (Method: B) (ESI+) m/z 217.0 [MH+], tR=0.20 min.

Example 18: 5-{2,5-dimethyl-7-[({4-[2-(methylamino)-1,3-thiazol-4-yl]phenyl}methyl)(propyl)amino]pyrazolo[1,5-a]pyrimidin-3-yl}-N,N,4-trimethylpyridin-2-amine (Compound 11)

11

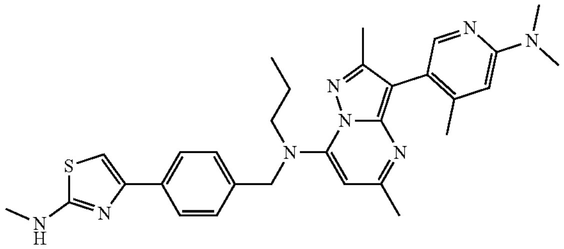

The title compound was prepared in a similar manner to the final step of Example 15 using intermediate 8A in place of N-(4-(1H-pyrazol-1-yl)benzyl)propan-1-amine (2-E). Purified on silica gel eluting with EtOAc/Hex. LCMS: (Method: E (ESI+) m/z 541.2 [MH+], tR=1.42 min.

Example 19: 5-{7-[({4-[2-(dimethylamino)-1,3-thiazol-4-yl]phenyl}methyl)(2-methoxyethyl)amino]-2,5-dimethylpyrazolo[1,5-a]pyrimidin-3-yl}-N,N,4-trimethylpyridin-2-amine (Compound 12)

12

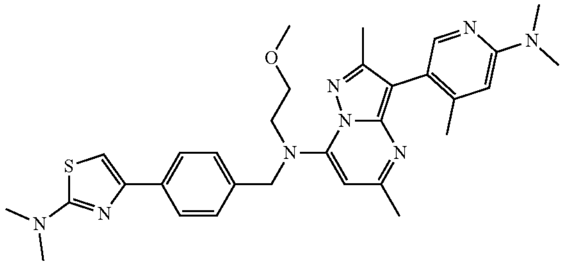

The title compound was prepared in a similar manner to the final step of Example 15 using intermediate 8B in place of N-(4-(1H-pyrazol-1-yl)benzyl)propan-1-amine (2-E). Purified by HPLC (Method: H). LCMS: (Method: E (ESI+) m/z 571 [MH+], tR=2.22 min.

Example 20: 5-{7-[({4-[2-(dimethylamino)-1,3-thiazol-4-yl]phenyl}methyl)(ethyl)amino]-2,5-dimethylpyrazolo[1,5-a]pyrimidin-3-yl}-N,N,4-trimethylpyridin-2-amine (Compound 13)

13

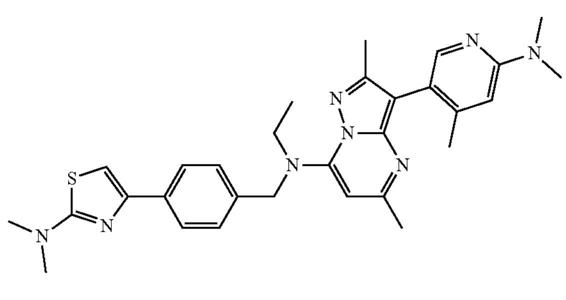

The title compound was prepared in a similar manner to the final step of Example 15 using intermediate 8C in place of N-(4-(1H-pyrazol-1-yl)benzyl)propan-1-amine (2-E). Purified by HPLC (Method: H). LCMS: (Method: E (ESI+) m/z 541.3 [NM+], tR=2.22 min.

Example 21: 5-{7-[({4-[2-(dimethylamino)-1,3-thiazol-4-yl]phenyl}methyl)(methyl)amino]-2,5-dimethylpyrazolo[1,5-a]pyrimidin-3-yl}-N,N,4-trimethylpyridin-2-amine (Compound 14)

14

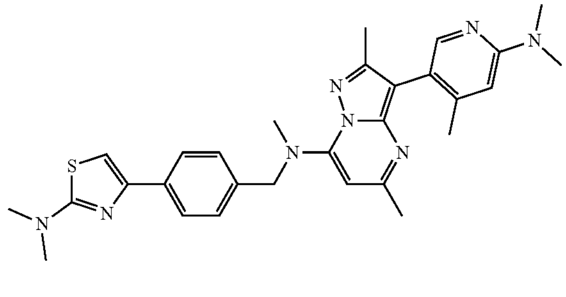

The title compound was prepared in a similar manner to the final step of Example 15 using intermediate 8D in place of N-(4-(1H-pyrazol-1-yl)benzyl)propan-1-amine (2-E). Purified by HPLC (Method: H). LCMS: (Method: E (ESI+) m/z 527 [MH+], tR=2.12 min.

The compounds of Examples 22-50 were prepared in a similar manner to Example 1 starting from step 2 using commercially available 4-iodo-N-methylbenzenemethanamine in place of N-(4-iodobenzyl)propan-1-amine (2-D) HCl to afford 5-(7-{[(4-iodophenyl)methyl](methyl)amino}-2,5-dimethylpyrazolo[1,5-a]pyrimidin-3-yl)-N,N,4-trimethylpyridin-2-amine and the reaction conditions of Synthesis Method A in place of the reaction conditions in step 3.

Synthesis Method A

A mixture of 5-(7-{[(4-iodophenyl)methyl](methyl)amino}-2,5-dimethylpyrazolo[1,5-a]pyrimidin-3-yl)-N,N,4-trimethylpyridin-2-amine (10 mg) and chloro[(tri-tert-butylphosphine)-2-(2-aminobiphenyl)]palladium(II) (10 mol %) was dissolved in dioxane (0.2 mL) and 1 M NaOH (0.1 mL) and then added to the appropriate boronate or boronic acid (2 equivalents). The resulting mixture was heated at 95° C. in a sealed vial for 3 h. The mixture was cooled, and purified by prep-HPLC.

Example 22: 5-[7-({[4-(dimethyl-1,3-thiazol-5-yl)phenyl]methyl}(methyl)amino)-2,5-dimethylpyrazolo[1,5-a]pyrimidin-3-yl]-N,N,4-trimethylpyridin-2-amine (Compound 15)

15

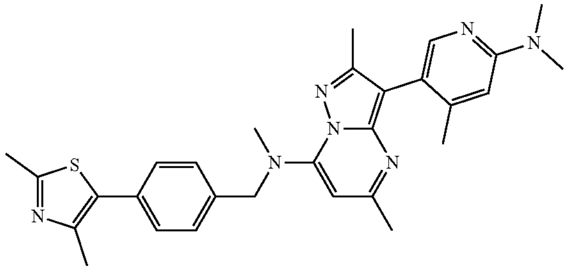

The title compound was prepared according to Synthesis Method A using 5-(7-{[(4-iodophenyl)methyl](methyl)amino}-2,5-dimethylpyrazolo[1,5-a]pyrimidin-3-yl)-N,N,4-trimethylpyridin-2-amine and 2,4-dimethyl-5-(tetramethyl-1,3,2-dioxaborolan-2-yl)-1,3-thiazole. Purified by HPLC (Method: F). LCMS: (Method: E) (ESI+) m/z 512.3 [MH+], tR=1.24 min.

Example 23: 5-{2,5-dimethyl-7-[methyl({[4-(1-methyl-1H-pyrazol-5-yl)phenyl]methyl})amino]pyrazolo[1,5-a]pyrimidin-3-yl}-N,N,4-trimethylpyridin-2-amine (Compound 16)

16

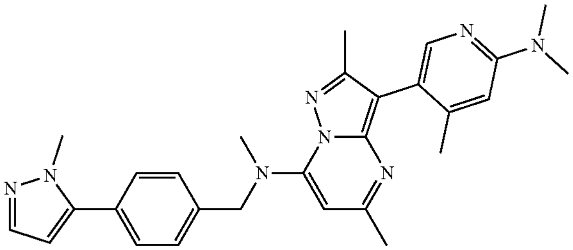

The title compound was prepared according to Synthesis Method A using 5-(7-{[(4-iodophenyl)methyl](methyl)amino}-2,5-dimethylpyrazolo[1,5-a]pyrimidin-3-yl)-N,N,4-trimethylpyridin-2-amine and (1-methyl-1H-pyrazol-5-yl)boronic acid. Purified by HPLC (Method: F). LCMS: (Method: E) (ESI+) m/z 481.3 [MH+], tR=1.16 min.

Example 24: 5-{2,5-dimethyl-7-[methyl({[4-(1-methyl-1H-pyrazol-3-yl)phenyl]methyl})amino]pyrazolo[1,5-a]pyrimidin-3-yl}-N,N,4-trimethylpyridin-2-amine (Compound 17)

17

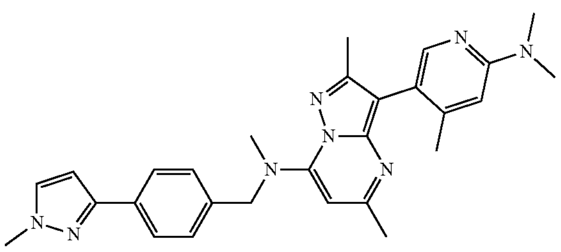

The title compound was prepared according to Synthesis Method A using 5-(7-{[(4-iodophenyl)methyl](methyl)amino}-2,5-dimethylpyrazolo[1,5-a]pyrimidin-3-yl)-N,N,4-trimethylpyridin-2-amine and (1-methyl-1H-pyrazol-3-yl) boronic acid. Purified by HPLC (Method: F). LCMS: (Method: E) (ESI+) m/z 481.3 [MH+], tR=1.18 min.

Example 25: 5-{2,5-dimethyl-7-[methyl({[4-(1-methyl-1H-pyrazol-4-yl)phenyl]methyl})amino]pyrazolo[1,5-a]pyrimidin-3-yl}-N,N,4-trimethylpyridin-2-amine (Compound 18)

18

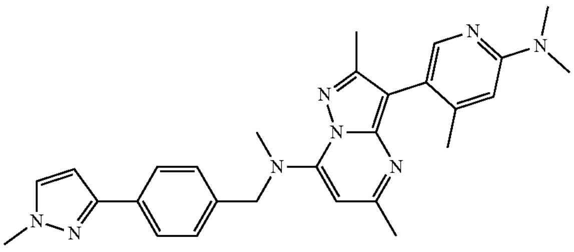

The title compound was prepared according to Synthesis Method A using 5-(7-{[(4-iodophenyl)methyl](methyl)amino}-2,5-dimethylpyrazolo[1,5-a]pyrimidin-3-yl)-N,N,4-trimethylpyridin-2-amine and 1-methyl-4-(tetramethyl-1,3,2-dioxaborolan-2-yl)-1H-pyrazole. Purified by HPLC (Method: F). LCMS: (Method: E) (ESI+) m/z 481.3 [MH+], tR=1.14 min.

Example 26: 5-{2,5-dimethyl-7-[methyl({[4-(1H-pyrazol-4-yl)phenyl]methyl})amino]pyrazolo[1,5-a]pyrimidin-3-yl}-N,N,4-trimethylpyridin-2-amine (Compound 19)

19

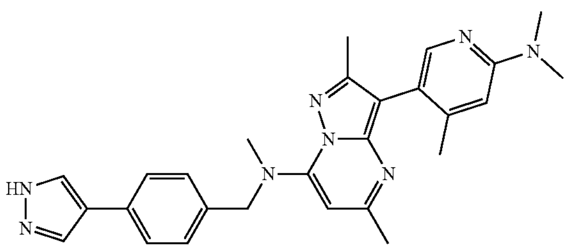

The title compound was prepared according to Synthesis Method A using 5-(7-{[(4-iodophenyl)methyl](methyl)amino}-2,5-dimethylpyrazolo[1,5-a]pyrimidin-3-yl)-N,N,4-trimethylpyridin-2-amine and (1H-pyrazol-4-yl)boronic acid. Purified by HPLC (method: C).

LCMS: (Method: F) (ESI+) m/z 467.25 [MH+], tR=1.06 min.

Example 27: 5-{2,5-dimethyl-7-[methyl({[4-(3-methyl-1H-pyrazol-4-yl)phenyl]methyl})amino]pyrazolo[1,5-a]pyrimidin-3-yl}-N,N,4-trimethylpyridin-2-amine (Compound 20)

20

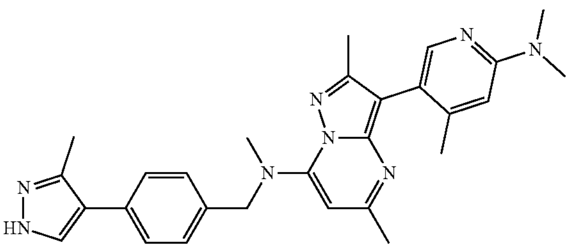

The title compound was prepared according to Synthesis Method A using 5-(7-{[(4-iodophenyl)methyl](methyl)amino}-2,5-dimethylpyrazolo[1,5-a]pyrimidin-3-yl)-N,N,4-trimethylpyridin-2-amine and (3-methyl-1H-pyrazol-4-yl) boronic. Purified by HPLC (Method: F). LCMS: (Method: E) (ESI+) m/z 481.3 [MH+], tR=1.09 min.

Example 28: 5-[7-({[4-(1,3-dimethyl-1H-pyrazol-5-yl)phenyl]methyl}(methyl)amino)-2,5-dimethylpyrazolo[1,5-a]pyrimidin-3-yl]-N,N,4-trimethylpyridin-2-amine (Compound 21)

21

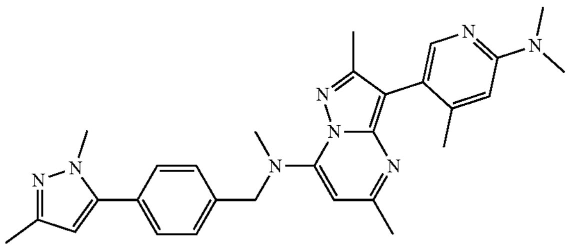

The title compound was prepared according to Synthesis Method A using 5-(7-{[(4-iodophenyl)methyl](methyl)amino}-2,5-dimethylpyrazolo[1,5-a]pyrimidin-3-yl)-N,N,4-trimethylpyridin-2-amine and (1,3-dimethyl-1H-pyrazol-5-yl)boronic acid. Purified by HPLC (Method: F). LCMS: (Method: E) (ESI+) m/z 495.3 [MH+], tR=1.20 min.

Example 29: 5-[7-{[4-(1,4-dimethyl-1H-pyrazol-3-yl)phenyl]methyl}(methyl)amino)-2,5-dimethylpyrazolo[1,5-a]pyrimidin-3-yl]-N,N,4-trimethylpyridin-2-amine (Compound 22)

22

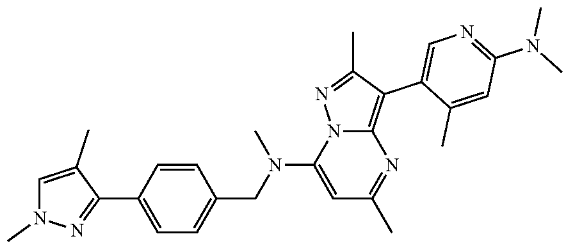

The title compound was prepared according to Synthesis Method A using 5-(7-{[(4-iodophenyl)methyl](methyl)amino}-2,5-dimethylpyrazolo[1,5-a]pyrimidin-3-yl)-N,N,4-trimethylpyridin-2-amine and (1,4-dimethyl-1H-pyrazol-3-yl)boronic acid. Purified by HPLC (Method: F). LCMS: (Method: E) (ESI+) m/z 495.3 [MH+], tR=1.25 min.

Example 30: 5-[7-({[4-(1,5-dimethyl-1H-pyrazol-3-yl)phenyl]methyl}(methyl)amino)-2,5-dimethylpyrazolo[1,5-a]pyrimidin-3-yl]-N,N,4-trimethylpyridin-2-amine (Compound 23)

23

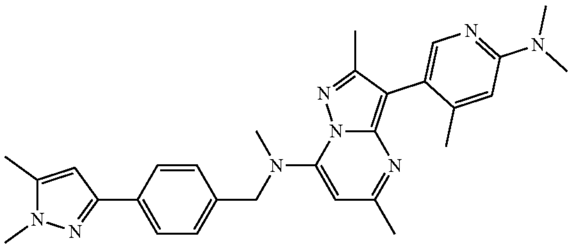

The title compound was prepared according to Synthesis Method A using 5-(7-{[(4-iodophenyl)methyl](methyl)amino}-2,5-dimethylpyrazolo[1,5-a]pyrimidin-3-yl)-N,N,4-trimethylpyridin-2-amine and 1,5-dimethyl-3-(tetramethyl-1,3,2-dioxaborolan-2-yl)-1H-pyrazole. Purified by HPLC (Method: F). LCMS: (Method: E) (ESI+) m/z 495.3 [MH+], tR=1.19 min.

Example 31: 5-[7-{[4-(1,4-dimethyl-1H-pyrazol-5-yl)phenyl]methyl}(methyl)amino)-2,5-dimethylpyrazolo[1,5-a]pyrimidin-3-yl]-N,N,4-trimethylpyridin-2-amine (Compound 24)

24

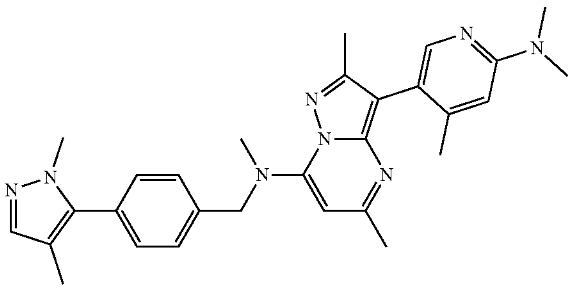

The title compound was prepared according to Synthesis Method A using 5-(7-{[(4-iodophenyl)methyl](methyl)amino}-2,5-dimethylpyrazolo[1,5-a]pyrimidin-3-yl)-N,N,4-trimethylpyridin-2-amine and 1,4-dimethyl-5-(tetramethyl-1,3,2-dioxaborolan-2-yl)-1H-pyrazole. Purified by HPLC (Method: F). LCMS: (Method: E) (ESI+) m/z 495.3 [MH+], tR=1.22 min.

Example 32: 5-[7-({[4-(1,5-dimethyl-1H-pyrazol-4-yl)phenyl]methyl}(methyl)amino)-2,5-dimethylpyrazolo[1,5-a]pyrimidin-3-yl]-N,N,4-trimethylpyridin-2-amine (Compound 25)

25

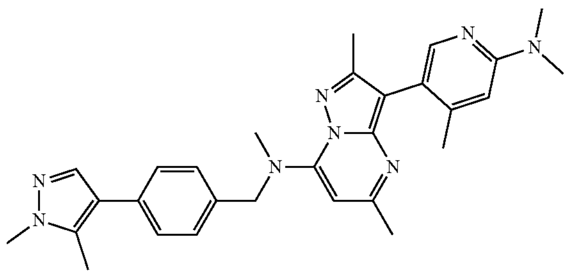

The title compound was prepared according to Synthesis Method A using 5-(7-{[(4-iodophenyl)methyl](methyl)amino}-2,5-dimethylpyrazolo[1,5-a]pyrimidin-3-yl)-N,N,4-trimethylpyridin-2-amine and 1,5-dimethyl-4-(tetramethyl-1,3,2-dioxaborolan-2-yl)-1H-pyrazole. Purified by HPLC (Method: F). LCMS: (Method: E) (ESI+) m/z 495.3 [MH+], tR=1.19 min.

Example 33: 5-[7-{[4-(1,3-dimethyl-1H-pyrazol-4-yl)phenyl]methyl}(methyl)amino)-2,5-dimethylpyrazolo[1,5-a]pyrimidin-3-yl]-N,N,4-trimethylpyridin-2-amine (Compound 26)

26

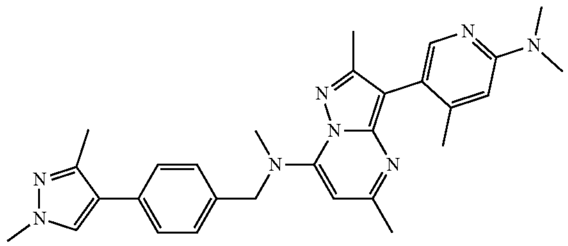

The title compound was prepared according to Synthesis Method A using 5-(7-{[(4-iodophenyl)methyl](methyl)amino}-2,5-dimethylpyrazolo[1,5-a]pyrimidin-3-yl)-N,N,4-trimethylpyridin-2-amine and (1,3-dimethyl-1H-pyrazol-4-yl)boronic acid. Purified by HPLC (Method: F). LCMS: (Method: E) (ESI+) m/z 495.3 [MH+], tR=1.18 min.

Example 34: 5-[7-({[4-(3-fluoropyridin-4-yl)phenyl]methyl}(methyl)amino)-2,5-dimethylpyrazolo[1,5-a]pyrimidin-3-yl]-N,N,4-trimethylpyridin-2-amine (Compound 27)

27

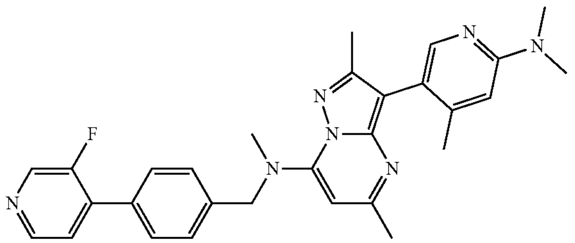

The title compound was prepared according to Synthesis Method A using 5-(7-{[(4-iodophenyl)methyl](methyl)amino}-2,5-dimethylpyrazolo[1,5-a]pyrimidin-3-yl)-N,N,4-trimethylpyridin-2-amine and (3-fluoropyridin-4-yl)boronic acid. Purified by HPLC (Method: F). LCMS: (Method: E) (ESI+) m/z 496.3 [MH+], tR=1.19 min.

Example 35: 5-[7-({[4-(2-fluoropyridin-4-yl)phenyl]methyl}(methyl)amino)-2,5-dimethylpyrazolo[1,5-a]pyrimidin-3-yl]-N,N,4-trimethylpyridin-2-amine (Compound 28)

28

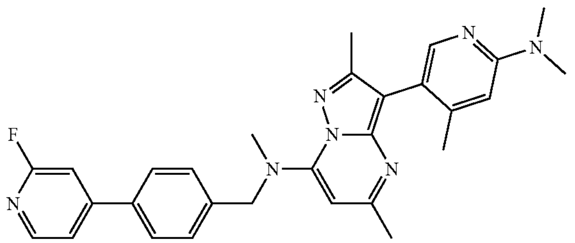

The title compound was prepared according to Synthesis Method A using 5-(7-{[(4-iodophenyl)methyl](methyl)amino}-2,5-dimethylpyrazolo[1,5-a]pyrimidin-3-yl)-N,N,4-trimethylpyridin-2-amine and (2-fluoropyridin-4-yl)boronic acid. Purified by HPLC (Method: F). LCMS: (Method: E) (ESI+) m/z 496.3 [MH+], tR=1.31 min.

Example 36: 5-[7-({[4-(5-fluoropyridin-3-yl)phenyl]methyl}(methyl)amino)-2,5-dimethylpyrazolo[1,5-a]pyrimidin-3-yl]-N,N,4-trimethylpyridin-2-amine (Compound 29)

29

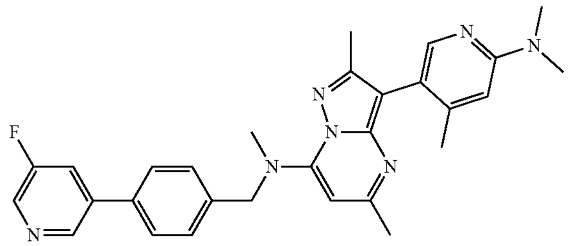

The title compound was prepared according to Synthesis Method A using 5-(7-{[(4-iodophenyl)methyl](methyl)amino}-2,5-dimethylpyrazolo[1,5-a]pyrimidin-3-yl)-N,N,4-trimethylpyridin-2-amine and (5-fluoropyridin-3-yl)boronic acid. Purified by HPLC (Method: F). LCMS: (Method: E) (ESI+) m/z 496.3 [MH+], tR=1.26 min.

Example 37: 5-[7-({[4-(5-methanesulfonylpyridin-3-yl)phenyl]methyl}(methyl)amino)-2,5-dimethylpyrazolo[1,5-a]pyrimidin-3-yl]-N,N,4-trimethylpyridin-2-amine (Compound 30)

30

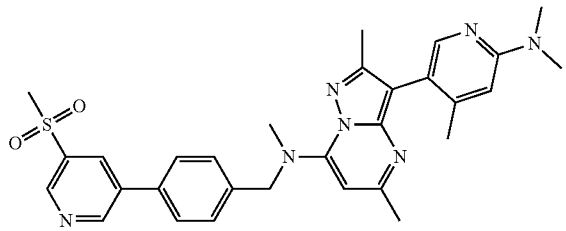

The title compound was prepared according to Synthesis Method A using 5-(7-{[(4-iodophenyl)methyl](methyl)amino}-2,5-dimethylpyrazolo[1,5-a]pyrimidin-3-yl)-N,N,4-trimethylpyridin-2-amine and 3-methanesulfonyl-5-(tetramethyl-1,3,2-dioxaborolan-2-yl)pyridine. Purified by HPLC (Method: F). LCMS: (Method: E) (ESI+) m/z 556.3 [MH+], tR=1.13 min.

Example 38: 3-{4-[({3-[6-(dimethylamino)-4-methylpyridin-3-yl]-2,5-dimethylpyrazolo[1,5-a]pyrimidin-7-yl}(methyl)amino)methyl]phenyl}pyridine-4-carbonitrile (Compound 31)

31

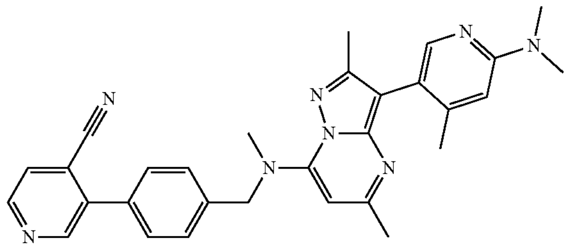

The title compound was prepared according to Synthesis Method A using 5-(7-{[(4-iodophenyl)methyl](methyl)amino}-2,5-dimethylpyrazolo[1,5-a]pyrimidin-3-yl)-N,N,4-trimethylpyridin-2-amine and 3-(tetramethyl-1,3,2-dioxaborolan-2-yl)pyridine-4-carbonitrile. Purified by HPLC (Method: F). LCMS: (Method: E) (ESI+) m/z 503.3 [MH+], tR=1.20 min.

Example 39: 4-{4-[({3-[6-(dimethylamino)-4-methylpyridin-3-yl]-2,5-dimethylpyrazolo[1,5-a]pyrimidin-7-yl}(methyl)amino)methyl]phenyl}pyridine-2-carboxylic acid (Compound 32)

32

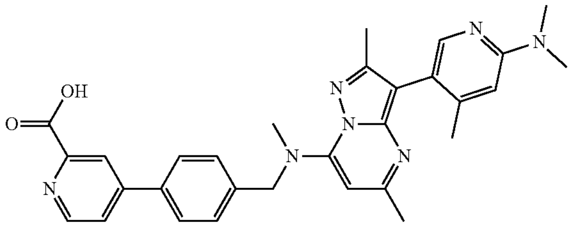

The title compound was prepared according to Synthesis Method A using 5-(7-{[(4-iodophenyl)methyl](methyl)amino}-2,5-dimethylpyrazolo[1,5-a]pyrimidin-3-yl)-N,N,4-trimethylpyridin-2-amine and 4-(dihydroxyboranyl)pyridine-2-carboxylic acid. Purified by HPLC (Method: G). LCMS: (Method: E) (ESI+) m/z 521.8 [MH+], tR=1.10 min.

Example 40: 5-[7-({[4-(5-methoxypyridin-3-yl)phenyl]methyl}(methyl)amino)-2,5-dimethylpyrazolo[1,5-a]pyrimidin-3-yl]-N,N,4-trimethylpyridin-2-amine (Compound 33)

33

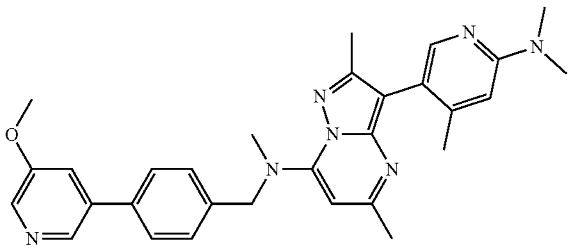

The title compound was prepared according to Synthesis Method A using 5-(7-{[(4-iodophenyl)methyl](methyl)amino}-2,5-dimethylpyrazolo[1,5-a]pyrimidin-3-yl)-N,N,4-trimethylpyridin-2-amine and (5-methoxypyridin-3-yl)boronic acid. Purified by HPLC (Method: F). LCMS: (Method: E) (ESI+) m/z 508.1 [MH+], tR=1.04 min.

Example 41: 5-{7-[({4-[6-(dimethylamino)pyridin-3-yl]phenyl}methyl)(methyl)amino]-2,5-dimethylpyrazolo[1,5-a]pyrimidin-3-yl}-N,N,4-trimethylpyridin-2-amine (Compound 34)

34

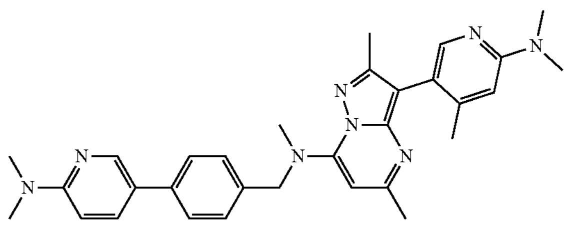

The title compound was prepared according to Synthesis Method A using 5-(7-{[(4-iodophenyl)methyl](methyl) amino}-2,5-dimethylpyrazolo[1,5-a]pyrimidin-3-yl)-N,N,4-trimethylpyridin-2-amine and [6-(dimethylamino)pyridin-3-yl]boronic acid. Purified by HPLC (Method: G). LCMS: (Method: E) (ESI+) m/z 521.3 [MH+], tR=0.95 min.

Example 42: 5-{4-[({3-[6-(dimethylamino)-4-methylpyridin-3-yl]-2,5-dimethylpyrazolo[1,5-a]pyrimidin-7-yl}(methyl)amino)methyl]phenyl}-N,N-dimethylpyrazin-2-amine (Compound 35)

35

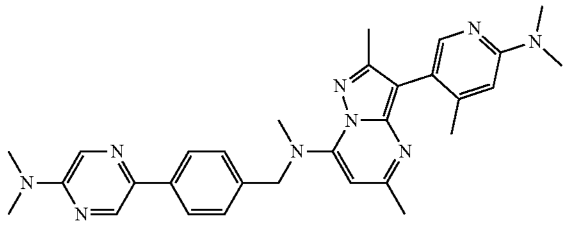

The title compound was prepared according to Synthesis Method A using 5-(7-{[(4-iodophenyl)methyl](methyl) amino}-2,5-dimethylpyrazolo[1,5-a]pyrimidin-3-yl)-N,N,4-trimethylpyridin-2-amine and N,N-dimethyl-5-(tetramethyl-1,3,2-dioxaborolan-2-yl)pyrazin-2-amine. Purified by HPLC (Method: F). LCMS: (Method: E) (ESI+) m/z 522.3 [MH+], tR=1.31 min.

Example 43: 5-[7-({[4-(4-methanesulfonylphenyl) phenyl]methyl}(methyl)amino)-2,5-dimethylpyrazolo[1,5-a]pyrimidin-3-yl]-N,N,4-trimethylpyridin-2-amine (Compound 36)

36

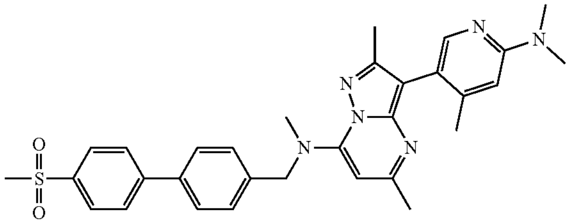

The title compound was prepared according to Synthesis Method A using 5-(7-{[(4-iodophenyl)methyl](methyl) amino}-2,5-dimethylpyrazolo[1,5-a]pyrimidin-3-yl)-N,N,4-trimethylpyridin-2-amine and (4-methanesulfonylphenyl) boronic acid. Purified by HPLC (Method: F). LCMS: (Method: E) (ESI+) m/z 555.3 [MH+], tR=1.26 min.

Example 44: 5-[7-({[4-(3-methanesulfonylphenyl) phenyl]methyl}(methyl)amino)-2,5-dimethylpyrazolo[1,5-a]pyrimidin-3-yl]-N,N,4-trimethylpyridin-2-amine (Compound 37)

37

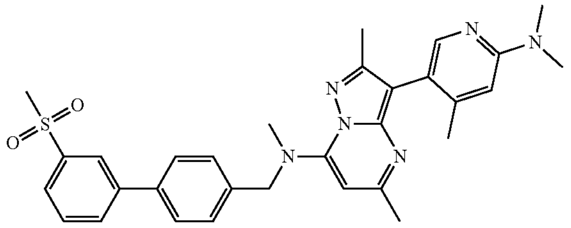

The title compound was prepared according to Synthesis Method A using 5-(7-{[(4-iodophenyl)methyl](methyl) amino}-2,5-dimethylpyrazolo[1,5-a]pyrimidin-3-yl)-N,N,4-trimethylpyridin-2-amine and (3-methanesulfonylphenyl) boronic acid. Purified by HPLC (Method: F). LCMS: (Method: E) (ESI+) m/z 555.3 [MH+], tR=1.27 min.

Example 45: 4-{4-[({3-[6-(dimethylamino)-4-methylpyridin-3-yl]-2,5-dimethylpyrazolo[1,5-a]pyrimidin-7-yl}(methyl)amino)methyl]phenyl}benzamide (Compound 38)

38

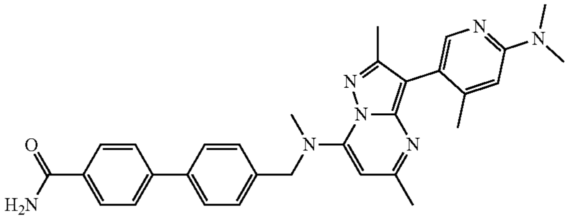

The title compound was prepared according to Synthesis Method A using 5-(7-{[(4-iodophenyl)methyl](methyl) amino}-2,5-dimethylpyrazolo[1,5-a]pyrimidin-3-yl)-N,N,4-trimethylpyridin-2-amine and (4-carbamoylphenyl)boronic acid. Purified by HPLC (Method: F). LCMS: (Method: E) (ESI+) m/z 520.3 [MH+], tR=1.13 min.

Example 46: 3-{4-[({3-[6-(dimethylamino)-4-methylpyridin-3-yl]-2,5-dimethylpyrazolo[1,5-a]pyrimidin-7-yl}(methyl)amino)methyl]phenyl}benzamide (Compound 39)

39

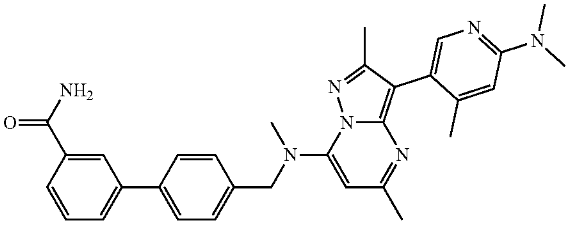

The title compound was prepared according to Synthesis Method A using 5-(7-{[(4-iodophenyl)methyl](methyl)amino}-2,5-dimethylpyrazolo[1,5-a]pyrimidin-3-yl)-N,N,4-trimethylpyridin-2-amine and (3-carbamoylphenyl)boronic acid. Purified by HPLC (Method: F). LCMS: (Method: E) (ESI+) m/z 520.3 [MH+], tR=1.17 min.

Example 47: 2-{4-[({3-[6-(dimethylamino)-4-methylpyridin-3-yl]-2,5-dimethylpyrazolo[1,5-a]pyrimidin-7-yl}(methyl)amino)methyl]phenyl}benzamide (Compound 40)

40

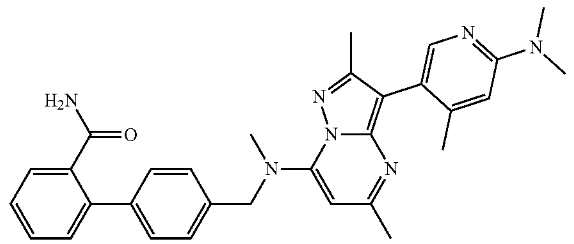

The title compound was prepared according to Synthesis Method A using 5-(7-{[(4-iodophenyl)methyl](methyl)amino}-2,5-dimethylpyrazolo[1,5-a]pyrimidin-3-yl)-N,N,4-trimethylpyridin-2-amine and (2-carbamoylphenyl)boronic acid. Purified by HPLC (Method: F). LCMS: (Method: E) (ESI+) m/z 520.3 [MH+], tR=1.13 min.

Example 48: 4-{4-[({3-[6-(dimethylamino)-4-methylpyridin-3-yl]-2,5-dimethylpyrazolo[1,5-a]pyrimidin-7-yl}(methyl)amino)methyl]phenyl}benzonitrile (Compound 41)

41

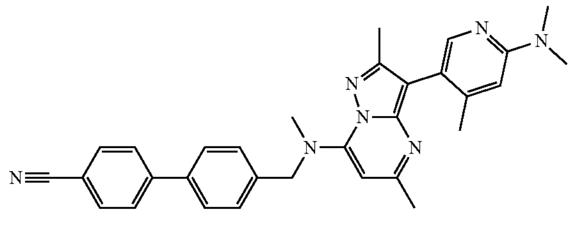

The title compound was prepared according to Synthesis Method A using 5-(7-{[(4-iodophenyl)methyl](methyl)amino}-2,5-dimethylpyrazolo[1,5-a]pyrimidin-3-yl)-N,N,4-trimethylpyridin-2-amine and (4-cyanophenyl)boronic acid. Purified by HPLC (Method: F). LCMS: (Method: E) (ESI+) m/z 502.3 [MH+], tR=1.44 min.

Example 49: 3-{4-[({3-[6-(dimethylamino)-4-methylpyridin-3-yl]-2,5-dimethylpyrazolo[1,5-a]pyrimidin-7-yl}(methyl)amino)methyl]phenyl}benzonitrile (Compound 42)

42

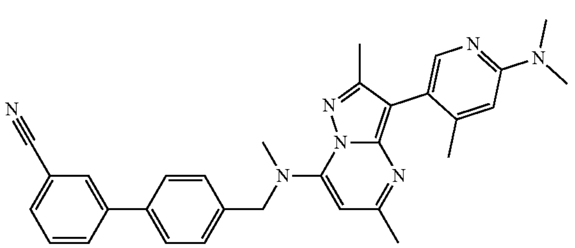

The title compound was prepared according to Synthesis Method A using 5-(7-{[(4-iodophenyl)methyl](methyl)amino}-2,5-dimethylpyrazolo[1,5-a]pyrimidin-3-yl)-N,N,4-trimethylpyridin-2-amine and (3-cyanophenyl)boronic acid. Purified by HPLC (Method: F). LCMS: (Method: E) (ESI+) m/z 502.3 [MH+], tR=1.46 min.

Example 50: 2-{4-[({3-[6-(dimethylamino)-4-methylpyridin-3-yl]-2,5-dimethylpyrazolo[1,5-a]pyrimidin-7-yl}(methyl)amino)methyl]phenyl}benzonitrile (Compound 43)

43

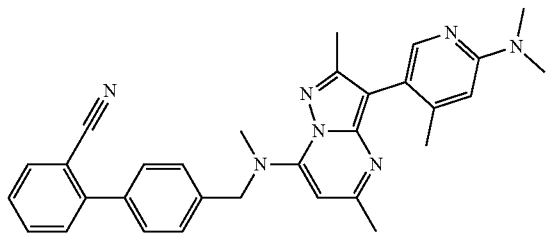

The title compound was prepared according to Synthesis Method A using 5-(7-{[(4-iodophenyl)methyl](methyl)amino}-2,5-dimethylpyrazolo[1,5-a]pyrimidin-3-yl)-N,N,4-trimethylpyridin-2-amine and (2-cyanophenyl)boronic acid. Purified by HPLC (Method: F. LCMS: (Method: E) (ESI+) m/z 502.3 [MH+], tR=1.41 min.

Tables 1 and 2 below provide the observed ion m/z ratios [MH+] for the listed compounds.

TABLE 1

| Compound # | Structure/Name | MW | LCMS (m/z) |
| --- | --- | --- | --- |
| 1 | 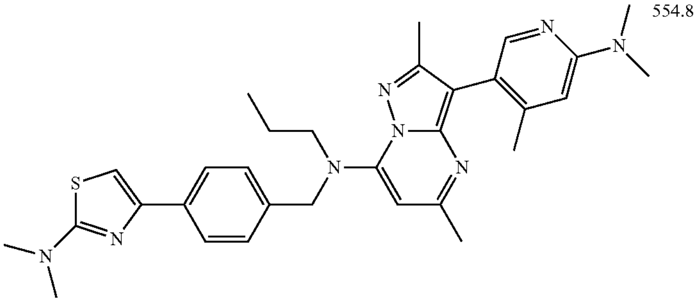 5-{7-[({4-[2-(dimethylamino)-1,3-thiazol-4-yl]phenyl}methyl)(propyl)amino]-2,5-dimethylpyrazolo[1,5-a]pyrimidin-3-yl}-N,N,4-trimethylpyridin-2-amine | 554.8 | 555 |
| 2 | 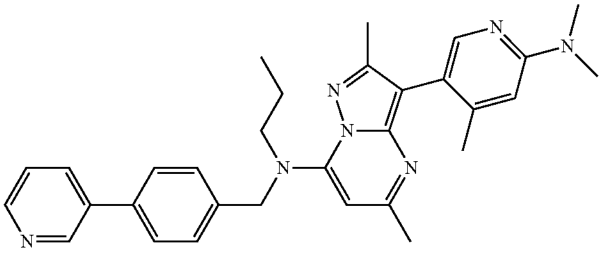 [SMILES: CCCN(Cc1ccc(-c2cccnc2)cc1)c1cc(C)nc2c(-c3cnc(N(C)C)cc3C)c(C)nn12] 5-{2,5-dimethyl-7-[propyl({[4-(pyridin-3-yl)phenyl]methyl})amino]pyrazolo[1,5-a]pyrimidin-3-yl}-N,N,4-trimethylpyridin-2-amine | 505.7 | 506.3 |
| 3 | 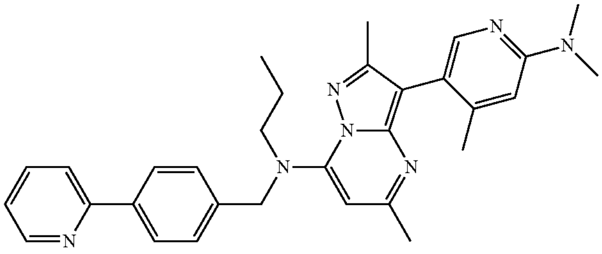 [SMILES: CCCN(Cc1ccc(-c2ccccn2)cc1)c1cc(C)nc2c(-c3cnc(N(C)C)cc3C)c(C)nn12] 5-{2,5-dimethyl-7-[propyl({[4-(pyridin-2-yl)phenyl]methyl})amino]pyrazolo[1,5-a]pyrimidin-3-yl}-N,N,4-trimethylpyridin-2-amine | 505.7 | 506.3 |
| 4 | 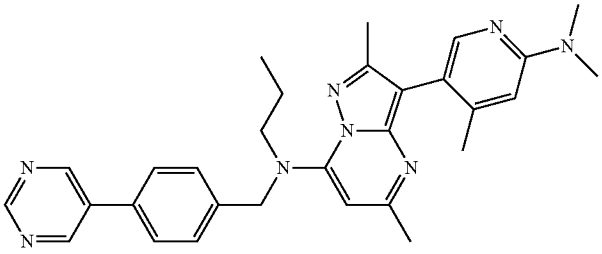 [SMILES: CCCN(Cc1ccc(-c2cncnc2)cc1)c1cc(C)nc2c(-c3cnc(N(C)C)cc3C)c(C)nn12] 5-{2,5-dimethyl-7-[propyl({[4-(pyrimidin-5-yl)phenyl]methyl})amino]pyrazolo[1,5-a]pyrimidin-3-yl}-N,N,4-trimethylpyridin-2-amine | 506.6 | 507.3 |

TABLE 1-continued

| Compound # | Structure/Name | MW | LCMS (m/z) |
|---|---|---|---|
| 5 | 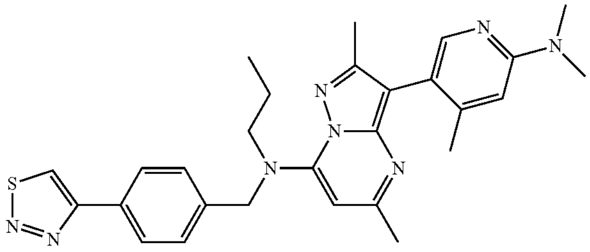 [SMILES: CCCN(Cc1ccc(-c2csnn2)cc1)c1cc(C)nc2c(-c3cnc(N(C)C)cc3C)c(C)nn12] 5-{2,5-dimethyl-7-[propyl({[4-(1,2,3-thiadiazol-4-yl)phenyl]methyl})amino]pyrazolo[1,5-a]pyrimidin-3-yl}-N,N,4-trimethylpyridin-2-amine | 512.7 | |
| 6 | 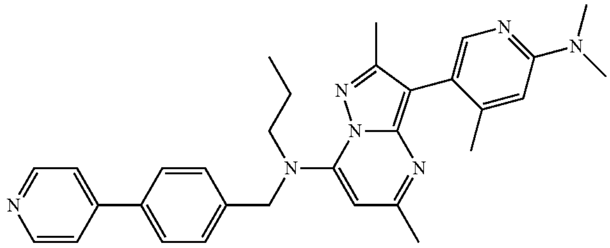 [SMILES: CCCN(Cc1ccc(-c2ccncc2)cc1)c1cc(C)nc2c(-c3cnc(N(C)C)cc3C)c(C)nn12] 5-{2,5-dimethyl-7-[propyl({[4-(pyridin-4-yl)phenyl]methyl})amino]pyrazolo[1,5-a]pyrimidin-3-yl}-N,N,4-trimethylpyridin-2-amine | 505.7 | 506.2 |
| 7 | 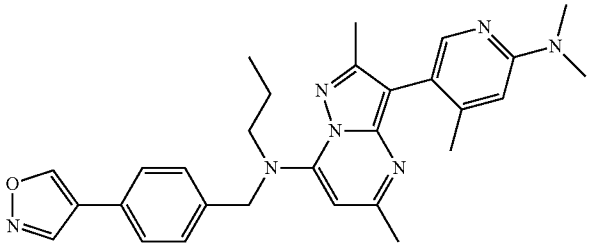 [SMILES: CCCN(Cc1ccc(-c2cnoc2)cc1)c1cc(C)nc2c(-c3cnc(N(C)C)cc3C)c(C)nn12] 5-[2,5-dimethyl-7-({[4-(1,2-oxazol-4-yl)phenyl]methyl}(propyl)amino)pyrazolo[1,5-a]pyrimidin-3-yl]-N,N,4-trimethylpyridin-2-amine | 495.6 | 495.3 |
| 9 | 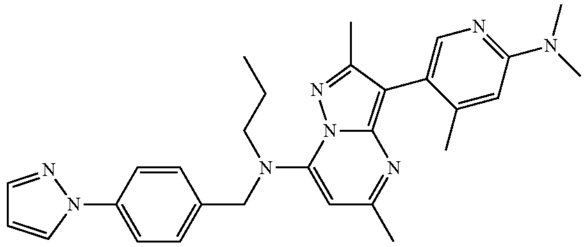 [SMILES: CCCN(Cc1ccc(-n2cccn2)cc1)c1cc(C)nc2c(-c3cnc(N(C)C)cc3C)c(C)nn12] 5-{2,5-dimethyl-7-[propyl({[4-(1H-pyrazol-1-yl)phenyl]methyl})amino]pyrazolo[1,5-a]pyrimidin-3-yl}-N,N,4-trimethylpyridin-2-amine | 494.6 | 495.3 |

TABLE 1-continued

| Compound # | Structure/Name | MW | LCMS (m/z) |
|---|---|---|---|
| 10 | 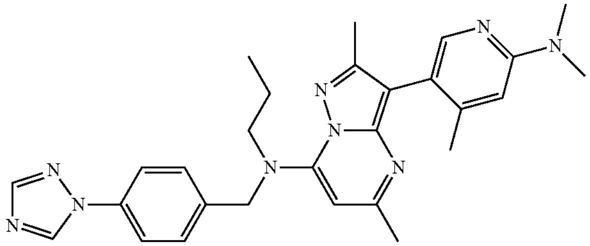 [SMILES: CCCN(Cc1ccc(-n2cncn2)cc1)c1cc(C)nc2c(-c3cnc(N(C)C)cc3C)c(C)nn12] 5-{2,5-dimethyl-7-[propyl({[4-(1H-1,2,4-triazol-1-yl)phenyl]methyl})amino]pyrazolo[1,5-a]pyrimidin-3-yl}-N,N,4-trimethylpyridin-2-amine | 495.6 | 496.3 |
| 11 | 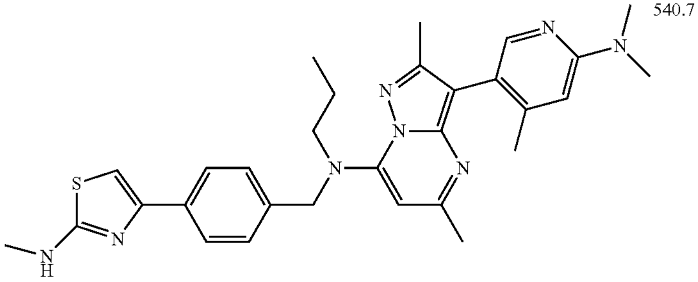 5-{2,5-dimethyl-7-[({4-[2-(methylamino)-1,3-thiazol-4-yl]phenyl}methyl)(propyl)amino]pyrazolo[1,5-a]pyrimidin-3-yl}-N,N,4-trimethylpyridin-2-amine | 540.7 | 541.2 |
| 12 | 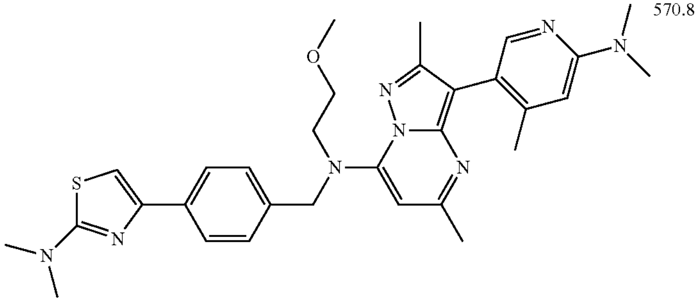 5-{7-[({4-[2-(dimethylamino)-1,3-thiazol-4-yl]phenyl}methyl)(2-methoxyethyl)amino]-2,5-dimethylpyrazolo[1,5-a]pyrimidin-3-yl}-N,N,4-trimethylpyridin-2-amine | 570.8 | 571.3 |
| 13 | 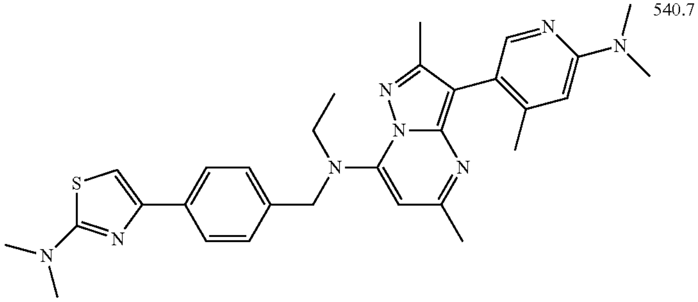 5-{7-[({4-[2-(dimethylamino)-1,3-thiazol-4-yl]phenyl}methyl)(ethyl)amino]-2,5-dimethylpyrazolo[1,5-a]pyrimidin-3-yl}-N,N,4-trimethylpyridin-2-amine | 540.7 | 541.3 |

TABLE 1-continued

| Compound # | Structure/Name | MW | LCMS (m/z) |
|---|---|---|---|
| 14 | 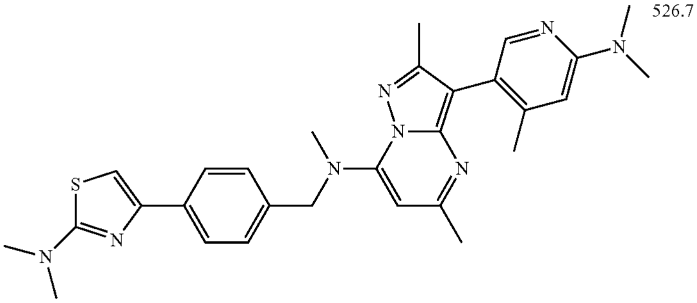<br>5-{7-[({4-[2-(dimethylamino)-1,3-thiazol-4-yl]phenyl}methyl)(methyl)amino]-2,5-dimethylpyrazolo[1,5-a]pyrimidin-3-yl}-N,N,4-trimethylpyridin-2-amine | 526.7 | 527.3 |
| 15 | 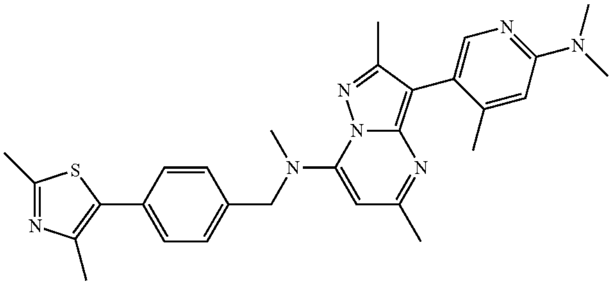<br>5-[7-({[4-(dimethyl-1,3-thiazol-5-yl)phenyl]methyl}(methyl)amino)-2,5-dimethylpyrazolo[1,5-a]pyrimidin-3-yl]-N,N,4-trimethylpyridin-2-amine | 511.7 | 512.3 |
| 16 | 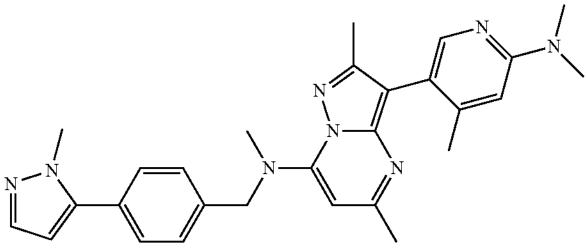 [SMILES: Cc1cc(N(C)Cc2ccc(-c3ccnn3C)cc2)n2nc(C)c(-c3cnc(N(C)C)cc3C)c2n1]<br>5-{2,5-dimethyl-7-[methyl({[4-(1-methyl-1H-pyrazol-5-yl)phenyl]methyl})amino]pyrazolo[1,5-a]pyrimidin-3-yl}-N,N,4-trimethylpyridin-2-amine | 480.6 | 481.3 |
| 17 | 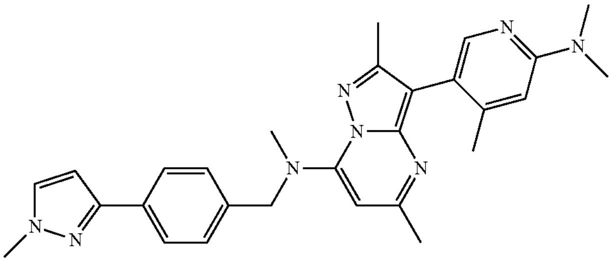<br>5-{2,5-dimethyl-7-[methyl({[4-(1-methyl-1H-pyrazol-3-yl)phenyl]methyl})amino]pyrazolo[1,5-a]pyrimidin-3-yl}-N,N,4-trimethylpyridin-2-amine | 480.6 | 481.3 |

TABLE 1-continued

| Compound # | Structure/Name | MW | LCMS (m/z) |
|---|---|---|---|
| 18 | 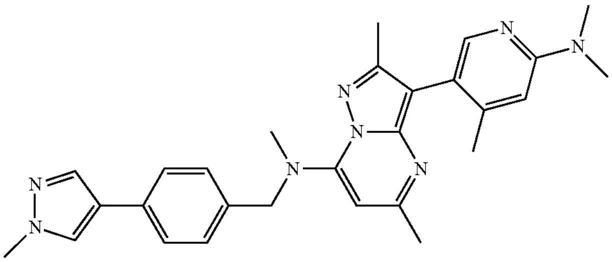 5-{2,5-dimethyl-7-[methyl({[4-(1-methyl-1H-pyrazol-4-yl)phenyl]methyl})amino]pyrazolo[1,5-a]pyrimidin-3-yl}-N,N,4-trimethylpyridin-2-amine | 480.6 | 481.3 |
| 19 | 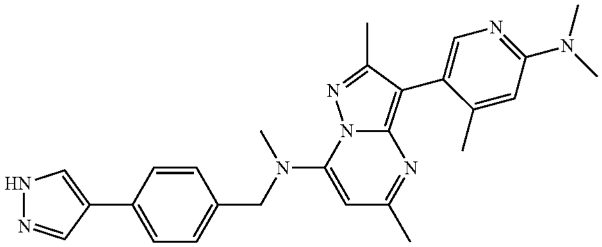 [SMILES: Cc1cc(N(C)Cc2ccc(-c3cn[nH]c3)cc2)n2nc(C)c(-c3cnc(N(C)C)cc3C)c2n1] 5-{2,5-dimethyl-7-[methyl({[4-(1H-pyrazol-4-yl)phenyl]methyl})amino]pyrazolo[1,5-a]pyrimidin-3-yl}-N,N,4-trimethylpyridin-2-amine | 466.6 | 467.25 |
| 20 | 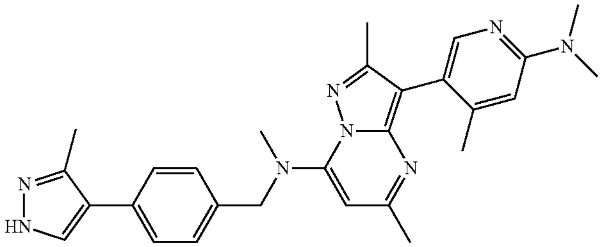 [SMILES: Cc1cc(N(C)Cc2ccc(-c3c[nH]nc3C)cc2)n2nc(C)c(-c3cnc(N(C)C)cc3C)c2n1] 5-{2,5-dimethyl-7-[methyl({[4-(3-methyl-1H-pyrazol-4-yl)phenyl]methyl})amino]pyrazolo[1,5-a]pyrimidin-3-yl}-N,N,4-trimethylpyridin-2-amine | 480.6 | 481.3 |
| 21 | 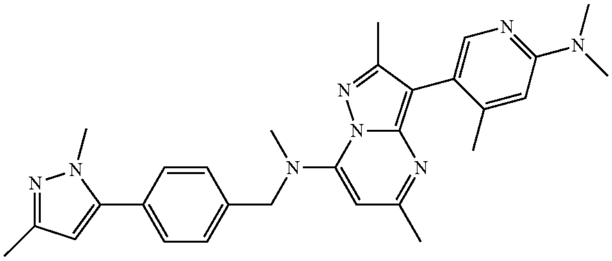 5-[7-({[4-(1,3-dimethyl-1H-pyrazol-5-yl)phenyl]methyl}(methyl)amino)-2,5-dimethylpyrazolo[1,5-a]pyrimidin-3-yl]-N,N,4-trimethylpyridin-2-amine | 494.6 | 495.3 |

TABLE 1-continued

| Compound # | Structure/Name | MW | LCMS (m/z) |
|---|---|---|---|
| 22 | 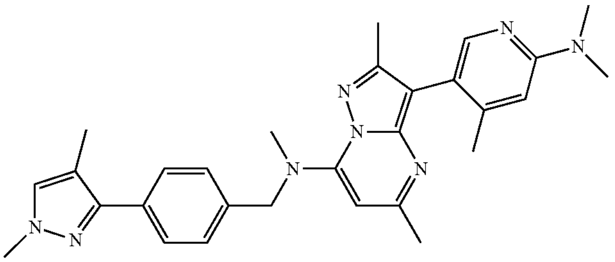 5-[7-({[4-(1,4-dimethyl-1H-pyrazol-3-yl)phenyl]methyl}(methyl)amino)-2,5-dimethylpyrazolo[1,5-a]pyrimidin-3-yl]-N,N,4-trimethylpyridin-2-amine | 494.6 | 495.3 |
| 23 | 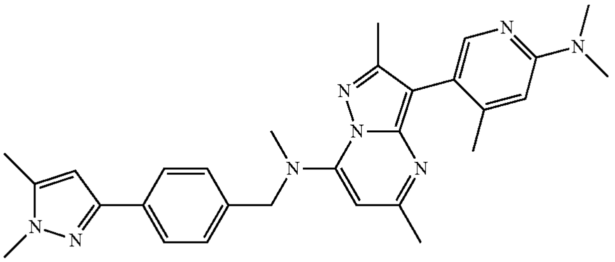 5-[7-({[4-(1,5-dimethyl-1H-pyrazol-3-yl)phenyl]methyl}(methyl)amino)-2,5-dimethylpyrazolo[1,5-a]pyrimidin-3-yl]-N,N,4-trimethylpyridin-2-amine | 494.6 | 495.3 |
| 24 | 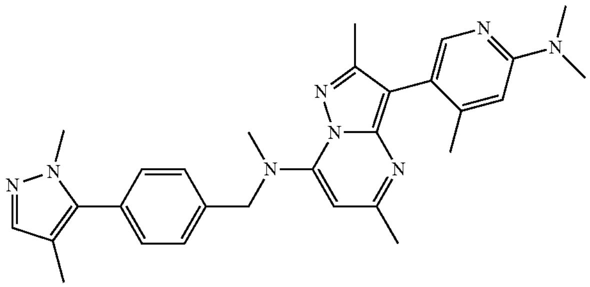 [SMILES: Cc1cc(N(C)Cc2ccc(-c3c(C)cnn3C)cc2)n2nc(C)c(-c3cnc(N(C)C)cc3C)c2n1] 5-[7-({[4-(1,4-dimethyl-1H-pyrazol-5-yl)phenyl]methyl}(methyl)amino)-2,5-dimethylpyrazolo[1,5-a]pyrimidin-3-yl]-N,N,4-trimethylpyridin-2-amine | 494.6 | 495.3 |
| 25 | 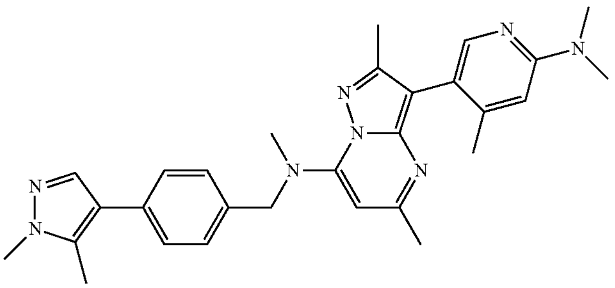 5-[7-({[4-(1,5-dimethyl-1H-pyrazol-4-yl)phenyl]methyl}(methyl)amino)-2,5-dimethylpyrazolo[1,5-a]pyrimidin-3-yl]-N,N,4-trimethylpyridin-2-amine | 494.6 | 495.3 |

TABLE 1-continued

| Compound # | Structure/Name | MW | LCMS (m/z) |
|---|---|---|---|
| 26 | 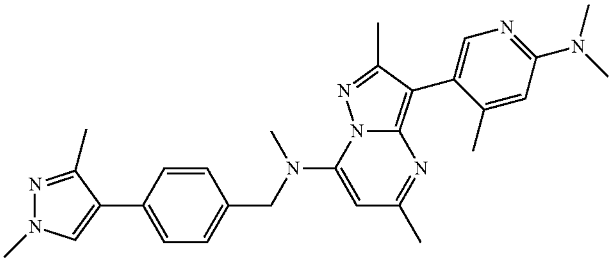 5-[7-({[4-(1,3-dimethyl-1H-pyrazol-4-yl)phenyl]methyl}(methyl)amino)-2,5-dimethylpyrazolo[1,5-a]pyrimidin-3-yl]-N,N,4-trimethylpyridin-2-amine | 494.6 | 495.3 |
| 27 | 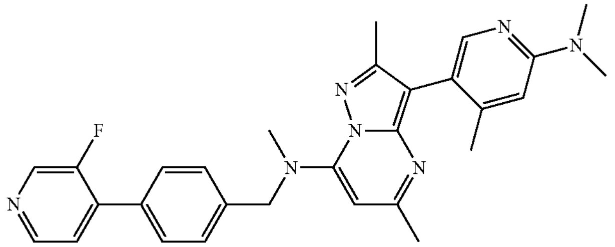 [SMILES: Cc1cc(N(C)Cc2ccc(-c3ccncc3F)cc2)n2nc(C)c(-c3cnc(N(C)C)cc3C)c2n1] 5-[7-({[4-(3-fluoropyridin-4-yl)phenyl]methyl}(methyl)amino)-2,5-dimethylpyrazolo[1,5-a]pyrimidin-3-yl]-N,N,4-trimethylpyridin-2-amine | 495.6 | 496.3 |
| 28 | 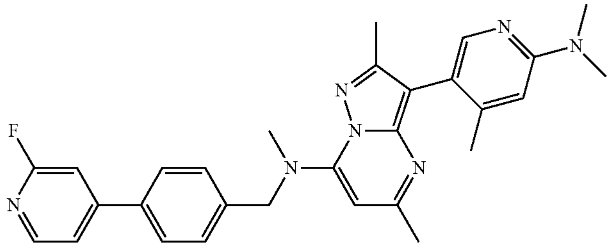 [SMILES: Cc1cc(N(C)Cc2ccc(-c3ccnc(F)c3)cc2)n2nc(C)c(-c3cnc(N(C)C)cc3C)c2n1] 5-[7-({[4-(2-fluoropyridin-4-yl)phenyl]methyl}(methyl)amino)-2,5-dimethylpyrazolo[1,5-a]pyrimidin-3-yl]-N,N,4-trimethylpyridin-2-amine | 495.6 | 496.3 |
| 29 | 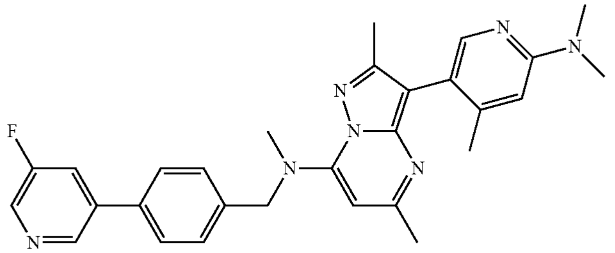 [SMILES: Cc1cc(N(C)Cc2ccc(-c3cncc(F)c3)cc2)n2nc(C)c(-c3cnc(N(C)C)cc3C)c2n1] 5-[7-({[4-(5-fluoropyridin-3-yl)phenyl]methyl}(methyl)amino)-2,5-dimethylpyrazolo[1,5-a]pyrimidin-3-yl]-N,N,4-trimethylpyridin-2-amine | 495.6 | 496.3 |

TABLE 1-continued

| Compound # | Structure/Name | MW | LCMS (m/z) |
|---|---|---|---|
| 30 | 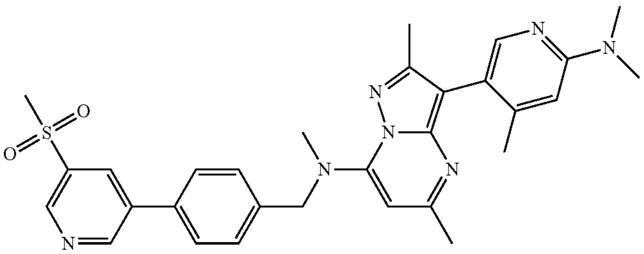 [SMILES: Cc1cc(N(C)Cc2ccc(-c3cncc(S(C)(=O)=O)c3)cc2)n2nc(C)c(-c3cnc(N(C)C)cc3C)c2n1]<br>5-[7-({[4-(5-methanesulfonylpyridin-3-yl)phenyl]methyl}(methyl)amino)-2,5-dimethylpyrazolo[1,5-a]pyrimidin-3-yl]-N,N,4-trimethylpyridin-2-amine | 555.7 | 556.3 |
| 31 | 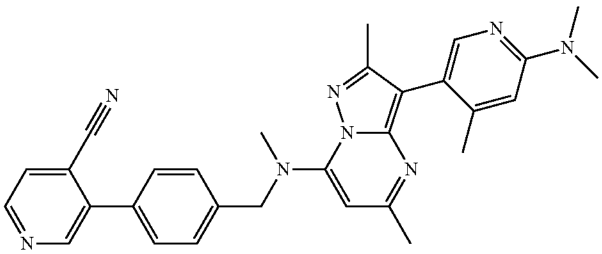 [SMILES: Cc1cc(N(C)Cc2ccc(-c3cnccc3C#N)cc2)n2nc(C)c(-c3cnc(N(C)C)cc3C)c2n1]<br>3-{4-[({3-[6-(dimethylamino)-4-methylpyridin-3-yl]-2,5-dimethylpyrazolo[1,5-a]pyrimidin-7-yl}(methyl)amino)methyl]phenyl}pyridine-4-carbonitrile | 502.6 | 503.3 |
| 32 | 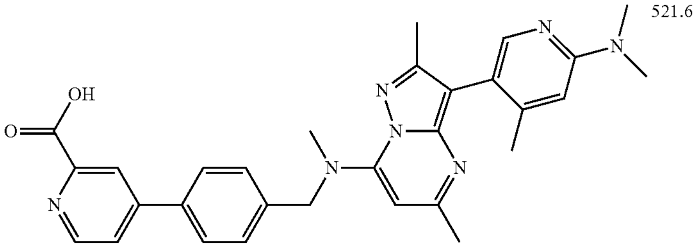<br>4-{4-[({3-[6-(dimethylamino)-4-methylpyridin-3-yl]-2,5-dimethylpyrazolo[1,5-a]pyrimidin-7-yl}(methyl)amino)methyl]phenyl}pyridine-2-carboxylic acid | 521.6 | 521.8 |
| 33 | 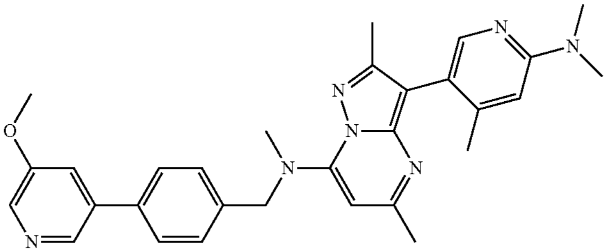 [SMILES: COc1cncc(-c2ccc(CN(C)c3cc(C)nc4c(-c5cnc(N(C)C)cc5C)c(C)nn34)cc2)c1]<br>5-[7-({[4-(5-methoxypyridin-3-yl)phenyl]methyl}(methyl)amino)-2,5-dimethylpyrazolo[1,5-a]pyrimidin-3-yl]-N,N,4-trimethylpyridin-2-amine | 507.6 | 508.3 |

TABLE 1-continued

| Compound # | Structure/Name | MW | LCMS (m/z) |
|---|---|---|---|
| 34 | 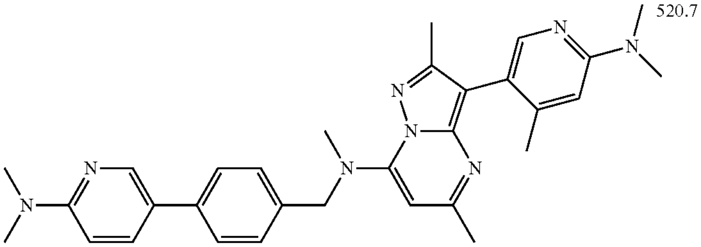<br>5-{7-[({4-[6-(dimethylamino)pyridin-3-yl]phenyl}methyl)(methyl)amino]-2,5-dimethylpyrazolo[1,5-a]pyrimidin-3-yl}-N,N,4-trimethylpyridin-2-amine | 520.7 | 521.3 |
| 35 | 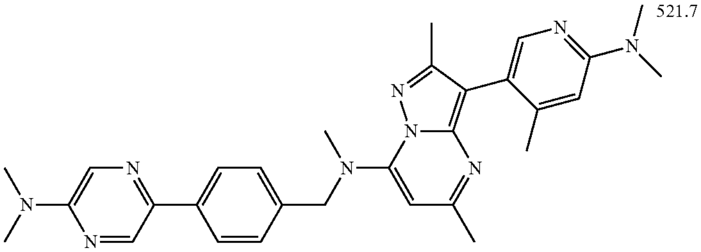<br>5-{4-[({3-[6-(dimethylamino)-4-methylpyridin-3-yl]-2,5-dimethylpyrazolo[1,5-a]pyrimidin-7-yl}(methyl)amino)methyl]phenyl}-N,N-dimethylpyrazin-2-amine | 521.7 | 522.3 |

TABLE 2

| Compound # | Structure/Name | MW | LCMS (m/z) |
|---|---|---|---|
| 8 | 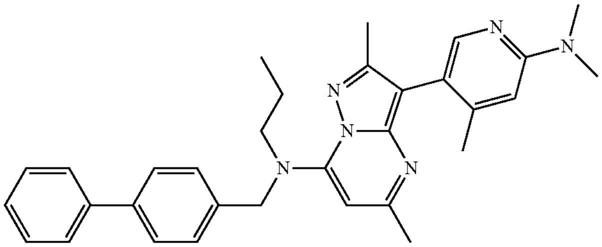 [SMILES: CCCN(Cc1ccc(-c2ccccc2)cc1)c1cc(C)nc2c(-c3cnc(N(C)C)cc3C)c(C)nn12]<br>5-(2,5-dimethyl-7-{[(4-phenylphenyl)methyl](propyl)amino}pyrazolo[1,5-a]pyrimidin-3-yl)-N,N,4-trimethylpyridin-2-amine | 504.7 | 505.4 |
| 36 | 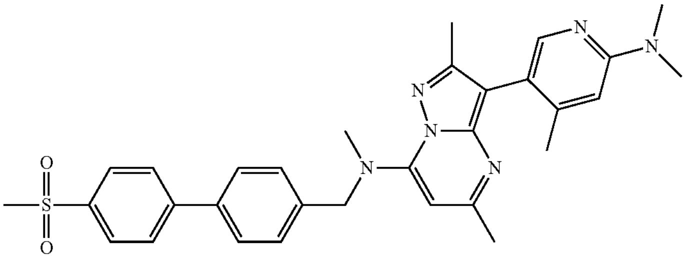<br>5-[7-({[4-(4-methanesulfonylphenyl)phenyl]methyl}(methyl)amino)-2,5-dimethylpyrazolo[1,5-a]pyrimidin-3-yl]-N,N,4-trimethylpyridin-2-amine | 554.7 | 555.3 |

TABLE 2-continued

| Compound # | Structure/Name | MW | LCMS (m/z) |
| --- | --- | --- | --- |
| 37 | 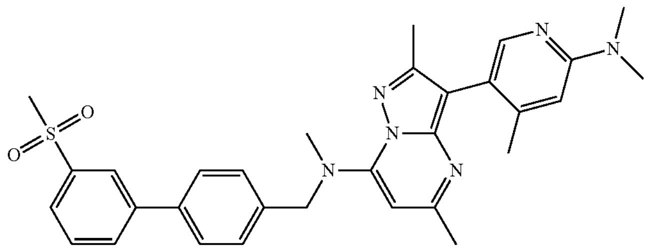 [SMILES: Cc1cc(N(C)Cc2ccc(-c3cccc(S(C)(=O)=O)c3)cc2)n2nc(C)c(-c3cnc(N(C)C)cc3C)c2n1] 5-[7-({[4-(3-methanesulfonylphenyl)phenyl]methyl}(methyl)amino)-2,5-dimethylpyrazolo[1,5-a]pyrimidin-3-yl]-N,N,4-trimethylpyridin-2-amine | 554.7 | 555.3 |
| 38 | 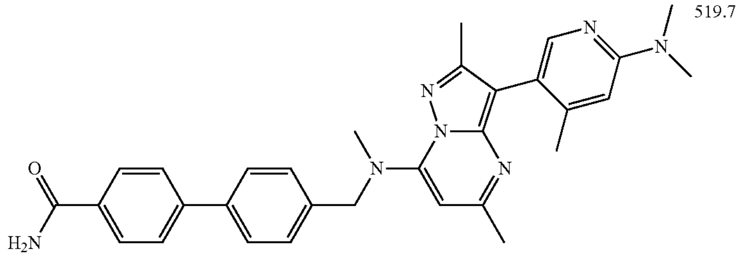 4-{4-[({3-[6-(dimethylamino)-4-methylpyridin-3-yl]-2,5-dimethylpyrazolo[1,5-a]pyrimidin-7-yl}(methyl)amino)methyl]phenyl}benzamide | 519.7 | 520.3 |
| 39 | 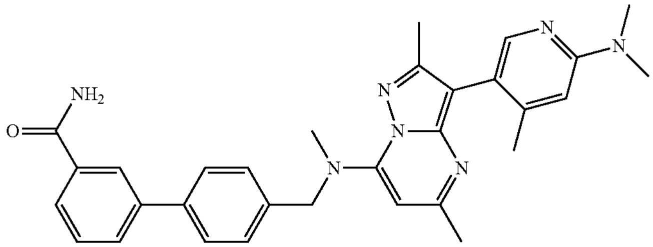 3-{4-[({3-[6-(dimethylamino)-4-methylpyridin-3-yl]-2,5-dimethylpyrazolo[1,5-a]pyrimidin-7-yl}(methyl)amino)methyl]phenyl}benzamide | 519.7 | 520.3 |
| 40 | 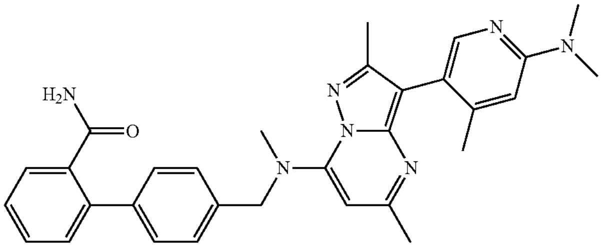 [SMILES: Cc1cc(N(C)Cc2ccc(-c3ccccc3C(N)=O)cc2)n2nc(C)c(-c3cnc(N(C)C)cc3C)c2n1] 2-{4-[({3-[6-(dimethylamino)-4-methylpyridin-3-yl]-2,5-dimethylpyrazolo[1,5-a]pyrimidin-7-yl}(methyl)amino)methyl]phenyl}benzamide | 519.7 | 520.3 |

TABLE 2-continued

| Compound # | Structure/Name | MW | LCMS (m/z) |
|---|---|---|---|
| 41 | 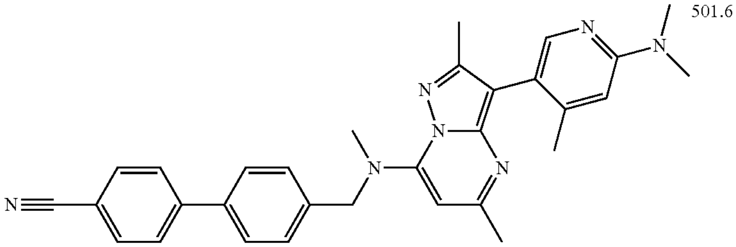 4-{4-[({3-[6-(dimethylamino)-4-methylpyridin-3-yl]-2,5-dimethylpyrazolo[1,5-a]pyrimidin-7-yl}(methyl)amino)methyl]phenyl}benzonitrile | 501.6 | 502.3 |
| 42 | 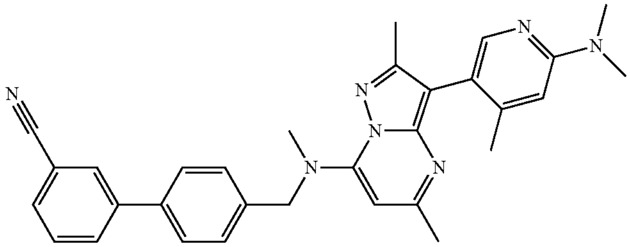 [SMILES: Cc1cc(N(C)Cc2ccc(-c3cccc(C#N)c3)cc2)n2nc(C)c(-c3cnc(N(C)C)cc3C)c2n1] 3-{4-[({3-[6-(dimethylamino)-4-methylpyridin-3-yl]-2,5-dimethylpyrazolo[1,5-a]pyrimidin-7-yl}(methyl)amino)methyl]phenyl}benzonitrile | 501.6 | 502.3 |
| 43 | 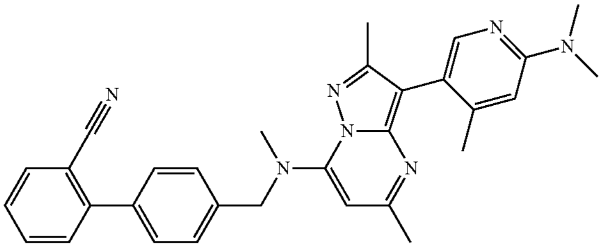 [SMILES: Cc1cc(N(C)Cc2ccc(-c3ccccc3C#N)cc2)n2nc(C)c(-c3cnc(N(C)C)cc3C)c2n1] 2-{4-[({3-[6-(dimethylamino)-4-methylpyridin-3-yl]-2,5-dimethylpyrazolo[1,5-a]pyrimidin-7-yl}(methyl)amino)methyl]phenyl}benzonitrile | 501.6 | 502.3 |

Example 51: General Preparation of Salt Forms of Compound 1

Salt forms of Compound 1 were prepared by creating slurries of Compound 1 Form I in various solvents around their saturation concentration. The vials were heated to −60° C. to dissolve solids, spiked with a stoichiometric volume of an aqueous counter-ion solution, and then allowed to slow-cool to room temperature. Solid forms were characterized via XRPD analysis.

Example 52: Solubility Determination

Solid forms of Compound 1 were combined with solvents providing the results shown in Tables 3 and 4 below.

TABLE 3

| Solubility (mg/mL FB) | Compound 1 | | | | |
|---|---|---|---|---|---|
| Measured pH Lot | −1 (FB) | −2 (FB) | −3 (HCl) | −4 (Maleate) | −5 (Mesylate) |
| 50 mM PB pH 1 | 14.9 pH NR | — | — | — | — |
| 50 mM PB pH 2 | 6.5 pH 2.7 | 3.3 pH 3.1 | 4.4 pH 2.9 | 3.9 pH 2.5 | 4.7 pH 3.0 |
| 50 mM CB pH 3 | 1.7 pH NR | 1.7 pH 3.3 | 0.8 pH 3.2 | 0.3 pH 3.2 | 1.0 pH 3.4 |
| 50 mM CB pH 4 | 0 pH 4.1 | 0 pH 4.1 | 0 pH 3.9 | 0 pH 3.9 | 0.1 pH 4.0 |
| 50 mM CB pH 5 | 0 pH 4.4 | 0 pH 5.0 | — | — | — |
| 50 mM CB pH 6 | 0 pH 6.1 | 0 pH 6.1 | 0 pH 5.8 | Below LOD pH 5.3 | 0 pH 5.1 |

TABLE 3-continued

| Solubility (mg/mL FB) | Compound 1 | | | | |
|---|---|---|---|---|---|
| Measured pH Lot | -1 (FB) | -2 (FB) | -3 (HCl) | -4 (Maleate) | -5 (Mesylate) |
| 50 mM PB pH 7 | 0 pH 7.0 | 0 pH 7.1 | — | — | — |
| 50 mM PB pH 8 | — | 0 pH 8.1 | 0 pH 7.5 | Below LOD pH 6.2 | 0 pH 6.7 |
| 50 mM BB pH 9 | — | — | Below LOD pH 8.7 | Below LOD pH 4.3 | 0.2 pH 3.2 |
| 100% $H_2O$ | 0 pH 6.7 | 0 pH 8.3 | 0.4 pH 3.3 | 0 pH 3.4 | 0.8 pH 3.5 |

PB = Phosphate Buffer; CB = Citrate Buffer; BB = Borate Buffer; FB = Free Base.

TABLE 4

| Solubility | Compound 1 | | |
|---|---|---|---|
| (mg/mL FB) Lot | -3 (HCl) | -4 (Maleate) | -5 (Mesylate) |
| Acetone | 0.4 | 4.1 | 1.0 |
| ACN | 0.7 | 3.6 | 3.1 |
| IPA | 0.8 | 1.9 | 2.3 |
| MeOH | 32.3 | 27.1 | 134.4 |
| DMSO | 0.9 | >2.5 | >2.1 |
| EtOAc | 0.1 | 1.2 | 0.6 |
| EtOH | 5.3 | 6.5 | 16.6 |

X-Ray Powder diffraction (XRPD), differential scanning calorimetry (DSC), thermal gravimetric analysis (TGA), and UV-Metric/pH-Metric Titration (SiriusT3) were used to characterize Form I of Compound 1. UPLC was used to evaluate solubility of each material in various vehicles.

Example 53: Characterization of Crystalline Forms of Compound 1

Form I of Compound 1 was prepared according to Example 2.

The XRPD analysis was performed on a Rigaku Powder X-Ray Diffractometer Miniflex Plus Serial Number ZD01936. For analysis, ~1-5 mg of sample was added to a XRPD zero-background sample holder. The powder was pressed down gently with a piece of weigh paper and the sample holder was placed in the sample changer. Run Parameters: Miniflex Counter Detector, Kb Filter, Scan Axis Theta/2-Theta, Mode Continuous, Start (deg) 3.0, Stop (deg) 45.0, Step (deg) 0.020, Speed (deg/min) 1.0, Spin-yes, Voltage (kV) 30, Current (mA) 15.

The XRPD diffractogram for Form I of Compound 1 is shown in FIG. 1. Select peak data is provided below.

X-Ray Powder Diffraction (XRPD) Compound 1 Form I (Select Peaks):

| # | 2-theta | Height (cps) |
|---|---|---|
| 1 | 11.2 | 10030 |
| 2 | 13.1 | 10741 |
| 3 | 15.1 | 11041 |
| 4 | 19.9 | 8451 |
| 5 | 22.5 | 29147 |

The DSC and TGA analysis were performed on TA Instruments Discovery DSC2500 (DSC) and TGA5500 (TGA) series. For the DSC analysis, ~1-3 mg of compound was weighed into a Tzero Pan and the Tzero lid was pressed on with tweezers. The pan was transferred to the DSC autosampler for analysis. The method for analysis was a ramp at 10° C./min to 350° C. Note: The reference pan was prepared with the same procedures, absent compound. For TGA analysis, a standard aluminum sample pan was placed into the platinum TGA pan and the blank was tared with the instrument. Approximately 1-5 mg of compound was added to the standard aluminum pan and analyzed at 10° C./min up to 375° C. Results: Weight loss due to solvent/water: Little-to-none. Onset Melt: 142.4° C., 72.177 J/g. FIG. 2 depicts exemplary DSC diffractogram and TGA thermogram of a sample of crystalline Form I of Compound 1.

Form II of Compound 1 was prepared by combining two batches of Compound 1 prepared as described in Example 1 using 5-(7-{[(4-iodophenyl)methyl](propyl)amino}-2,5-dimethylpyrazolo[1,5-a]pyrimidin-3-yl)-N,N,4-trimethylpyridin-2-amine (4-D, 6.5 g and 12 g batches). The combined material (32.5 g, combined theoretical mass) was crystallized from MTBE/heptane by dissolving the material in a minimum amount of MTBE and then adding a small amount of heptane and some seed crystals of Form I of Compound 1 prepared in Example 2. The resulting mixture was stirred at rt overnight to provide a white solid which was collected by filtration to afford a first isolate. The obtained solid was placed under suction to afford a second isolate (26 g). The second isolate was dried over NaOH pellets in a vacuum desiccator overnight to afford a third isolate (23.2 g). The third isolate was identified as Compound 1 in crystalline Form II by XRPD. The XRPD diffractogram of Compound 1 Form II is shown in FIG. 3.

X-Ray Powder Diffraction (XRPD) Compound 1 Form II (Select Peaks):

| # | 2-theta | Height (cps) |
|---|---|---|
| 1 | 4.9 | 5488 |
| 2 | 10.4 | 29191 |
| 3 | 14.8 | 8798 |
| 4 | 19.1 | 21013 |
| 5 | 24.0 | 11450 |

The DSC was performed as described above for Form I of Compound 1. Onset Melt: 139.4° C., 142.6° C. FIG. 4 depicts exemplary DSC diffractogram of a sample of crystalline Form II of Compound 1.

Form III of Compound 1 was prepared by heating wet solid Form I of Compound 1 crystallized from IPA:water (~2.85:1.71) overnight at ~67° C. The XRPD diffractogram is shown in FIG. 5.

X-Ray Powder Diffraction (XRPD) Compound 1 Form III (Select Peaks):

| # | 2-theta | Height (cps) |
|---|---|---|
| 1 | 9.7 | 6373 |
| 2 | 11.3 | 22959 |
| 3 | 15.6 | 4697 |
| 4 | 19.5 | 10611 |
| 5 | 25.3 | 11457 |

The DSC was performed as described above for Form I of Compound 1. Onset Melt: 84.5° C. FIG. 6 depicts exemplary DSC diffractogram of a sample of crystalline Form III of Compound 1.

Example 54: pKa Determination of Compound 1

The pKa was determined using a SiriusT3 (Serial: T317136) with a UV-metric co-solvent titration assay and a pH-metric co-solvent titration assay. For the UV-metric, 10 mM sample was prepared in DMSO with phosphate buffer and placed on the instrument along with a blank prepared with the same composition, absent compound. For pH-metric, an appropriate weight of sample was added to a glass vial to meet buffer capacity requirements, absent of diluent. For each test, pKa was measured in three water:$CH_3OH$ ratios. The reported pKas are extrapolated graphically via the Yasuda-Shedlovsky method.

The pKas of Compound 1 were found by the UV-metric method to be 4.07±0.06, 4.80±0.06, and 7.00±0.02. The pKas of Compound 1 were found by the pH-metric method to be 4.06±0.08, 4.77±0.09, and 6.90±0.13. Overall, the two methods indicated that Compound 1 has 3 pKas of approximately 4.1, 4.8, and 7.0.

Example 55: Preparation of Compound 1 Hydrochloric Acid Salt

The hydrochloric acid salt of Compound 1 was prepared by creating slurries of free base Compound 1 in various solvents around their saturation concentration. The vials were heated to ~60° C. to dissolve solids, spiked with a stoichiometric volume of an aqueous counter-ion solution (HCl), and then allowed to slow-cool to room temperature. Solid forms were characterized via XRPD. FIG. 7 depicts an exemplary XRPD diffractogram of a sample of the Compound 1 HCl Salt Form I.

The XRPD analysis was performed on a Rigaku Powder X-Ray Diffractometer Miniflex Plus Serial Number ZD01936. For analysis, ~1-5 mg of sample was added to a XRPD zero-background sample holder. The powder was pressed down gently with a piece of weigh paper and the sample holder was placed in the sample changer. Run Parameters: Miniflex Counter Detector, Kb Filter, Scan Axis Theta/2-Theta, Mode Continuous, Start (deg) 3.0, Stop (deg) 45.0, Step (deg) 0.020, Speed (deg/min) 1.0, Spin-yes, Voltage (kV) 30, Current (mA) 15.

X-Ray Powder Diffraction (XRPD) Compound 1 HCl Salt Form I (Select Peaks):

| # | 2-theta | Height (cps) |
|---|---|---|
| 1 | 10.6 | 6973 |
| 2 | 14.4 | 10475 |
| 3 | 22.0 | 11174 |
| 4 | 24.2 | 11396 |
| 5 | 25.8 | 10588 |

The DSC and TGA analysis were performed as described above in Example 20 for Form I of Compound 1. Results: Weight loss due to solvent/water: Little-to-none. Onset Melt: 249.8° C., 179.91 J/g. FIG. 8 depicts exemplary DSC diffractogram and TGA thermogram of a sample of the Compound 1 HCl Salt Form I.

Example 56: Preparation of Compound 1 Maleate Salt Form

The maleate salt of Compound 1 was prepared by creating slurries of free base Compound 1 in various solvents around their saturation concentration. The vials were heated to ~60° C. to dissolve solids, spiked with a stoichiometric volume of an aqueous counter-ion solution (maleic acid), and then allowed to slow-cool to room temperature. Solid forms were characterized via XRPD diffractogram as shown in FIG. 9 depicts an exemplary XRPD diffractogram of a sample of Compound 1 maleate salt Form I.

The XRPD analysis was performed on a Rigaku Powder X-Ray Diffractometer Miniflex Plus Serial Number ZD01936. For analysis, ~1-5 mg of sample was added to a XRPD zero-background sample holder. The powder was pressed down gently with a piece of weigh paper and the sample holder was placed in the sample changer. Run Parameters: Miniflex Counter Detector, Kb Filter, Scan Axis Theta/2-Theta, Mode Continuous, Start (deg) 3.0, Stop (deg) 45.0, Step (deg) 0.020, Speed (deg/min) 1.0, Spin-yes, Voltage (kV) 30, Current (mA) 15.

Powder X-Ray Diffraction (XRPD) Compound 1 Maleate Salt Form I (Select Peaks):

| # | 2-theta | Height (cps) |
|---|---|---|
| 1 | 8.1 | 16151 |
| 2 | 14.3 | 6262 |
| 3 | 15.8 | 10802 |
| 4 | 19.5 | 9600 |
| 5 | 24.3 | 12029 |

The DSC and TGA analysis were performed as described above in Example 20 for Form I of Compound 1. Results: Weight loss due to solvent/water: Little-to-none. Onset Melt: 188.45° C., 100.13 J/g. FIG. 10 depicts exemplary DSC diffractogram and TGA thermogram of a sample of Compound 1 Maleate Salt Form I.

Example 57: Preparation of Compound 1 Mesylate Salt Form I

The mesylate salt of Compound 1 was prepared by creating slurries of free base Compound 1 in various solvents around their saturation concentration. The vials were heated to ~60° C. to dissolve solids, spiked with a stoichiometric volume of an aqueous counter-ion solution (methanesulfonic acid), and then allowed to slow-cool to room temperature. FIG. 11 depicts an exemplary XRPD of a sample of the methanesulfonic acid salt of Compound 1.

The XRPD analysis was performed on a Rigaku Powder X-Ray Diffractometer Miniflex Plus Serial Number ZD01936. For analysis, ~1-5 mg of sample was added to a XRPD zero-background sample holder. The powder was pressed down gently with a piece of weigh paper and the sample holder was placed in the sample changer. Run Parameters: Miniflex Counter Detector, Kb Filter, Scan Axis Theta/2-Theta, Mode Continuous, Start (deg) 3.0, Stop (deg) 45.0, Step (deg) 0.020, Speed (deg/min) 1.0, Spin-yes, Voltage (kV) 30, Current (mA) 15.

Preparation of Compound 1 Mesylate Salt Form I

A mixture of Form I or Form III of Compound 1 (8 g, 14.4 mmol.) in acetone (12 V; 96 mL) was stirred and heated to 53±5° C. to fully dissolve Compound 1. The resulting mixture was polish filtered at 50±5° C. to remove any insoluble material. The filtrate was stirred and heated to 53±5° C. A filtered, aqueous solution of methanesulfonic acid (21.5 wt % MSA, 0.644 g, 0.1 eq MSA) was added to the filtrate to afford a mixture. Seeds of Compound 1 Mesylate salt form I (80 mg, 1% seed load) were added to the mixture. The resulting suspension was stirred for 30 minutes at 53±5° C., ensuring the seeds did not dissolve. Subsequently, a filtered, aqueous solution of methanesulfonic acid (5.80 g, 21.5 wt % MSA, 0.9 eq MSA) was pumped into the mixture over 6 h using a linear addition rate. Notably, if using Form III of Compound 1 as starting material, the water content in the MSA solution was adjusted by the KF value of Form III of Compound 1. The total amount of water in the final crystallization solvent system was adjusted to be 5%. After the aqueous MSA solution addition, the suspension was cooled to 20±5° C. over 4 h using a linear ramp (7.5° C./h). Once the suspension reached 20±5° C., the suspension was stirred for no less than 1 h at 20±5° C. The suspension was then filtered, and the mother liquor was collected in a clean vessel. The filtered solids were washed (2×2 V) with a filtered, pre-made Acetone/$H_2O$ solution (19:1, 32 mL). The resulting solids were dried on the filter under vacuum with a nitrogen sweep at 50° C. for 16 h. The resulting solids were recovered as an off-white powder with 90% isolated yield of Compound 1 Mesylate salt form I. The form was confirmed by comparing analytical data to analytical data of previously prepared material.

Scale-Up Preparation of Compound 1 Mesylate Salt Form I

A mixture of Form III of Compound 1-hydrate (75 g) in acetone (12 V; 1800 mL) was treated with water (86 mL). The formed slurry was heated to 50° C. with stirring (200 rpm). Subsequently, the stirring mixture was treated with methanesulfonic acid (0.4 eq., 7 mL) at 50° C. The mixture turned white to tan color but solids remained. The mixture was treated with methanesulfonic acid in two additions (1.5 mL and 2 mL, 0.2 eq.) at 54° C. The mixture became homogeneous. The mixture was seeded with previously prepared Compound 1 mesylate salt (1.5 g) and within 15 min it became a white slurry. The mixture was slowly treated with methanesulfonic acid (0.5 eq., 7.6 mL) over 1 hr. The mixture was stirred at 50-55° C. for 30 min. Subsequently, ramp cooling of 10 deg/hr was set up. The mixture was cooled to 24° C. The mixture was stirred overnight at room temperature. The solid was collected by filtration (20 min) and washed with acetone:water (19:1-2 V). The wash took 20 min, very slow. During wash the mixture was stirred constantly to prevent clogging. The collected solid was placed under vacuum oven at 50° C. for 18 h affording Compound 1 Mesylate salt form I (155 g, 88% isolated yield). The form was confirmed by comparing analytical data to analytical data of previously prepared material.

X-Ray Powder Diffraction (XRPD) Mesylate Salt Form I (Select Peaks):

| # | 2-theta | Height (cps) |
|---|---|---|
| 1 | 8.2 | 4156 |
| 2 | 13.0 | 28645 |
| 3 | 14.9 | 9196 |
| 4 | 19.7 | 14013 |
| 5 | 22.3 | 9850 |

The DSC and TGA analysis were performed as described above in Example 20 for Form I of Compound 1. Results: Weight loss due to solvent/water: Little-to-none. Onset Melt: 188.45° C., 100.13 J/g. FIG. 12 depicts exemplary DSC diffractogram and TGA thermogram of a sample of Compound 1 Mesylate Salt Form I.

Example 58: Preparation of Compound 1 Esylate Salt Form

The ethanesulfonic acid salt of Compound 1 was prepared by creating slurries of free base Compound 1 in various solvents around their saturation concentration. The vials were heated to ~60° C. to dissolve solids, spiked with a stoichiometric volume of an aqueous counter-ion solution (ethanesulfonic acid), and then allowed to slow-cool to room temperature. FIG. 13 depicts an exemplary XRPD of a sample of the ethanesulfonic acid salt of Compound 1.

The XRPD analysis was performed on a Rigaku Powder X-Ray Diffractometer Miniflex Plus Serial Number ZD01936. For analysis, ~1-5 mg of sample was added to a XRPD zero-background sample holder. The powder was pressed down gently with a piece of weigh paper and the sample holder was placed in the sample changer. Run Parameters: Miniflex Counter Detector, Kb Filter, Scan Axis Theta/2-Theta, Mode Continuous, Start (deg) 3.0, Stop (deg) 45.0, Step (deg) 0.020, Speed (deg/min) 1.0, Spin-yes, Voltage (kV) 30, Current (mA) 15.

X-Ray Powder Diffraction (XRPD) Esylate Salt Form I (Select Peaks):

| # | 2-theta | Height (cps) |
|---|---|---|
| 1 | 8.6 | 2517 |
| 2 | 13.0 | 22301 |
| 3 | 14.4 | 13872 |
| 4 | 17.4 | 4391 |
| 5 | 19.6 | 8561 |

The DSC and TGA analysis were performed as described above in Example 20 for Form I of Compound 1. Results: Weight loss due to solvent/water: 2.084%. Onset Melt: 194.55° C. FIG. 14 depicts exemplary DSC diffractogram and TGA thermogram of a sample of Compound 1 Esylate Salt Form I.

Example 59: Preparation of Compound 1 Aspartate Salt Form

The aspartic acid salt of Compound 1 was prepared by creating slurries of free base Compound 1 in various solvents around their saturation concentration. The vials were heated to ~60° C. to dissolve solids, spiked with a stoichiometric volume of an aqueous counter-ion solution (aspartic acid), and then allowed to slow-cool to room temperature. FIG. 15 depicts an exemplary XRPD of a sample of the aspartic acid salt of Compound 1.

The XRPD analysis was performed on a Rigaku Powder X-Ray Diffractometer Miniflex Plus Serial Number ZD01936. For analysis, ~1-5 mg of sample was added to a XRPD zero-background sample holder. The powder was pressed down gently with a piece of weigh paper and the sample holder was placed in the sample changer. Run Parameters: Miniflex Counter Detector, Kb Filter, Scan Axis Theta/2-Theta, Mode Continuous, Start (deg) 3.0, Stop (deg) 45.0, Step (deg) 0.020, Speed (deg/min) 1.0, Spin-yes, Voltage (kV) 30, Current (mA) 15.

X-Ray Powder Diffraction (XRPD) Aspartate Salt Form I (Select Peaks):

| # | 2-theta | Height (cps) |
|---|---|---|
| 1 | 9.6 | 7988 |
| 2 | 11.6 | 3048 |
| 3 | 19.4 | 11363 |
| 4 | 23.5 | 48241 |
| 5 | 35.7 | 9981 |

The DSC and TGA analysis were performed as described above in Example 20 for Form I of Compound 1. Results:

Weight loss due to solvent/water: 1.831%. FIG. 16 depicts exemplary DSC diffractogram and TGA thermogram of a sample of Compound 1 Aspartate Salt Form I.

Example 60: Solubility Determination of Compound 1 Form I

The solubility of Compound 1 Form I was evaluated in various vehicles in an attempt to achieve doses of 0.5 mg/mL (IV) and 1.0 mg/mL (PO). Samples were prepared at 1 mg/mL and diluted to 0.5 mg/mL if they did not appear to produce a solution. Vortex mixing and sonication were used to dissolve particles, then samples were transferred to 0.22 μm nylon centrifuge tube filters and centrifuged for approximately 2 minutes @10,000 rpm. All samples were diluted with the method diluent (if necessary) and analyzed by HPLC providing the results shown in the below Table.

| Solvent | Final/ Actual pH | [Compound 1] (mg/mL) | Solubility <USP 34> |
|---|---|---|---|
| 50 mM Citrate, pH 2 | 3.1 | 3.3 | Slightly Soluble |
| 50 mM Citrate, pH 3 | 3.3 | 1.7 | Slightly Soluble |
| 50 mM Citrate, pH 4 | 4.1 | ~0 | Practically Insoluble |
| 50 mM Citrate, pH 5 | 5.0 | ~0 | Practically Insoluble |
| 50 mM Citrate, pH 6 | 6.1 | ~0 | Practically Insoluble |
| 50 mM Citrate, pH 7 | 7.1 | ~0 | Practically Insoluble |
| 50 mM Phosphate, pH 8 | 8.1 | Below LOD | Practically Insoluble |
| 10% HP-β-CD in Water | 8.2 | ~0 | Practically Insoluble |
| 1% TW80 in Water | 7.6 | ~0 | Practically Insoluble |
| 1% Poloxamer 188 in Water | 8.0 | ~0 | Practically Insoluble |
| 100% Water | 8.3 | ~0 | Practically Insoluble |

Example 61: $CRF_1$ Receptor Antagonist Activity

The association ($k_1$) and dissociation ($k_{-1}$) rate constants defining binding of the Compounds to the $CRF_1$ receptor were determined by the method described in Fleck et al. (*J. Pharmacology and Experimental Therapeutics,* 341(2):518-531, 2012) (hereinafter "Fleck et al." and incorporated by reference in its entirety). As described therein, the activity of a $CRF_1$ receptor antagonist can be expressed as the kinetically derived affinity ($K_i$) calculated from the association ($k_1$) and dissociation ($k_{-1}$) rate constants by the following equation:

$$K_i = k_{-1}/k_1$$

Additionally, the half-life of drug dissociation from the receptor ($t_{1/2}$), which is equal to the median residence time, is calculated from the dissociation rate constant ($k_{-1}$) by the following equation:

$$t_{1/2} = 0.693/k_{-1}$$

The Compounds listed in Table 5 were evaluated according to these procedures, and the kinetic $K_i$ was determined and found to be as follows:

TABLE 5

Binding data for representative $CRF_1$ Receptor Antagonists

| Compound | $k_1$ ($10^6 M^{-1} min^{-1}$) | $k^{-1}$ ($min^{-1}$) | Dissociation $t_{1/2}$ (min) | Kinetic $K_i$ (nM) |
|---|---|---|---|---|
| 1 | 4.9 ± 1.7 | <0.001 | >693 | <0.22 |
| 2 | 5.3 ± 0.78 | <0.001 | >693 | <0.19 |
| 3 | 2.9 ± 0.92 | <0.001 | >693 | <0.36 |
| 8 | 9.1 ± 4.1 | <0.001 | >693 | <0.12 |
| 9 | 3.5 ± 1.1 | <0.001 | >693 | <0.29 |
| 10 | 2.2 | 0.0021 | 330 | 0.95 |
| 11 | 2.4 +/− 0.2 | 0.0017 | 483 | 0.72 |

Example 62: Lowering of ACTH in Adrenalectomized Rats

Compound 1 is a potent $CRF_1$ antagonist possessing a kinetic Ki<0.22 nM and a dissociation $t_{1/2}$>693 minutes (Table 5 above). When administered orally to ADX rats in a method defined in Fleck et al., 10 mg/kg single dose of Compound 1 significantly lowered the plasma ACTH levels for up to 5 hours (n=11/group).

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

Various references such as patents, patent applications, and publications are cited herein, the disclosures of which are hereby incorporated by reference herein in their entireties.

SEQUENCE LISTING

Not Applicable

What is claimed is:

1. A compound of Formula (I):

(I)

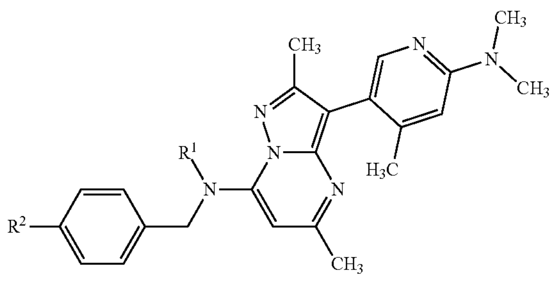

or a pharmaceutically acceptable salt or stereoisomer thereof, wherein:

$R^1$ is H or $C_{1-6}$ alkyl;

$R^2$ is $C_{3-10}$ cycloalkyl, 4- to 14-membered heterocycloalkyl, $C_{6-10}$ aryl, or 5- to 10-membered heteroaryl;

wherein the $C_{3-10}$ cycloalkyl, 4- to 14-membered heterocycloalkyl, $C_{6-10}$ aryl, or 5- to 10-membered heteroaryl is optionally substituted with 1, 2, 3, 4, or 5 substituents independently selected from the group consisting of halo, CN, $NO_2$, $C_{1-6}$ alkyl, $C_{1-6}$ haloalkyl, $C_{1-4}$ alkylene-Cy, $C_{2-6}$ alkenyl, $C_{2-6}$ alkynyl, $C(NR^e)NR^cR^d$, $C(O)R^b$, $C(O)NR^cR^d$, $C(O)OR^a$, $NR^cR^d$, $NR^cC(N^e)NR^cR^d$, $NR^cC(O)R^b$, $NR^cC(O)NR^cR^d$, $NR^cC(O)OR^a$, $NR^cS(O)R^b$, $NR^cS(O)_2R^b$, $NR^cS(O)_2NR^cR^d$, $OR^a$, $OC(O)R^b$, $OC(O)NR^cR^d$, $SR^a$, $S(O)R^b$, $S(O)NR^cR^d$, $S(O)_2R^b$, $S(O)_2NR^cR^d$, and Cy; and wherein each $C_{1-6}$ alkyl, $C_{2-6}$ alkenyl, and $C_{2-6}$ alkynyl substituent is optionally and independently substituted with 1, 2, or 3 substituents independently selected from the group consisting of halo, CN, $NO_2$, $C_{1-6}$ haloalkyl, $C(NR^e)NR^cR^d$, $C(O)R^b$, $C(O)NR^cR^d$, $C(O)OR^a$, $NR^cR^d$, $NR^cC(R^e)NR^cR^d$, $NR^cC(O)R^b$, $NR^cC(O)NR^cR^d$, $NR^cC(O)OR^a$, $NR^cS(O)R^b$, $NR^cS(O)_2R^b$, $NR^cS(O)_2NR^cR^d$, $OR^a$, $OC(O)R^b$, $OC(O)NR^cR^d$, $SR^a$, $S(O)R^b$, $S(O)NR^cR^d$, $S(O)_2R^b$, and $S(O)_2NR^cR^d$;

each Cy is independently $C_{3-10}$ cycloalkyl, 4- to 14-membered heterocycloalkyl, $C_{6-10}$ aryl, or 5- to 10-membered heteroaryl, wherein each $C_{3-10}$ cycloalkyl, 4- to 14-membered heterocycloalkyl, $C_{6-10}$ aryl, and 5- to 10-membered heteroaryl is optionally and independently substituted with 1, 2, 3, 4, or 5 substituents independently selected from the group consisting of halo, CN, $NO_2$, $C_{1-6}$ alkyl, $C_{1-6}$ haloalkyl, $C_{1-4}$ alkylene-$C_{3-7}$ cycloalkyl, $C_{1-4}$ alkylene-4- to 10-membered heterocycloalkyl, $C_{1-4}$ alkylene-$C_{6-10}$ aryl, $C_{1-4}$ alkylene-5- to 10-membered heteroaryl, $C_{2-6}$ alkenyl, $C_{2-6}$ alkynyl, $C(NR^{e1})NR^{c1}R^{d1}$, $C(O)R^{b1}$, $C(O)NR^{c1}R^{d1}$, $C(O)OR^{a1}$, $NR^{c1}R^{d1}$, $NR^{c1}C(NR^{e1})NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)R^{b1}$, $NR^{c1}S(O)_2R^{b1}$, $NR^{c1}S(O)_2NR^{c1}R^{d1}$, $OR^{a1}$, $OC(O)R^{b1}$, $OC(O)NR^{c1}R^{d1}$, $SR^{a1}$, $S(O)R^{b1}$, $S(O)NR^{c1}R^{d1}$, $S(O)_2R^{b1}$, and $S(O)_2NR^{c1}R^{d1}$;

each $R^a$ is independently H, $C_{1-6}$ alkyl, $C_{1-6}$ haloalkyl, $C_{1-4}$ alkylene-$C_{3-7}$ cycloalkyl, $C_{1-4}$ alkylene-4- to 10-membered heterocycloalkyl, $C_{1-4}$ alkylene-$C_{6-10}$ aryl, $C_{1-4}$ alkylene-5- to 10-membered heteroaryl, $C_{2-6}$ alkenyl, $C_{2-6}$ alkynyl, $C_{3-7}$ cycloalkyl, $C_{6-10}$ aryl, 4- to 10-membered heterocycloalkyl, or 5- to 10-membered heteroaryl, wherein each $C_{1-6}$ alkyl, $C_{2-6}$ alkenyl, $C_{2-6}$ alkynyl, $C_{1-4}$ alkylene-$C_{3-7}$ cycloalkyl, $C_{1-4}$ alkylene-4- to 10-membered heterocycloalkyl, $C_{1-4}$ alkylene-$C_{6-10}$ aryl, $C_{1-4}$ alkylene-5- to 10-membered heteroaryl, $C_{2-6}$ alkenyl, $C_{2-6}$ alkynyl, $C_{3-7}$ cycloalkyl, $C_{6-10}$ aryl, 4- to 10-membered heterocycloalkyl, and 5- to 10-membered heteroaryl is optionally and independently substituted with 1, 2, 3, 4, or 5 substituents independently selected from the group consisting of halo, CN, $C_{1-4}$ alkyl, $C_{1-4}$ haloalkyl, $C_{2-6}$ alkenyl, $C_{2-6}$ alkynyl, $C(NR^{e2})NR^{c2}R^{d2}$, $C(O)R^{b2}$, $C(O)NR^{c2}R^{d2}$, $C(O)OR^{a2}$, $NR^{c2}R^{d2}$, $NR^{c2}C(NR^{e2})NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)_2R^{b2}$, $NR^{c2}S(O)_2NR^{c2}R^{d2}$, $OR^{a2}$, $OC(O)R^{b2}$, $OC(O)NR^{c2}R^{d2}$, $SR^{a2}$, $S(O)R^{b2}$, $S(O)NR^{c2}R^{d2}$, $S(O)_2R^{b2}$, and $S(O)_2NR^{c2}R^{d2}$;

each $R^b$ is independently H, $C_{1-6}$ alkyl, $C_{1-6}$ haloalkyl, $C_{1-4}$ alkylene-$C_{3-7}$ cycloalkyl, $C_{1-4}$ alkylene-4- to 10-membered heterocycloalkyl, $C_{1-4}$ alkylene-$C_{6-10}$ aryl, $C_{1-4}$ alkylene-5- to 10-membered heteroaryl, $C_{2-6}$ alkenyl, $C_{2-6}$ alkynyl, $C_{3-7}$ cycloalkyl, $C_{6-10}$ aryl, 4- to 10-membered heterocycloalkyl, or 5- to 10-membered heteroaryl, wherein each $C_{1-6}$ alkyl, $C_{2-6}$ alkenyl, $C_{2-6}$ alkynyl, $C_{1-4}$ alkylene-$C_{3-7}$ cycloalkyl, $C_{1-4}$ alkylene-4- to 10-membered heterocycloalkyl, $C_{1-4}$ alkylene-$C_{6-10}$ aryl, $C_{1-4}$ alkylene-5- to 10-membered heteroaryl, $C_{2-6}$ alkenyl, $C_{2-6}$ alkynyl, $C_{3-7}$ cycloalkyl, $C_{6-10}$ aryl, 4- to 10-membered heterocycloalkyl, and 5- to 10-membered heteroaryl is optionally and independently substituted with 1, 2, 3, 4, or 5 substituents independently selected from the group consisting of halo, CN, $C_{1-4}$ alkyl, $C_{1-4}$ haloalkyl, $C_{2-6}$ alkenyl, $C_{2-6}$ alkynyl, $C(NR^{e2})NR^{c2}R^{d2}$, $C(O)R^{b2}$, $C(O)NR^{c2}R^{d2}$, $C(O)OR^{a2}$, $NR^{c2}R^{d2}$, $NR^{c2}C(NR^{e2})NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)_2R^{b2}$, $NR^{c2}S(O)_2NR^{c2}R^{d2}$, $OR^{a2}$, $OC(O)R^{b2}$, $OC(O)NR^{c2}R^{d2}$, $SR^{a2}$, $S(O)R^{b2}$, $S(O)NR^{c2}R^{d2}$, $S(O)_2R^{b2}$, and $S(O)_2NR^{c2}R^{d2}$;

each $R^c$ is independently H, $C_{1-6}$ alkyl, $C_{1-6}$ haloalkyl, $C_{1-4}$ alkylene-$C_{3-7}$ cycloalkyl, $C_{1-4}$ alkylene-4- to 10-membered heterocycloalkyl, $C_{1-4}$ alkylene-$C_{6-10}$ aryl, $C_{1-4}$ alkylene-5- to 10-membered heteroaryl, $C_{2-6}$ alkenyl, $C_{2-6}$ alkynyl, $C_{3-7}$ cycloalkyl, $C_{6-10}$ aryl, 4- to 10-membered heterocycloalkyl, or 5- to 10-membered heteroaryl, wherein each $C_{1-6}$ alkyl, $C_{2-6}$ alkenyl, $C_{2-6}$ alkynyl, $C_{1-4}$ alkylene-$C_{3-7}$ cycloalkyl, $C_{1-4}$ alkylene-4- to 10-membered heterocycloalkyl, $C_{1-4}$ alkylene-$C_{6-10}$ aryl, $C_{1-4}$ alkylene-5- to 10-membered heteroaryl, $C_{2-6}$ alkenyl, $C_{2-6}$ alkynyl, $C_{3-7}$ cycloalkyl, $C_{6-10}$ aryl, 4- to 10-membered heterocycloalkyl, and 5- to 10-membered heteroaryl is optionally and independently substituted with 1, 2, 3, 4, or 5 substituents independently selected from the group consisting of halo, CN, $C_{1-4}$ alkyl, $C_{1-4}$ haloalkyl, $C_{2-6}$ alkenyl, $C_{2-6}$ alkynyl, $C(NR^{e2})NR^{c2}R^{d2}$, $C(O)R^{b2}$, $C(O)NR^{c2}R^{d2}$, $C(O)OR^{a2}$, $NR^{c2}R^{d2}$, $NR^{c2}C(NR^{e2})NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)_2R^{b2}$, $NR^{c2}S(O)_2NR^{c2}R^{d2}$, $OR^{a2}$, $OC(O)R^{b2}$, $OC(O)NR^{c2}R^{d2}$, $SR^{a2}$, $S(O)R^{b2}$, $S(O)NR^{c2}R^{d2}$, $S(O)_2R^{b2}$, and $S(O)_2NR^{c2}R^{d2}$;

each $R^d$ is independently H, $C_{1-6}$ alkyl, $C_{1-6}$ haloalkyl, $C_{1-4}$ alkylene-$C_{3-7}$ cycloalkyl, $C_{1-4}$ alkylene-4- to 10-membered heterocycloalkyl, $C_{1-4}$ alkylene-$C_{6-10}$ aryl, $C_{1-4}$ alkylene-5- to 10-membered heteroaryl, $C_{2-6}$ alkenyl, $C_{2-6}$ alkynyl, $C_{3-7}$ cycloalkyl, $C_{6-10}$ aryl, 4- to 10-membered heterocycloalkyl, or 5- to 10-membered heteroaryl, wherein each $C_{1-6}$ alkyl, $C_{2-6}$ alkenyl, $C_{2-6}$ alkynyl, $C_{1-4}$ alkylene-$C_{3-7}$ cycloalkyl, $C_{1-4}$ alkylene-4- to 10-membered heterocycloalkyl, $C_{1-4}$ alkylene-$C_{6-10}$ aryl, $C_{1-4}$ alkylene-5- to 10-membered heteroaryl, $C_{2-6}$ alkenyl, $C_{2-6}$ alkynyl, $C_{3-7}$ cycloalkyl, $C_{6-10}$ aryl, 4- to 10-membered heterocycloalkyl, and 5- to 10-membered heteroaryl is optionally and independently substituted with 1, 2, 3, 4, or 5 substituents independently selected from the group consisting of halo, CN, $C_{1-4}$ alkyl, $C_{1-4}$ haloalkyl, $C_{2-6}$ alkenyl, $C_{2-6}$ alkynyl, $C(NR^{e2})NR^{c2}R^{d2}$, $C(O)R^{b2}$, $C(O)NR^{c2}R^{d2}$, $C(O)OR^{a2}$, $NR^{c2}R^{d2}$, $NR^{c2}C(NR^{e2})NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)_2R^{b2}$, $NR^{c2}S(O)_2NR^{c2}R^{d2}$, $OR^{a2}$, $OC(O)R^{b2}$, $OC(O)NR^{c2}R^{d2}$, $SR^{a2}$, $S(O)R^{b2}$, $S(O)NR^{c2}R^{d2}$, $S(O)_2R^{b2}$, and $S(O)_2NR^{c2}R^{d2}$; or any $R^c$ and $R^d$, taken together with the nitrogen atom to which they are attached, independently forms a 4- to 7-membered heterocycloalkyl, wherein each 4- to 7-membered heterocycloalkyl is optionally and independently substituted with 1, 2, or 3 substituents independently selected from the group consisting of halo, CN, $C_{1-4}$ alkyl, $C_{1-4}$ haloalkyl, $C(NR^{e2})NR^{c2}R^{d2}$, $C(O)R^{b2}$, $C(O)NR^{c2}R^{d2}$, $C(O)OR^{a2}$, $NR^{c2}R^{d2}$, $NR^{c2}C$ $(NR^{e2})NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)_2R^{b2}$, $NR^{c2}S(O)_2NR^{c2}R^{d2}$, $OR^{a2}$, $OC(O)R^{b2}$, $OC(O)NR^{c2}R^{d2}$, $SR^{a2}$, $S(O)R^{b2}$, $S(O)NR^{c2}R^{d2}$, $S(O)_2R^{b2}$, and $S(O)_2NR^{c2}R^{d2}$;

each $R^{a1}$ is independently H, $C_{1-6}$ alkyl, $C_{1-6}$ haloalkyl, $C_{1-4}$ alkylene-$C_{3-7}$ cycloalkyl, $C_{1-4}$ alkylene-4- to 10-membered heterocycloalkyl, $C_{1-4}$ alkylene-$C_{6-10}$ aryl, $C_{1-4}$ alkylene-5- to 10-membered heteroaryl, $C_{2-6}$ alkenyl, $C_{2-6}$ alkynyl, $C_{3-7}$ cycloalkyl, $C_{6-10}$ aryl, 4- to 10-membered heterocycloalkyl, or 5- to 10-membered heteroaryl, wherein each $C_{1-6}$ alkyl, $C_{2-6}$ alkenyl, $C_{2-6}$ alkynyl, $C_{1-4}$ alkylene-$C_{3-7}$ cycloalkyl, $C_{1-4}$ alkylene-4- to 10-membered heterocycloalkyl, $C_{1-4}$ alkylene-$C_{6-10}$ aryl, $C_{1-4}$ alkylene-5- to 10-membered heteroaryl, $C_{2-6}$ alkenyl, $C_{2-6}$ alkynyl, $C_{3-7}$ cycloalkyl, $C_{6-10}$ aryl, 4- to 10-membered heterocycloalkyl, and 5- to 10-membered heteroaryl is optionally and independently substituted with 1, 2, 3, 4, or 5 substituents independently selected from the group consisting of halo, CN, $C_{1-4}$ alkyl, $C_{1-4}$ haloalkyl, $C_{2-6}$ alkenyl, $C_{2-6}$ alkynyl, $C(NR^{e2})NR^{c2}R^{d2}$, $C(O)R^{b2}$, $C(O)NR^{c2}R^{d2}$, $C(O)OR^{a2}$, $NR^{c2}R^{d2}$, $NR^{c2}C(NR^{e2})NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)_2R^{b2}$, $NR^{c2}S(O)_2NR^{c2}R^{d2}$, $OR^{a2}$, $OC(O)R^{b2}$, $OC(O)NR^{c2}R^{d2}$, $SR^{a2}$, $S(O)R^{b2}$, $S(O)NR^{c2}R^{d2}$, $S(O)_2R^{b2}$, and $S(O)_2NR^{c2}R^{d2}$;

each $R^{b1}$ is independently H, $C_{1-6}$ alkyl, $C_{1-6}$ haloalkyl, $C_{1-4}$ alkylene-$C_{3-7}$ cycloalkyl, $C_{1-4}$ alkylene-4- to 10-membered heterocycloalkyl, $C_{1-4}$ alkylene-$C_{6-10}$ aryl, $C_{1-4}$ alkylene-5- to 10-membered heteroaryl, $C_{2-6}$ alkenyl, $C_{2-6}$ alkynyl, $C_{3-7}$ cycloalkyl, $C_{6-10}$ aryl, 4- to 10-membered heterocycloalkyl, or 5- to 10-membered heteroaryl, wherein each $C_{1-6}$ alkyl, $C_{2-6}$ alkenyl, $C_{2-6}$ alkynyl, $C_{1-4}$ alkylene-$C_{3-7}$ cycloalkyl, $C_{1-4}$ alkylene-4- to 10-membered heterocycloalkyl, $C_{1-4}$ alkylene-$C_{6-10}$ aryl, $C_{1-4}$ alkylene-5- to 10-membered heteroaryl, $C_{2-6}$ alkenyl, $C_{2-6}$ alkynyl, $C_{3-7}$ cycloalkyl, $C_{6-10}$ aryl, 4- to 10-membered heterocycloalkyl, and 5- to 10-membered heteroaryl is optionally and independently substituted with 1, 2, 3, 4, or 5 substituents independently selected from the group consisting of halo, CN, $C_{1-4}$ alkyl, $C_{1-4}$ haloalkyl, $C_{2-6}$ alkenyl, $C_{2-6}$ alkynyl, $C(NR^{e2})NR^{c2}R^{d2}$, $C(O)R^{b2}$, $C(O)NR^{c2}R^{d2}$, $C(O)OR^{a2}$, $NR^{c2}R^{d2}$, $NR^{c2}C(NR^{e2})NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)_2R^{b2}$, $NR^{c2}S(O)_2NR^{c2}R^{d2}$, $OR^{a2}$, $OC(O)R^{b2}$, $OC(O)NR^{c2}R^{d2}$, $SR^{a2}$, $S(O)R^{b2}$, $S(O)NR^{c2}R^{d2}$, $S(O)_2R^{b2}$, and $S(O)_2NR^{c2}R^{d2}$;

each $R^{c1}$ is independently H, $C_{1-6}$ alkyl, $C_{1-6}$ haloalkyl, $C_{1-4}$ alkylene-$C_{3-7}$ cycloalkyl, $C_{1-4}$ alkylene-4- to 10-membered heterocycloalkyl, $C_{1-4}$ alkylene-$C_{6-10}$ aryl, $C_{1-4}$ alkylene-5- to 10-membered heteroaryl, $C_{2-6}$ alkenyl, $C_{2-6}$ alkynyl, $C_{3-7}$ cycloalkyl, $C_{6-10}$ aryl, 4- to 10-membered heterocycloalkyl, or 5- to 10-membered heteroaryl, wherein each $C_{1-6}$ alkyl, $C_{2-6}$ alkenyl, $C_{2-6}$ alkynyl, $C_{1-4}$ alkylene-$C_{3-7}$ cycloalkyl, $C_{1-4}$ alkylene-4- to 10-membered heterocycloalkyl, $C_{1-4}$ alkylene-$C_{6-10}$ aryl, $C_{1-4}$ alkylene-5- to 10-membered heteroaryl, $C_{2-6}$ alkenyl, $C_{2-6}$ alkynyl, $C_{3-7}$ cycloalkyl, $C_{6-10}$ aryl, 4- to 10-membered heterocycloalkyl, and 5- to 10-membered heteroaryl is optionally and independently substituted with 1, 2, 3, 4, or 5 substituents independently selected from the group consisting of halo, CN, $C_{1-4}$ alkyl, $C_{1-4}$ haloalkyl, $C_{2-6}$ alkenyl, $C_{2-6}$ alkynyl, $C(NR^{e2})NR^{c2}R^{d2}$, $C(O)R^{b2}$, $C(O)NR^{c2}R^{d2}$, $C(O)OR^{a2}$, $NR^{c2}R^{d2}$, $NR^{c2}C(NR^{e2})NR^{c2}R^{d2}$, $NR^{c2}C(O)R^{b2}$, $NR^{c2}C(O)NR^{c2}R^{d2}$, $NR^{c2}C(O)OR^{a}2$, $NR^{c2}S(O)_2R^{b2}$, $NR^{c2}S(O)_2NR^{c2}R^{d2}$, $OR^{a2}$, $OC(O)R^{b2}$, $OC(O)NR^{c2}R^{d2}$, $SR^{a2}$, $S(O)R^{b2}$, $S(O)NR^{c2}R^{d2}$, $S(O)_2R^{b2}$, and $S(O)_2NR^{c2}R^{d2}$;

each $R^{d1}$ is independently H, $C_{1-6}$ alkyl, $C_{1-6}$ haloalkyl, $C_{1-4}$ alkylene-$C_{3-7}$ cycloalkyl, $C_{1-4}$ alkylene-4- to 10-membered heterocycloalkyl, $C_{1-4}$ alkylene-$C_{6-10}$ aryl, $C_{1-4}$ alkylene-5- to 10-membered heteroaryl, $C_{2-6}$ alkenyl, $C_{2-6}$ alkynyl, $C_{3-7}$ cycloalkyl, $C_{6-10}$ aryl, 4- to 10-membered heterocycloalkyl, or 5- to 10-membered heteroaryl, wherein each $C_{1-6}$ alkyl, $C_{2-6}$ alkenyl, $C_{2-6}$ alkynyl, $C_{1-4}$ alkylene-$C_{3-7}$ cycloalkyl, $C_{1-4}$ alkylene-4- to 10-membered heterocycloalkyl, $C_{1-4}$ alkylene-$C_{6-10}$ aryl, $C_{1-4}$ alkylene-5- to 10-membered heteroaryl, $C_{2-6}$ alkenyl, $C_{2-6}$ alkynyl, $C_{3-7}$ cycloalkyl, $C_{6-10}$ aryl, 4- to 10-membered heterocycloalkyl, and 5- to 10-membered heteroaryl is optionally and independently substituted with 1, 2, 3, 4, or 5 substituents independently selected from the group consisting of halo, CN, $C_{1-4}$ alkyl, $C_{1-4}$ haloalkyl, $C_{2-6}$ alkenyl, $C_{2-6}$ alkynyl, $C(NR^{e2})NR^{c2}R^{d2}$, $C(O)R^{b2}$, $C(O)NR^{c2}R^{d2}$, $C(O)OR^{a2}$, $NR^{c2}R^{d2}$, $NR^{c2}C(NR^{e2})NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)_2R^{b2}$, $NR^{c2}S(O)_2NR^{c2}R^{d2}$, $OR^{a2}$, $OC(O)R^{b2}$, $OC(O)NR^{c2}R^{d2}$, $SR^{a2}$, $S(O)R^{b2}$, $S(O)NR^{c2}R^{d2}$, $S(O)_2R^{b2}$, and $S(O)_2NR^{c2}R^{d2}$; or any $R^{c1}$ and $R^{d1}$, taken together with the nitrogen atom to which they are attached, independently forms a 4- to 7-membered heterocycloalkyl, wherein each 4- to 7-membered heterocycloalkyl is optionally and independently substituted with 1, 2, or 3 substituents independently selected from the group consisting of halo, CN, $C_{1-4}$ alkyl, $C_{1-4}$ haloalkyl, $C(NR^{e2})NR^{c2}R^{d2}$, $C(O)R^{b2}$, $C(O)NR^{c2}R^{d2}$, $C(O)OR^{a2}$, $NR^{c2}R^{d2}$, $NR^{c2}C(NR^{c2})NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)_2R^{b2}$, $NR^{c2}S(O)_2NR^{c2}R^{d2}$ $OR^{a2}$, $OC(O)R^{b2}$, $OC(O)NR^{c2}R^{d2}$, $SR^{a2}$, $S(O)R^{b2}$, $S(O)NR^{c2}R^{d2}$, $S(O)_2R^{b2}$, and $S(O)_2NR^{c2}R^{d2}$;

each $R^{a2}$ is independently H, $C_{1-6}$ alkyl, $C_{1-6}$ haloalkyl, $C_{1-4}$ alkylene-$C_{3-7}$ cycloalkyl, $C_{1-4}$ alkylene-4- to 10-membered heterocycloalkyl, $C_{1-4}$ alkylene-$C_{6-10}$ aryl, $C_{1-4}$ alkylene-5- to 10-membered heteroaryl, $C_{2-6}$ alkenyl, $C_{2-6}$ alkynyl, $C_{3-7}$ cycloalkyl, 4- to 10-membered heterocycloalkyl, $C_{6-10}$ aryl, or 5- to 10-membered heteroaryl, wherein each $C_{1-6}$ alkyl, $C_{1-6}$ haloalkyl, $C_{1-4}$ alkylene-$C_{3-7}$ cycloalkyl, $C_{1-4}$ alkylene-4- to 10-membered heterocycloalkyl, $C_{1-4}$ alkylene-$C_{6-10}$ aryl, $C_{1-4}$ alkylene-5- to 10-membered heteroaryl, $C_{2-6}$ alkenyl, $C_{2-6}$ alkynyl, $C_{3-7}$ cycloalkyl, 4- to 10-membered heterocycloalkyl, $C_{6-10}$ aryl, and 5- to 10-membered heteroaryl is optionally and independently substituted with 1, 2, or 3 substituents independently selected from the group consisting of halo, CN, $C_{1-6}$ alkyl, $C_{1-6}$ haloalkyl, $NH_2$, OH, $OC_{1-6}$ alkyl, and $OC_{1-6}$ haloalkyl;

each $R^{b2}$ is independently H, $C_{1-6}$ alkyl, $C_{1-6}$ haloalkyl, $C_{1-4}$ alkylene-$C_{3-7}$ cycloalkyl, $C_{1-4}$ alkylene-4- to 10-membered heterocycloalkyl, $C_{1-4}$ alkylene-$C_{6-10}$ aryl, $C_{1-4}$ alkylene-5- to 10-membered heteroaryl, $C_{2-6}$ alkenyl, $C_{2-6}$ alkynyl, $C_{3-7}$ cycloalkyl, 4- to 10-membered heterocycloalkyl, $C_{6-10}$ aryl, or 5- to 10-membered heteroaryl, wherein each $C_{1-6}$ alkyl, $C_{1-6}$ haloalkyl, $C_{1-4}$ alkylene-$C_{3-7}$ cycloalkyl, $C_{1-4}$ alkylene-4- to 10-membered heterocycloalkyl, $C_{1-4}$ alkylene-$C_{6-10}$ aryl, $C_{1-4}$ alkylene-5- to 10-membered heteroaryl, $C_{2-6}$ alkenyl, $C_{2-6}$ alkynyl, $C_{3-7}$ cycloalkyl, 4- to 10-membered heterocycloalkyl, $C_{6-10}$ aryl, and 5- to 10-membered heteroaryl is optionally and independently substituted with 1, 2, or 3 substituents independently selected from the group consisting of halo, CN, $C_{1-6}$ alkyl, $C_{1-6}$ haloalkyl, $NH_2$, OH, $OC_{1-6}$ alkyl, and $OC_{1-6}$ haloalkyl;

each $R^{c2}$ is independently H, $C_{1-6}$ alkyl, $C_{1-6}$ haloalkyl, $C_{1-4}$ alkylene-$C_{3-7}$ cycloalkyl, $C_{1-4}$ alkylene-4- to 10-membered heterocycloalkyl, $C_{1-4}$ alkylene-$C_{6-10}$ aryl, $C_{1-4}$ alkylene-5- to 10-membered heteroaryl, $C_{2-6}$ alkenyl, $C_{2-6}$ alkynyl, $C_{3-7}$ cycloalkyl, 4- to 10-membered heterocycloalkyl, $C_{6-10}$ aryl, or 5- to 10-membered heteroaryl, wherein each $C_{1-6}$ alkyl, $C_{1-6}$ haloalkyl, $C_{1-4}$ alkylene-$C_{3-7}$ cycloalkyl, $C_{1-4}$ alkylene-4- to 10-membered heterocycloalkyl, $C_{1-4}$ alkylene-$C_{6-10}$ aryl, $C_{1-4}$ alkylene-5- to 10-membered heteroaryl, $C_{2-6}$ alkenyl, $C_{2-6}$ alkynyl, $C_{3-7}$ cycloalkyl, 4- to 10-membered heterocycloalkyl, $C_{6-10}$ aryl, and 5- to 10-membered heteroaryl is optionally and independently substituted with 1, 2, or 3 substituents independently selected from the group consisting of halo, CN, $C_{1-6}$ alkyl, $C_{1-6}$ haloalkyl, $NH_2$, OH, $OC_{1-6}$ alkyl, and $OC_{1-6}$ haloalkyl;

each $R^{d2}$ is independently H, $C_{1-6}$ alkyl, $C_{1-6}$ haloalkyl, $C_{1-4}$ alkylene-$C_{3-7}$ cycloalkyl, $C_{1-4}$ alkylene-4- to 10-membered heterocycloalkyl, $C_{1-4}$ alkylene-$C_{6-10}$ aryl, $C_{1-4}$ alkylene-5- to 10-membered heteroaryl, $C_{2-6}$ alkenyl, $C_{2-6}$ alkynyl, $C_{3-7}$ cycloalkyl, 4- to 10-membered heterocycloalkyl, $C_{6-10}$ aryl, or 5- to 10-membered heteroaryl, wherein each $C_{1-6}$ alkyl, $C_{1-6}$ haloalkyl, $C_{1-4}$ alkylene-$C_{3-7}$ cycloalkyl, $C_{1-4}$ alkylene-4- to 10-membered heterocycloalkyl, $C_{1-4}$ alkylene-$C_{6-10}$ aryl, $C_{1-4}$ alkylene-5- to 10-membered heteroaryl, $C_{2-6}$ alkenyl, $C_{2-6}$ alkynyl, $C_{3-7}$ cycloalkyl, 4- to 10-membered heterocycloalkyl, $C_{6-10}$ aryl, and 5- to 10-membered heteroaryl is optionally and independently substituted with 1, 2, or 3 substituents independently selected from the group consisting of halo, CN, $C_{1-6}$ alkyl, $C_{1-6}$ haloalkyl, $NH_2$, OH, $OC_{1-6}$ alkyl, and $OC_{1-6}$ haloalkyl;

each $R^e$ is independently H, CN, or $C_{1-4}$ alkyl;

each $R^{e1}$ is independently H, CN, or $C_{1-4}$ alkyl; and each $R^{e2}$ is independently H, CN, or $C_{1-4}$ alkyl;

with the provisos that:

(1) any ring-forming carbon atom or any ring-forming nitrogen atom of any aforementioned heterocycloalkyl is optionally and independently substituted with one =O substituent; and (2) any ring-forming sulfur atom of any aforementioned heterocycloalkyl is optionally and independently substituted with one or two =O substituents.

2. The compound of claim 1, or a pharmaceutically acceptable salt or stereoisomer thereof, wherein $R^1$ is $C_{1-6}$ alkyl.

3. The compound of claim 1, or a pharmaceutically acceptable salt or stereoisomer thereof, wherein $R^1$ is $CH_2CH_2CH_3$.

4. The compound of claim 1, or a pharmaceutically acceptable salt or stereoisomer thereof, wherein $R^2$ is $C_{6-10}$ aryl or 5- to 10-membered heteroaryl;

wherein the $C_{6-10}$ aryl or 5- to 10-membered heteroaryl is optionally substituted with 1, 2, 3, 4, or 5 substituents independently selected from the group consisting of halo, CN, $NO_2$, $C_{1-6}$ alkyl, $C_{1-6}$ haloalkyl, $C_{1-4}$ alkylene-Cy, $C_{2-6}$ alkenyl, $C_{2-6}$ alkynyl, $C(NR^e)NR^cR^d$, $C(O)R^b$, $C(O)NR^cR^d$, $C(O)OR^a$, $NR^cR^d$, $NR^cC(NR^e)NR^cR^d$, $C(O)R^b$, $NR^cC(O)NR^cR^d$, $NR^cC(O)OR^a$, $NR^cS(O)R^b$, $NR^cS(O)_2R^b$, $NR^cS(O)_2NR^cR^d$, $OR^a$, $OC(O)R^b$, $OC(O)NR^cR^d$, $SR^a$, $S(O)R^b$, $S(O)NR^cR^d$, $S(O)_2R^b$, $S(O)_2NR^cR^d$, and Cy; and wherein each $C_{1-6}$ alkyl, $C_{2-6}$ alkenyl, and $C_{2-6}$ alkynyl substituent is optionally and independently substituted with 1, 2, or 3 substituents independently selected from the group consisting of halo, CN, $NO_2$, $C_{1-6}$ haloalkyl, $C(NR^e)NR^cR^d$, $C(O)R^b$, $C(O)NR^cR^d$, $C(O)OR^a$, $NR^cR^d$, $NR^cC(NR^e)NR^cR^d$, $NR^cC(O)R^b$, $NR^cC(O)NR^cR^d$, $NR^cC(O)OR^a$, $NR^cS(O)R^b$, $NR^cS(O)_2R^b$, $NR^cS(O)_2NR^cR^d$, $OR^a$, $OC(O)R^b$, $OC(O)NR^cR^d$, $SR^a$, $S(O)R^b$, $S(O)NR^cR^d$, $S(O)_2R^b$, and $S(O)_2NR^cR^d$.

5. The compound of claim 1, or a pharmaceutically acceptable salt or stereoisomer thereof, wherein $R^2$ is phenyl or 5- or 6-membered heteroaryl;

wherein the phenyl or 5- or 6-membered heteroaryl is optionally substituted with 1, 2, 3, 4, or 5 substituents independently selected from the group consisting of halo, CN, $NO_2$, $C_{1-6}$ alkyl, $C_{1-6}$ haloalkyl, $C_{1-4}$ alkylene-Cy, $C_{2-6}$ alkenyl, $C_{2-6}$ alkynyl, $C(NR^e)NR^cR^d$, $C(O)R^b$, $C(O)NR^cR^d$, $C(O)OR^a$, $NR^cR^d$, $NR^cC(NR^e)NR^cR^d$, $NR^cC(O)R^b$, $NR^cC(O)NR^cR^d$, $NR^cC(O)OR^a$, $NR^cS(O)R^b$, $NR^cS(O)_2R^b$, $NR^cS(O)_2NR^cR^d$, $OR^a$, $OC(O)R^b$, $OC(O)NR^cR^d$, $SR^a$, $S(O)R^b$, $S(O)NR^cR^d$, $S(O)_2R^b$, $S(O)_2NR^cR^d$, and Cy; and wherein each $C_{1-6}$ alkyl, $C_{2-6}$ alkenyl, and $C_{2-6}$ alkynyl substituent is optionally and independently substituted with 1, 2, or 3 substituents independently selected from the group consisting of halo, CN, $NO_2$, $C_{1-6}$ haloalkyl, $C(NR^e)NR^cR^d$, $C(O)R^b$, $C(O)NR^cR^d$, $C(O)OR^a$, $NR^cR^d$, $NR^cC(R^e)NR^cR^d$, $NR^cC(O)R^b$, $NR^cC(O)NR^cR^d$, $C(O)OR^a$, $NR^cS(O)R^b$, $NR^cS(O)_2R^b$, $NR^cS(O)_2NR^cR^d$, $OR^a$, $OC(O)R^b$, $OC(O)NR^cR^d$, $SR^a$, $S(O)R^b$, $S(O)NR^cR^d$, $S(O)_2R^b$, and $S(O)_2NR^cR^d$.

6. The compound of claim 1, or a pharmaceutically acceptable salt or stereoisomer thereof, wherein $R^2$ is phenyl, pyrazolyl, isoxazolyl, thiazolyl, triazolyl, thiadiazolyl, pyridinyl, or pyrimidinyl;

wherein the phenyl, pyrazolyl, isoxazolyl, thiazolyl, triazolyl, thiadiazolyl, pyridinyl, or pyrimidinyl is optionally substituted with 1, 2, 3, 4, or 5 substituents independently selected from the group consisting of halo, CN, $NO_2$, $C_{1-6}$ alkyl, $C_{1-6}$ haloalkyl, $C_{1-4}$ alkylene-Cy, $C_{2-6}$ alkenyl, $C_{2-6}$ alkynyl, $C(NR^e)NR^cR^d$, $C(O)R^b$, $C(O)NR^cR^d$, $C(O)OR^a$, $NR^cR^d$, $R^cC(NR^e)NR^cR^d$, $NR^cC(O)R^b$, $NR^cC(O)NR^d$, $NR^cC(O)OR^a$, $NR^cS(O)R^b$, $NR^cS(O)_2R^b$, $NR^cS(O)_2NR^cR^d$, $OR^a$, $OC(O)R^b$, $OC(O)NR^cR^d$, $SR^a$, $S(O)R^b$, $S(O)NR^cR^d$, $S(O)_2R^b$, $S(O)_2NR^cR^d$, and Cy; and wherein each $C_{1-6}$ alkyl, $C_{2-6}$ alkenyl, and $C_{2-6}$ alkynyl substituent is optionally and independently substituted with 1, 2, or 3 substituents independently selected from the group consisting of halo, CN, $NO_2$, $C_{1-6}$ haloalkyl, $C(NR^e)NR^cR^d$, $C(O)R^b$, $C(O)NR^cR^d$, $C(O)OR^a$, $NR^cR^d$, $NR^cC(NR^e)NR^cR^d$, $NR^cC(O)R^b$, $NR^cC(O)NR^cR^d$, $NR^cC(O)OR^a$, $NR^cS(O)R^b$, $NR^cS(O)_2R^b$, $NR^cS(O)_2NR^cR^d$, $OR^a$, $OC(O)R^b$, $OC(O)NR^cR^d$, $SR^a$, $S(O)R^b$, $S(O)NR^cR^d$, $S(O)_2R^b$, and $S(O)_2NR^cR^d$.

7. The compound of claim 1, or a pharmaceutically acceptable salt or stereoisomer thereof, wherein $R^2$ is phenyl, pyrazol-1-yl, isoxazol-4-yl, 2-(dimethylamino)thiazol-4-yl, 1,2,4-triazol-1-yl, 1,2,3-thiadiazol-4-yl, pyridin-2-yl, pyridin-3-yl, pyridin-4-yl, or pyrimidin-5-yl.

8. The compound of claim 1, or a pharmaceutically acceptable salt or stereoisomer thereof, wherein:

$R^1$ is $C_{1-6}$ alkyl;

$R^2$ is $C_{6-10}$ aryl or 5- to 10-membered heteroaryl, wherein the $C_{6-10}$ aryl or 5- to 10-membered heteroaryl is optionally substituted with 1 or 2 substituents independently selected from the group consisting of halo, CN, $NO_2$, $C_{1-6}$ alkyl, $C_{1-6}$ haloalkyl, $C(O)R^b$, $C(O)NR^cR^d$, $C(O)OR^a$, $NR^cR^d$, $NR^cC(O)R^b$, $NR^cC(O)NR^cR^d$, $NR^cC(O)OR^a$, $NR^cS(O)_2R^b$, $NR^cS(O)_2NR^cR^d$, $OR^a$, $OC(O)R^b$, $S(O)_2R^b$, and $S(O)_2NR^cR^d$;

each $R^a$ is independently H, $C_{1-6}$ alkyl, or $C_{1-6}$ haloalkyl, wherein each $C_{1-6}$ alkyl is optionally and independently substituted with 1 or 2 substituents independently selected from the group consisting of halo, CN, $C_{1-4}$ alkyl, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)_2R^{b2}$, $NR^{c2}S(O)_2NR^{c2}R^{d2}$, $OR^{a2}$, $OC(O)R^{b2}$, $SR^{a2}$, $S(O)_2R^{b2}$, and $S(O)_2NR^{c2}R^{d2}$;

each $R^b$ is independently H, $C_{1-6}$ alkyl, or $C_{1-6}$ haloalkyl, wherein each $C_{1-6}$ alkyl is optionally and independently substituted with 1 or 2 substituents independently selected from the group consisting of halo, CN, $C_{1-4}$ alkyl, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)_2R^{b2}$, $NR^{c2}S(O)_2NR^{c2}R^{d2}$, $OR^{a2}$, $OC(O)R^{b2}$, $SR^{a2}$, $S(O)_2R^{b2}$, and $S(O)_2NR^{c2}R^{d2}$;

each $R^c$ is independently H, $C_{1-6}$ alkyl, or $C_{1-6}$ haloalkyl, wherein each $C_{1-6}$ alkyl is optionally and independently substituted with 1 or 2 substituents independently selected from the group consisting of halo, CN, $C_{1-4}$ alkyl, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)_2R^{b2}$, $NR^{c2}S(O)_2NR^{c2}R^{d2}$, $OR^{a2}$, $OC(O)R^{b2}$, $SR^{a2}$, $S(O)_2R^{b2}$, and $S(O)_2NR^{c2}R^{d2}$;

each $R^d$ is independently H, $C_{1-6}$ alkyl, or $C_{1-6}$ haloalkyl, wherein each $C_{1-6}$ alkyl is optionally and independently substituted with 1 or 2 substituents independently selected from the group consisting of halo, CN, $C_{1-4}$ alkyl, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)_2R^{b2}$, $NR^{c2}S(O)_2NR^{c2}R^{d2}$, $OR^{a2}$, $OC(O)R^{b2}$, $SR^{a2}$, $S(O)_2R^{b2}$, and $S(O)_2NR^{c2}R^{d2}$; or any $R^c$ and $R^d$, taken together with the nitrogen atom to which they are attached, independently forms a 4- to 7-membered heterocycloalkyl, wherein each 4- to 7-membered heterocycloalkyl is optionally and independently substituted with 1, 2, or 3 substituents independently selected from the group consisting of halo, CN, $C_{1-4}$ alkyl, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)_2R^{b2}$, $NR^{c2}S(O)_2NR^{c2}R^{d2}$, $OR^{a2}$, $OC(O)R^{b2}$, $SR^{a2}$, $S(O)_2R^{b2}$, and $S(O)_2NR^{c2}R^{d2}$;

each $R^{a2}$ is independently H, $C_{1-6}$ alkyl, or $C_{1-6}$ haloalkyl, wherein each $C_{1-6}$ alkyl is optionally and independently substituted with 1, 2, or 3 substituents independently selected from the group consisting of halo, CN, $C_{1-6}$ alkyl, $C_{1-6}$ haloalkyl, $NH_2$, OH, $OC_{1-6}$ alkyl, and $OC_{1-6}$ haloalkyl;

each $R^{b2}$ is independently H, $C_{1-6}$ alkyl, or $C_{1-6}$ haloalkyl, wherein each $C_{1-6}$ alkyl is optionally and independently substituted with 1, 2, or 3 substituents independently selected from the group consisting of halo, CN, $C_{1-6}$ alkyl, $C_{1-6}$ haloalkyl, $NH_2$, OH, $OC_{1-6}$ alkyl, and $OC_{1-6}$ haloalkyl;

each $R^{c2}$ is independently H, $C_{1-6}$ alkyl, or $C_{1-6}$ haloalkyl, wherein each $C_{1-6}$ alkyl is optionally and independently substituted with 1, 2, or 3 substituents independently selected from the group consisting of halo, CN, $C_{1-6}$ alkyl, $C_{1-6}$ haloalkyl, $NH_2$, OH, $OC_{1-6}$ alkyl, and $OC_{1-6}$ haloalkyl; and each $R^{d2}$ is independently H, $C_{1-6}$ alkyl, or $C_{1-6}$ haloalkyl, wherein each $C_{1-6}$ alkyl is optionally and independently substituted with 1, 2, or 3 substituents independently selected from the group consisting of halo, CN, $C_{1-6}$ alkyl, $C_{1-6}$ haloalkyl, $NH_2$, OH, $OC_{1-6}$ alkyl, and $OC_{1-6}$ haloalkyl.

9. The compound of claim 1, wherein the compound is selected from the group consisting of:

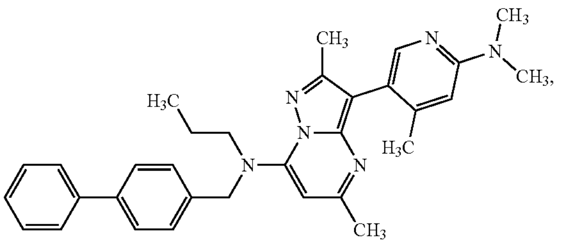

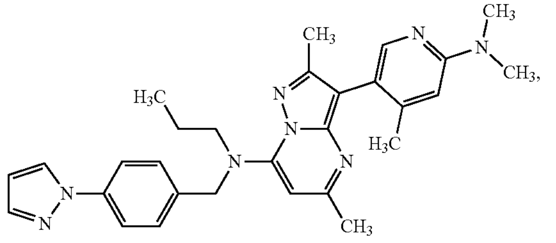

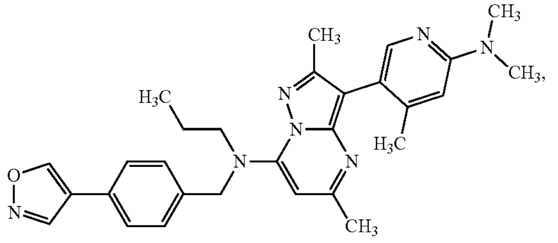

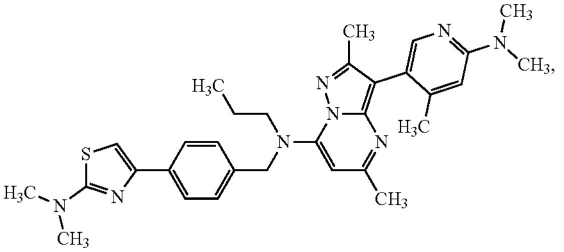

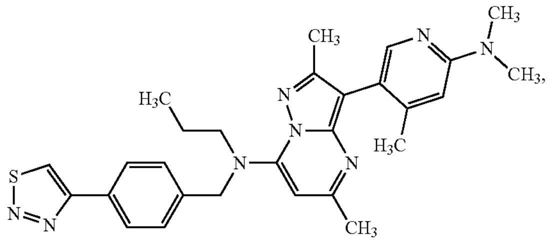

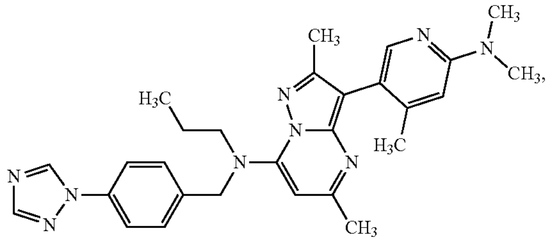

-continued

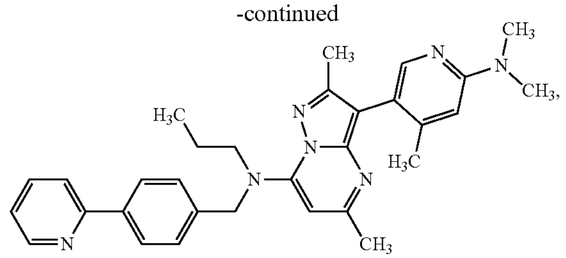

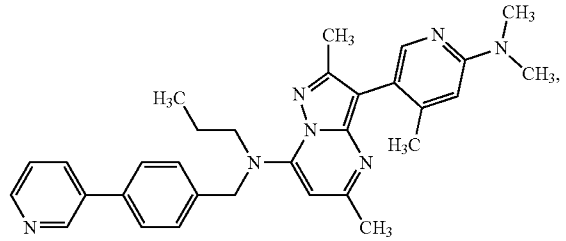

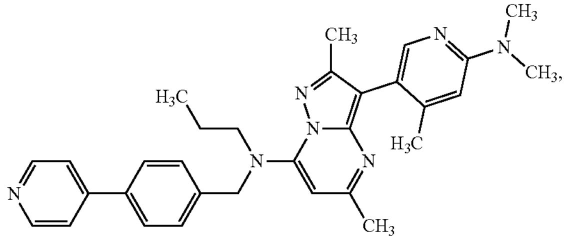

and

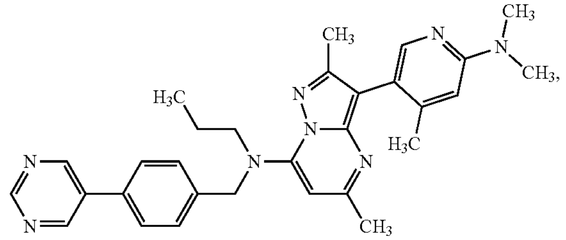

or a pharmaceutically acceptable salt thereof.

10. A pharmaceutical composition comprising at least one pharmaceutically acceptable carrier and a compound of claim 1, or a pharmaceutically acceptable salt or stereoisomer thereof.

11. A method for reducing the level of at least one biomarker in a subject in need thereof, wherein the method comprises administering to the subject a therapeutically effective amount of a compound of claim 1, or a pharmaceutically acceptable salt or stereoisomer thereof;

wherein reducing the level of at least one biomarker in the subject is effective to reduce the level of the at least one biomarker in the subject compared to the level of the at least one biomarker in the subject prior to administration of the therapeutically effective amount of the compound of claim 1, or a pharmaceutically acceptable salt or stereoisomer thereof; and wherein the at least one biomarker in the subject is selected from the group consisting of (a) androstenedione, (b) 17-hydroxyprogesterone (17-OHP), and (c) testosterone.

12. A method for reducing the severity of at least one symptom of congenital adrenal hyperplasia (CAH) in a subject in need thereof, wherein the method comprises administering to the subject a therapeutically effective amount of a compound of claim 1, or a pharmaceutically acceptable salt or stereoisomer thereof;

wherein the at least one symptom of congenital adrenal hyperplasia (CAH) in the subject is selected from the group consisting of acne, a fertility problem, growth impairment, hirsutism, and precocious puberty.

13. A method for reducing the dosage of corticosteroid needed by a subject to treat congenital adrenal hyperplasia (CAH) in the subject, wherein the method comprises administering to the subject a therapeutically effective amount of a compound of claim 1, or a pharmaceutically acceptable salt or stereoisomer thereof.

14. A method for reducing the severity of at least one side effect of glucocorticoid treatment in a subject having congenital adrenal hyperplasia (CAH), wherein the method comprises administering to the subject a therapeutically effective amount of a compound of claim 1, or a pharmaceutically acceptable salt or stereoisomer thereof;

wherein the at least one side effect of glucocorticoid treatment in the subject is selected from the group consisting of acne, adrenal suppression, akathisia, anxiety, avascular necrosis of the bone, cataract, central serous chorioretinopathy, cognitive impairment, coronary heart disease, a Cushingoid feature, Cushing's syndrome, delayed wound healing, delirium, dementia, depression, dermatoprosis, diabetes mellitus, dyslipidemia, easy bruising, ecchymosis, an erosion, euphoria, gastritis, gastrointestinal bleeding, glaucoma, growth suppression, hair loss, heart failure, hepatic steatosis, hirsutism, hyperglycemia, hypertension, irritability, ischemic heart disease, a mood change, mood lability, mydriasis, myopathy, an opportunistic ocular infection, osteoporosis, pancreatitis, peptic ulcer, a predisposition to an infection, ptosis, purpura, psychosis, a reactivation of a latent infection, skin atrophy, striae, suppression of cell-mediated immunity, visceral perforation, and weight gain.

15. A method for treating congenital adrenal hyperplasia (CAH) in a subject in need thereof, wherein the method comprises administering to the subject a therapeutically effective amount of a compound of claim 1, or a pharmaceutically acceptable salt or stereoisomer thereof.

16. The method of claim 15, wherein the congenital adrenal hyperplasia (CAH) is classic congenital adrenal hyperplasia.

17. The method of claim 16, wherein the classic congenital adrenal hyperplasia is due to 21-hydroxylase deficiency.

18. The method of claim 16, wherein the subject has a mutation in the CYP21A2 gene located on chromosome 6p21.

19. The method of claim 16, wherein the subject does not have a mutation of the 11β-hydroxylase gene CYP11B1 (11β-OH CAH).

20. The method of claim 16, wherein the method further comprises administering to the subject a therapeutically effective amount of a glucocorticoid.

21. The method of claim 20, wherein the glucocorticoid is selected from the group consisting of dexamethasone, hydrocortisone, prednisolone, and prednisone.

22. A method for treating congenital adrenal hyperplasia (CAH) in a subject in need thereof, wherein the method comprises:

(i) measuring the level of at least one biomarker in a biological sample obtained from the subject, wherein the at least one biomarker obtained from the subject is selected from the group consisting of (a) androstenedione, (b) 17-hydroxyprogesterone (17-OHP), and (c) testosterone;

(ii) analyzing the level of the at least one biomarker in the biological sample obtained from the subject to determine if the level of the at least one biomarker in the biological sample obtained from the subject is elevated compared to a healthy subject not having congenital adrenal hyperplasia (CAH); and (iii) administering to the subject a therapeutically effective amount of a compound of claim 1, or a pharmaceutically acceptable salt or stereoisomer thereof, if the subject is determined to have an elevated level of at least one biomarker selected from the group consisting of (a) androstenedione, (b) 17-hydroxyprogesterone (17-OHP), and (c) testosterone.

23. A compound having the structure:

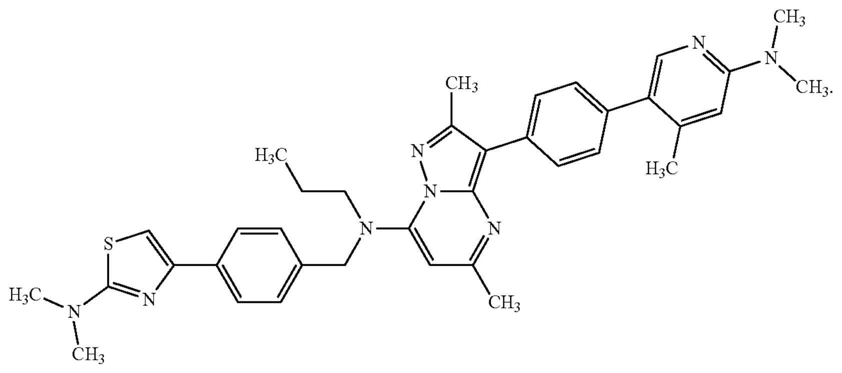 [SMILES: CCCN(Cc1ccc(-c2csc(N(C)C)n2)cc1)c1cc(C)nc2c(-c3ccc(-c4cnc(N(C)C)cc4C)cc3)c(C)nn12]

24. A pharmaceutical composition comprising at least one pharmaceutically acceptable carrier and the compound of claim 23.

25. A method for reducing the level of at least one biomarker in a subject in need thereof, wherein the method comprises administering to the subject a therapeutically effective amount of the compound of claim 23;

wherein reducing the level of at least one biomarker in the subject is effective to reduce the level of the at least one biomarker in the subject compared to the level of the at least one biomarker in the subject prior to administration of the therapeutically effective amount of the compound of claim 23; and wherein the at least one biomarker in the subject is selected from the group consisting of (a) androstenedione, (b) 17-hydroxyprogesterone (17-OHP), and (c) testosterone.

26. A method for reducing the severity of at least one symptom of congenital adrenal hyperplasia (CAH) in a subject in need thereof, wherein the method comprises administering to the subject a therapeutically effective amount of the compound of claim 23;

wherein the at least one symptom of congenital adrenal hyperplasia (CAH) in the subject is selected from the group consisting of acne, a fertility problem, growth impairment, hirsutism, and precocious puberty.

27. A method for reducing the dosage of corticosteroid needed by a subject to treat congenital adrenal hyperplasia (CAH) in the subject, wherein the method comprises administering to the subject a therapeutically effective amount of the compound of claim 23.

28. A method for reducing the severity of at least one side effect of glucocorticoid treatment in a subject having congenital adrenal hyperplasia (CAH), wherein the method comprises administering to the subject a therapeutically effective amount of the compound of claim 23;

wherein the at least one side effect of glucocorticoid treatment in the subject is selected from the group consisting of acne, adrenal suppression, akathisia, anxiety, avascular necrosis of the bone, cataract, central serous chorioretinopathy, cognitive impairment, coronary heart disease, a Cushingoid feature, Cushing's syndrome, delayed wound healing, delirium, dementia, depression, dermatoprosis, diabetes mellitus, dyslipidemia, easy bruising, ecchymosis, an erosion, euphoria, gastritis, gastrointestinal bleeding, glaucoma, growth suppression, hair loss, heart failure, hepatic steatosis, hirsutism, hyperglycemia, hypertension, irritability, ischemic heart disease, a mood change, mood lability, mydriasis, myopathy, an opportunistic ocular infection, osteoporosis, pancreatitis, peptic ulcer, a predisposition to an infection, ptosis, purpura, psychosis, a reactivation of a latent infection, skin atrophy, striae, suppression of cell-mediated immunity, visceral perforation, and weight gain.

29. A method for treating congenital adrenal hyperplasia (CAH) in a subject in need thereof, wherein the method comprises administering to the subject a therapeutically effective amount of the compound of claim 23.

30. The method of claim 29, wherein the congenital adrenal hyperplasia (CAH) is classic congenital adrenal hyperplasia.

31. The method of claim 30, wherein the classic congenital adrenal hyperplasia is due to 21-hydroxylase deficiency.

32. The method of claim 30, wherein the subject has a mutation in the CYP21A2 gene located on chromosome 6p21.

33. The method of claim 30, wherein the subject does not have a mutation of the 11b-hydroxylase gene CYP11B1 (11b-OH CAH).

34. The method of claim 30, wherein the method further comprises administering to the subject a therapeutically effective amount of a glucocorticoid.

35. The method of claim 34, wherein the glucocorticoid is selected from the group consisting of dexamethasone, hydrocortisone, prednisolone, and prednisone.

36. A method for treating congenital adrenal hyperplasia (CAH) in a subject in need thereof, wherein the method comprises:

(i) measuring the level of at least one biomarker in a biological sample obtained from the subject, wherein the at least one biomarker obtained from the subject is selected from the group consisting of (a) androstenedione, (b) 17-hydroxyprogesterone (17-OHP), and (c) testosterone;

(ii) analyzing the level of the at least one biomarker in the biological sample obtained from the subject to determine if the level of the at least one biomarker in the biological sample obtained from the subject is elevated compared to a healthy subject not having congenital adrenal hyperplasia (CAH); and (iii) administering to the subject a therapeutically effective amount of the compound of claim 23, if the subject is determined to have an elevated level of at least one biomarker selected from the group consisting of (a) androstenedione, (b) 17-hydroxyprogesterone (17-OHP), and (c) testosterone.

* * * * *